US008796180B2

(12) United States Patent
Gross et al.

(10) Patent No.: US 8,796,180 B2
(45) Date of Patent: Aug. 5, 2014

(54) AMINOQUINAZOLINE COMPOUNDS FOR COMBATING INVERTEBRATE PESTS

(75) Inventors: Steffen Gross, Ludwigshafen (DE); Matthias Pohlman, Freinsheim (DE); Arun Narine, Mannheim (DE); Claudia Rosenbaum, Heidelberg (DE); Prashant Deshmukh, Mannheim (DE); Joachim Dickhaut, Heidelberg (DE); Nina Gertrud Bandur, Mannheim (DE); Karsten Koerber, Eppelheim (DE); Florian Kaiser, Mannheim (DE); Wolfgang Von Deyn, Neustadt (DE); Juergen Langewald, Mannheim (DE); Deborah L. Culbertson, Fuquay Varina, NC (US); Cecille Ebuenga, Los Banos (PH)

(73) Assignee: BASF SE, Ludwigshafen (DE)

( * ) Notice: Subject to any disclaimer, the term of this patent is extended or adjusted under 35 U.S.C. 154(b) by 137 days.

(21) Appl. No.: 13/497,374

(22) PCT Filed: Sep. 15, 2010

(86) PCT No.: PCT/EP2010/063502
§ 371 (c)(1),
(2), (4) Date: Mar. 21, 2012

(87) PCT Pub. No.: WO2011/036074
PCT Pub. Date: Mar. 31, 2011

(65) Prior Publication Data
US 2012/0178622 A1    Jul. 12, 2012

Related U.S. Application Data

(60) Provisional application No. 61/245,322, filed on Sep. 24, 2009.

(51) Int. Cl.
*A01N 43/54* (2006.01)
*A61K 31/517* (2006.01)
*C07D 239/72* (2006.01)
*C07D 401/00* (2006.01)

(52) U.S. Cl.
USPC ............... 504/240; 514/266.1; 514/266.2; 544/283; 544/284

(58) Field of Classification Search
USPC ............. 504/240; 514/266.1, 266.2; 544/283, 544/284
See application file for complete search history.

(56) References Cited

U.S. PATENT DOCUMENTS
6,613,772 B1    9/2003    Schindler

FOREIGN PATENT DOCUMENTS

| | | |
|---|---|---|
| DE | 197 56 388 | 6/1999 |
| EP | 0 393 999 | 10/1990 |
| WO | WO 02/24667 | 3/2002 |
| WO | WO 2004/030672 | 4/2004 |
| WO | WO 2004/092196 | 10/2004 |
| WO | WO 2005/087742 | 9/2005 |
| WO | WO 2007/125331 | 11/2007 |
| WO | WO 2010/100189 | 9/2010 |

OTHER PUBLICATIONS

International Search Report completed Dec. 15, 2010, in International Application No. PCT/EP2010/063502, filed Sep. 15, 2010.
English language translation of the International Preliminary Report on Patentability dated Dec. 22, 2011, from corresponding International Application No. PCT/EP2010/063502, filed Sep. 15, 2010.

*Primary Examiner* — Paul V. Ward
(74) *Attorney, Agent, or Firm* — Brinks Gilson & Lione

(57) ABSTRACT

The invention relates to aminoquinazoline compounds or the enantiomers or veterinarily acceptable salts thereof which are useful for combating or controlling invertebrate pests, in particular arthropod pests and nematodes. The invention also relates to methods for controlling invertebrate pests by using these compounds and to plant propagation material and to agricultural and veterinary compositions comprising said compounds.

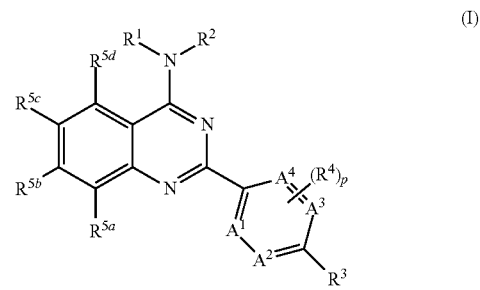

wherein $A^1, A^2, A^3, A^4, R^1, R^2, R^3, R^4, R^{5a}, R^{5b}, R^{5c}, R^{5d}$ and p are defined as in the description.

22 Claims, No Drawings

AMINOQUINAZOLINE COMPOUNDS FOR COMBATING INVERTEBRATE PESTS

This application is a National Stage application of International Application No. PCT/EP2010/063502, filed Sep. 15, 2010, which claims the benefit of U.S. Provisional Application No. 61/245,322, filed Sep. 24, 2009, the entire contents of which are hereby incorporated herein by reference.

The present invention relates to aminoquinazoline compounds or the enantiomers or veterinarily acceptable salts thereof which are useful for combating or controlling invertebrate pests, in particular arthropod pests and nematodes. The invention also relates to methods for controlling invertebrate pests by using these compounds and to plant propagation material and to agricultural and veterinary compositions comprising said compounds.

Invertebrate pests and in particular arthropods and nematodes destroy growing and harvested crops and attack wooden dwelling and commercial structures, causing large economic loss to the food supply and to property. While a large number of pesticidal agents are known, due to the ability of target pests to develop resistance to said agents, there is an ongoing need for new agents for combating invertebrate pests, in particular insects, arachnids and nematodes.

WO 2005/087742 describes quinoline derivatives usable as agents in the control of pests for crop protection, human and animal health, acting as ethanolamine kinase inhibitors.

EP-A-393999 describes quinazolinylsulfonylureidoazines useful as herbicides.

DE-A-19756388 describes substituted 2-aryl-4-amino-quinazolines and their use as cardiovascular agents for treatment of circulatory diseases, blood pressure, angina, pectoris, heart insufficiency, thrombosis or arterosclorosis and to modulate the production of cGMP.

WO 2002/24667 describes 4-amino-quinazolines as glycoprotein IbIX antagonists.

WO 2004/030672 describes the use of 4-amino-quinazolines as anti cancer agents and PKB inhibitors.

WO 2004/092196 describes among other quinazolines derivatives compounds for modulating protein kinase enzymatic activity.

It is an object of the present invention to provide compounds that have a good pesticidal activity, in particular insecticidal activity, and show a broad activity spectrum against a large number of different invertebrate pests, especially against difficult to control arthropod pests and/or nematodes.

It has been found that these objectives can be achieved by aminoquinazoline compounds of the formula I below, by their steroisomers and by their salts and N-oxides, in particular their agriculturally or veterinarily acceptable salts.

Therefore, in a first aspect, the invention relates to aminoquinazoline compounds of the formula I and the salts and N-oxides thereof

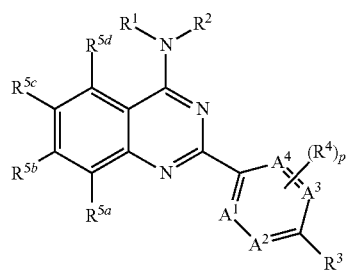

(I)

wherein
$A^1$, $A^2$, $A^3$ and $A^4$ are N, NX or $CR^4$ wherein X is a lone pair or O, with the proviso that at most three of $A^1$, $A^2$, $A^3$ and $A^4$ are N or NX;

$R^1$, $R^2$ are selected independently from one another from the group consisting of hydrogen, CN, $NO_2$, $C_1$-$C_{10}$-alkyl, $C_3$-$C_8$-cycloalkyl, $C_2$-$C_{10}$-alkenyl, $C_2$-$C_{10}$-alkynyl,
wherein the carbon atoms of the aforementioned aliphatic and cycloaliphatic radicals may be unsubstituted or substituted with one or more $R^{6-}$;
$Si(R^{11})_2R^{12}$, $OR^7$, $S(O)_mR^7$, $NR^8R^9$, $N=C(R^6)_2$, $C(=O)R^6$, $C(=S)R^6$, $C(=NR^8)R^6$ and a 3-, 4-, 5-, 6- or 7-membered heterocyclic ring,
wherein said heterocyclic ring
is saturated or partially saturated,
comprises 1, 2 or 3 heteroatoms selected from oxygen, nitrogen and/or sulfur, wherein the nitrogen and/or the sulfur atom(s) may be oxidized,
is unsubstituted or substituted with one to five $R^{10}$, and
wherein one or two $CH_2$ groups in said heterocyclic ring may be replaced by one or two C=O groups;

$R^3$ is selected from the group consisting of hydrogen, halogen, cyano, azido, nitro, SCN, $SF_5$, $C_1$-$C_{10}$-alkyl, $C_3$-$C_8$-cycloalkyl, $C_2$-$C_{10}$-alkenyl, $C_2$-$C_{10}$-alkynyl,
wherein the carbon atoms of the aforementioned aliphatic and cycloaliphatic radicals may be unsubstituted or substituted with one or more $R^6$;
$Si(R^{11})_2R^{12}$, $OR^7$, $N(R^8)R^9$, $N=C(R^6)_2$, $C(=O)R^6$, $C(=S)R^6$, $C(=NR^8)R^6$, phenyl
which may be substituted with 1, 2, 3, 4 or 5 radicals $R^{10}$;
and a 3-, 4-, 5-, 6- or 7-membered heterocyclic ring,
wherein said heterocyclic ring
is saturated or partially saturated,
comprises 1, 2 or 3 heteroatoms or heteroatom groups selected from N, O, S, NO, SO and $SO_2$,
is unsubstituted or substituted with one to five radicals $R^{10}$, and
wherein one or two $CH_2$ groups in said heterocyclic ring may be replaced by one or two C=O groups;

each $R^4$ is selected independently from the group consisting of hydrogen, halogen, cyano, azido, nitro, SCN, $SF_5$, $C_1$-$C_{10}$-alkyl, $C_3$-$C_8$-cycloalkyl, $C_2$-$C_{10}$-alkenyl, $C_2$-$C_{10}$-alkynyl,
wherein the carbon atoms of the aforementioned aliphatic and cycloaliphatic radicals may be unsubstituted or substituted with one or more $R^6$;
$Si(R^{11})_2R^{12}$, $OR^7$, $S(O)_mR^7$, $N(R^8)R^9$, $N=C(R^6)_2$, $C(=O)R^6$, $C(=S)R^6$, $C(=NR^8)R^6$, $C(=O)N(R^8)R^9$, $C(=S)N(R^8)R^9$, phenyl
which may be substituted with 1, 2, 3, 4 or 5 radicals $R^{10}$;
and a 3-, 4-, 5-, 6- or 7-membered heterocyclic ring,
wherein said heterocyclic ring
is saturated or partially unsaturated or aromatic,
comprises 1, 2 or 3 heteroatoms or heteroatom groups selected from N, O, S, NO, SO and $SO_2$,
is unsubstituted or substituted with one to five radicals $R^{10}$, and
wherein one or two $CH_2$ groups in said saturated or partially saturated rings may be replaced by one or two C=O groups;

or two radicals $R^4$ bound on adjacent carbon atoms together form a group selected from $-CH_2CH_2CH_2CH_2-$, $-CH=CH-CH=CH-$, $-N=CH-CH=CH-$, $-CH=N-CH=CH-$, $-N=CH-N=CH-$, $-OCH_2CH_2CH_2-$, $-OCH=CHCH_2-$, $-CH_2OCH_2CH_2-$, $-OCH_2CH_2O-$, $-OCH_2OCH_2-$, $-CH_2CH_2CH_2-$, —CH=CHCH$_2$—, —CH$_2$CH$_2$O—, —CH=CHO—, —CH$_2$OCH$_2$—, —CH$_2$C(=O)O—, —C(=O)OCH$_2$—, —O(CH$_2$)O—, —SCH$_2$CH$_2$CH$_2$—, —SCH=CHCH$_2$—, —CH$_2$SCH$_2$CH$_2$—, —SCH$_2$CH$_2$S—, —SCH$_2$SCH$_2$—, —CH$_2$CH$_2$S—, —CH=CHS—, —CH$_2$SCH$_2$—, —CH$_2$C(=S)S—, —C(=S)SCH$_2$—, —S(CH$_2$)S—, —CH$_2$CH$_2$NR$^8$—, —CH$_2$CH=N—, —CH=CH—NR$^8$—, —OCH=N— and —SCH=N—, wherein in each of the above group, one to five hydrogen atoms independently of each other may be replaced by one to five substituents selected from halogen, methyl, halomethyl, hydroxyl, methoxy and halomethoxy, or one or two CH$_2$ groups of the above groups may be replaced by one or two C=O groups;

R$^{5a}$ is selected from the group consisting of hydrogen, halogen, cyano, azido, nitro, SCN, SF$_5$, C$_1$-C$_{10}$-alkyl, C$_3$-C$_8$-cycloalkyl, C$_2$-C$_{10}$-alkenyl, C$_2$-C$_{10}$-alkynyl, wherein the carbon atoms of the aforementioned aliphatic and cycloaliphatic radicals may be unsubstituted or substituted with one or more R$^6$;

Si(R$^{11}$)$_2$R$^{12}$, OR$^7$, S(O)$_m$R$^7$, N(R$^8$)R$^9$, N=C(R$^6$)$_2$, C(=O)R$^6$, C(=S)R$^6$, C(=NR$^8$)R$^6$, phenyl which may be substituted with 1, 2, 3, 4 or 5 radicals R$^{10}$; and a 3-, 4-, 5-, 6- or 7-membered heterocyclic ring, wherein said heterocyclic ring is saturated or partially unsaturated or aromatic, comprises 1, 2 or 3 heteroatoms or heteroatom groups selected from N, O, S, NO, SO and SO$_2$, is unsubstituted or substituted with one to five radicals R$^{10}$, and wherein one or two CH$_2$ groups in said saturated or partially saturated rings may be replaced by one or two C=O groups;

or R$^{5a}$ may form together with the adjacent carbon atom R$^{5b}$ a 5- or 6-membered ring which is at least substituted with one halogen;

R$^{5b}$ is selected from the group consisting of C$_1$-C$_6$-alkyl, C$_3$-C$_6$-cycloalkyl, C$_1$-C$_6$-alkoxy and C$_1$-C$_6$-cycloalkoxy, wherein each mentioned radical is at least substituted with one halogen, may be further partially or fully halogenated, and may be substituted with one to five radicals R$^6$;

or R$^{5b}$ may form together with the adjacent carbon atom R$^{5c}$ or R$^{5a}$ a 5- or 6-membered ring which is at least substituted with one halogen;

R$^{5c}$ is selected from the group consisting of hydrogen, halogen, cyano, azido, nitro, SCN, SF$_5$, C$_1$-C$_{10}$-alkyl, C$_3$-C$_8$-cycloalkyl, C$_2$-C$_{10}$-alkenyl, C$_2$-C$_{10}$-alkynyl, wherein the carbon atoms of the aforementioned aliphatic and cycloaliphatic radicals may be unsubstituted or substituted with one or more R$^6$;

Si(R$^{11}$)$_2$R$^{12}$, OR$^7$, S(O)$_m$R$^7$, N(R$^8$)R$^9$, N=C(R$^6$)$_2$, C(=O)OR$^7$, C(=S)OR$^7$, C(=NR$^8$)R$^6$, C(=O)N(R$^8$)R$^9$, C(=S)N(R$^8$)R$^9$, phenyl which may be substituted with 1, 2, 3, 4 or 5 radicals R$^{10}$; and a 3-, 4-, 5-, 6- or 7-membered heterocyclic ring, wherein said heterocyclic ring is saturated, partially unsaturated or aromatic, comprises 1, 2 or 3 heteroatoms or heteroatom groups selected from N, O, S, NO, SO and SO$_2$, is unsubstituted or substituted with one to five radicals R$^{10}$, and wherein one or two CH$_2$ groups in said saturated or partially saturated rings may be replaced by one or two C=O groups;

or R$^{5c}$ may form together with the adjacent carbon atom R$^{5b}$ or R$^{5d}$ a 5- or 6-membered ring which is at least substituted with one halogen in case of R$^{5b}$ beings involved;

R$^{5d}$ is selected from the group consisting of hydrogen, halogen, cyano, azido, nitro, SCN, SF$_5$, C$_1$-C$_{10}$-alkyl, C$_3$-C$_8$-cycloalkyl, C$_2$-C$_{10}$-alkenyl, C$_2$-C$_{10}$-alkynyl, wherein the carbon atoms of the aforementioned aliphatic and cycloaliphatic radicals may be unsubstituted or substituted with one or more R$^6$;

Si(R$^{11}$)$_2$R$^{12}$, OR$^7$, S(O)$_m$N(R$^8$)R$^9$, N(R$^8$)R$^9$, N=C(R$^6$)$_2$, C(=O)R$^6$, C(=S)R$^6$, C(=NR$^8$)R$^6$, phenyl which may be substituted with 1, 2, 3, 4 or 5 radicals R$^{10}$; and a 3-, 4-, 5-, 6- or 7-membered heterocyclic ring, wherein said heterocyclic ring is saturated, partially unsaturated or aromatic, comprises 1, 2 or 3 heteroatoms or heteroatom groups selected from N, O, S, NO, SO and SO$_2$, is unsubstituted or substituted with one to five radicals R$^{10}$, and wherein one or two CH$_2$ groups in said saturated or partially saturated rings may be replaced by one or two C=O groups;

or R$^{5d}$ may form together with the adjacent carbon atom R$^{5c}$ or with R$^1$ or R$^2$ a 5- or 6-membered ring;

R$^6$ is independently selected independently from the group consisting of hydrogen, halogen, cyano, azido, nitro, SCN, SF$_5$, C$_1$-C$_6$-alkyl, C$_1$-C$_6$-alkoxy, C$_1$-C$_6$-alkylthio, C$_1$-C$_6$-alkylsulfinyl, C$_1$-C$_6$-alkylsulfonyl, C$_3$-C$_8$-cycloalkyl, C$_3$-C$_8$-cycloalkyl-C$_1$-C$_4$-alkyl, C$_2$-C$_6$-alkenyl, C$_2$-C$_6$-alkynyl, wherein the carbon atom of the aforementioned aliphatic and cycloaliphatic radicals may be substituted with one or more R$^c$;

Si(R$^{11}$)$_2$R$^{12}$, OR$^o$, O(CO)R$^c$, O(CS)R$^c$, S(O)$_m$R$^o$, S(O)$_m$N(R'')$_2$, S(CO)R$^c$, S(CS)R$^c$, S(C=NR'')R$^c$, N(R'')$_2$, N(R'')C(=O)R$^c$, N(R'')C(=S)R$^c$, NS(O)$_m$R$^o$, N=C(R$^c$)$_2$, C(=O)R$^c$, C(=S)R$^c$, C(=NR'')R$^c$, C(=O)N(R'')$_2$, C(=S)N(R'')$_2$, phenyl which may be substituted with 1, 2, 3, 4 or 5 radicals R$^{10}$; and a 3-, 4-, 5-, 6- or 7-membered heterocyclic ring, wherein said heterocyclic ring is saturated, partially unsaturated or aromatic, comprises 1, 2 or 3 heteroatoms or heteroatom groups selected from N, O, S, NO, SO and SO$_2$, is unsubstituted or substituted with one to five radicals R$^{10}$, and wherein one or two CH$_2$ groups in said saturated or partially saturated rings may be replaced by one or two O=O groups;

or two vicinally bound radicals R$^6$ together form a group selected from =C(R$^c$)$_2$, =S(O)$_m$R$^o$, =S(O)$_m$N(R'')$_2$, =NR'' and =NN(R'')$_2$;

R$^7$ is independently selected independently from the group consisting of hydrogen, cyano, C$_1$-C$_6$-alkyl, C$_1$-C$_6$-alkoxy, C$_1$-C$_6$-alkylthio, C$_1$-C$_6$-alkylsulfinyl, C$_1$-C$_6$-alkylsulfonyl, C$_3$-C$_8$-cycloalkyl, C$_3$-C$_8$-cycloalkyl-C$_1$-C$_4$-alkyl, C$_2$-C$_6$-alkenyl, C$_2$-C$_6$-alkynyl, wherein the carbon atom of the aforementioned aliphatic and cycloaliphatic radicals may be substituted with one or more R$^c$;

Si(R$^{11}$)$_2$R$^{12}$, OR$^o$, O(CO)R$^c$, O(CS)R$^c$, S(O)$_m$R$^o$, S(O)$_m$N(R'')$_2$, S(CO)R$^c$, S(CS)R$^c$, S(C=NR'')R$^c$, N(R'')$_2$, N(R'')C(=O)R$^c$, N(R'')C(=S)R$^c$, NS(O)$_m$R$^o$, N=C(R$^c$)$_2$, C(=O)R$^c$, C(=S)R$^c$, C(=NR'')R$^c$, C(=O)N(R'')$_2$, C(=S)N(R'')$_2$, phenyl which may be substituted with 1, 2, 3, 4 or 5 radicals $R^{10}$;
and a 3-, 4-, 5-, 6- or 7-membered heterocyclic ring,
  wherein said heterocyclic ring
    is saturated, partially unsaturated or aromatic,
    comprises 1, 2 or 3 heteroatoms or heteroatom groups selected from N, O, S, NO, SO and $SO_2$,
    is unsubstituted or substituted with one to five radicals $R^{10}$, and
    wherein one or two $CH_2$ groups in said saturated or partially saturated rings may be replaced by one or two C=O groups;
with the proviso that $R^7$ is not $C_1$-$C_6$-alkoxy or $C_1$-$C_6$-haloalkoxy if it is bound to an oxygen atom;
$R^8$, $R^9$ are selected independently from one another and independently of each occurrence from the group consisting of hydrogen, CN, $NO_2$, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_3$-$C_8$-cycloalkyl, $C_3$-$C_8$-cycloalkyl-$C_1$-$C_4$-alkyl, $C_2$-$C_6$-alkenyl, $C_2$-$C_6$-alkynyl,
  wherein the carbon atom of the aforementioned aliphatic and
  cycloaliphatic radicals may be substituted with one or more $R^c$;
  $Si(R^{11})_2R^{12}$, $OR^o$, $O(CO)R^c$, $O(CS)R^c$, $S(O)_mR^o$, $S(O)_mN(R'')_2$, $S(CO)R^c$, $S(CS)R^c$, $S(C=NR'')R^c$, $N(R'')_2$, $N(R'')C(=O)R^c$, $N(R'')C(=S)R^c$, $NS(O)_mR^o$, $N=C(R^c)_2$, $C(=O)R^c$, $C(=S)R^c$, $C(=NR'')R^c$, $C(=O)N(R'')_2$, $C(=S)N(R'')_2$ phenyl
  which may be substituted with 1, 2, 3, 4 or 5 radicals $R^{10}$;
  and a 3-, 4-, 5-, 6- or 7-membered heterocyclic ring,
  wherein said heterocyclic ring
    is saturated, partially unsaturated or aromatic,
    comprises 1, 2 or 3 heteroatoms or heteroatom groups selected from N, O, S, NO, SO and $SO_2$,
    is unsubstituted or substituted with one to five radicals $R^{10}$, and
    wherein one or two $CH_2$ groups in said saturated or partially saturated rings may be replaced by one or two C=O groups;
$R^{10}$ is independently selected independently from the group consisting of halogen, cyano, azido, nitro, SCN, $SF_5$, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_3$-$C_8$-cycloalkyl, $C_3$-$C_8$-cycloalkyl-$C_1$-$C_4$-alkyl, $C_2$-$C_6$-alkenyl, $C_2$-$C_6$-alkynyl,
  wherein the carbon atom of the aforementioned aliphatic and
  cycloaliphatic radicals may be substituted with one or more $R^c$;
  $Si(R^{11})_2R^{12}$, $OR^o$, $O(CO)R^c$, $O(CS)R^c$, $S(O)_mR^o$, $S(O)_mN(R^c)_2$, $S(CO)R^c$, $S(CS)R^c$, $S(C=NR'')R^c$, $N(R'')_2$, $N(R'')C(=O)R^c$, $N(R'')C(=S)R^c$, $NS(O)_mR^o$, $N=C(R^c)_2$, $C(=O)R^c$, $C(=S)R^c$, $C(=NR'')R^c$, $C(=O)N(R'')_2$, $C(=S)N(R'')_2$, phenyl
  which may be substituted with one to five radicals independently selected independently from halogen, cyano, nitro, $C_1$-$C_6$-alkyl, $C_1$-$C_6$-haloalkyl, $C_1$-$C_6$-alkoxy and $C_1$-$C_6$-haloalkoxy;
  and a 3-, 4-, 5-, 6- or 7-membered heterocyclic ring,
  wherein said heterocyclic ring
    is saturated or unsaturated,
    comprises 1, 2 or 3 heteroatoms or heteroatom groups selected from N, O, S, NO, SO and $SO_2$,
    is unsubstituted or substituted with one to five radicals independently selected independently from halogen, cyano, nitro, $C_1$-$C_6$-alkyl, $C_1$-$C_6$-haloalkyl, $C_1$-$C_6$-alkoxy and $C_1$-$C_6$-haloalkoxy;
or two radicals $R^{10}$ bound on adjacent atoms together form a group selected from —$CH_2CH_2CH_2CH_2$—, —CH=CH—CH=CH—, —N=CH—CH=CH—, —CH=N—CH=CH—, —N=CH—N=CH—, —$OCH_2CH_2CH_2$—, —OCH=$CHCH_2$—, —$CH_2OCH_2CH_2$—, —$OCH_2CH_2O$—, —$OCH_2OCH_2$—, —$CH_2CH_2CH_2$—, —CH=$CHCH_2$—, —$CH_2CH_2O$—, —CH=CHO—, —$CH_2OCH_2$—, —$CH_2C$(=O)O—, —C(=O)$OCH_2$—, —O($CH_2$)O—, —$SCH_2CH_2CH_2$—, —SCH=$CHCH_2$—, —$CH_2SCH_2CH_2$—, —$SCH_2CH_2S$—, —$SCH_2SCH_2$—, —$CH_2CH_2S$—, —CH=CHS—, —$CH_2SCH_2$—, —$CH_2C$(=S)S—, —C(=S)$SCH_2$—, —S($CH_2$)S—, —$CH_2CH_2NR^8$—, —$CH_2$CH=N—, —CH=CH—$NR^8$—, —OCH=N— and —SCH=N—,
  wherein in each of the above groups,
    one to five hydrogen atoms independently of each other may be replaced by one to five substituents selected from halogen, methyl, halomethyl, hydroxyl, methoxy and halomethoxy, or
    one or two or more $CH_2$ groups of the above groups may be replaced by one or two C=O groups;
$R^{11}$, $R^{12}$ are selected independently of each other and independently of each occurrence from the group consisting of $C_1$-$C_4$-alkyl, $C_3$-$C_6$-cycloalkyl, $C_1$-$C_4$-alkoxy-$C_1$-$C_4$-alkyl, phenyl and benzyl;
$R^c$ is independently selected independently from the group consisting of hydrogen, halogen, cyano, azido, nitro, SCN, $SF_5$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkyl, $C_3$-$C_8$-cycloalkyl-$C_1$-$C_4$-alkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl, and a 3-, 4-, 5-, 6- or 7-membered heterocyclic ring,
  wherein said heterocyclic ring
    is saturated, partially unsaturated or aromatic,
    comprises 1, 2 or 3 heteroatoms or heteroatom groups selected from CO, N, O, S, NO, SO and $SO_2$,
    is unsubstituted or substituted with one to five radicals, which are selected independently of each other from halogen, cyano, nitro, $C_1$-$C_4$-alkyl, $C_1$-$C_4$-haloalkyl, $C_1$-$C_4$-alkoxy and $C_1$-$C_4$-haloalkoxy;
$R^o$ is independently selected independently from the group consisting of hydrogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfonyl, $C_1$-$C_6$-haloalkylsulfinyl, $C_3$-$C_8$-cycloalkyl, $C_3$-$C_8$-cycloalkyl-$C_1$-$C_4$-alkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl, and a 3-, 4-, 5-, 6- or 7-membered heterocyclic ring,
  wherein said heterocyclic ring
    is saturated, partially unsaturated or aromatic,
    comprises 1, 2 or 3 heteroatoms or heteroatom groups selected from CO, N, O, S, NO, SO and $SO_2$,
    is unsubstituted or substituted with one to five radicals, which are selected independently of each other from halogen, cyano, nitro, $C_1$-$C_4$-alkyl, $C_1$-$C_4$-haloalkyl, $C_1$-$C_4$-alkoxy and $C_1$-$C_4$-haloalkoxy;
with the proviso that $R^o$ is not $C_1$-$C_6$-alkoxy or $C_1$-$C_6$-haloalkoxy if it is bound to an oxygen atom;
$R''$ is independently selected independently from the group consisting of hydrogen, CN, $NO_2$, $C_1$-$C_6$-alkoxy, $C_1$-$C_6$-haloalkoxy, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkyl, $C_3$-$C_8$-cycloalkyl-$C_1$-$C_4$-alkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl, and a 3-, 4-, 5-, 6- or 7-membered saturated heterocyclic ring, wherein said heterocyclic ring is saturated, partially unsaturated or aromatic, comprises 1, 2 or 3 heteroatoms or heteroatom groups selected from CO, N, O, S, NO, SO and $SO_2$, is unsubstituted or substituted with one to five radicals, which are selected independently of each other from halogen, cyano, nitro, $C_1$-$C_4$-alkyl, $C_1$-$C_4$-haloalkyl, $C_1$-$C_4$-alkoxy and $C_1$-$C_4$-haloalkoxy;

m is independently 0, 1 or 2;

p is 0, 1, 2, 3 or 4;

or enantiomers or diastereoisomers thereof or their agriculturally or veterinarily acceptable salts.

The present invention also provides a composition comprising at least one compound of the formula I as defined herein and/or an agriculturally acceptable salt thereof and at least one inert solid/liquid and/or solid carrier The present invention also provides an agricultural composition comprising at least one compound of the formula I as defined herein and at least one agriculturally acceptable liquid and/or solid carrier.

The present invention also provides a veterinary composition comprising at least one compound of the formula I as defined herein and/or a veterinarily acceptable salt thereof and at least one liquid and/or solid carrier.

The present invention also provides a method for controlling or combating invertebrate pests attack or infestation which method comprises treating the pests, their food supply, their habitat or their breeding, ground or a cultivated plant, plant propagation materials (such as seed), soil, area, material or environment in which the pests are growing or may grow, with a pesticidally effective amount of at least one compound of formula I or salt thereof as defined herein.

The present invention also relates to plant propagation material, in particular to seed, comprising at least one compound of formula I or an composition comprising at least one compound of formula I or an agriculturally acceptable salt thereof as defined herein.

The present invention further relates to a method for treating or protecting an animal from infestation or infection by parasites which comprises bringing the animal in contact with a parasiticidally effective amount of a compound of the formula I or a veterinarily acceptable salt thereof as defined herein. Bringing the animal in contact with the compound I, its salt or the veterinary composition of the invention means applying or administering it to the animal.

If used, the term "steroisomers" encompasses both optical isomers, such as enantiomers or diastereomers, the latter existing due to more than one center of chirality in the molecule, as well as geometrical isomers (cis/trans isomers).

Depending on the substitution pattern, the compounds of the formula I may have one or more centers of chirality, in which case they are present as mixtures of enantiomers or diastereomers. The invention provides both the pure enantiomers or diastereomers and their mixtures and the use according to the invention of the pure enantiomers or diastereomers of the compound I or its mixtures. Suitable compounds of the formula I also include all possible geometrical stereoisomers (cis/trans isomers) and mixtures thereof. Cis/trans isomers may be present with respect to an imine group.

The compounds of the present invention may be amorphous or may exist in one or more different crystalline states (polymorphs) which may have a different macroscopic properties such as stability or show different biological properties such as activities. The present invention includes both amorphous and crystalline compounds of the formula I, mixtures of different crystalline states of the respective compound I, as well as amorphous or crystalline salts thereof.

Salts of the compounds of the formula I are preferably agriculturally and veterinarily acceptable salts. They can be formed in a customary method, e.g. by reacting the compound with an acid of the anion in question if the compound of formula I has a basic functionality or by reacting an acidic compound of formula I with a suitable base.

Suitable agriculturally acceptable salts are especially the salts of those cations or the acid addition salts of those acids whose cations and anions, respectively, do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH^{4+}$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethylammonium, bis(2-hydroxyethyl)ammonium, benzyltrimethylammonium and benzyl-triethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting a compound of formula I with an acid of the corresponding anion, preferably of hydrochloric acid, hydrobromic acid, sulfuric acid, phosphoric acid or nitric acid.

By the term "veterinarily acceptable salts" is meant salts of those cations or anions which are known and accepted in the art for the formation of salts for veterinary use. Suitable acid addition salts, e.g. formed by compounds of formula I containing a basic nitrogen atom, e.g. an amino group, include salts with inorganic acids, for example hydrochlorids, sulphates, phosphates, and nitrates and salts of organic acids for example acetic acid, maleic acid, dimaleic acid, fumaric acid, difumaric acid, methane sulfenic acid, methane sulfonic acid, and succinic acid.

The term "invertebrate pest" as used herein encompasses animal populations, such as insects, arachnids and nematodes, which may attack plants, thereby causing substantial damage to the plants attacked, as well as ectoparasites which may infest animals, in particular warm blooded animals such as e.g. mammals or birds, or other higher animals such as reptiles, amphibians or fish, thereby causing substantial damage to the animals infested.

The term "plant propagation material" as used herein includes all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "plants" comprises any types of plants including "non-cultivated plants" and in particular "cultivated plants".

The term "non-cultivated plants" refers to any wild type species or related species or related genera of a cultivated plant.

The term "cultivated plants" as used herein includes plants which have been modified by breeding, mutagenesis or genetic engineering. Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transitional modification of protein(s) (oligo- or polypeptides) poly for example by glycosylation or polymer additions such as prenylated, acetylated or farnesylated moieties or PEG moieties (e.g. as disclosed in Biotechnol Prog. 2001 July-August; 17(4):720-8, Protein Eng Des Sel. 2004 January; 17(1):57-66, Nat. Protoc. 2007; 2(5):1225-35, Curr. Opin. Chem. Biol. 2006 October; 10(5): 487-91. Epub 2006 August 28, Biomaterials. 2001 March; 22(5):405-17, Bioconjug Chem. 2005 January-Feb.; 16(1): 113-21).

The term "cultivated plants" as used herein further includes plants that have been rendered tolerant to applications of specific classes of herbicides, such as hydroxy-phenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A-0242236, EP-A-242246) or oxynil herbicides (see e.g. U.S. Pat. No. 5,559,024) as a result of conventional methods of breeding or genetic engineering. Several cultivated plants have been rendered tolerant to herbicides by conventional methods of breeding (mutagenesis), for example Clearfield® summer rape (Canola) being tolerant to imidazolinones, e.g. imazamox. Genetic engineering methods have been used to render cultivated plants, such as soybean, cotton, corn, beets and rape, tolerant to herbicides, such as glyphosate and glufosinate, some of which are commercially available under the trade names RoundupReady® (glyphosate) and LibertyLink® (glufosinate).

The term "cultivated plants" as used herein further includes plants that are by the use of recombinant DNA techniques capable to synthesize one or more insecticidal proteins, especially those known from the bacterial genus bacillus, particularly from bacillus thuringiensis, such as ä-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, for example Photorhabdus spp. or Xenorhabdus spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, for example WO 02/015701). Further examples of such toxins or genetically modified plants capable of synthesizing such toxins are disclosed, for example, in EP-A 374 753, WO 93/007278, WO 95/34656, EP-A 427 529, EP-A 451 878, WO 03/018810 and WO 03/052073. These insecticidal proteins contained in the genetically modified plants impart to the plants producing these proteins protection from harmful pests from certain taxonomic groups of arthropods insects, particularly to beetles (Coleoptera), flies (Diptera), and butterflies and moths (Lepidoptera) and to plant parasitic nematodes (Nematoda).

The term "cultivated plants" as used herein further includes plants that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, for example EP-A 0 392 225), plant disease resistance genes (for example potato cultivars, which express resistance genes acting against Phytophthora infestans derived from the mexican wild potato Solanum bulbocastanum) or T4-lyso-zym (e.g. potato cultivars capable of synthesizing these proteins with increased resistance against bacteria such as Erwinia amylvora).

The term "cultivated plants" as used herein further includes plants that are by the use of recombinant DNA techniques capable to synthesize one or more proteins to increase the productivity (e.g. bio mass production, grain yield, starch content, oil content or protein content), tolerance to drought, salinity or other growth limiting environ-mental factors or tolerance to pests and fungal, bacterial or viral pathogens of those plants.

The term "cultivated plants" as used herein further includes plants that contain by the use of recombinant DNA techniques a modified amount of substances of content or new substances of content, specifically to improve human or animal nutrition, for example oil crops that produce health-promoting long-chain omega-3 fatty acids or unsaturated omega-9 fatty acids (e.g. Nexera® rape).

The term "cultivated plants" as used herein further includes plants that contain by the use of recombinant DNA techniques a modified amount of substances of content or new substances of content, specifically to improve raw material production, for example potatoes that produce increased amounts of amylopectin (e.g. Amflora® potato).

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine, chlorine or bromine.

The term "$C_1$-$C_{10}$-alkyl" as used herein and in the alkyl moieties of alkoxy, alkylthio, alkylsulfinyl, alkylsulfonyl, alkylcarbonyl, alkoxycarbonyl and the like refers to saturated straight-chain or branched hydrocarbon radicals having 1 to 2 ("$C_1$-$C_2$-alkyl"), 1 to 4 ("$C_1$-$C_4$-alkyl"), 1 to 6 ("$C_1$-$C_6$-alkyl"), 1 to 8 ("$C_1$-$C_8$-alkyl") or 1 to 10 ("$C_1$-$C_{10}$-alkyl") carbon atoms. $C_1$-$C_2$-alkyl is methyl or ethyl. $C_1$-$C_4$-alkyl is additionally propyl, isopropyl, butyl, 1-methylpropyl (sec-butyl), 2-methylpropyl (isobutyl) or 1,1-dimethylethyl (tert-butyl). $C_1$-$C_6$-alkyl is additionally also, for example, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl. $C_1$-$C_8$-alkyl is additionally also, for example, heptyl, octyl, 2-ethylhexyl and positional isomers thereof. $C_1$-$C_{10}$-alkyl is additionally also, for example, nonyl, decyl and positional isomers thereof.

The term "$C_1$-$C_{10}$-haloalkyl" as used herein, which is also expressed as "$C_1$-$C_{10}$-alkyl which is partially or fully halogenated", refers to straight-chain or branched alkyl groups having 1 to 2 ("$C_1$-$C_2$-haloalkyl"), 1 to 4 ("$C_1$-$C_4$-haloalkyl"), 1 to 6 ("$C_1$-$C_6$-haloalkyl"), 1 to 8 ("$C_1$-$C_8$-haloalkyl") or 1 to 10 ("$C_1$-$C_{10}$-haloalkyl") carbon atoms (as mentioned above), where some or all of the hydrogen atoms in these groups are replaced by halogen atoms as mentioned above: in particular $C_1$-$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl or 1,1,1-trifluoroprop-2-yl.

"Halomethyl" is methyl in which 1, 2 or 3 of the hydrogen atoms are replaced by halogen atoms. Examples are bromomethyl, chloromethyl, fluoromethyl, dichloromethyl, trichloromethyl, difluoromethyl, trifluoromethyl, chlorofluoromethyl, dichlorofluoromethyl, chlorodifluoromethyl and the like.

The term "$C_2$-$C_{10}$-alkenyl" as used herein and in the alkenyl moiety of alkenyloxy and the like refers to monounsaturated straight-chain or branched hydrocarbon radicals having 2 to 4 ("$C_2$-$C_4$-alkenyl"), 2 to 6 ("$C_2$-$C_6$-alkenyl"), 2 to 8 ("$C_2$-$C_8$-alkenyl"), 3 to 8 ("$C_3$-$C_8$-alkenyl"), 2 to 10 ("$C_2$-$C_{10}$-alkenyl") or 3 to 10 ("$C_3$-$C_{10}$-alkenyl") carbon atoms and a double bond in any position, for example $C_2$-$C_4$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl or 2-methyl-2-propenyl; $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl and the like, or $C_2$-$C_{10}$-alkenyl, such as the radicals mentioned for $C_2$-$C_6$-alkenyl and additionally 1-heptenyl, 2-heptenyl, 3-heptenyl, 1-octenyl, 2-octenyl, 3-octenyl, 4-octenyl, 1-nonenyl, 2-nonenyl, 3-nonenyl, 4-nonenyl, 1-decenyl, 2-decenyl, 3-decenyl, 4-decenyl, 5-decenyl and the positional isomers thereof.

The term "$C_2$-$C_{10}$-haloalkenyl" as used herein, which is also expressed as "$C_1$-$C_{10}$-alkenyl which is partially or fully halogenated", and the haloalkenyl moieties in haloalkenyloxy, haloalkenylcarbonyl and the like refers to unsaturated straight-chain or branched hydrocarbon radicals having 2 to 4 ("$C_2$-$C_4$-haloalkenyl"), 2 to 6 ("$C_2$-$C_6$-haloalkenyl"), 2 to 8 ("$C_2$-$C_6$-haloalkenyl") or 2 to 10 ("$C_2$-$C_{10}$-haloalkenyl") carbon atoms and a double bond in any position (as mentioned above), where some or all of the hydrogen atoms in these groups are replaced by halogen atoms as mentioned above, in particular fluorine, chlorine and bromine, for example chlorovinyl, chloroallyl and the like.

The term "$C_2$-$C_{10}$-alkynyl" as used herein and the alkynyl moieties in alkynyloxy, alkynylcarbonyl and the like refers to straight-chain or branched hydrocarbon groups having 2 to 4 ("$C_2$-$C_4$-alkynyl"), 2 to 6 ("$C_2$-$C_6$-alkynyl"), 2 to 8 ("$C_2$-$C_8$-alkynyl"), 3 to 8 ("$C_3$-$C_8$-alkynyl"), 2 to 10 ("$C_2$-$C_{10}$-alkynyl") or 3 to 10 ("$C_3$-$C_8$-alkynyl") carbon atoms and one or two triple bonds in any position, for example $C_2$-$C_4$-alkynyl, such as ethynyl, 1-propynyl, 2-propynyl, 1-butynyl, 2-butynyl, 3-butynyl, 1-methyl-2-propynyl and the like, $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl and the like;

The term "$C_2$-$C_{10}$-haloalkynyl" as used herein, which is also expressed as "$C_1$-$C_{10}$-alkynyl which is partially or fully halogenated", and the haloalkynyl moieties in haloalkynyloxy, haloalkynylcarbonyl and the like refers to unsaturated straight-chain or branched hydrocarbon radicals having 2 to 4 ("$C_2$-$C_4$-haloalkynyl"), 3 to 4 ("$C_3$-$C_4$-haloalkynyl"), 2 to 6 ("$C_2$-$C_6$-haloalkynyl"), 3 to 6 ("$C_3$-$C_6$-haloalkynyl"), 2 to 8 ("$C_2$-$C_8$-haloalkynyl"), 3 to 8 ("$C_3$-$C_8$-haloalkynyl"), 2 to 10 ("$C_2$-$C_{10}$-haloalkynyl") or 3 to 10 ("$C_3$-$C_{10}$-haloalkynyl") carbon atoms and one or two triple bonds in any position (as mentioned above), where some or all of the hydrogen atoms in these groups are replaced by halogen atoms as mentioned above, in particular fluorine, chlorine and bromine;

The term "$C_3$-$C_8$-cycloalkyl" as used herein refers to mono- or bi- or polycyclic saturated hydrocarbon radicals having 3 to 8, in particular 3 to 6 carbon atoms ("$C_3$-$C_6$-cycloalkyl"). Examples of monocyclic radicals having 3 to 6 carbon atoms comprise cyclopropyl, cyclobutyl, cyclopentyl and cyclohexyl. Examples of monocyclic radicals having 3 to 8 carbon atoms comprise cyclopropyl, cyclobutyl, cyclopentyl, cyclohexyl, cycloheptyl and cyclooctyl. Examples of bicyclic radicals having 7 or 8 carbon atoms comprise bicyclo[2.2.1]heptyl, bicyclo[3.1.1]heptyl, bicyclo[2.2.2]octyl and bicyclo[3.2.1]octyl.

The term "$C_3$-$C_8$-halocycloalkyl" as used herein, which is also expressed as "$C_3$-$C_8$-cycloalkyl which is partially or fully halogenated", and the halocycloalkyl moieties in halocycloalkoxy, halocycloalkylcarbonyl and the like refers to mono- or bi- or polycyclic saturated hydrocarbon groups having 3 to 8 ("$C_3$-$C_8$-halocycloalkyl") or preferably 3 to 6 ("$C_3$-$C_6$-halocycloalkyl") carbon ring members (as mentioned above) in which some or all of the hydrogen atoms are replaced by halogen atoms as mentioned above, in particular fluorine, chlorine and bromine.

The term "$C_3$-$C_8$-cycloalkyl-$C_1$-$C_4$-alkyl" refers to a $C_3$-$C_8$-cycloalkyl group as defined above which is bound to the remainder of the molecule via a $C_1$-$C_4$-alkyl group, as defined above. Examples are cyclopropylmethyl, cyclopropylethyl, cyclopropylpropyl, cyclobutylmethyl, cyclobutylethyl, cyclobutylpropyl, cyclopentylmethyl, cycloppentylethyl, cyclopentylpropyl, cyclohexylmethyl, cyclohexylethyl, cyclohexylpropyl, and the like.

The term "$C_1$-$C_2$-alkoxy" is a $C_1$-$C_2$-alkyl group, as defined above, attached via an oxygen atom. The term "$C_1$-$C_4$-alkoxy" is a $C_1$-$C_4$-alkyl group, as defined above, attached via an oxygen atom. The term "$C_1$-$C_6$-alkoxy" is a $C_1$-$C_6$-alkyl group, as defined above, attached via an oxygen atom. The term "$C_1$-$C_{10}$-alkoxy" is a $C_1$-$C_{10}$-alkyl group, as defined above, attached via an oxygen atom. $C_1$-$C_2$-alkoxy is methoxy or ethoxy. $C_1$-$C_4$-alkoxy is additionally, for example, n-propoxy, 1-methylethoxy (isopropoxy), butoxy, 1-methylpropoxy (sec-butoxy), 2-methylpropoxy (isobutoxy) or 1,1-dimethylethoxy (tert-butoxy). $C_1$-$C_6$-alkoxy is additionally, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy. $C_1$-$C_8$-alkoxy is additionally, for example, heptyloxy, octyloxy, 2-ethylhexyloxy and positional isomers thereof. $C_1$-$C_{10}$-alkoxy is additionally, for example, nonyloxy, decyloxy and positional isomers thereof.

The term "$C_1$-$C_2$-haloalkoxy" is a $C_1$-$C_2$-haloalkyl group, as defined above, attached via an oxygen atom. The term "$C_1$-$C_4$-haloalkoxyl" is a $C_1$-$C_4$-haloalkyl group, as defined above, attached via an oxygen atom. The term "$C_1$-$C_6$-haloalkoxy" is a $C_1$-$C_6$-haloalkyl group, as defined above, attached via an oxygen atom. The term "$C_1$-$C_{10}$-haloalkoxy" is a $C_1$-$C_{10}$-haloalkyl group, as defined above, attached via an oxygen atom. $C_1$-$C_2$-Haloalkoxy is, for example, $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or $OC_2F_5$. $C_1$-$C_4$-Haloalkoxy is additionally, for example, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy. $C_1$-$C_6$-Haloalkoxy is additionally, for example, 5-fluoropentoxy, 5-chloropentoxy, 5-brompentoxy, 5-iodopentoxy, undecafluoropentoxy, 6-fluorohexoxy, 6-chlorohexoxy, 6-bromohexoxy, 6-iodohexoxy or dodecafluorohexoxy.

The term "$C_1$-$C_2$-alkylthio" is a $C_1$-$C_2$-alkyl group, as defined above, attached via a sulfur atom. The term "$C_1$-$C_4$-alkylthio" is a $C_1$-$C_4$-alkyl group, as defined above, attached via a sulfur atom. The term "$C_1$-$C_6$-alkylthio" is a $C_1$-$C_6$-alkyl group, as defined above, attached via a sulfur atom. The term "$C_1$-$C_{10}$-alkylthio" is a $C_1$-$C_{10}$-alkyl group, as defined above, attached via a sulfur atom. $C_1$-$C_2$-alkylthio is methylthio or ethylthio. $C_1$-$C_4$-alkylthio is additionally, for example, n-propylthio, 1-methylethylthio (isopropylthio), butylthio, 1-methylpropylthio (sec-butylthio), 2-methylpropylthio (isobutylthio) or 1,1-dimethylethylthio (tert-butylthio). $C_1$-$C_6$-alkylthio is additionally, for example, pentylthio, 1-methylbutylthio, 2-methylbutylthio, 3-methylbutylthio, 1,1-dimethylpropylthio, 1,2-dimethylpropylthio, 2,2-dimethylpropylthio, 1-ethylpropylthio, hexylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio. $C_1$-$C_8$-alkylthio is additionally, for example, heptylthio, octylthio, 2-ethylhexylthio and positional isomers thereof. $C_1$-$C_{10}$-alkylthio is additionally, for example, nonylthio, decylthio and positional isomers thereof.

The term "$C_1$-$C_2$-haloalkylthio" is a $C_1$-$C_2$-haloalkyl group, as defined above, attached via a sulfur atom. The term "$C_1$-$C_4$-haloalkylthio" is a $C_1$-$C_4$-haloalkyl group, as defined above, attached via a sulfur atom. The term "$C_1$-$C_6$-haloalkylthio" is a $C_1$-$C_6$-haloalkyl group, as defined above, attached via a sulfur atom. The term "$C_1$-$C_{10}$-haloalkylthio" is a $C_1$-$C_{10}$-haloalkyl group, as defined above, attached via a sulfur atom. $C_1$-$C_2$-haloalkylthio is, for example, $SCH_2F$, $SCHF_2$, $SCF_3$, $SCH_2Cl$, $SCHCl_2$, $SCCl_3$, chlorofluoromethylthio, dichlorofluoromethylthio, chlorodifluoromethylthio, 2-fluoroethylthio, 2-chloroethylthio, 2-bromoethylthio, 2-iodoethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or $SC_2F_5$. $C_1$-$C_4$-Haloalkylthio is additionally, for example, 2-fluoropropylthio, 3-fluoropropylthio, 2,2-difluoropropylthio, 2,3-difluoropropylthio, 2-chloropropylthio, 3-chloropropylthio, 2,3-dichloropropylthio, 2-bromopropylthio, 3-bromopropylthio, 3,3,3-trifluoropropylthio, 3,3,3-trichloropropylthio, $SCH_2$—$C_2F_5$, $SCF_2$—$C_2F_5$, 1-($CH_2F$)-2-fluoroethylthio, 1-($CH_2Cl$)-2-chloroethylthio, 1-($CH_2Br$)-2-bromoethylthio, 4-fluorobutylthio, 4-chlorobutylthio, 4-bromobutylthio or nonafluorobutylthio. $C_1$-$C_6$-Haloalkylthio is additionally, for example, 5-fluoropentylthio, 5-chloropentylthio, 5-brompentylthio, 5-iodopentylthio, undecafluoropentylthio, 6-fluorohexylthio, 6-chlorohexylthio, 6-bromohexylthio, 6-iodohexylthio or dodecafluorohexylthio.

The term "$C_1$-$C_2$-alkylsulfinyl" is a $C_1$-$C_2$-alkyl group, as defined above, attached via a sulfinyl [S(O)] group. The term "$C_1$-$C_4$-alkylsulfinyl" is a $C_1$-$C_4$-alkyl group, as defined above, attached via a sulfinyl [S(O)] group. The term "$C_1$-$C_6$-alkylsulfinyl" is a $C_1$-$C_6$-alkyl group, as defined above, attached via a sulfinyl [S(O)] group. The term "$C_1$-$C_{10}$-alkylsulfinyl" is a $C_1$-$C_{10}$-alkyl group, as defined above, attached via a sulfinyl [S(O)] group. $C_1$-$C_2$-Alkylsulfinyl is methylsulfinyl or ethylsulfinyl. $C_1$-$C_4$-Alkylsulfinyl is additionally, for example, n-propylsulfinyl, 1-methylethylsulfinyl (isopropylsulfinyl), butylsulfinyl, 1-methylpropylsulfinyl (sec-butylsulfinyl), 2-methylpropylsulfinyl (isobutylsulfinyl) or 1,1-dimethylethylsulfinyl (tert-butylsulfinyl). $C_1$-$C_6$-Alkylsulfinyl is additionally, for example, pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl. $C_1$-$C_8$-Alkylsulfinyl is additionally, for example, heptylsulfinyl, octylsulfinyl, 2-ethylhexylsulfinyl and positional isomers thereof. $C_1$-$C_{10}$-Alkylsulfinyl is additionally, for example, nonylsulfinyl, decylsulfinyl and positional isomers thereof.

The term "$C_1$-$C_2$-haloalkylsulfinyl" is a $C_1$-$C_2$-haloalkyl group, as defined above, attached via a sulfinyl [S(O)] group. The term "$C_1$-$C_4$-haloalkylsulfinyl" is a $C_1$-$C_4$-haloalkyl group, as defined above, attached via a sulfinyl [S(O)] group. The term "$C_1$-$C_6$-haloalkylsulfinyl" is a $C_1$-$C_6$-haloalkyl group, as defined above, attached via a sulfinyl [S(O)] group. The term "$C_1$-$C_{10}$-haloalkylsulfinyl" is a $C_1$-$C_{10}$-haloalkyl group, as defined above, attached via a sulfinyl [S(O)] group. $C_1$-$C_2$-Haloalkylsulfinyl is, for example, S(O)CH$_2$F, S(O)CHF$_2$, S(O)CF$_3$, S(O)CH$_2$Cl, S(O)CHCl$_2$, S(O)CCl$_3$, chlorofluoromethylsulfinyl, dichlorofluoromethylsulfinyl, chlorodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2-chloro-2-fluoroethylsulfinyl, 2-chloro-2,2-difluoroethylsulfinyl, 2,2-dichloro-2-fluoroethylsulfinyl, 2,2,2-trichloroethylsulfinyl or S(O)C$_2$F$_5$. $C_1$-$C_4$-Haloalkylsulfinyl is additionally, for example, 2-fluoropropylsulfinyl, 3-fluoropropylsulfinyl, 2,2-difluoropropylsulfinyl, 2,3-difluoropropylsulfinyl, 2-chloropropylsulfinyl, 3-chloropropylsulfinyl, 2,3-dichloropropylsulfinyl, 2-bromopropylsulfinyl, 3-bromopropylsulfinyl, 3,3,3-trifluoropropylsulfinyl, 3,3,3-trichloropropylsulfinyl, S(O)CH$_2$—C$_2$F$_5$, S(O)CF$_2$—C$_2$F$_5$, 1-(CH$_2$F)-2-fluoroethylsulfinyl, 1-(CH$_2$Cl)-2-chloroethylsulfinyl, 1-(CH$_2$Br)-2-bromoethylsulfinyl, 4-fluorobutylsulfinyl, 4-chlorobutylsulfinyl, 4-bromobutylsulfinyl or nonafluorobutylsulfinyl. $C_1$-$C_6$-Haloalkylsulfinyl is additionally, for example, 5-fluoropentylsulfinyl, 5-chloropentylsulfinyl, 5-brompentylsulfinyl, 5-iodopentylsulfinyl, undecafluoropentylsulfinyl, 6-fluorohexylsulfinyl, 6-chlorohexylsulfinyl, 6-bromohexylsulfinyl, 6-iodohexylsulfinyl or dodecafluorohexylsulfinyl.

The term "$C_1$-$C_2$-alkylsulfonyl" is a $C_1$-$C_2$-alkyl group, as defined above, attached via a sulfonyl [S(O)$_2$] group. The term "$C_1$-$C_4$-alkylsulfonyl" is a $C_1$-$C_4$-alkyl group, as defined above, attached via a sulfonyl [S(O)$_2$] group. The term "$C_1$-$C_6$-alkylsulfonyl" is a $C_1$-$C_6$-alkyl group, as defined above, attached via a sulfonyl [S(O)$_2$] group. The term "$C_1$-$C_{10}$-alkylsulfonyl" is a $C_1$-$C_{10}$-alkyl group, as defined above, attached via a sulfonyl [S(O)$_2$] group. $C_1$-$C_2$-Alkylsulfonyl is methylsulfonyl or ethylsulfonyl. $C_1$-$C_4$-Alkylsulfonyl is additionally, for example, n-propylsulfonyl, 1-methylethylsulfonyl (isopropylsulfonyl), butylsulfonyl, 1-methylpropylsulfonyl (sec-butylsulfonyl), 2-methylpropylsulfonyl (isobutylsulfonyl) or 1,1-dimethylethylsulfonyl (tert-butylsulfonyl). $C_1$-$C_6$-Alkylsulfonyl is additionally, for example, pentylsulfonyl, 1-methylbutylsulfonyl, 2-methylbutylsulfonyl, 3-methylbutylsulfonyl, 1,1-dimethylpropylsulfonyl, 1,2-dinnethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl. $C_1$-$C_8$-Alkylsulfonyl is additionally, for example, heptylsulfonyl, octylsulfonyl, 2-ethylhexylsulfonyl and positional isomers thereof. $C_1$-$C_{10}$-Alkylsulfonyl is additionally, for example, nonylsulfonyl, decylsulfonyl and positional isomers thereof.

The term "$C_1$-$C_2$-haloalkylsulfonyl" is a $C_1$-$C_2$-haloalkyl group, as defined above, attached via a sulfonyl [S(O)$_2$] group. The term "$C_1$-$C_4$-haloalkylsulfonyl" is a $C_1$-$C_4$-haloalkyl group, as defined above, attached via a sulfonyl [S(O)$_2$] group. The term "$C_1$-$C_8$-haloalkylsulfonyl" is a $C_1$-$C_8$-haloalkyl group, as defined above, attached via a sulfonyl [S(O)$_2$] group. The term "$C_1$-$C_{10}$-haloalkylsulfonyl" is a $C_1$-$C_{10}$-haloalkyl group, as defined above, attached via a sulfonyl [S(O)$_2$] group. $C_1$-$C_2$-Haloalkylsulfonyl is, for example, S(O)$_2$CH$_2$F, S(O)$_2$CHF$_2$, S(O)$_2$CF$_3$, S(O)$_2$CH$_2$Cl, S(O)$_2$CHCl$_2$, S(O)$_2$CCl$_3$, chlorofluoromethylsulfonyl, dichlorofluoromethylsulfonyl, chlorodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl or S(O)$_2$C$_2$F$_5$. $C_1$-$C_4$-Haloalkylsulfonyl is additionally, for example, 2-fluoropropylsulfonyl, 3-fluoropropylsulfonyl, 2,2-difluoropropylsulfonyl, 2,3-difluoropropylsulfonyl, 2-chloropropylsulfonyl, 3-chloropropylsulfonyl, 2,3-dichloropropylsulfonyl, 2-bromopropylsulfonyl, 3-bromopropylsulfonyl, 3,3,3-trifluoropropylsulfonyl, 3,3,3-trichloropropylsulfonyl, S(O)$_2$CH$_2$—C$_2$F$_5$, S(O)$_2$CF$_2$—C$_2$F$_5$, 1-(CH$_2$F)-2-fluoroethylsulfonyl, 1-(CH$_2$Cl)-2-chloroethylsulfonyl, 1-(CH$_2$Br)-2-bromoethylsulfonyl, 4-fluorobutylsulfonyl, 4-chlorobutylsulfonyl, 4-bromobutylsulfonyl or nonafluorobutylsulfonyl. $C_1$-$C_6$-Haloalkylsulfonyl is additionally, for example, 5-fluoropentylsulfonyl, 5-chloropentylsulfonyl, 5-brompentylsulfonyl, 5-iodopentylsulfonyl, undecafluoropentylsulfonyl, 6-fluorohexylsulfonyl, 6-chlorohexylsulfonyl, 6-bromohexylsulfonyl, 6-iodohexylsulfonyl or dodecafluorohexylsulfonyl.

The term "3-, 4-, 5-, 6- or 7-membered saturated, partially unsaturated or aromatic heterocyclic ring containing 1, 2 or 3 heteroatoms or heteroatom groups (if one or two or at most three heteroatoms of the heterocyclic ring are oxidzed) selected from N, O, S, NO, SO and SO$_2$, as ring members" as used herein refers to monocyclic radicals, the monocyclic radicals being saturated, partially unsaturated or aromatic.

The heterocyclic radical may be attached to the remainder of the molecule via a carbon ring member or via a nitrogen ring member.

Examples of 3-, 4-, 5-, 6- or 7-membered saturated heterocyclic ring include: Oxiranyl, aziridinyl, azetidinyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-pyrazolidinyl, 4-pyrazolidinyl, 5-pyrazolidinyl, 2-imidazolidinyl, 4-imidazolidinyl, 2-oxazolidinyl, 4-oxazolidinyl, 5-oxazolidinyl, 3-isoxazolidinyl, 4-isoxazolidinyl, 5-isoxazolidinyl, 2-thiazolidinyl, 4-thiazolidinyl, 5-thiazolidinyl, 3-isothiazolidinyl, 4-isothiazolidinyl, 5-isothiazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2-tetrahydropyranyl, 4-tetrahydropyranyl, 1,3-dioxan-5-yl, 1,4-dioxan-2-yl, 2-piperidinyl, 3-piperidinyl, 4-piperidinyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl, 2-morphollnyl, 3-morpholinyl, 2-thiomorpholinyl, 3-thiomorpholinyl, 1-oxothiomorpholin-2-yl, 1-oxothiomorpholin-3-yl, 1,1-dioxothiomorpholin-2-yl, 1,1-dioxothiomorpholin-3-yl, hexahydroazepin-1-, -2-, -3- or -4-yl, hexahydrooxepinyl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl and the like.

Examples of 3-, 4-, 5-, 6- or 7-membered partially unsaturated heterocyclic ring include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4-di- or tetrahydropyridazinyl, 2-di- or tetrahydropyrimidinyl, 4-di- or tetrahydropyrimidinyl, 5-di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H]azepin-1-, -2-, -3-, -4-, -5-, -6- or -7-yl, 3,4,5,6-tetrahydro[2H]azepin-2-, -3-, -4-, -5-, -6- or -7-yl, 2,3,4,7-tetrahydro[1'-1]azepin-1-, -2-, -3-, -4-, -5-, -6- or -7-yl, 2,3,6,7-tetrahydro[1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or 2,3,4,7-tetrahydro[1H]oxepin-2-, -3-, -4-, -5-, -6- or -7-yl, 2,3,6,7-tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl and tetrahydro-1,4-dioxepinyl.

3-, 4-, 5-, 6- or 7-membered aromatic heterocyclic ring is 5- or 6-membered aromatic heterocyclic (hetaryl). Examples are: 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl.

The remarks made below concerning preferred embodiments of the variables of the compounds of formula I, especially with respect to their substituents $A^1$, $A^2$, $A^3$, $A^4$, $R^1$, $R^2$, $R^3$, $R^4$, $R^{5a}$, $R^{5b}$, $R^{5c}$, $R^{5d}$, $R^6$, $R^7$, $R^8$, $R^9$, $R^{10}$, $R^{11}$, $R^{12}$, $R^c$, $R^n$, $R^o$, m, and p the features of the use and method according to the invention and of the composition of the invention are valid both on their own and, in particular, in every possible combination with each other.

The radical A when used in the text is as following defined:

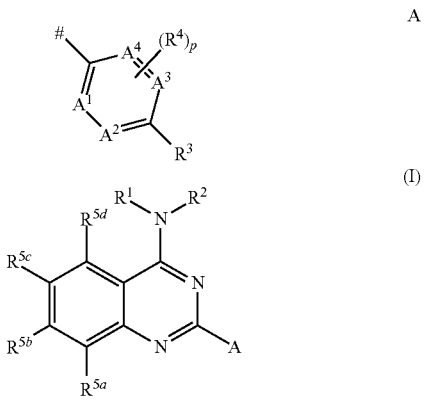

wherein # denotes the binding site to the remainder of formula I and wherein the variables p, $R^3$, $R^4$, $A^1$, $A^2$, $A^3$ and $A^4$ are as defined in formula I.

As a matter of course, the p radicals $R^4$ replace a hydrogen atom on a carbon ring atom. For instance, if $A^1$, $A^2$, $A^3$ or $A^4$ is defined to be CH and if this position is to be substituted by a radical $R^4$, then $A^1$, $A^2$, $A^3$ or $A^4$ is of course a substituted C—$R^4$. If there is more than one radical $R^4$, these substituents $R^4$ can be the same or different.

Preferably, at most two of $A^1$, $A^2$, $A^3$ and $A^4$ are N.

In a preferred embodiment, A', $A^2$, $A^3$ and $A^4$ are $CR^4$. In the case that more than one substituent $R^4$ is present in the radical A, the different $R^4$ are selected independently from each other. In case p is 2, the two substituents $R^4$ are preferably bound on the position of $A^1$ and $A^2$. In case p is 1, the substituent $R^4$ is preferably bound on the position of $A^1$ or $A^2$.

In analogy to the above cited meaning of A, $A^3$ and $A^4$ are respectively equivalent to $A^2$ and $A^1$ and thus have the same definition of preferencies.

Preferably, three of $A^1$, $A^2$, $A^3$ and $A^4$ are CH and the remaining radical is a substituted $CR^4$. Even more preferably, $A^2$, $A^3$, $A^4$ and $A^1$ are CH.

In one embodiment, $R^3$ is selected from the group consisting of hydrogen, halogen, cyano, azido, nitro, SCN, $SF_5$, $C_1$-$C_{10}$-alkyl, $C_3$-$C_8$-cycloalkyl, $C_2$-$C_{10}$-alkenyl, $C_2$-$C_{10}$-alkynyl,
wherein the carbon atoms of the aforementioned aliphatic and cycloaliphatic radicals may be unsubstituted or substituted with one or more $R^6$;

Si(R$^{11}$)$_2$R$^{12}$, OR$^7$, S(O)$_m$R$^7$, N(R$^8$)R$^9$, N=C(R$^6$)$_2$, C(=O)R$^6$, C(=S)R$^6$, C(=NR$^8$)R$^6$, phenyl which may be substituted by 1, 2, 3, 4 or 5 radicals R$^{10}$; and a 3-, 4-, 5-, 6- or 7-membered heterocyclic ring,
wherein said heterocyclic ring
  is saturated, partially unsaturated or aromatic,
  comprises 1, 2 or 3 heteroatoms or heteroatom groups selected from N, O, S, NO, SO and SO$_2$,
  is unsubstituted or substituted by one to five radicals R$^{10}$ and wherein one or two CH$_2$ groups in said saturated or partially saturated heterocyclic rings may be replaced by one or two C=O groups.

In another embodiment, R$^3$ is selected from the group consisting of hydrogen, halogen, cyano, azido, nitro, SCN, SF$_5$, C$_1$-C$_6$-alkyl, C$_3$-C$_6$-cycloalkyl, C$_1$-C$_6$-alkoxy, C$_1$-C$_6$-cycloalkoxy wherein the last four mentioned radicals are preferably at least substituted by one halogen, Si(R$^{11}$)$_2$R$^{12}$, OR$^7$, S(O)$_m$R$^7$, N(R$^8$)R$^9$, N=C(R$^6$)$_2$, C(=O)R$^6$, C(=S)R$^6$ and C(=NR$^8$)R$^6$.

Within these embodiments, R$^3$ is preferably selected from the group consisting of hydrogen, halogen, cyano, nitro, SR$^7$, C$_1$-C$_6$-alkyl, C$_3$-C$_6$-cycloalkyl, C$_1$-C$_6$-alkoxy and C$_3$-C$_6$-cycloalkoxy wherein the four last mentioned group are preferably at least substituted by one halogen and wherein the five last mentioned radicals may be substituted by one to five radicals R$^6$.

More preferably, R$^3$ is selected from the group consisting of halogen, cyano, nitro, C$_1$-C$_6$-alkyl, C$_1$-C$_6$-alkoxy wherein the two last mentioned radicals are at least by one halogen.

Even more preferably, R$^3$ is selected from the group consisting of fluorine, chlorine, bromine, iodine, cyano, NO$_2$, CF$_3$, CHF$_2$, CH$_2$F, CF$_2$Cl, CFCl$_2$, CCl$_3$, OCF$_3$, OCHF$_2$ and OCF$_2$CHF$_2$.

More particularly, R$^3$ is preferably fluorine or chlorine or bromine.

In an embodiment,
R$^4$ is selected independently from the group consisting of hydrogen, halogen, cyano, azido, nitro, SCN, SF$_5$, C$_1$-C$_{10}$ alkyl, C$_3$-C$_8$-cycloalkyl, C$_2$-C$_{10}$-alkenyl, alkynyl, wherein the carbon atoms of the aforementioned aliphatic and cycloaliphatic radicals may be unsubstituted or substituted with one or more R$^6$;
Si(R$^{11}$)$_2$R$^{12}$, OR$^7$, S(O)$_m$R$^7$, N(R$^8$)R$^9$, N=C(R$^6$)$_2$, C(=O)R$^6$, C(=S)R$^6$, C(=NR$^8$)R$^6$, C(=O)N(R$^8$)R$^9$, C(=S)N(R$^8$)R$^9$, phenyl which may be substituted by 1, 2, 3, 4 or 5 radicals R$^{10}$; and
a 3-, 4-, 5-, 6- or 7-membered heterocyclic ring,
wherein said heterocyclic ring
  is saturated or partially unsaturated or aromatic,
  comprises 1, 2 or 3 heteroatoms or heteroatom groups selected from N, O, S, NO, SO and SO$_2$
  is unsubstituted or substituted by one to five radicals R$^{10}$ and
  wherein one or two CH$_2$ groups in said saturated or partially saturated heterocyclic rings may be replaced by one or two C=O groups;
or two radicals R$^4$ bound on adjacent carbon atoms together form a group selected from —CH$_2$CH$_2$CH$_2$CH$_2$—, —CH=CH—CH=CH—, —N=CH—CH=CH—, —CH=N—CH=CH—, —N=CH—N=CH—, —OCH$_2$CH$_2$CH$_2$—, —OCH=CHCH$_2$—, —CH$_2$OCH$_2$CH$_2$—, —OCH$_2$CH$_2$O—, —OCH$_2$OCH$_2$—, —CH$_2$CH$_2$CH$_2$—, —CH=CHCH$_2$—, —CH$_2$CH$_2$O, —CH=CHO—, —CH$_2$OCH$_2$—, —CH$_2$C(=O)O—, —C(=O)OCH$_2$—, —O(CH$_2$)O, —SCH$_2$CH$_2$—, —SCH=CHCH$_2$—, —CH$_2$SCH$_2$CH$_2$—, —SCH$_2$CH$_2$S—, —SCH$_2$SCH$_2$—, —CH$_2$CH$_2$S—, —CH=CHS—, —CH$_2$SCH$_2$—, —CH$_2$C(=S)S—, —C(=S)SCH$_2$—, —S(CH$_2$)S—, —CH$_2$CH$_2$NR$^8$—, —CH$_2$CH=N—, —CH=CH—NR$^8$—, —OCH=N— and —SCH=N—,
wherein in each of the above groups one to five hydrogen atoms may be replaced by one to five substituents selected from halogen, methyl, halomethyl, hydroxyl, methoxy and halomethoxy or one or two CH$_2$ groups of the above groups may be replaced by one or two C=O groups.

In another embodiment,
R$^4$ is selected from the group consisting of hydrogen, halogen, cyano, azido, nitro, SCN, SF$_5$, C$_1$-C$_{10}$-alkyl, C$_3$-C$_8$-cycloalkyl, C$_2$-C$_{10}$-alkenyl, C$_2$-C$_{10}$-alkynyl,
wherein the carbon atoms of the aforementioned aliphatic and cycloaliphatic radicals may be unsubstituted or substituted with one or more R$^6$;
Si(R$^{11}$)$_2$R$^{12}$, OR$^7$, S(O)$_m$R$^7$, N(R$^8$)R$^9$, N=C(R$^6$)$_2$, C(=O)R$^6$, C(=S)R$^6$, C(=NR$^8$)R$^6$, C(=O)N(R$^8$)R$^9$, C(=S)N(R$^8$)R$^9$, phenyl,
which may be substituted by 1, 2, 3, 4 or 5 radicals R$^{10}$; and
a 3-, 4-, 5-, 6- or 7-membered heterocyclic ring,
wherein said heterocyclic ring
  is saturated or partially unsaturated or aromatic,
  comprises 1, 2 or 3 heteroatoms or heteroatom groups selected from N, O, S, NO SO and SO$_2$,
  is unsubstituted or substituted by one to five radicals R$^{10}$ and
  wherein one or two CH$_2$ groups in said saturated or partially saturated rings may be replaced by one or two C=O groups.

In a further embodiment,
R$^4$ is selected from the group consisting of hydrogen, halogen, cyano, azido, nitro, SCN, SF$_5$, C$_3$-C$_5$-cycloalkyl, C$_2$-C$_{10}$-alkenyl, C$_2$-C$_{10}$-alkynyl,
wherein the carbon atoms of the aforementioned aliphatic and cycloaliphatic radicals may be unsubstituted or substituted with one or more R$^6$;
Si(R$^{11}$)$_2$R$^{12}$, OR$^7$, S(O)$_m$R$^7$, N(R$^8$)R$^9$, N=C(R$^6$)$_2$, C(=O)R$^6$, C(=S)R$^6$, C(=NR$^8$)R$^6$, C(=O)N(R$^8$)R$^9$ and C(=S)N(R$^8$)R$^9$.

Within these embodiments, R$^4$ is preferably selected from the group consisting of hydrogen, halogen, cyano, nitro, C$_1$-C$_6$-alkyl, C$_3$-C$_6$-cycloalkyl, C$_1$-C$_6$-alkoxy and C$_1$-C$_6$-cycloalkoxy wherein the four last mentioned radicals if substituted are preferably substituted by one halogen and wherein the five last mentioned groups may be substituted by one to five radicals R$^6$.

More preferably, R$^4$ is selected from the group consisting of hydrogen, halogen, cyano, nitro, C$_1$-C$_6$-alkyl and C$_1$-C$_6$-haloalkyl.

Even more preferably, R$^4$ is selected from the group consisting of hydrogen, fluorine, chlorine, bromine, iodine, CF$_3$ and CHF$_2$.

More particularly, R$^4$ is hydrogen.

Examples of suitable radicals A are the radicals numbered A1a1 to A1a98 which are radicals of the formula A as above depicted wherein A$^2$, A$^3$, A$^4$ are CH, A$^1$ is CR$^4$, and R$^4$ and R$^3$ are as defined in one row of the following Table B (radicals A1a1 to A1a98):

TABLE B

| Radical A | R$^3$ | R$^4$ |
| --- | --- | --- |
| A1a1 | F | H |
| A1a2 | Cl | H |
| A1a3 | Br | H |

TABLE B-continued

| Radical A | $R^3$ | $R^4$ |
|---|---|---|
| A1a4 | I | H |
| A1a5 | CN | H |
| A1a6 | $NO_2$ | H |
| A1a7 | $CF_3$ | H |
| A1a8 | $CHF_2$ | H |
| A1a9 | $CH_2F$ | H |
| A1a10 | $CF_2Cl$ | H |
| A1a11 | $CFCl_2$ | H |
| A1a12 | $CCl_3$ | H |
| A1a13 | $OCHF_2$ | H |
| A1a14 | $SCF_3$ | H |
| A1a15 | F | F |
| A1a16 | Cl | F |
| A1a17 | Br | F |
| A1a18 | I | F |
| A1a19 | CN | F |
| A1a20 | $NO_2$ | F |
| A1a21 | $CF_3$ | F |
| A1a22 | $CHF_2$ | F |
| A1a23 | $CH_2F$ | F |
| A1a24 | $CF_2Cl$ | F |
| A1a25 | $CFCl_2$ | F |
| A1a26 | $CCl_3$ | F |
| A1a27 | $OCHF_2$ | F |
| A1a28 | $SCF_3$ | F |
| A1a29 | F | Cl |
| A1a30 | Cl | Cl |
| A1a31 | Br | Cl |
| A1a32 | I | Cl |
| A1a33 | CN | Cl |
| A1a34 | $NO_2$ | Cl |
| A1a35 | $CF_3$ | Cl |
| A1a36 | $CHF_2$ | Cl |
| A1a37 | $CH_2F$ | Cl |
| A1a38 | $CF_2Cl$ | Cl |
| A1a39 | $CFCl_2$ | Cl |
| A1a40 | $CCl_3$ | Cl |
| A1a41 | $OCHF_2$ | Cl |
| A1a42 | $SCF_3$ | Cl |
| A1a43 | F | Br |
| A1a44 | Cl | Br |
| A1a45 | Br | Br |
| A1a46 | I | Br |
| A1a47 | CN | Br |
| A1a48 | $NO_2$ | Br |
| A1a49 | $CF_3$ | Br |
| A1a50 | $CHF_2$ | Br |
| A1a51 | $CH_2F$ | Br |
| A1a52 | $CF_2Cl$ | Br |
| A1a53 | $CFCl_2$ | Br |
| A1a54 | $CCl_3$ | Br |
| A1a55 | $OCHF_2$ | Br |
| A1a56 | $SCF_3$ | Br |
| A1a57 | F | CN |
| A1a58 | Cl | CN |
| A1a59 | Br | CN |
| A1a60 | I | CN |
| A1a61 | CN | CN |
| A1a62 | $NO_2$ | CN |
| A1a63 | $CF_3$ | CN |
| A1a64 | $CHF_2$ | CN |
| A1a65 | $CH_2F$ | CN |
| A1a66 | $CF_2Cl$ | CN |
| A1a67 | $CFCl_2$ | CN |
| A1a68 | $CCl_3$ | CN |
| A1a69 | $OCHF_2$ | CN |
| A1a70 | $SCF_3$ | CN |
| A1a71 | F | Me |
| A1a72 | Cl | Me |
| A1a73 | Br | Me |
| A1a74 | I | Me |
| A1a75 | CN | Me |
| A1a76 | $NO_2$ | Me |
| A1a77 | $CF_3$ | Me |
| A1a78 | $CHF_2$ | Me |
| A1a79 | $CH_2F$ | Me |
| A1a80 | $CF_2Cl$ | Me |
| A1a81 | $CFCl_2$ | Me |
| A1a82 | $CCl_3$ | Me |
| A1a83 | $OCHF_2$ | Me |
| A1a84 | $SCF_3$ | Me |
| A1a85 | F | $CF_3$ |
| A1a86 | Cl | $CF_3$ |
| A1a87 | Br | $CF_3$ |
| A1a88 | I | $CF_3$ |
| A1a89 | CN | $CF_3$ |
| A1a90 | $NO_2$ | $CF_3$ |
| A1a91 | $CF_3$ | $CF_3$ |
| A1a92 | $CHF_2$ | $CF_3$ |
| A1a93 | $CH_2F$ | $CF_3$ |
| A1a94 | $CF_2Cl$ | $CF_3$ |
| A1a95 | $CFCl_2$ | $CF_3$ |
| A1a96 | $CCl_3$ | $CF_3$ |
| A1a97 | $OCHF_2$ | $CF_3$ |
| A1a98 | $SCF_3$ | $CF_3$ |

Analog to the above listed Table B, further examples of suitable radicals A are the radicals of the formula A numbered A1a99 to A1a197 wherein $A^1$, $A^3$, $A^4$ are CH, $A^2$ is $CR^4$, and $R^4$ and $R^3$ for each radical A have the meaning of one line in Table B.

In a particular embodiment of the invention, each example of radical A numbered A1a1 to A1a197 is a preferred radical A in formula I.

In an embodiment, $R^{5a}$ is selected from the group consisting of hydrogen, halogen, cyano, azido, nitro, —SCN, $SF_5$, $C_1$-$C_{10}$-alkyl, $C_3$-$C_8$-cycloalkyl, $C_2$-$C_{10}$-alkenyl, $C_2$-$C_{10}$-alkynyl,
  wherein the carbon atoms of the aforementioned aliphatic and cycloaliphatic radicals may be unsubstituted or substituted with one or more $R^6$,
  $Si(R^{11})_2R^{12}$, $OR^7$, $S(O)_mR^7$, $N(R^8)R^9$, $N=C(R^6)_2$, $C(=O)R^6$, $C(=S)R^6$, $C(=NR^8)R^6$, phenyl,
  which may be substituted by 1, 2, 3, 4 or 5 radicals $R^{10}$;
  and a 3-, 4-, 5-, 6- or 7-membered heterocyclic ring
  wherein said heterocyclic ring
    is saturated or partially unsaturated or aromatic,
    comprises 1, 2 or 3 heteroatoms or heteroatom groups selected from N, O, S, NO, SO and $SO_2$,
    is unsubstituted or substituted by one to five radicals $R^{10}$, and
    wherein one or two $CH_2$ groups in said saturated or partially saturated rings may be by one or two C═O groups;
or $R^{5a}$ may form together with the adjacent carbon atom $R^{5b}$ a 5- or 6-membered ring which is at least substituted by one halogen.

More preferably, $R^{5a}$ is selected from the group consisting of hydrogen, halogen, cyano, azido, nitro, $C_1$-$C_{10}$-alkyl, $C_3$-$C_8$-cycloalkyl, $C_2$-$C_{10}$-alkenyl, $C_2$-$C_{10}$-alkynyl,
  wherein the carbon atoms of the aforementioned aliphatic and cycloaliphatic radicals may be unsubstituted or substituted with one or more $R^6$;
  $Si(R^{11})_2R^{12}$, $OR^7$, $S(O)_mR^7$, $N(R^8)R^9$, $N=C(R^6)_2$, $C(=O)R^6$, $C(=S)R^6$ and $C(=NR^8)R^6$.

More preferably, $R^{5a}$ is selected from the group consisting of hydrogen, halogen, cyano, nitro, $SCF_3$, $SOCF_3$, $C_1$-$C_6$-alkyl, $C_3$-$C_6$-cycloalkyl, $C_1$-$C_6$-alkoxy and $C_1$-$C_6$-cycloalkoxy wherein the last four mentioned radicals may be substituted by one halogen.

More preferably, $R^{5a}$ is selected from the group consisting of hydrogen, halogen, cyano, nitro, $C_1$-$C_6$-alkyl, $C_3$-$C_6$-cycloalkyl, $C_1$-$C_6$-alkoxy (e.g. $OCF_3$, $OCHF_2$, $OCF_2CHF_2$) and $C_1$-$C_6$-cycloalkoxy wherein the five last mentioned group may be substituted by halogen.

Even more preferably, $R^{5a}$ is selected from the group consisting of hydrogen, halogen, $C_1$-$C_6$-alkyl and $C_1$-$C_6$-haloalkyl.

Even more preferably, $R^{5a}$ is selected from the group consisting of hydrogen, fluorine, chlorine, bromine, iodine, $CH_3$, $CF_3$, $CHF_2$, $CH_2F$, $CF_2Cl$, $CFCl_2$ and $CCl_3$.

Even more preferably, $R^{5a}$ is selected from the group consisting of hydrogen, fluorine, chlorine, bromine, iodine, $CF_3$ and $CHF_2$.

More particularly, $R^{5a}$ is hydrogen.

In a embodiment, $R^{5b}$ is selected from the group consisting of $C_1$-$C_6$-alkyl, $C_3$-$C_6$-cycloalkyl, alkoxy and $C_1$-$C_6$-cycloalkoxy, wherein each mentioned radical
 is at least substituted with one halogen,
 may be further partially or fully halogenated and
 may be substituted with one to five radicals $R^6$;
or may form together with the adjacent carbon atom $R^{5c}$ or $R^{5a}$ a 5- or 6-membered ring which is at least substituted with one halogen.

Within the above embodiment, $R^{5b}$ is preferably selected from the group consisting of $C_1$-$C_6$-alkyl, $C_3$-$C_6$-cycloalkyl, $C_1$-$C_6$-alkoxy and $C_1$-$C_6$-cycloalkoxy and wherein each mentioned radical is at least substituted with one halogen.

Within the above embodiments, $R^{5b}$ is preferably selected from the group consisting of $C_1$-$C_6$-haloalkyl and $C_1$-$C_6$-haloalkoxy.

Even more preferably, $R^{5b}$ is selected from the group consisting of $CF_3$, $CHF_2$, $CH_2F$, $CF_2F_3$, $CF(CF_3)_2$, $COH(CF_3)_2$, $CF_2Cl$, $CFCl_2$, $CCl_3$, $OCF_3$, $OCHF_2$, $OCF_2CF_3$, $OCF_2CHF_2$, $OCF(CF_3)_2$, $OCF_2Cl$, $OCFCl_2$ and $OCCl_3$.

Even more preferably, $R^{5b}$ is selected from the group consisting of $CF_3$, $CHF_2$, $CF_2F_3$, $CF(CF_3)_2$, $COH(CF_3)_2$, $CF_2Cl$, $CFCl_2$, $CCl_3$, $OCF_3$, $OCHF_2$, $OCF_2CF_3$, $OCF_2CHF_2$, $OCF(CF_3)_2$, $OCF_2Cl$, $OCFCl_2$ and $OCCl_3$.

More particularly $R^{5b}$ is $CF_3$.

Preferably, $R^{5c}$ is selected from the group consisting of hydrogen, halogen, $C_1$-$C_6$-alkyl, $C_3$-$C_8$-cycloalkyl, $C_2$-$C_6$-alkenyl and $C_2$-$C_6$-alkynyl, wherein the last four mentioned groups may be partially or fully halogenated and/or may be substituted with one to five radicals $R^6$.

More preferably, $R^{5c}$ is selected from the group consisting of hydrogen, halogen, $C_1$-$C_6$-alkyl and $C_1$-$C_6$-haloalkyl.

More particularly, $R^{5c}$ is hydrogen.

Preferably, $R^{5d}$ is selected from the group consisting of hydrogen, halogen, $C_1$-$C_6$-alkyl, $C_3$-$C_8$-cycloalkyl, $C_2$-$C_6$-alkenyl and $C_2$-$C_6$-alkynyl, wherein the last four mentioned groups may be partially or fully halogenated and/or may be substituted with one to five radicals $R^6$.

More preferably, $R^{5d}$ is selected from the group consisting of hydrogen, halogen, $C_1$-$C_6$-alkyl and $C_1$-$C_6$-haloalkyl.

More particularly, $R^{5d}$ is hydrogen.

In case $R^6$ is a substituent on an alkyl, alkenyl or alkynyl group, it is preferably selected from the group consisting of
 hydrogen, halogen, cyano, azido, nitro, SCN, $SF_5$, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_3$-$C_8$-cycloalkyl, $C_3$-$C_8$-cycloalkyl-$C_1$-$C_4$-alkyl, $C_2$-$C_6$-alkenyl, $C_2$-$C_6$-alkynyl, wherein the carbon atom of the aforementioned aliphatic and cycloaliphatic radicals may be substituted with one or more $R^c$;
 $Si(R^{11})_2R^{12}$, $OR^o$, $O(CO)R^c$, $O(CS)R^c$, $S(O)_mR^o$, $S(O)_mN(R'')_2$, $S(CO)R^c$, $S(CS)R^c$, $S(C=NR'')R^c$, $N(R'')_2$, $N(R'')C(=O)R^c$, $N(R'')C(=S)R^c$, $NS(O)_nR^o$, $N=C(R^c)_2$, $C(=O)R^c$, $C(=S)R^c$, $C(=NR'')R^c$, $C(=O)N(R'')_2$, $C(=S)N(R'')_2$, phenyl,
 which may be substituted by 1, 2, 3, 4 or 5 radicals $R^{10}$, and
 a 3-, 4-, 5-, 6- or 7-membered heterocyclic ring,
  wherein said heterocyclic ring
   is saturated or partially unsaturated or aromatic,
   comprises 1, 2 or 3 heteroatoms or heteroatom groups selected from N, O, S, NO, SO and $SO_2$,
   is unsubstituted or substituted with one to five radicals $R^{10}$, and
   wherein one or two $CH_2$ groups in said saturated or partially saturated heterocyclic rings may be replaced by one or two C=O groups.

In case $R^6$ is a substituent on an alkyl, alkenyl or alkynyl group, it is more preferably selected from the group consisting of
 halogen, cyano, $C_3$-$C_8$-cycloalkyl, $C_3$-$C_8$-halocycloalkyl, $OR^o$, $SR^o$, phenyl,
 which may be substituted with 1, 2, 3, 4 or 5 radicals $R^{10}$, and
 a 3-, 4-, 5-, 6- or 7-membered heterocyclic ring,
  wherein said heterocyclic ring
   is saturated or partially unsaturated or aromatic,
   comprises 1, 2 or 3 heteroatoms or heteroatom groups selected from N, O, S, NO, SO and $SO_2$,
   is unsubstituted or substituted with one or more radicals $R^{10}$;
 wherein $R^o$ and $R^{10}$ have one of the meanings given above or in particular one of the preferred meanings given below.

In case $R^6$ is a substituent on an alkyl, alkenyl or alkynyl group, it is even more preferably selected from the group consisting of halogen, cyano, $C_3$-$C_6$-cycloalkyl, $C_3$-$C_6$-halocycloalkyl, $C_1$-$C_4$-alkoxy, $C_1$-$C_4$-haloalkoxy, $C_1$-$C_4$-alkylthio, $C_1$-$C_4$-haloalkylthio, phenyl which may be substituted with 1, 2, 3, 4 or 5 radicals $R^{10}$, and a 5- or 6-membered heteroaromatic ring containing 1, 2 or 3 heteroatoms selected from N, O and S, wherein the heteroaromatic ring may be substituted with one or more radicals $R^{10}$; and
wherein $R^{10}$ has one of the meanings given above or in particular one of the preferred meanings given below.

In case $R^6$ is a substituent on an alkyl, alkenyl or alkynyl group, it is in particular selected from the group consisting of halogen and a 5- or 6-membered heteroaromatic ring containing 1, 2 or 3 heteroatoms selected from N, O and S, wherein the heteroaromatic ring is unsubstituted or substituted with one or more radicals $R^{10}$; and
wherein $R^{10}$ has one of the meanings given above or in particular one of the preferred meanings given below.

In case $R^6$ is a substituent on a cycloalkyl group, it is preferably selected from the group consisting of halogen, cyano, azido, nitro, SCN, $SF_5$, $C_1$-$C_6$-alkyl, $C_1$-$C_6$-haloalkyl, $C_1$-$C_6$-alkoxy-$C_1$-$C_6$-alkyl, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, $Si(R^{11})_2R^{12}$, $OR^o$, $O(CO)R^c$, $O(CS)R^c$, $S(O)_mR^o$, $S(O)_mN(R'')_2$, $S(CO)R^c$, $S(CS)R^c$, $S(C=NR'')R^c$, $N(R'')_2$, $N(R'')C(=O)R^c$, $N(R'')C(=S)R^c$, $NS(O)_mR^o$, $N=C(R^c)_2$, $C(=O)R^c$, $C(=S)R^c$, $C(=NR'')R^c$, $C(=O)N(R'')_2$, $C(=S)N(R'')_2$, phenyl which may be substituted by 1, 2, 3, 4 or 5 radicals $R^{10}$, and a 3-, 4-, 5-, 6- or 7-membered heterocyclic ring, wherein said heterocyclic ring is saturated or partially unsaturated or aromatic, comprises 1, 2 or 3 heteroatoms or heteroatom groups selected from N, O, S, NO, SO and $SO_2$ and wherein said heterocyclic ring is unsubstituted or substituted with one or more radicals $R^{10}$;

or two vicinally bound radicals $R^6$ together form a group selected from $=C(R^c)_2$, $S(O)_mR^c$, $=S(O)_mN(R'')_2$, $=NR''$, and $=NN(R'')_2$;

or two radicals $R^6$, together with the carbon atoms to which they are bound, form a 3-, 4-, 5-, 6-, 7- or 8-membered saturated or partially unsaturated carbocyclic or heterocyclic ring containing 1, 2 or 3 heteroatoms or heteroatom groups selected from N, O, S, NO, SO and $SO_2$;

wherein $R^c$, $R''$, $R^o$, $R^{10}$, $R^{11}$ and $R^{12}$ have one of the meanings given above or in particular one of the preferred meanings given below.

In case $R^6$ is a substituent on a cycloalkyl group, it is more preferably selected from the group consisting of halogen, cyano, $C_1$-$C_6$-alkyl, $C_1$-$C_6$-haloalkyl, $C_1$-$C_6$-alkoxy-$C_1$-$C_6$-alkyl, $OR^o$, $SR^o$, $S(O)_mR^o$, $S(O)_mN(R'')_2$, $N(R'')_2$, $C(=O)N(R'')_2$, $C(=S)N(R'')_2$, $C(=O)R^o$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted with one or more radicals $R^{10}$;

wherein $R^c$, $R''$, $R^o$ and $R^{10}$ have one of the meanings given above or in particular one of the preferred meanings given below.

In case $R^6$ is a substituent on a cycloalkyl group, it is even more preferably selected from the group consisting of halogen, $C_1$-$C_4$-alkyl, $C_1$-$C_3$-haloalkyl, $C_1$-$C_4$-alkoxy and $C_1$-$C_3$-haloalkoxy. In particular, $R^6$ as a substituent on a cycloalkyl group is selected from halogen, $C_1$-$C_4$-alkyl and $C_1$-$C_3$-haloalkyl.

In case $R^6$ is a substituent on $C(=O)$, $C(=S)$ or $C(=NR^8)$, it is preferably selected from the group consisting of hydrogen, $C_1$-$C_6$-alkyl, $C_1$-$C_6$-haloalkyl, $C_1$-$C_6$-alkoxy $C_1$-$C_6$-alkyl, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, $-OR^o$, $-SR^o$, $-N(R'')_2$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, wherein the heterocyclic ring may be substituted with one or more radicals $R^{10}$;

wherein $R^c$, $R''$, $R^o$ and $R^{10}$ have one of the meanings given above or in particular one of the preferred meanings given below.

In case $R^6$ is a substituent on $C(=O)$, $C(=S)$ or $C(=NR^8)$, it is more preferably selected from the group consisting of $C_1$-$C_6$-alkyl, $C_1$-$C_6$-haloalkyl, $C_3$-$C_8$-cycloalkyl, $C_3$-$C_8$-halocycloalkyl, $C_1$-$C_6$-alkoxy, $C_1$-$C_6$-haloalkoxy, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, wherein the heterocyclic ring may be substituted by one or more radicals $R^{10}$;

wherein $R^{10}$ has one of the meanings given above or in particular one of the preferred meanings given below.

In case $R^6$ is a substituent on $C(=O)$, $C(=S)$ or $C(=NR^8)$, it is even more preferably selected from the group consisting of $C_1$-$C_4$-alkyl, $C_1$-$C_4$-haloalkyl, $C_3$-$C_6$-cycloalkyl, $C_3$-$C_6$-halocycloalkyl, $C_1$-$C_4$-alkoxy, $C_1$-$C_3$-haloalkoxy, phenyl which may be substituted with 1, 2, 3, 4 or 5 radicals $R^{10}$, and a 5- or 6-membered heteroaromatic ring containing 1, 2 or 3 heteroatoms selected from N, O and S, wherein the heteroaromatic ring may be substituted with one or more radicals $R^{10}$;

wherein $R^{10}$ has one of the meanings given above or in particular one of the preferred meanings given below.

Preferably, each $R^7$ is independently selected from the group consisting of hydrogen, $C_1$-$C_6$-alkyl, $C_1$-$C_6$-haloalkyl, $C_3$-$C_8$-cycloalkyl, $C_3$-$C_8$-halocycloalkyl, $C_3$-$C_8$-cycloalkyl-$C_1$-$C_4$-alkyl, phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, wherein the heterocyclic ring is unsubstituted or substituted with. 1, 2, 3 or 4, preferably 1 or 2, more preferably 1, radicals $R^{10}$, wherein $R^{10}$ has one of the meanings given above or in particular one of the preferred meanings given below.

More preferably, each $R^7$ is independently selected from the group consisting of hydrogen, $C_1$-$C_6$-alkyl, $C_1$-$C_6$-haloalkyl, phenyl which is unsubstituted or substituted by 1, 2, 3, 4 or 5 radicals $R^{10}$; and a 5- or 6-membered heteroaromatic ring containing 1, 2 or 3 heteroatoms selected from N, O and S, wherein the heteroaromatic ring may be substituted by one or more radicals $R^{10}$; where $R^{10}$ has one of the meanings given above or in particular one of the preferred meanings given below.

$R^8$ and $R^9$ are independently of each other and independently of each occurrence preferably selected from the group consisting of hydrogen, $C_1$-$C_6$-alkyl, $C_1$-$C_6$-haloalkyl, $C_3$-$C_8$-cycloalkyl, $C_3$-$C_8$-halocycloalkyl, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, where the heterocyclic ring may be substituted by one or more radicals $R^{10}$; and wherein $R^{10}$ has one of the meanings given above or in particular one of the preferred meanings given below.

$R^8$ and $R^9$ are independently of each other and independently of each occurrence more preferably selected from the group consisting of hydrogen, $C_1$-$C_6$-alkyl, $C_1$-$C_6$-haloalkyl, phenyl which may be substituted by 1, 2, 3, 4 or 5 radicals $R^{10}$, and a 5- or 6-membered heteroaromatic ring containing 1, 2 or 3 heteroatoms selected from N, O and S, as ring members, wherein the heteroaromatic ring is unsubstituted or substituted by one or more radicals $R^{10}$; and wherein $R^{10}$ has one of the meanings given above or in particular one of the preferred meanings given below.

In particular, $R^8$ and $R^9$ are independently of each other and independently of each occurrence selected from the group consisting of hydrogen and $C_1$-$C_4$-alkyl. Preferably, each $R^{10}$ is independently selected from the group consisting of halogen, cyano, $C_1$-$C_{10}$-alkyl which may be partially or fully halogenated and/or may be substituted by one or more radicals $R^c$, $C_3$-$C_8$-cycloalkyl which may be partially or fully halogenated and/or may be substituted by one or more radicals $R^c$, $OR^o$, $O(CO)R^c$, $O(CS)R^c$, $S(O)_mR^o$, $S(O)_mN(R'')_2$, $N(R'')_2$, $C(=O)R^c$, $C(=O)N(R'')_2$, phenyl which may be substituted by 1, 2, 3, 4 or 5 radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy; and a 3-, 4-, 5-, 6- or 7-membered saturated or unsaturated heterocyclic ring containing 1, 2 or 3 heteroatoms or heteroatom groups selected from N, O, S, NO, SO and $SO_2$, as ring members, which may be substituted by one or more radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy;

or two radicals $R^{10}$ bound on adjacent atoms together form a group selected from $-CH_2CH_2CH_2CH_2-$, $-CH=CH-CH=CH-$, $-N=CH-CH=CH-$, $-CH=N-CH=CH-$, $-N=CH-N=CH-$, $-OCH_2CH_2CH_2-$, —OCH═CHCH$_2$—, —CH$_2$OCH$_2$CH$_2$—, —OCH$_2$CH$_2$O—, —OCH$_2$OCH$_2$—, —CH$_2$CH$_2$CH$_2$—, —CH═CHCH$_2$—, —CH$_2$CH$_2$O—, —CH═CHO—, —CH$_2$OCH$_2$—, —CH$_2$C(═O)O—, —C(═O)OCH$_2$—, and —O(CH$_2$)O—, thus forming, together with the atoms to which they are bound, a 5- or 6-membered ring, where the hydrogen atoms of the above groups may be replaced by one or more substituents selected from halogen, methyl, halomethyl, hydroxyl, methoxy and halomethoxy or one or more CH$_2$ groups of the above groups may be replaced by a C═O group, where $R^c$, $R''$ and $R^o$ have one of the general or in particular one of the preferred meanings given above.

More preferably, each $R^{10}$ is independently selected from the group consisting of halogen, cyano, $C_1$-$C_{10}$-alkyl which may be partially or fully halogenated and/or may be substituted by one or more radicals $R^c$, —$OR''$, —$N(R'')_2$, $C(═O)R^c$, —$C(═O)OR^o$, —$C(═O)N(R'')_2$, phenyl which may be substituted by 1, 2, 3, 4 or 5 radicals independently selected from halogen, cyano, nitro, $C_1$-$C_6$-alkyl, $C_1$-$C_6$-alkoxy and $C_1$-$C_6$-haloalkoxy; and a 3-, 4-, 5-, 6- or 7-membered saturated or unsaturated heterocyclic ring containing 1, 2 or 3 heteroatoms or heteroatom groups selected from N, O, S, NO, SO and SO$_2$, as ring members, which may be substituted by one or more radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy;

where $R^c$, $R''$, $R^o$ have one of the general or in particular one of the preferred meanings given above.

Even more preferably, each $R^{10}$ is independently selected from the group consisting of halogen, $C_1$-$C_4$-alkyl, $C_1$-$C_4$-haloalkyl, $C_1$-$C_4$-alkoxy and $C_1$-$C_4$-haloalkoxy. In particular, each $R^{10}$ is independently selected from the group consisting of halogen, $C_1$-$C_4$-alkyl and $C_1$-$C_4$-haloalkyl and is specifically halogen, more specifically chlorine.

Preferably, $R^{11}$ and $R^{12}$ are, independently of each other and independently of each occurrence, selected from $C_1$-$C_4$-alkyl and are in particular methyl.

A very preferred embodiment of the invention relates to the compounds of the formula (I-a)

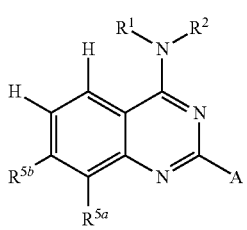

(I-a)

wherein

A has one of the general meaning as defined here above;

A is in particular one of the preferred radical A numbered A1a1 to A1a197 as defined in table B above.

$R^{5b}$, $R^{5a}$, $R^1$ and $R^2$ have one of the general meaning or one of the preferred meaning as here above defined.

In particular, $R^{5b}$, $R^1$, and $R^2$ have the meaning Ib numbered Ib1 to Ib1168 as defined in each line of the following Table C. It is to note that $R^1$ and $R^2$ are permutable in the meaning of Ib1009 to Ib1168.

TABLE C

| Ib | $R^{5b}$ | $R^1$ | $R^2$ |
|---|---|---|---|
| Ib1 | CF$_3$ | Me | Me |
| Ib2 | CHF$_2$ | Me | Me |
| Ib3 | CF$_2$CF$_3$ | Me | Me |
| Ib4 | CF(CF$_3$)$_2$ | Me | Me |
| Ib5 | COH(CF$_3$)$_2$ | Me | Me |
| Ib6 | CF$_2$Cl | Me | Me |
| Ib7 | CFCl$_2$ | Me | Me |
| Ib8 | CCl$_3$ | Me | Me |
| Ib9 | OCF$_3$ | Me | Me |
| Ib10 | OCHF$_2$ | Me | Me |
| Ib11 | OCF$_2$CF$_3$ | Me | Me |
| Ib12 | OCF$_2$CHF$_2$ | Me | Me |
| Ib13 | OCF(CF$_3$)$_2$ | Me | Me |
| Ib14 | OCF$_2$Cl | Me | Me |
| Ib15 | OCFCl$_2$ | Me | Me |
| Ib16 | OCCl$_3$ | Me | Me |
| Ib17 | CF$_3$ | Me | Et |
| Ib18 | CHF$_2$ | Me | Et |
| Ib19 | CF$_2$CF$_3$ | Me | Et |
| Ib20 | CF(CF$_3$)$_2$ | Me | Et |
| Ib21 | COH(CF$_3$)$_2$ | Me | Et |
| Ib22 | CF$_2$Cl | Me | Et |
| Ib23 | CFCl$_2$ | Me | Et |
| Ib24 | CCl$_3$ | Me | Et |
| Ib25 | OCF$_3$ | Me | Et |
| Ib26 | OCHF$_2$ | Me | Et |
| Ib27 | OCF$_2$CF$_3$ | Me | Et |
| Ib28 | OCF$_2$CHF$_2$ | Me | Et |
| Ib29 | OCF(CF$_3$)$_2$ | Me | Et |
| Ib30 | OCF$_2$Cl | Me | Et |
| Ib31 | OCFCl$_2$ | Me | Et |
| Ib32 | OCCl$_3$ | Me | Et |
| Ib33 | CF$_3$ | Me | Pr |
| Ib34 | CHF$_2$ | Me | Pr |
| Ib35 | CF$_2$CF$_3$ | Me | Pr |
| Ib36 | CF(CF$_3$)$_2$ | Me | Pr |
| Ib37 | COH(CF$_3$)$_2$ | Me | Pr |
| Ib38 | CF$_2$Cl | Me | Pr |
| Ib39 | CFCl$_2$ | Me | Pr |
| Ib40 | CCl$_3$ | Me | Pr |
| Ib41 | OCF$_3$ | Me | Pr |
| Ib42 | OCHF$_2$ | Me | Pr |
| Ib43 | OCF$_2$CF$_3$ | Me | Pr |
| Ib44 | OCF$_2$CHF$_2$ | Me | Pr |
| Ib45 | OCF(CF3)2 | Me | Pr |
| Ib46 | OCF$_2$Cl | Me | Pr |
| Ib47 | OCFCl$_2$ | Me | Pr |
| Ib48 | OCCl$_3$ | Me | Pr |
| Ib49 | CF$_3$ | Me | iPr |
| Ib50 | CHF$_2$ | Me | iPr |
| Ib51 | CF$_2$CF$_3$ | Me | iPr |
| Ib52 | CF(CF$_3$)$_2$ | Me | iPr |
| Ib53 | COH(CF$_3$)$_2$ | Me | iPr |
| Ib54 | CF$_2$Cl | Me | iPr |
| Ib55 | CFCl$_2$ | Me | iPr |
| Ib56 | CCl$_3$ | Me | iPr |
| Ib57 | OCF$_3$ | Me | iPr |
| Ib58 | OCHF$_2$ | Me | iPr |
| Ib59 | OCF$_2$CF$_3$ | Me | iPr |
| Ib60 | OCF$_2$CHF$_2$ | Me | iPr |
| Ib61 | OCF(CF$_3$)$_2$ | Me | iPr |
| Ib62 | OCF$_2$Cl | Me | iPr |
| Ib63 | OCFCl$_2$ | Me | iPr |
| Ib64 | OCCl$_3$ | Me | iPr |
| Ib65 | CF$_3$ | Me | Bu |
| Ib66 | CHF$_2$ | Me | Bu |
| Ib67 | CF$_2$CF$_3$ | Me | Bu |
| Ib68 | CF(CF$_3$)$_2$ | Me | Bu |
| Ib69 | COH(CF$_3$)$_2$ | Me | Bu |
| Ib70 | CF$_2$Cl | Me | Bu |
| Ib71 | CFCl$_2$ | Me | Bu |
| Ib72 | CCl$_3$ | Me | Bu |
| Ib73 | OCF$_3$ | Me | Bu |
| Ib74 | OCHF$_2$ | Me | Bu |
| Ib75 | OCF$_2$CF$_3$ | Me | Bu |
| Ib76 | OCF$_2$CHF$_2$ | Me | Bu |
| Ib77 | OCF(CF$_3$)$_2$ | Me | Bu |
| Ib78 | OCF$_2$Cl | Me | Bu |

TABLE C-continued

| Ib | R$^{5b}$ | R$^1$ | R$^2$ |
|---|---|---|---|
| Ib79 | OCFCl$_2$ | Me | Bu |
| Ib80 | OCCl$_3$ | Me | Bu |
| Ib81 | CF$_3$ | Me | Pn |
| Ib82 | CHF$_2$ | Me | Pn |
| Ib83 | CF$_2$CF$_3$ | Me | Pn |
| Ib84 | CF(CF$_3$)$_2$ | Me | Pn |
| Ib85 | COH(CF$_3$)$_2$ | Me | Pn |
| Ib86 | CF$_2$Cl | Me | Pn |
| Ib87 | CFCl$_2$ | Me | Pn |
| Ib88 | CCl$_3$ | Me | Pn |
| Ib89 | OCF$_3$ | Me | Pn |
| Ib90 | OCHF$_2$ | Me | Pn |
| Ib91 | OCF$_2$CF$_3$ | Me | Pn |
| Ib92 | OCF$_2$CHF$_2$ | Me | Pn |
| Ib93 | OCF(CF$_3$)$_2$ | Me | Pn |
| Ib94 | OCF$_2$Cl | Me | Pn |
| Ib95 | OCFCl$_2$ | Me | Pn |
| Ib96 | OCCl$_3$ | Me | Pn |
| Ib97 | CF$_3$ | Me | Me—cPr |
| Ib98 | CHF$_2$ | Me | Me—cPr |
| Ib99 | CF$_2$CF$_3$ | Me | Me—cPr |
| Ib100 | CF(CF$_3$)$_2$ | Me | Me—cPr |
| Ib101 | COH(CF$_3$)$_2$ | Me | Me—cPr |
| Ib102 | CF$_2$Cl | Me | Me—cPr |
| Ib103 | CFCl$_2$ | Me | Me—cPr |
| Ib104 | CCl$_3$ | Me | Me—cPr |
| Ib105 | OCF$_3$ | Me | Me—cPr |
| Ib106 | OCHF$_2$ | Me | Me—cPr |
| Ib107 | OCF$_2$CF$_3$ | Me | Me—cPr |
| Ib108 | OCF$_2$CHF$_2$ | Me | Me—cPr |
| Ib109 | OCF(CF3)2 | Me | Me—cPr |
| Ib110 | OCF$_2$Cl | Me | Me—cPr |
| Ib111 | OCFCl$_2$ | Me | Me—cPr |
| Ib112 | OCCl$_3$ | Me | Me—cPr |
| Ib113 | CF$_3$ | Me | allyl |
| Ib114 | CHF$_2$ | Me | allyl |
| Ib115 | CF$_2$CF$_3$ | Me | allyl |
| Ib116 | CF(CF$_3$)$_2$ | Me | allyl |
| Ib117 | COH(CF$_3$)$_2$ | Me | allyl |
| Ib118 | CF$_2$Cl | Me | allyl |
| Ib119 | CFCl$_2$ | Me | allyl |
| Ib120 | CCl$_3$ | Me | allyl |
| Ib121 | OCF$_3$ | Me | allyl |
| Ib122 | OCHF$_2$ | Me | allyl |
| Ib123 | OCF$_2$CF$_3$ | Me | allyl |
| Ib124 | OCF$_2$CHF$_2$ | Me | allyl |
| Ib125 | OCF(CF$_3$)$_2$ | Me | allyl |
| Ib126 | OCF$_2$Cl | Me | allyl |
| Ib127 | OCFCl$_2$ | Me | allyl |
| Ib128 | OCCl$_3$ | Me | allyl |
| Ib129 | CF$_3$ | Me | propargyl |
| Ib130 | CHF$_2$ | Me | propargyl |
| Ib131 | CF$_2$CF$_3$ | Me | propargyl |
| Ib132 | CF(CF$_3$)$_2$ | Me | propargyl |
| Ib133 | COH(CF$_3$)$_2$ | Me | propargyl |
| Ib134 | CF$_2$Cl | Me | propargyl |
| Ib135 | CFCl$_2$ | Me | propargyl |
| Ib136 | CCl$_3$ | Me | propargyl |
| Ib137 | OCF$_3$ | Me | propargyl |
| Ib138 | OCHF$_2$ | Me | propargyl |
| Ib139 | OCF$_2$CF$_3$ | Me | propargyl |
| Ib140 | OCF$_2$CHF$_2$ | Me | propargyl |
| Ib141 | OCF(CF$_3$)$_2$ | Me | propargyl |
| Ib142 | OCF$_2$Cl | Me | propargyl |
| Ib143 | OCFCl$_2$ | Me | propargyl |
| Ib144 | OCCl$_3$ | Me | propargyl |
| Ib145 | CF$_3$ | Me | Me—CN |
| Ib146 | CHF$_2$ | Me | Me—CN |
| Ib147 | CF$_2$CF$_3$ | Me | Me—CN |
| Ib148 | CF(CF$_3$)$_2$ | Me | Me—CN |
| Ib149 | COH(CF$_3$)$_2$ | Me | Me—CN |
| Ib150 | CF$_2$Cl | Me | Me—CN |
| Ib151 | CFCl$_2$ | Me | Me—CN |
| Ib152 | CCl$_3$ | Me | Me—CN |
| Ib153 | OCF$_3$ | Me | Me—CN |
| Ib154 | OCHF$_2$ | Me | Me—CN |
| Ib155 | OCF$_2$CF$_3$ | Me | Me—CN |
| Ib156 | OCF$_2$CHF$_2$ | Me | Me—CN |
| Ib157 | OCF(CF$_3$)$_2$ | Me | Me—CN |
| Ib158 | OCF$_2$Cl | Me | Me—CN |
| Ib159 | OCFCl$_2$ | Me | Me—CN |
| Ib160 | OCCl$_3$ | Me | Me—CN |
| Ib161 | CF$_3$ | Et | Et |
| Ib162 | CHF$_2$ | Et | Et |
| Ib163 | CF$_2$CF$_3$ | Et | Et |
| Ib164 | CF(CF$_3$)$_2$ | Et | Et |
| Ib165 | COH(CF$_3$)$_2$ | Et | Et |
| Ib166 | CF$_2$Cl | Et | Et |
| Ib167 | CFCl$_2$ | Et | Et |
| Ib168 | CCl$_3$ | Et | Et |
| Ib169 | OCF$_3$ | Et | Et |
| Ib170 | OCHF$_2$ | Et | Et |
| Ib171 | OCF$_2$CF$_3$ | Et | Et |
| Ib172 | OCF$_2$CHF$_2$ | Et | Et |
| Ib173 | OCF(CF$_3$)$_2$ | Et | Et |
| Ib174 | OCF$_2$Cl | Et | Et |
| Ib175 | OCFCl$_2$ | Et | Et |
| Ib176 | OCCl$_3$ | Et | Et |
| Ib177 | CF$_3$ | Et | Pr |
| Ib178 | CHF$_2$ | Et | Pr |
| Ib179 | CF$_2$CF$_3$ | Et | Pr |
| Ib180 | CF(CF$_3$)$_2$ | Et | Pr |
| Ib181 | COH(CF$_3$)$_2$ | Et | Pr |
| Ib182 | CF$_2$Cl | Et | Pr |
| Ib183 | CFCl$_2$ | Et | Pr |
| Ib184 | CCl$_3$ | Et | Pr |
| Ib185 | OCF$_3$ | Et | Pr |
| Ib186 | OCHF$_2$ | Et | Pr |
| Ib187 | OCF$_2$CF$_3$ | Et | Pr |
| Ib188 | OCF$_2$CHF$_2$ | Et | Pr |
| Ib189 | OCF(CF3)2 | Et | Pr |
| Ib190 | OCF$_2$Cl | Et | Pr |
| Ib191 | OCFCl$_2$ | Et | Pr |
| Ib192 | OCCl$_3$ | Et | Pr |
| Ib193 | CF$_3$ | Et | iPr |
| Ib194 | CHF$_2$ | Et | iPr |
| Ib195 | CF$_2$CF$_3$ | Et | iPr |
| Ib196 | CF(CF$_3$)$_2$ | Et | iPr |
| Ib197 | COH(CF$_3$)$_2$ | Et | iPr |
| Ib198 | CF$_2$Cl | Et | iPr |
| Ib199 | CFCl$_2$ | Et | iPr |
| Ib200 | CCl$_3$ | Et | iPr |
| Ib201 | OCF$_3$ | Et | iPr |
| Ib202 | OCHF$_2$ | Et | iPr |
| Ib203 | OCF$_2$CF$_3$ | Et | iPr |
| Ib204 | OCF$_2$CHF$_2$ | Et | iPr |
| Ib205 | OCF(CF$_3$)$_2$ | Et | iPr |
| Ib206 | OCF$_2$Cl | Et | iPr |
| Ib207 | OCFCl$_2$ | Et | iPr |
| Ib208 | OCCl$_3$ | Et | iPr |
| Ib209 | CF$_3$ | Et | Bu |
| Ib210 | CHF$_2$ | Et | Bu |
| Ib211 | CF$_2$CF$_3$ | Et | Bu |
| Ib212 | CF(CF$_3$)$_2$ | Et | Bu |
| Ib213 | COH(CF$_3$)$_2$ | Et | Bu |
| Ib214 | CF$_2$Cl | Et | Bu |
| Ib215 | CFCl$_2$ | Et | Bu |
| Ib216 | CCl$_3$ | Et | Bu |
| Ib217 | OCF$_3$ | Et | Bu |
| Ib218 | OCHF$_2$ | Et | Bu |
| Ib219 | OCF$_2$CF$_3$ | Et | Bu |
| Ib220 | OCF$_2$CHF$_2$ | Et | Bu |
| Ib221 | OCF(CF$_3$)$_2$ | Et | Bu |
| Ib222 | OCF$_2$Cl | Et | Bu |
| Ib223 | OCFCl$_2$ | Et | Bu |
| Ib224 | OCCl$_3$ | Et | Bu |
| Ib225 | CF$_3$ | Et | Pn |
| Ib226 | CHF$_2$ | Et | Pn |
| Ib227 | CF$_2$CF$_3$ | Et | Pn |
| Ib228 | CF(CF$_3$)$_2$ | Et | Pn |
| Ib229 | COH(CF$_3$)$_2$ | Et | Pn |
| Ib230 | CF$_2$Cl | Et | Pn |
| Ib231 | CFCl$_2$ | Et | Pn |
| Ib232 | CCl$_3$ | Et | Pn |
| Ib233 | OCF$_3$ | Et | Pn |
| Ib234 | OCHF$_2$ | Et | Pn |

TABLE C-continued

| Ib | R$^{5b}$ | R$^1$ | R$^2$ |
|---|---|---|---|
| Ib235 | OCF$_2$CF$_3$ | Et | Pn |
| Ib236 | OCF$_2$CHF$_2$ | Et | Pn |
| Ib237 | OCF(CF$_3$)$_2$ | Et | Pn |
| Ib238 | OCF$_2$Cl | Et | Pn |
| Ib239 | OCFCl$_2$ | Et | Pn |
| Ib240 | OCCl$_3$ | Et | Pn |
| Ib241 | CF$_3$ | Et | Me—cPr |
| Ib242 | CHF$_2$ | Et | Me—cPr |
| Ib243 | CF$_2$CF$_3$ | Et | Me—cPr |
| Ib244 | CF(CF$_3$)$_2$ | Et | Me—cPr |
| Ib245 | COH(CF$_3$)$_2$ | Et | Me—cPr |
| Ib246 | CF$_2$Cl | Et | Me—cPr |
| Ib247 | CFCl$_2$ | Et | Me—cPr |
| Ib248 | CCl$_3$ | Et | Me—cPr |
| Ib249 | OCF$_3$ | Et | Me—cPr |
| Ib250 | OCHF$_2$ | Et | Me—cPr |
| Ib251 | OCF$_2$CF$_3$ | Et | Me—cPr |
| Ib252 | OCF$_2$CHF$_2$ | Et | Me—cPr |
| Ib253 | OCF(CF3)2 | Et | Me—cPr |
| Ib254 | OCF$_2$Cl | Et | Me—cPr |
| Ib255 | OCFCl$_2$ | Et | Me—cPr |
| Ib256 | OCCl$_3$ | Et | Me—cPr |
| Ib257 | CF$_3$ | Et | allyl |
| Ib258 | CHF$_2$ | Et | allyl |
| Ib259 | CF$_2$CF$_3$ | Et | allyl |
| Ib260 | CF(CF$_3$)$_2$ | Et | allyl |
| Ib261 | COH(CF$_3$)$_2$ | Et | allyl |
| Ib262 | CF$_2$Cl | Et | allyl |
| Ib263 | CFCl$_2$ | Et | allyl |
| Ib264 | CCl$_3$ | Et | allyl |
| Ib265 | OCF$_3$ | Et | allyl |
| Ib266 | OCHF$_2$ | Et | allyl |
| Ib267 | OCF$_2$CF$_3$ | Et | allyl |
| Ib268 | OCF$_2$CHF$_2$ | Et | allyl |
| Ib269 | OCF(CF$_3$)$_2$ | Et | allyl |
| Ib270 | OCF$_2$Cl | Et | allyl |
| Ib271 | OCFCl$_2$ | Et | allyl |
| Ib272 | OCCl$_3$ | Et | allyl |
| Ib273 | CF$_3$ | Et | propargyl |
| Ib274 | CHF$_2$ | Et | propargyl |
| Ib275 | CF$_2$CF$_3$ | Et | propargyl |
| Ib276 | CF(CF$_3$)$_2$ | Et | propargyl |
| Ib277 | COH(CF$_3$)$_2$ | Et | propargyl |
| Ib278 | CF$_2$Cl | Et | propargyl |
| Ib279 | CFCl$_2$ | Et | propargyl |
| Ib280 | CCl$_3$ | Et | propargyl |
| Ib281 | OCF$_3$ | Et | propargyl |
| Ib282 | OCHF$_2$ | Et | propargyl |
| Ib283 | OCF$_2$CF$_3$ | Et | propargyl |
| Ib284 | OCF$_2$CHF$_2$ | Et | propargyl |
| Ib285 | OCF(CF$_3$)$_2$ | Et | propargyl |
| Ib286 | OCF$_2$Cl | Et | propargyl |
| Ib287 | OCFCl$_2$ | Et | propargyl |
| Ib288 | OCCl$_3$ | Et | propargyl |
| Ib289 | CF$_3$ | Et | Me—CN |
| Ib290 | CHF$_2$ | Et | Me—CN |
| Ib291 | CF$_2$CF$_3$ | Et | Me—CN |
| Ib292 | CF(CF$_3$)$_2$ | Et | Me—CN |
| Ib293 | COH(CF$_3$)$_2$ | Et | Me—CN |
| Ib294 | CF$_2$Cl | Et | Me—CN |
| Ib295 | CFCl$_2$ | Et | Me—CN |
| Ib296 | CCl$_3$ | Et | Me—CN |
| Ib297 | OCF$_3$ | Et | Me—CN |
| Ib298 | OCHF$_2$ | Et | Me—CN |
| Ib299 | OCF$_2$CF$_3$ | Et | Me—CN |
| Ib300 | OCF$_2$CHF$_2$ | Et | Me—CN |
| Ib301 | OCF(CF$_3$)$_2$ | Et | Me—CN |
| Ib302 | OCF$_2$Cl | Et | Me—CN |
| Ib303 | OCFCl$_2$ | Et | Me—CN |
| Ib304 | OCCl$_3$ | Et | Me—CN |
| Ib305 | CF$_3$ | Pr | Pr |
| Ib306 | CHF$_2$ | Pr | Pr |
| Ib307 | CF$_2$CF$_3$ | Pr | Pr |
| Ib308 | CF(CF$_3$)$_2$ | Pr | Pr |
| Ib309 | COH(CF$_3$)$_2$ | Pr | Pr |
| Ib310 | CF$_2$Cl | Pr | Pr |
| Ib311 | CFCl$_2$ | Pr | Pr |
| Ib312 | CCl$_3$ | Pr | Pr |
| Ib313 | OCF$_3$ | Pr | Pr |
| Ib314 | OCHF$_2$ | Pr | Pr |
| Ib315 | OCF$_2$CF$_3$ | Pr | Pr |
| Ib316 | OCF$_2$CHF$_2$ | Pr | Pr |
| Ib317 | OCF(CF3)2 | Pr | Pr |
| Ib318 | OCF$_2$Cl | Pr | Pr |
| Ib319 | OCFCl$_2$ | Pr | Pr |
| Ib320 | OCCl$_3$ | Pr | Pr |
| Ib321 | CF$_3$ | Pr | iPr |
| Ib322 | CHF$_2$ | Pr | iPr |
| Ib323 | CF$_2$CF$_3$ | Pr | iPr |
| Ib324 | CF(CF$_3$)$_2$ | Pr | iPr |
| Ib325 | COH(CF$_3$)$_2$ | Pr | iPr |
| Ib326 | CF$_2$Cl | Pr | iPr |
| Ib327 | CFCl$_2$ | Pr | iPr |
| Ib328 | CCl$_3$ | Pr | iPr |
| Ib329 | OCF$_3$ | Pr | iPr |
| Ib330 | OCHF$_2$ | Pr | iPr |
| Ib331 | OCF$_2$CF$_3$ | Pr | iPr |
| Ib332 | OCF$_2$CHF$_2$ | Pr | iPr |
| Ib333 | OCF(CF$_3$)$_2$ | Pr | iPr |
| Ib334 | OCF$_2$Cl | Pr | iPr |
| Ib335 | OCFCl$_2$ | Pr | iPr |
| Ib336 | OCCl$_3$ | Pr | iPr |
| Ib337 | CF$_3$ | Pr | Bu |
| Ib338 | CHF$_2$ | Pr | Bu |
| Ib339 | CF$_2$CF$_3$ | Pr | Bu |
| Ib340 | CF(CF$_3$)$_2$ | Pr | Bu |
| Ib341 | COH(CF$_3$)$_2$ | Pr | Bu |
| Ib342 | CF$_2$Cl | Pr | Bu |
| Ib343 | CFCl$_2$ | Pr | Bu |
| Ib344 | CCl$_3$ | Pr | Bu |
| Ib345 | OCF$_3$ | Pr | Bu |
| Ib346 | OCHF$_2$ | Pr | Bu |
| Ib347 | OCF$_2$CF$_3$ | Pr | Bu |
| Ib348 | OCF$_2$CHF$_2$ | Pr | Bu |
| Ib349 | OCF(CF$_3$)$_2$ | Pr | Bu |
| Ib350 | OCF$_2$Cl | Pr | Bu |
| Ib351 | OCFCl$_2$ | Pr | Bu |
| Ib352 | OCCl$_3$ | Pr | Bu |
| Ib353 | CF$_3$ | Pr | Pn |
| Ib354 | CHF$_2$ | Pr | Pn |
| Ib355 | CF$_2$CF$_3$ | Pr | Pn |
| Ib356 | CF(CF$_3$)$_2$ | Pr | Pn |
| Ib357 | COH(CF$_3$)$_2$ | Pr | Pn |
| Ib358 | CF$_2$Cl | Pr | Pn |
| Ib359 | CFCl$_2$ | Pr | Pn |
| Ib360 | CCl$_3$ | Pr | Pn |
| Ib361 | OCF$_3$ | Pr | Pn |
| Ib362 | OCHF$_2$ | Pr | Pn |
| Ib363 | OCF$_2$CF$_3$ | Pr | Pn |
| Ib364 | OCF$_2$CHF$_2$ | Pr | Pn |
| Ib365 | OCF(CF$_3$)$_2$ | Pr | Pn |
| Ib366 | OCF$_2$Cl | Pr | Pn |
| Ib367 | OCFCl$_2$ | Pr | Pn |
| Ib368 | OCCl$_3$ | Pr | Pn |
| Ib369 | CF$_3$ | Pr | Me—cPr |
| Ib370 | CHF$_2$ | Pr | Me—cPr |
| Ib371 | CF$_2$CF$_3$ | Pr | Me—cPr |
| Ib372 | CF(CF$_3$)$_2$ | Pr | Me—cPr |
| Ib373 | COH(CF$_3$)$_2$ | Pr | Me—cPr |
| Ib374 | CF$_2$Cl | Pr | Me—cPr |
| Ib375 | CFCl$_2$ | Pr | Me—cPr |
| Ib376 | CCl$_3$ | Pr | Me—cPr |
| Ib377 | OCF$_3$ | Pr | Me—cPr |
| Ib378 | OCHF$_2$ | Pr | Me—cPr |
| Ib379 | OCF$_2$CF$_3$ | Pr | Me—cPr |
| Ib380 | OCF$_2$CHF$_2$ | Pr | Me—cPr |
| Ib381 | OCF(CF3)2 | Pr | Me—cPr |
| Ib382 | OCF$_2$Cl | Pr | Me—cPr |
| Ib383 | OCFCl$_2$ | Pr | Me—cPr |
| Ib384 | OCCl$_3$ | Pr | Me—cPr |
| Ib385 | CF$_3$ | Pr | allyl |
| Ib386 | CHF$_2$ | Pr | allyl |
| Ib387 | CF$_2$CF$_3$ | Pr | allyl |
| Ib388 | CF(CF$_3$)$_2$ | Pr | allyl |
| Ib389 | COH(CF$_3$)$_2$ | Pr | allyl |
| Ib390 | CF$_2$Cl | Pr | allyl |

TABLE C-continued

| Ib | R$^{5b}$ | R$^1$ | R$^2$ |
|---|---|---|---|
| Ib391 | CFCl$_2$ | Pr | allyl |
| Ib392 | CCl$_3$ | Pr | allyl |
| Ib393 | OCF$_3$ | Pr | allyl |
| Ib394 | OCHF$_2$ | Pr | allyl |
| Ib395 | OCF$_2$CF$_3$ | Pr | allyl |
| Ib396 | OCF$_2$CHF$_2$ | Pr | allyl |
| Ib397 | OCF(CF$_3$)$_2$ | Pr | allyl |
| Ib398 | OCF$_2$Cl | Pr | allyl |
| Ib399 | OCFCl$_2$ | Pr | allyl |
| Ib400 | OCCl$_3$ | Pr | allyl |
| Ib401 | CF$_3$ | Pr | propargyl |
| Ib402 | CHF$_2$ | Pr | propargyl |
| Ib403 | CF$_2$CF$_3$ | Pr | propargyl |
| Ib404 | CF(CF$_3$)$_2$ | Pr | propargyl |
| Ib405 | COH(CF$_3$)$_2$ | Pr | propargyl |
| Ib406 | CF$_2$Cl | Pr | propargyl |
| Ib407 | CFCl$_2$ | Pr | propargyl |
| Ib408 | CCl$_3$ | Pr | propargyl |
| Ib409 | OCF$_3$ | Pr | propargyl |
| Ib410 | OCHF$_2$ | Pr | propargyl |
| Ib411 | OCF$_2$CF$_3$ | Pr | propargyl |
| Ib412 | OCF$_2$CHF$_2$ | Pr | propargyl |
| Ib413 | OCF(CF$_3$)$_2$ | Pr | propargyl |
| Ib414 | OCF$_2$Cl | Pr | propargyl |
| Ib415 | OCFCl$_2$ | Pr | propargyl |
| Ib416 | OCCl$_3$ | Pr | propargyl |
| Ib417 | CF$_3$ | Pr | Me—CN |
| Ib418 | CHF$_2$ | Pr | Me—CN |
| Ib419 | CF$_2$CF$_3$ | Pr | Me—CN |
| Ib420 | CF(CF$_3$)$_2$ | Pr | Me—CN |
| Ib421 | COH(CF$_3$)$_2$ | Pr | Me—CN |
| Ib422 | CF$_2$Cl | Pr | Me—CN |
| Ib423 | CFCl$_2$ | Pr | Me—CN |
| Ib424 | CCl$_3$ | Pr | Me—CN |
| Ib425 | OCF$_3$ | Pr | Me—CN |
| Ib426 | OCHF$_2$ | Pr | Me—CN |
| Ib427 | OCF$_2$CF$_3$ | Pr | Me—CN |
| Ib428 | OCF$_2$CHF$_2$ | Pr | Me—CN |
| Ib429 | OCF(CF$_3$)$_2$ | Pr | Me—CN |
| Ib430 | OCF$_2$Cl | Pr | Me—CN |
| Ib431 | OCFCl$_2$ | Pr | Me—CN |
| Ib432 | OCCl$_3$ | Pr | Me—CN |
| Ib433 | CF$_3$ | Pr | Pr |
| Ib434 | CHF$_2$ | Pr | Pr |
| Ib435 | CF$_2$CF$_3$ | Pr | Pr |
| Ib436 | CF(CF$_3$)$_2$ | Pr | Pr |
| Ib437 | COH(CF$_3$)$_2$ | Pr | Pr |
| Ib438 | CF$_2$Cl | Pr | Pr |
| Ib439 | CFCl$_2$ | Pr | Pr |
| Ib440 | CCl$_3$ | Pr | Pr |
| Ib441 | OCF$_3$ | Pr | Pr |
| Ib442 | OCHF$_2$ | Pr | Pr |
| Ib443 | OCF$_2$CF$_3$ | Pr | Pr |
| Ib444 | OCF$_2$CHF$_2$ | Pr | Pr |
| Ib445 | OCF(CF3)2 | Pr | Pr |
| Ib446 | OCF$_2$Cl | Pr | Pr |
| Ib447 | OCFCl$_2$ | Pr | Pr |
| Ib448 | OCCl$_3$ | Pr | Pr |
| Ib449 | CF$_3$ | Pr | iPr |
| Ib450 | CHF$_2$ | Pr | iPr |
| Ib451 | CF$_2$CF$_3$ | Pr | iPr |
| Ib452 | CF(CF$_3$)$_2$ | Pr | iPr |
| Ib453 | COH(CF$_3$)$_2$ | Pr | iPr |
| Ib454 | CF$_2$Cl | Pr | iPr |
| Ib455 | CFCl$_2$ | Pr | iPr |
| Ib456 | CCl$_3$ | Pr | iPr |
| Ib457 | OCF$_3$ | Pr | iPr |
| Ib458 | OCHF$_2$ | Pr | iPr |
| Ib459 | OCF$_2$CF$_3$ | Pr | iPr |
| Ib460 | OCF$_2$CHF$_2$ | Pr | iPr |
| Ib461 | OCF(CF$_3$)$_2$ | Pr | iPr |
| Ib462 | OCF$_2$Cl | Pr | iPr |
| Ib463 | OCFCl$_2$ | Pr | iPr |
| Ib464 | OCCl$_3$ | Pr | iPr |
| Ib465 | CF$_3$ | Pr | Bu |
| Ib466 | CHF$_2$ | Pr | Bu |
| Ib467 | CF$_2$CF$_3$ | Pr | Bu |
| Ib468 | CF(CF$_3$)$_2$ | Pr | Bu |
| Ib469 | COH(CF$_3$)$_2$ | Pr | Bu |
| Ib470 | CF$_2$Cl | Pr | Bu |
| Ib471 | CFCl$_2$ | Pr | Bu |
| Ib472 | CCl$_3$ | Pr | Bu |
| Ib473 | OCF$_3$ | Pr | Bu |
| Ib474 | OCHF$_2$ | Pr | Bu |
| Ib475 | OCF$_2$CF$_3$ | Pr | Bu |
| Ib476 | OCF$_2$CHF$_2$ | Pr | Bu |
| Ib477 | OCF(CF$_3$)$_2$ | Pr | Bu |
| Ib478 | OCF$_2$Cl | Pr | Bu |
| Ib479 | OCFCl$_2$ | Pr | Bu |
| Ib480 | OCCl$_3$ | Pr | Bu |
| Ib481 | CF$_3$ | Pr | Pn |
| Ib482 | CHF$_2$ | Pr | Pn |
| Ib483 | CF$_2$CF$_3$ | Pr | Pn |
| Ib484 | CF(CF$_3$)$_2$ | Pr | Pn |
| Ib485 | COH(CF$_3$)$_2$ | Pr | Pn |
| Ib486 | CF$_2$Cl | Pr | Pn |
| Ib487 | CFCl$_2$ | Pr | Pn |
| Ib488 | CCl$_3$ | Pr | Pn |
| Ib489 | OCF$_3$ | Pr | Pn |
| Ib490 | OCHF$_2$ | Pr | Pn |
| Ib491 | OCF$_2$CF$_3$ | Pr | Pn |
| Ib492 | OCF$_2$CHF$_2$ | Pr | Pn |
| Ib493 | OCF(CF$_3$)$_2$ | Pr | Pn |
| Ib494 | OCF$_2$Cl | Pr | Pn |
| Ib495 | OCFCl$_2$ | Pr | Pn |
| Ib496 | OCCl$_3$ | Pr | Pn |
| Ib497 | CF$_3$ | Pr | Me—cPr |
| Ib498 | CHF$_2$ | Pr | Me—cPr |
| Ib499 | CF$_2$CF$_3$ | Pr | Me—cPr |
| Ib500 | CF(CF$_3$)$_2$ | Pr | Me—cPr |
| Ib501 | COH(CF$_3$)$_2$ | Pr | Me—cPr |
| Ib502 | CF$_2$Cl | Pr | Me—cPr |
| Ib503 | CFCl$_2$ | Pr | Me—cPr |
| Ib504 | CCl$_3$ | Pr | Me—cPr |
| Ib505 | OCF$_3$ | Pr | Me—cPr |
| Ib506 | OCHF$_2$ | Pr | Me—cPr |
| Ib507 | OCF$_2$CF$_3$ | Pr | Me—cPr |
| Ib508 | OCF$_2$CHF$_2$ | Pr | Me—cPr |
| Ib509 | OCF(CF3)2 | Pr | Me—cPr |
| Ib510 | OCF$_2$Cl | Pr | Me—cPr |
| Ib511 | OCFCl$_2$ | Pr | Me—cPr |
| Ib512 | OCCl$_3$ | Pr | Me—cPr |
| Ib513 | CF$_3$ | Pr | allyl |
| Ib514 | CHF$_2$ | Pr | allyl |
| Ib515 | CF$_2$CF$_3$ | Pr | allyl |
| Ib516 | CF(CF$_3$)$_2$ | Pr | allyl |
| Ib517 | COH(CF$_3$)$_2$ | Pr | allyl |
| Ib518 | CF$_2$Cl | Pr | allyl |
| Ib519 | CFCl$_2$ | Pr | allyl |
| Ib520 | CCl$_3$ | Pr | allyl |
| Ib521 | OCF$_3$ | Pr | allyl |
| Ib522 | OCHF$_2$ | Pr | allyl |
| Ib523 | OCF$_2$CF$_3$ | Pr | allyl |
| Ib524 | OCF$_2$CHF$_2$ | Pr | allyl |
| Ib525 | OCF(CF$_3$)$_2$ | Pr | allyl |
| Ib526 | OCF$_2$Cl | Pr | allyl |
| Ib527 | OCFCl$_2$ | Pr | allyl |
| Ib528 | OCCl$_3$ | Pr | allyl |
| Ib529 | CF$_3$ | Pr | propargyl |
| Ib530 | CHF$_2$ | Pr | propargyl |
| Ib531 | CF$_2$CF$_3$ | Pr | propargyl |
| Ib532 | CF(CF$_3$)$_2$ | Pr | propargyl |
| Ib533 | COH(CF$_3$)$_2$ | Pr | propargyl |
| Ib534 | CF$_2$Cl | Pr | propargyl |
| Ib535 | CFCl$_2$ | Pr | propargyl |
| Ib536 | CCl$_3$ | Pr | propargyl |
| Ib537 | OCF$_3$ | Pr | propargyl |
| Ib538 | OCHF$_2$ | Pr | propargyl |
| Ib539 | OCF$_2$CF$_3$ | Pr | propargyl |
| Ib540 | OCF$_2$CHF$_2$ | Pr | propargyl |
| Ib541 | OCF(CF$_3$)$_2$ | Pr | propargyl |
| Ib542 | OCF$_2$Cl | Pr | propargyl |
| Ib543 | OCFCl$_2$ | Pr | propargyl |
| Ib544 | OCCl$_3$ | Pr | propargyl |
| Ib545 | CF$_3$ | Pr | Me—CN |
| Ib546 | CHF$_2$ | Pr | Me—CN |

TABLE C-continued

| Ib | $R^{5b}$ | $R^1$ | $R^2$ |
|---|---|---|---|
| Ib547 | $CF_2CF_3$ | Pr | Me—CN |
| Ib548 | $CF(CF_3)_2$ | Pr | Me—CN |
| Ib549 | $COH(CF_3)_2$ | Pr | Me—CN |
| Ib550 | $CF_2Cl$ | Pr | Me—CN |
| Ib551 | $CFCl_2$ | Pr | Me—CN |
| Ib552 | $CCl_3$ | Pr | Me—CN |
| Ib553 | $OCF_3$ | Pr | Me—CN |
| Ib554 | $OCHF_2$ | Pr | Me—CN |
| Ib555 | $OCF_2CF_3$ | Pr | Me—CN |
| Ib556 | $OCF_2CHF_2$ | Pr | Me—CN |
| Ib557 | $OCF(CF_3)_2$ | Pr | Me—CN |
| Ib558 | $OCF_2Cl$ | Pr | Me—CN |
| Ib559 | $OCFCl_2$ | Pr | Me—CN |
| Ib560 | $OCCl_3$ | Pr | Me—CN |
| Ib561 | $CF_3$ | iPr | iPr |
| Ib562 | $CHF_2$ | iPr | iPr |
| Ib563 | $CF_2CF_3$ | iPr | iPr |
| Ib564 | $CF(CF_3)_2$ | iPr | iPr |
| Ib565 | $COH(CF_3)_2$ | iPr | iPr |
| Ib566 | $CF_2Cl$ | iPr | iPr |
| Ib567 | $CFCl_2$ | iPr | iPr |
| Ib568 | $CCl_3$ | iPr | iPr |
| Ib569 | $OCF_3$ | iPr | iPr |
| Ib570 | $OCHF_2$ | iPr | iPr |
| Ib571 | $OCF_2CF_3$ | iPr | iPr |
| Ib572 | $OCF_2CHF_2$ | iPr | iPr |
| Ib573 | $OCF(CF_3)_2$ | iPr | iPr |
| Ib574 | $OCF_2Cl$ | iPr | iPr |
| Ib575 | $OCFCl_2$ | iPr | iPr |
| Ib576 | $OCCl_3$ | iPr | iPr |
| Ib577 | $CF_3$ | iPr | Bu |
| Ib578 | $CHF_2$ | iPr | Bu |
| Ib579 | $CF_2CF_3$ | iPr | Bu |
| Ib580 | $CF(CF_3)_2$ | iPr | Bu |
| Ib581 | $COH(CF_3)_2$ | iPr | Bu |
| Ib582 | $CF_2Cl$ | iPr | Bu |
| Ib583 | $CFCl_2$ | iPr | Bu |
| Ib584 | $CCl_3$ | iPr | Bu |
| Ib585 | $OCF_3$ | iPr | Bu |
| Ib586 | $OCHF_2$ | iPr | Bu |
| Ib587 | $OCF_2CF_3$ | iPr | Bu |
| Ib588 | $OCF_2CHF_2$ | iPr | Bu |
| Ib589 | $OCF(CF_3)_2$ | iPr | Bu |
| Ib590 | $OCF_2Cl$ | iPr | Bu |
| Ib591 | $OCFCl_2$ | iPr | Bu |
| Ib592 | $OCCl_3$ | iPr | Bu |
| Ib593 | $CF_3$ | iPr | Pn |
| Ib594 | $CHF_2$ | iPr | Pn |
| Ib595 | $CF_2CF_3$ | iPr | Pn |
| Ib596 | $CF(CF_3)_2$ | iPr | Pn |
| Ib597 | $COH(CF_3)_2$ | iPr | Pn |
| Ib598 | $CF_2Cl$ | iPr | Pn |
| Ib599 | $CFCl_2$ | iPr | Pn |
| Ib600 | $CCl_3$ | iPr | Pn |
| Ib601 | $OCF_3$ | iPr | Pn |
| Ib602 | $OCHF_2$ | iPr | Pn |
| Ib603 | $OCF_2CF_3$ | iPr | Pn |
| Ib604 | $OCF_2CHF_2$ | iPr | Pn |
| Ib605 | $OCF(CF_3)_2$ | iPr | Pn |
| Ib606 | $OCF_2Cl$ | iPr | Pn |
| Ib607 | $OCFCl_2$ | iPr | Pn |
| Ib608 | $OCCl_3$ | iPr | Pn |
| Ib609 | $CF_3$ | iPr | Me—cPr |
| Ib610 | $CHF_2$ | iPr | Me—cPr |
| Ib611 | $CF_2CF_3$ | iPr | Me—cPr |
| Ib612 | $CF(CF_3)_2$ | iPr | Me—cPr |
| Ib613 | $COH(CF_3)_2$ | iPr | Me—cPr |
| Ib614 | $CF_2Cl$ | iPr | Me—cPr |
| Ib615 | $CFCl_2$ | iPr | Me—cPr |
| Ib616 | $CCl_3$ | iPr | Me—cPr |
| Ib617 | $OCF_3$ | iPr | Me—cPr |
| Ib618 | $OCHF_2$ | iPr | Me—cPr |
| Ib619 | $OCF_2CF_3$ | iPr | Me—cPr |
| Ib620 | $OCF_2CHF_2$ | iPr | Me—cPr |
| Ib621 | $OCF(CF3)2$ | iPr | Me—cPr |
| Ib622 | $OCF_2Cl$ | iPr | Me—cPr |
| Ib623 | $OCFCl_2$ | iPr | Me—cPr |
| Ib624 | $OCCl_3$ | iPr | Me—cPr |
| Ib625 | $CF_3$ | iPr | allyl |
| Ib626 | $CHF_2$ | iPr | allyl |
| Ib627 | $CF_2CF_3$ | iPr | allyl |
| Ib628 | $CF(CF_3)_2$ | iPr | allyl |
| Ib629 | $COH(CF_3)_2$ | iPr | allyl |
| Ib630 | $CF_2Cl$ | iPr | allyl |
| Ib631 | $CFCl_2$ | iPr | allyl |
| Ib632 | $CCl_3$ | iPr | allyl |
| Ib633 | $OCF_3$ | iPr | allyl |
| Ib634 | $OCHF_2$ | iPr | allyl |
| Ib635 | $OCF_2CF_3$ | iPr | allyl |
| Ib636 | $OCF_2CHF_2$ | iPr | allyl |
| Ib637 | $OCF(CF_3)_2$ | iPr | allyl |
| Ib638 | $OCF_2Cl$ | iPr | allyl |
| Ib639 | $OCFCl_2$ | iPr | allyl |
| Ib640 | $OCCl_3$ | iPr | allyl |
| Ib641 | $CF_3$ | iPr | propargyl |
| Ib642 | $CHF_2$ | iPr | propargyl |
| Ib643 | $CF_2CF_3$ | iPr | propargyl |
| Ib644 | $CF(CF_3)_2$ | iPr | propargyl |
| Ib645 | $COH(CF_3)_2$ | iPr | propargyl |
| Ib646 | $CF_2Cl$ | iPr | propargyl |
| Ib647 | $CFCl_2$ | iPr | propargyl |
| Ib648 | $CCl_3$ | iPr | propargyl |
| Ib649 | $OCF_3$ | iPr | propargyl |
| Ib650 | $OCHF_2$ | iPr | propargyl |
| Ib651 | $OCF_2CF_3$ | iPr | propargyl |
| Ib652 | $OCF_2CHF_2$ | iPr | propargyl |
| Ib653 | $OCF(CF_3)_2$ | iPr | propargyl |
| Ib654 | $OCF_2Cl$ | iPr | propargyl |
| Ib655 | $OCFCl_2$ | iPr | propargyl |
| Ib656 | $OCCl_3$ | iPr | propargyl |
| Ib657 | $CF_3$ | iPr | Me—CN |
| Ib658 | $CHF_2$ | iPr | Me—CN |
| Ib659 | $CF_2CF_3$ | iPr | Me—CN |
| Ib660 | $CF(CF_3)_2$ | iPr | Me—CN |
| Ib661 | $COH(CF_3)_2$ | iPr | Me—CN |
| Ib662 | $CF_2Cl$ | iPr | Me—CN |
| Ib663 | $CFCl_2$ | iPr | Me—CN |
| Ib664 | $CCl_3$ | iPr | Me—CN |
| Ib665 | $OCF_3$ | iPr | Me—CN |
| Ib666 | $OCHF_2$ | iPr | Me—CN |
| Ib667 | $OCF_2CF_3$ | iPr | Me—CN |
| Ib668 | $OCF_2CHF_2$ | iPr | Me—CN |
| Ib669 | $OCF(CF_3)_2$ | iPr | Me—CN |
| Ib670 | $OCF_2Cl$ | iPr | Me—CN |
| Ib671 | $OCFCl_2$ | iPr | Me—CN |
| Ib672 | $OCCl_3$ | iPr | Me—CN |
| Ib673 | $CF_3$ | Bu | Bu |
| Ib674 | $CHF_2$ | Bu | Bu |
| Ib675 | $CF_2CF_3$ | Bu | Bu |
| Ib676 | $CF(CF_3)_2$ | Bu | Bu |
| Ib677 | $COH(CF_3)_2$ | Bu | Bu |
| Ib678 | $CF_2Cl$ | Bu | Bu |
| Ib679 | $CFCl_2$ | Bu | Bu |
| Ib680 | $CCl_3$ | Bu | Bu |
| Ib681 | $OCF_3$ | Bu | Bu |
| Ib682 | $OCHF_2$ | Bu | Bu |
| Ib683 | $OCF_2CF_3$ | Bu | Bu |
| Ib684 | $OCF_2CHF_2$ | Bu | Bu |
| Ib685 | $OCF(CF_3)_2$ | Bu | Bu |
| Ib686 | $OCF_2Cl$ | Bu | Bu |
| Ib687 | $OCFCl_2$ | Bu | Bu |
| Ib688 | $OCCl_3$ | Bu | Bu |
| Ib689 | $CF_3$ | Bu | Pn |
| Ib690 | $CHF_2$ | Bu | Pn |
| Ib691 | $CF_2CF_3$ | Bu | Pn |
| Ib692 | $CF(CF_3)_2$ | Bu | Pn |
| Ib693 | $COH(CF_3)_2$ | Bu | Pn |
| Ib694 | $CF_2Cl$ | Bu | Pn |
| Ib695 | $CFCl_2$ | Bu | Pn |
| Ib696 | $CCl_3$ | Bu | Pn |
| Ib697 | $OCF_3$ | Bu | Pn |
| Ib698 | $OCHF_2$ | Bu | Pn |
| Ib699 | $OCF_2CF_3$ | Bu | Pn |
| Ib700 | $OCF_2CHF_2$ | Bu | Pn |
| Ib701 | $OCF(CF_3)_2$ | Bu | Pn |
| Ib702 | $OCF_2Cl$ | Bu | Pn |

TABLE C-continued

| Ib | R$^{5b}$ | R$^1$ | R$^2$ |
|---|---|---|---|
| Ib703 | OCFCl$_2$ | Bu | Pn |
| Ib704 | OCCl$_3$ | Bu | Pn |
| Ib705 | CF$_3$ | Bu | Me—cPr |
| Ib706 | CHF$_2$ | Bu | Me—cPr |
| Ib707 | CF$_2$CF$_3$ | Bu | Me—cPr |
| Ib708 | CF(CF$_3$)$_2$ | Bu | Me—cPr |
| Ib709 | COH(CF$_3$)$_2$ | Bu | Me—cPr |
| Ib710 | CF$_2$Cl | Bu | Me—cPr |
| Ib711 | CFCl$_2$ | Bu | Me—cPr |
| Ib712 | CCl$_3$ | Bu | Me—cPr |
| Ib713 | OCF$_3$ | Bu | Me—cPr |
| Ib714 | OCHF$_2$ | Bu | Me—cPr |
| Ib715 | OCF$_2$CF$_3$ | Bu | Me—cPr |
| Ib716 | OCF$_2$CHF$_2$ | Bu | Me—cPr |
| Ib717 | OCF(CF3)2 | Bu | Me—cPr |
| Ib718 | OCF$_2$Cl | Bu | Me—cPr |
| Ib719 | OCFCl$_2$ | Bu | Me—cPr |
| Ib720 | OCCl$_3$ | Bu | Me—cPr |
| Ib721 | CF$_3$ | Bu | allyl |
| Ib722 | CHF$_2$ | Bu | allyl |
| Ib723 | CF$_2$CF$_3$ | Bu | allyl |
| Ib724 | CF(CF$_3$)$_2$ | Bu | allyl |
| Ib725 | COH(CF$_3$)$_2$ | Bu | allyl |
| Ib726 | CF$_2$Cl | Bu | allyl |
| Ib727 | CFCl$_2$ | Bu | allyl |
| Ib728 | CCl$_3$ | Bu | allyl |
| Ib729 | OCF$_3$ | Bu | allyl |
| Ib730 | OCHF$_2$ | Bu | allyl |
| Ib731 | OCF$_2$CF$_3$ | Bu | allyl |
| Ib732 | OCF$_2$CHF$_2$ | Bu | allyl |
| Ib733 | OCF(CF$_3$)$_2$ | Bu | allyl |
| Ib734 | OCF$_2$Cl | Bu | allyl |
| Ib735 | OCFCl$_2$ | Bu | allyl |
| Ib736 | OCCl$_3$ | Bu | allyl |
| Ib737 | CF$_3$ | Bu | propargyl |
| Ib738 | CHF$_2$ | Bu | propargyl |
| Ib739 | CF$_2$CF$_3$ | Bu | propargyl |
| Ib740 | CF(CF$_3$)$_2$ | Bu | propargyl |
| Ib741 | COH(CF$_3$)$_2$ | Bu | propargyl |
| Ib742 | CF$_2$Cl | Bu | propargyl |
| Ib743 | CFCl$_2$ | Bu | propargyl |
| Ib744 | CCl$_3$ | Bu | propargyl |
| Ib745 | OCF$_3$ | Bu | propargyl |
| Ib746 | OCHF$_2$ | Bu | propargyl |
| Ib747 | OCF$_2$CF$_3$ | Bu | propargyl |
| Ib748 | OCF$_2$CHF$_2$ | Bu | propargyl |
| Ib749 | OCF(CF$_3$)$_2$ | Bu | propargyl |
| Ib750 | OCF$_2$Cl | Bu | propargyl |
| Ib751 | OCFCl$_2$ | Bu | propargyl |
| Ib752 | OCCl$_3$ | Bu | propargyl |
| Ib753 | CF$_3$ | Bu | Me—CN |
| Ib754 | CHF$_2$ | Bu | Me—CN |
| Ib755 | CF$_2$CF$_3$ | Bu | Me—CN |
| Ib756 | CF(CF$_3$)$_2$ | Bu | Me—CN |
| Ib757 | COH(CF$_3$)$_2$ | Bu | Me—CN |
| Ib758 | CF$_2$Cl | Bu | Me—CN |
| Ib759 | CFCl$_2$ | Bu | Me—CN |
| Ib760 | CCl$_3$ | Bu | Me—CN |
| Ib761 | OCF$_3$ | Bu | Me—CN |
| Ib762 | OCHF$_2$ | Bu | Me—CN |
| Ib763 | OCF$_2$CF$_3$ | Bu | Me—CN |
| Ib764 | OCF$_2$CHF$_2$ | Bu | Me—CN |
| Ib765 | OCF(CF$_3$)$_2$ | Bu | Me—CN |
| Ib766 | OCF$_2$Cl | Bu | Me—CN |
| Ib767 | OCFCl$_2$ | Bu | Me—CN |
| Ib768 | OCCl$_3$ | Bu | Me—CN |
| Ib769 | CF$_3$ | Pn | Pn |
| Ib770 | CHF$_2$ | Pn | Pn |
| Ib771 | CF$_2$CF$_3$ | Pn | Pn |
| Ib772 | CF(CF$_3$)$_2$ | Pn | Pn |
| Ib773 | COH(CF$_3$)$_2$ | Pn | Pn |
| Ib774 | CF$_2$Cl | Pn | Pn |
| Ib775 | CFCl$_2$ | Pn | Pn |
| Ib776 | CCl$_3$ | Pn | Pn |
| Ib777 | OCF$_3$ | Pn | Pn |
| Ib778 | OCHF$_2$ | Pn | Pn |
| Ib779 | OCF$_2$CF$_3$ | Pn | Pn |
| Ib780 | OCF$_2$CHF$_2$ | Pn | Pn |
| Ib781 | OCF(CF$_3$)$_2$ | Pn | Pn |
| Ib782 | OCF$_2$Cl | Pn | Pn |
| Ib783 | OCFCl$_2$ | Pn | Pn |
| Ib784 | OCCl$_3$ | Pn | Pn |
| Ib785 | CF$_3$ | Pn | Me—cPr |
| Ib786 | CHF$_2$ | Pn | Me—cPr |
| Ib787 | CF$_2$CF$_3$ | Pn | Me—cPr |
| Ib788 | CF(CF$_3$)$_2$ | Pn | Me—cPr |
| Ib789 | COH(CF$_3$)$_2$ | Pn | Me—cPr |
| Ib790 | CF$_2$Cl | Pn | Me—cPr |
| Ib791 | CFCl$_2$ | Pn | Me—cPr |
| Ib792 | CCl$_3$ | Pn | Me—cPr |
| Ib793 | OCF$_3$ | Pn | Me—cPr |
| Ib794 | OCHF$_2$ | Pn | Me—cPr |
| Ib795 | OCF$_2$CF$_3$ | Pn | Me—cPr |
| Ib796 | OCF$_2$CHF$_2$ | Pn | Me—cPr |
| Ib797 | OCF(CF3)2 | Pn | Me—cPr |
| Ib798 | OCF$_2$Cl | Pn | Me—cPr |
| Ib799 | OCFCl$_2$ | Pn | Me—cPr |
| Ib800 | OCCl$_3$ | Pn | Me—cPr |
| Ib801 | CF$_3$ | Pn | allyl |
| Ib802 | CHF$_2$ | Pn | allyl |
| Ib803 | CF$_2$CF$_3$ | Pn | allyl |
| Ib804 | CF(CF$_3$)$_2$ | Pn | allyl |
| Ib805 | COH(CF$_3$)$_2$ | Pn | allyl |
| Ib806 | CF$_2$Cl | Pn | allyl |
| Ib807 | CFCl$_2$ | Pn | allyl |
| Ib808 | CCl$_3$ | Pn | allyl |
| Ib809 | OCF$_3$ | Pn | allyl |
| Ib810 | OCHF$_2$ | Pn | allyl |
| Ib811 | OCF$_2$CF$_3$ | Pn | allyl |
| Ib812 | OCF$_2$CHF$_2$ | Pn | allyl |
| Ib813 | OCF(CF$_3$)$_2$ | Pn | allyl |
| Ib814 | OCF$_2$Cl | Pn | allyl |
| Ib815 | OCFCl$_2$ | Pn | allyl |
| Ib816 | OCCl$_3$ | Pn | allyl |
| Ib817 | CF$_3$ | Pn | propargyl |
| Ib818 | CHF$_2$ | Pn | propargyl |
| Ib819 | CF$_2$CF$_3$ | Pn | propargyl |
| Ib820 | CF(CF$_3$)$_2$ | Pn | propargyl |
| Ib821 | COH(CF$_3$)$_2$ | Pn | propargyl |
| Ib822 | CF$_2$Cl | Pn | propargyl |
| Ib823 | CFCl$_2$ | Pn | propargyl |
| Ib824 | CCl$_3$ | Pn | propargyl |
| Ib825 | OCF$_3$ | Pn | propargyl |
| Ib826 | OCHF$_2$ | Pn | propargyl |
| Ib827 | OCF$_2$CF$_3$ | Pn | propargyl |
| Ib828 | OCF$_2$CHF$_2$ | Pn | propargyl |
| Ib829 | OCF(CF$_3$)$_2$ | Pn | propargyl |
| Ib830 | OCF$_2$Cl | Pn | propargyl |
| Ib831 | OCFCl$_2$ | Pn | propargyl |
| Ib832 | OCCl$_3$ | Pn | propargyl |
| Ib833 | CF$_3$ | Pn | Me—CN |
| Ib834 | CHF$_2$ | Pn | Me—CN |
| Ib835 | CF$_2$CF$_3$ | Pn | Me—CN |
| Ib836 | CF(CF$_3$)$_2$ | Pn | Me—CN |
| Ib837 | COH(CF$_3$)$_2$ | Pn | Me—CN |
| Ib838 | CF$_2$Cl | Pn | Me—CN |
| Ib839 | CFCl$_2$ | Pn | Me—CN |
| Ib840 | CCl$_3$ | Pn | Me—CN |
| Ib841 | OCF$_3$ | Pn | Me—CN |
| Ib842 | OCHF$_2$ | Pn | Me—CN |
| Ib843 | OCF$_2$CF$_3$ | Pn | Me—CN |
| Ib844 | OCF$_2$CHF$_2$ | Pn | Me—CN |
| Ib845 | OCF(CF$_3$)$_2$ | Pn | Me—CN |
| Ib846 | OCF$_2$Cl | Pn | Me—CN |
| Ib847 | OCFCl$_2$ | Pn | Me—CN |
| Ib848 | OCCl$_3$ | Pn | Me—CN |
| Ib849 | CF$_3$ | Me—cPr | Me—cPr |
| Ib850 | CHF$_2$ | Me—cPr | Me—cPr |
| Ib851 | CF$_2$CF$_3$ | Me—cPr | Me—cPr |
| Ib852 | CF(CF$_3$)$_2$ | Me—cPr | Me—cPr |
| Ib853 | COH(CF$_3$)$_2$ | Me—cPr | Me—cPr |
| Ib854 | CF$_2$Cl | Me—cPr | Me—cPr |
| Ib855 | CFCl$_2$ | Me—cPr | Me—cPr |
| Ib856 | CCl$_3$ | Me—cPr | Me—cPr |
| Ib857 | OCF$_3$ | Me—cPr | Me—cPr |
| Ib858 | OCHF$_2$ | Me—cPr | Me—cPr |

TABLE C-continued

| Ib | R$^{5b}$ | R$^1$ | R$^2$ |
|---|---|---|---|
| Ib859 | OCF$_2$CF$_3$ | Me—cPr | Me—cPr |
| Ib860 | OCF$_2$CHF$_2$ | Me—cPr | Me—cPr |
| Ib861 | OCF(CF3)2 | Me—cPr | Me—cPr |
| Ib862 | OCF$_2$Cl | Me—cPr | Me—cPr |
| Ib863 | OCFCl$_2$ | Me—cPr | Me—cPr |
| Ib864 | OCCl$_3$ | Me—cPr | Me—cPr |
| Ib865 | CF$_3$ | Me—cPr | allyl |
| Ib866 | CHF$_2$ | Me—cPr | allyl |
| Ib867 | CF$_2$CF$_3$ | Me—cPr | allyl |
| Ib868 | CF(CF$_3$)$_2$ | Me—cPr | allyl |
| Ib869 | COH(CF$_3$)$_2$ | Me—cPr | allyl |
| Ib870 | CF$_2$Cl | Me—cPr | allyl |
| Ib871 | CFCl$_2$ | Me—cPr | allyl |
| Ib872 | CCl$_3$ | Me—cPr | allyl |
| Ib873 | OCF$_3$ | Me—cPr | allyl |
| Ib874 | OCHF$_2$ | Me—cPr | allyl |
| Ib875 | OCF$_2$CF$_3$ | Me—cPr | allyl |
| Ib876 | OCF$_2$CHF$_2$ | Me—cPr | allyl |
| Ib877 | OCF(CF$_3$)$_2$ | Me—cPr | allyl |
| Ib878 | OCF$_2$Cl | Me—cPr | allyl |
| Ib879 | OCFCl$_2$ | Me—cPr | allyl |
| Ib880 | OCCl$_3$ | Me—cPr | allyl |
| Ib881 | CF$_3$ | Me—cPr | propargyl |
| Ib882 | CHF$_2$ | Me—cPr | propargyl |
| Ib883 | CF$_2$CF$_3$ | Me—cPr | propargyl |
| Ib884 | CF(CF$_3$)$_2$ | Me—cPr | propargyl |
| Ib885 | COH(CF$_3$)$_2$ | Me—cPr | propargyl |
| Ib886 | CF$_2$Cl | Me—cPr | propargyl |
| Ib887 | CFCl$_2$ | Me—cPr | propargyl |
| Ib888 | CCl$_3$ | Me—cPr | propargyl |
| Ib889 | OCF$_3$ | Me—cPr | propargyl |
| Ib890 | OCHF$_2$ | Me—cPr | propargyl |
| Ib891 | OCF$_2$CF$_3$ | Me—cPr | propargyl |
| Ib892 | OCF$_2$CHF$_2$ | Me—cPr | propargyl |
| Ib893 | OCF(CF$_3$)$_2$ | Me—cPr | propargyl |
| Ib894 | OCF$_2$Cl | Me—cPr | propargyl |
| Ib895 | OCFCl$_2$ | Me—cPr | propargyl |
| Ib896 | OCCl$_3$ | Me—cPr | propargyl |
| Ib897 | CF$_3$ | Me—cPr | Me—CN |
| Ib898 | CHF$_2$ | Me—cPr | Me—CN |
| Ib899 | CF$_2$CF$_3$ | Me—cPr | Me—CN |
| Ib900 | CF(CF$_3$)$_2$ | Me—cPr | Me—CN |
| Ib901 | COH(CF$_3$)$_2$ | Me—cPr | Me—CN |
| Ib902 | CF$_2$Cl | Me—cPr | Me—CN |
| Ib903 | CFCl$_2$ | Me—cPr | Me—CN |
| Ib904 | CCl$_3$ | Me—cPr | Me—CN |
| Ib905 | OCF$_3$ | Me—cPr | Me—CN |
| Ib906 | OCHF$_2$ | Me—cPr | Me—CN |
| Ib907 | OCF$_2$CF$_3$ | Me—cPr | Me—CN |
| Ib908 | OCF$_2$CHF$_2$ | Me—cPr | Me—CN |
| Ib909 | OCF(CF$_3$)$_2$ | Me—cPr | Me—CN |
| Ib910 | OCF$_2$Cl | Me—cPr | Me—CN |
| Ib911 | OCFCl$_2$ | Me—cPr | Me—CN |
| Ib912 | OCCl$_3$ | Me—cPr | Me—CN |
| Ib913 | CF$_3$ | allyl | allyl |
| Ib914 | CHF$_2$ | allyl | allyl |
| Ib915 | CF$_2$CF$_3$ | allyl | allyl |
| Ib916 | CF(CF$_3$)$_2$ | allyl | allyl |
| Ib917 | COH(CF$_3$)$_2$ | allyl | allyl |
| Ib918 | CF$_2$Cl | allyl | allyl |
| Ib919 | CFCl$_2$ | allyl | allyl |
| Ib920 | CCl$_3$ | allyl | allyl |
| Ib921 | OCF$_3$ | allyl | allyl |
| Ib922 | OCHF$_2$ | allyl | allyl |
| Ib923 | OCF$_2$CF$_3$ | allyl | allyl |
| Ib924 | OCF$_2$CHF$_2$ | allyl | allyl |
| Ib925 | OCF(CF$_3$)$_2$ | allyl | allyl |
| Ib926 | OCF$_2$Cl | allyl | allyl |
| Ib927 | OCFCl$_2$ | allyl | allyl |
| Ib928 | OCCl$_3$ | allyl | allyl |
| Ib929 | CF$_3$ | allyl | propargyl |
| Ib930 | CHF$_2$ | allyl | propargyl |
| Ib931 | CF$_2$CF$_3$ | allyl | propargyl |
| Ib932 | CF(CF$_3$)$_2$ | allyl | propargyl |
| Ib933 | COH(CF$_3$)$_2$ | allyl | propargyl |
| Ib934 | CF$_2$Cl | allyl | propargyl |
| Ib935 | CFCl$_2$ | allyl | propargyl |
| Ib936 | CCl$_3$ | allyl | propargyl |
| Ib937 | OCF$_3$ | allyl | propargyl |
| Ib938 | OCHF$_2$ | allyl | propargyl |
| Ib939 | OCF$_2$CF$_3$ | allyl | propargyl |
| Ib940 | OCF$_2$CHF$_2$ | allyl | propargyl |
| Ib941 | OCF(CF$_3$)$_2$ | allyl | propargyl |
| Ib942 | OCF$_2$Cl | allyl | propargyl |
| Ib943 | OCFCl$_2$ | allyl | propargyl |
| Ib944 | OCCl$_3$ | allyl | propargyl |
| Ib945 | CF$_3$ | allyl | Me—CN |
| Ib946 | CHF$_2$ | allyl | Me—CN |
| Ib947 | CF$_2$CF$_3$ | allyl | Me—CN |
| Ib948 | CF(CF$_3$)$_2$ | allyl | Me—CN |
| Ib949 | COH(CF$_3$)$_2$ | allyl | Me—CN |
| Ib950 | CF$_2$Cl | allyl | Me—CN |
| Ib951 | CFCl$_2$ | allyl | Me—CN |
| Ib952 | CCl$_3$ | allyl | Me—CN |
| Ib953 | OCF$_3$ | allyl | Me—CN |
| Ib954 | OCHF$_2$ | allyl | Me—CN |
| Ib955 | OCF$_2$CF$_3$ | allyl | Me—CN |
| Ib956 | OCF$_2$CHF$_2$ | allyl | Me—CN |
| Ib957 | OCF(CF$_3$)$_2$ | allyl | Me—CN |
| Ib958 | OCF$_2$Cl | allyl | Me—CN |
| Ib959 | OCFCl$_2$ | allyl | Me—CN |
| Ib960 | OCCl$_3$ | allyl | Me—CN |
| Ib961 | CF$_3$ | propargyl | propargyl |
| Ib962 | CHF$_2$ | propargyl | propargyl |
| Ib963 | CF$_2$CF$_3$ | propargyl | propargyl |
| Ib964 | CF(CF$_3$)$_2$ | propargyl | propargyl |
| Ib965 | COH(CF$_3$)$_2$ | propargyl | propargyl |
| Ib966 | CF$_2$Cl | propargyl | propargyl |
| Ib967 | CFCl$_2$ | propargyl | propargyl |
| Ib968 | CCl$_3$ | propargyl | propargyl |
| Ib969 | OCF$_3$ | propargyl | propargyl |
| Ib970 | OCHF$_2$ | propargyl | propargyl |
| Ib971 | OCF$_2$CF$_3$ | propargyl | propargyl |
| Ib972 | OCF$_2$CHF$_2$ | propargyl | propargyl |
| Ib973 | OCF(CF$_3$)$_2$ | propargyl | propargyl |
| Ib974 | OCF$_2$Cl | propargyl | propargyl |
| Ib975 | OCFCl$_2$ | propargyl | propargyl |
| Ib976 | OCCl$_3$ | propargyl | propargyl |
| Ib977 | CF$_3$ | propargyl | Me—CN |
| Ib978 | CHF$_2$ | propargyl | Me—CN |
| Ib979 | CF$_2$CF$_3$ | propargyl | Me—CN |
| Ib980 | CF(CF$_3$)$_2$ | propargyl | Me—CN |
| Ib981 | COH(CF$_3$)$_2$ | propargyl | Me—CN |
| Ib982 | CF$_2$Cl | propargyl | Me—CN |
| Ib983 | CFCl$_2$ | propargyl | Me—CN |
| Ib984 | CCl$_3$ | propargyl | Me—CN |
| Ib985 | OCF$_3$ | propargyl | Me—CN |
| Ib986 | OCHF$_2$ | propargyl | Me—CN |
| Ib987 | OCF$_2$CF$_3$ | propargyl | Me—CN |
| Ib988 | OCF$_2$CHF$_2$ | propargyl | Me—CN |
| Ib989 | OCF(CF$_3$)$_2$ | propargyl | Me—CN |
| Ib990 | OCF$_2$Cl | propargyl | Me—CN |
| Ib991 | OCFCl$_2$ | propargyl | Me—CN |
| Ib992 | OCCl$_3$ | propargyl | Me—CN |
| Ib993 | CF$_3$ | Me—CN | Me—CN |
| Ib994 | CHF$_2$ | Me—CN | Me—CN |
| Ib995 | CF$_2$CF$_3$ | Me—CN | Me—CN |
| Ib996 | CF(CF$_3$)$_2$ | Me—CN | Me—CN |
| Ib997 | COH(CF$_3$)$_2$ | Me—CN | Me—CN |
| Ib998 | CF$_2$Cl | Me—CN | Me—CN |
| Ib999 | CFCl$_2$ | Me—CN | Me—CN |
| Ib1000 | CCl$_3$ | Me—CN | Me—CN |
| Ib1001 | OCF$_3$ | Me—CN | Me—CN |
| Ib1002 | OCHF$_2$ | Me—CN | Me—CN |
| Ib1003 | OCF$_2$CF$_3$ | Me—CN | Me—CN |
| Ib1004 | OCF$_2$CHF$_2$ | Me—CN | Me—CN |
| Ib1005 | OCF(CF$_3$)$_2$ | Me—CN | Me—CN |
| Ib1006 | OCF$_2$Cl | Me—CN | Me—CN |
| Ib1007 | OCFCl$_2$ | Me—CN | Me—CN |
| Ib1008 | OCCl$_3$ | Me—CN | Me—CN |
| Ib1009 | CF$_3$ | H | Me |
| Ib1010 | CHF$_2$ | H | Me |
| Ib1011 | CF$_2$CF$_3$ | H | Me |
| Ib1012 | CF(CF$_3$)$_2$ | H | Me |
| Ib1013 | COH(CF$_3$)$_2$ | H | Me |
| Ib1014 | CF$_2$Cl | H | Me |

TABLE C-continued

| Ib | R$^{5b}$ | R$^1$ | R$^2$ |
|---|---|---|---|
| Ib1015 | CFCl$_2$ | H | Me |
| Ib1016 | CCl$_3$ | H | Me |
| Ib1017 | OCF$_3$ | H | Me |
| Ib1018 | OCHF$_2$ | H | Me |
| Ib1019 | OCF$_2$CF$_3$ | H | Me |
| Ib1020 | OCF$_2$CHF$_2$ | H | Me |
| Ib1021 | OCF(CF$_3$)$_2$ | H | Me |
| Ib1022 | OCF$_2$Cl | H | Me |
| Ib1023 | OCFCl$_2$ | H | Me |
| Ib1024 | OCCl$_3$ | H | Me |
| Ib1025 | CF$_3$ | H | Et |
| Ib1026 | CHF$_2$ | H | Et |
| Ib1027 | CF$_2$CF$_3$ | H | Et |
| Ib1028 | CF(CF$_3$)$_2$ | H | Et |
| Ib1029 | COH(CF$_3$)$_2$ | H | Et |
| Ib1030 | CF$_2$Cl | H | Et |
| Ib1031 | CFCl$_2$ | H | Et |
| Ib1032 | CCl$_3$ | H | Et |
| Ib1033 | OCF$_3$ | H | Et |
| Ib1034 | OCHF$_2$ | H | Et |
| Ib1035 | OCF$_2$CF$_3$ | H | Et |
| Ib1036 | OCF$_2$CHF$_2$ | H | Et |
| Ib1037 | OCF(CF$_3$)$_2$ | H | Et |
| Ib1038 | OCF$_2$Cl | H | Et |
| Ib1039 | OCFCl$_2$ | H | Et |
| Ib1040 | OCCl$_3$ | H | Et |
| Ib1041 | CF$_3$ | H | Pr |
| Ib1042 | CHF$_2$ | H | Pr |
| Ib1043 | CF$_2$CF$_3$ | H | Pr |
| Ib1044 | CF(CF$_3$)$_2$ | H | Pr |
| Ib1045 | COH(CF$_3$)$_2$ | H | Pr |
| Ib1046 | CF$_2$Cl | H | Pr |
| Ib1047 | CFCl$_2$ | H | Pr |
| Ib1048 | CCl$_3$ | H | Pr |
| Ib1049 | OCF$_3$ | H | Pr |
| Ib1050 | OCHF$_2$ | H | Pr |
| Ib1051 | OCF$_2$CF$_3$ | H | Pr |
| Ib1052 | OCF$_2$CHF$_2$ | H | Pr |
| Ib1053 | OCF(CF3)2 | H | Pr |
| Ib1054 | OCF$_2$Cl | H | Pr |
| Ib1055 | OCFCl$_2$ | H | Pr |
| Ib1056 | OCCl$_3$ | H | Pr |
| Ib1057 | CF$_3$ | H | iPr |
| Ib1058 | CHF$_2$ | H | iPr |
| Ib1059 | CF$_2$CF$_3$ | H | iPr |
| Ib1060 | CF(CF$_3$)$_2$ | H | iPr |
| Ib1061 | COH(CF$_3$)$_2$ | H | iPr |
| Ib1062 | CF$_2$Cl | H | iPr |
| Ib1063 | CFCl$_2$ | H | iPr |
| Ib1064 | CCl$_3$ | H | iPr |
| Ib1065 | OCF$_3$ | H | iPr |
| Ib1066 | OCHF$_2$ | H | iPr |
| Ib1067 | OCF$_2$CF$_3$ | H | iPr |
| Ib1068 | OCF$_2$CHF$_2$ | H | iPr |
| Ib1069 | OCF(CF$_3$)$_2$ | H | iPr |
| Ib1070 | OCF$_2$Cl | H | iPr |
| Ib1071 | OCFCl$_2$ | H | iPr |
| Ib1072 | OCCl$_3$ | H | iPr |
| Ib1073 | CF$_3$ | H | Bu |
| Ib1074 | CHF$_2$ | H | Bu |
| Ib1075 | CF$_2$CF$_3$ | H | Bu |
| Ib1076 | CF(CF$_3$)$_2$ | H | Bu |
| Ib1077 | COH(CF$_3$)$_2$ | H | Bu |
| Ib1078 | CF$_2$Cl | H | Bu |
| Ib1079 | CFCl$_2$ | H | Bu |
| Ib1080 | CCl$_3$ | H | Bu |
| Ib1081 | OCF$_3$ | H | Bu |
| Ib1082 | OCHF$_2$ | H | Bu |
| Ib1083 | OCF$_2$CF$_3$ | H | Bu |
| Ib1084 | OCF$_2$CHF$_2$ | H | Bu |
| Ib1085 | OCF(CF$_3$)$_2$ | H | Bu |
| Ib1086 | OCF$_2$Cl | H | Bu |
| Ib1087 | OCFCl$_2$ | H | Bu |
| Ib1088 | OCCl$_3$ | H | Bu |
| Ib1089 | CF$_3$ | H | Pn |
| Ib1090 | CHF$_2$ | H | Pn |
| Ib1091 | CF$_2$CF$_3$ | H | Pn |
| Ib1092 | CF(CF$_3$)$_2$ | H | Pn |
| Ib1093 | COH(CF$_3$)$_2$ | H | Pn |
| Ib1094 | CF$_2$Cl | H | Pn |
| Ib1095 | CFCl$_2$ | H | Pn |
| Ib1096 | CCl$_3$ | H | Pn |
| Ib1097 | OCF$_3$ | H | Pn |
| Ib1098 | OCHF$_2$ | H | Pn |
| Ib1099 | OCF$_2$CF$_3$ | H | Pn |
| Ib1100 | OCF$_2$CHF$_2$ | H | Pn |
| Ib1101 | OCF(CF$_3$)$_2$ | H | Pn |
| Ib1102 | OCF$_2$Cl | H | Pn |
| Ib1103 | OCFCl$_2$ | H | Pn |
| Ib1104 | OCCl$_3$ | H | Pn |
| Ib1105 | CF$_3$ | H | Me—cPr |
| Ib1106 | CHF$_2$ | H | Me—cPr |
| Ib1107 | CF$_2$CF$_3$ | H | Me—cPr |
| Ib1108 | CF(CF$_3$)$_2$ | H | Me—cPr |
| Ib1109 | COH(CF$_3$)$_2$ | H | Me—cPr |
| Ib1110 | CF$_2$Cl | H | Me—cPr |
| Ib1111 | CFCl$_2$ | H | Me—cPr |
| Ib1112 | CCl$_3$ | H | Me—cPr |
| Ib1113 | OCF$_3$ | H | Me—cPr |
| Ib1114 | OCHF$_2$ | H | Me—cPr |
| Ib1115 | OCF$_2$CF$_3$ | H | Me—cPr |
| Ib1116 | OCF$_2$CHF$_2$ | H | Me—cPr |
| Ib1117 | OCF(CF3)2 | H | Me—cPr |
| Ib1118 | OCF$_2$Cl | H | Me—cPr |
| Ib1119 | OCFCl$_2$ | H | Me—cPr |
| Ib1120 | OCCl$_3$ | H | Me—cPr |
| Ib1121 | CF$_3$ | H | allyl |
| Ib1122 | CHF$_2$ | H | allyl |
| Ib1123 | CF$_2$CF$_3$ | H | allyl |
| Ib1124 | CF(CF$_3$)$_2$ | H | allyl |
| Ib1125 | COH(CF$_3$)$_2$ | H | allyl |
| Ib1126 | CF$_2$Cl | H | allyl |
| Ib1127 | CFCl$_2$ | H | allyl |
| Ib1128 | CCl$_3$ | H | allyl |
| Ib1129 | OCF$_3$ | H | allyl |
| Ib1130 | OCHF$_2$ | H | allyl |
| Ib1131 | OCF$_2$CF$_3$ | H | allyl |
| Ib1132 | OCF$_2$CHF$_2$ | H | allyl |
| Ib1133 | OCF(CF$_3$)$_2$ | H | allyl |
| Ib1134 | OCF$_2$Cl | H | allyl |
| Ib1135 | OCFCl$_2$ | H | allyl |
| Ib1136 | OCCl$_3$ | H | allyl |
| Ib1137 | CF$_3$ | H | propargyl |
| Ib1138 | CHF$_2$ | H | propargyl |
| Ib1139 | CF$_2$CF$_3$ | H | propargyl |
| Ib1140 | CF(CF$_3$)$_2$ | H | propargyl |
| Ib1141 | COH(CF$_3$)$_2$ | H | propargyl |
| Ib1142 | CF$_2$Cl | H | propargyl |
| Ib1143 | CFCl$_2$ | H | propargyl |
| Ib1144 | CCl$_3$ | H | propargyl |
| Ib1145 | OCF$_3$ | H | propargyl |
| Ib1146 | OCHF$_2$ | H | propargyl |
| Ib1147 | OCF$_2$CF$_3$ | H | propargyl |
| Ib1148 | OCF$_2$CHF$_2$ | H | propargyl |
| Ib1149 | OCF(CF$_3$)$_2$ | H | propargyl |
| Ib1150 | OCF$_2$Cl | H | propargyl |
| Ib1151 | OCFCl$_2$ | H | propargyl |
| Ib1152 | OCCl$_3$ | H | propargyl |
| Ib1153 | CF$_3$ | H | Me—CN |
| Ib1154 | CHF$_2$ | H | Me—CN |
| Ib1155 | CF$_2$CF$_3$ | H | Me—CN |
| Ib1156 | CF(CF$_3$)$_2$ | H | Me—CN |
| Ib1157 | COH(CF$_3$)$_2$ | H | Me—CN |
| Ib1158 | CF$_2$Cl | H | Me—CN |
| Ib1159 | CFCl$_2$ | H | Me—CN |
| Ib1160 | CCl$_3$ | H | Me—CN |
| Ib1161 | OCF$_3$ | H | Me—CN |
| Ib1162 | OCHF$_2$ | H | Me—CN |
| Ib1163 | OCF$_2$CF$_3$ | H | Me—CN |
| Ib1164 | OCF$_2$CHF$_2$ | H | Me—CN |
| Ib1165 | OCF(CF$_3$)$_2$ | H | Me—CN |
| Ib1166 | OCF$_2$Cl | H | Me—CN |
| Ib1167 | OCFCl$_2$ | H | Me—CN |
| Ib1168 | OCCl$_3$ | H | Me—CN |

Following annotation when used in the text are defined as follows:

Me is methyl or —CH$_3$;
Et is ethyl or —CH$_2$CH$_3$;
Pr is propyl or —(CH$_2$)$_2$CH$_3$,
iPr is isopropyl or —CH(CH$_3$)$_2$;
Bu is butyl or (CH$_2$)$_3$CH$_3$;
Pn is pentyl or (CH$_2$)$_4$CH$_3$;
Me-cPr is methylcyclopropyl;
Me-CN is cyanomethyl.

Examples of compounds of this particular preferred embodiment of such compounds are the compounds I-a given in the following tables 1 to 13.

Table 1 Compounds of the formula I-a and their salts, wherein $R^{5c}$ and $R^{5d}$ are hydrogen, $R^{5a}$ is H and the remaining variables $R^1$, $R^2$, $R^{5b}$ band A correspond to each combination of the radicals numbered A1a1 to A1a197 with each row of Table C numbered Ib1 to Ib1168.

Table 2 Compounds of the formula I-a and their salts, wherein $R^{5c}$ and $R^{5d}$ are hydrogen, $R^{5a}$ is F and the remaining variables $R^1$, $R^2$, $R^{5b}$ and A correspond to each combination of the radicals numbered A1a1 to A1a197 with each row of Table C numbered Ib1 to Ib1168.

Table 3 Compounds of the formula I-a and their salts, wherein $R^{5c}$ and $R^{5d}$ are hydrogen, $R^{5a}$ is Cl and the remaining variables $R^1$, $R^2$, $R^{5b}$ and A correspond to each combination of the radicals numbered A1a1 to A1a197 with each row of Table C numbered Ib1 to Ib1168.

Table 4 Compounds of the formula I-a and their salts, wherein $R^{5c}$ and $R^{5d}$ are hydrogen, $R^{5a}$ is Br and the remaining variables $R^1$, $R^2$, $R^{5b}$ and A correspond to each combination of the radicals numbered A1a1 to A1a197 with each row of Table C numbered Ib1 to Ib1168.

Table 5 Compounds of the formula I-a and their salts, wherein $R^{5c}$ and $R^{5d}$ are hydrogen, $R^{5a}$ is I and the remaining variables $R^1$, $R^2$, $R^{5b}$ and A correspond to each combination of the radicals numbered A1a1 to A1a197 with each row of Table C numbered Ib1 to Ib1168.

Table 6 Compounds of the formula I-a and their salts, wherein $R^{5c}$ and $R^{5d}$ are hydrogen, $R^{5a}$ is CN and the remaining variables $R^1$, $R^2$, $R^{5b}$ and A correspond to each combination of the radicals numbered A1a1 to A1a197 with each row of Table C numbered Ib1 to Ib1168.

Table 7 Compounds of the formula I-a and their salts, wherein $R^{5c}$ and $R^{5d}$ are hydrogen, $R^{5a}$ is NO$_2$ and the remaining variables $R^1$, $R^2$, $R^{5b}$ and A correspond to each combination of the radicals numbered A1a1 to A1a197 with each row of Table C numbered Ib1 to Ib1168.

Table 8 Compounds of the formula I-a and their salts, wherein $R^{5c}$ and $R^{5d}$ are hydrogen, $R^{5a}$ is CH$_3$ and the remaining variables $R^1$, $R^2$, $R^{5b}$ and A correspond to each combination of the radicals numbered A1a1 to A1a197 with each row of Table C numbered Ib1 to Ib1168.

Table 9 Compounds of the formula I-a and their salts, wherein $R^{5c}$ and $R^{5d}$ are hydrogen, $R^{5a}$ is CF$_3$ and the remaining variables $R^1$, $R^2$, $R^{5b}$ and A correspond to each combination of the radicals numbered A1a1 to A1a197 with each row of Table C numbered Ib1 to Ib1168.

Table 10 Compounds of the formula I-a and their salts, wherein $R^{5c}$ and $R^{5d}$ are hydrogen, $R^{5a}$ is CHF$_2$ and the remaining variables $R^1$, $R^2$, $R^{5b}$ and A correspond to each combination of the radicals numbered A1a1 to A1a197 with each row of Table C numbered Ib1 to Ib1168.

Table 11 Compounds of the formula I-a and their salts, wherein $R^{5c}$ and $R^{5d}$ are hydrogen, $R^{5a}$ is OCF$_3$ and the remaining variables $R^1$, $R^2$, $R^{5b}$ and A correspond to each combination of the radicals numbered A1a1 to A1a197 with each row of Table C numbered Ib1 to Ib1168.

Table 12 Compounds of the formula I-a and their salts, wherein $R^{5c}$ and $R^{5d}$ are hydrogen, $R^{5a}$ is OCHF$_2$ and the remaining variables $R^1$, $R^2$, $R^{5b}$ and A correspond to each combination of the radicals numbered A1a1 to A1a197 with each row of Table C numbered Ib1 to Ib1168.

Table 13 Compounds of the formula I-a and their salts, wherein $R^{5c}$ and $R^{5d}$ are hydrogen, $R^{5a}$ is SCF$_3$ and the remaining variables $R^1$, $R^2$, $R^{5b}$ and A correspond to each combination of the radicals numbered A1a1 to A1a197 with each row of Table C numbered Ib1 to Ib1168.

Each example of the compounds of formula I-a as defined in the tables 1 to 13 constitutes a preferred embodiment of the invention.

Especially preferred embodiment of the invention are the compounds I-a wherein $R^{5a}$, is hydrogen, $A^2$, $A^3$, $A^4$ are CH, and the remaining variables $R^1$, $R^2$, $R^3$, $R^4$, $R^{5b}$, $A^1$ are defined in each row of the following Table D (variables $R^1$, $R^2$, $R^3$, $R^4$, $R^{5b}$, $A^1$ are defined in radical A and Ib being respectively defined in table B and C):

TABLE D

| Radical A | Ib |
|---|---|
| A1a1 | Ib1 |
| A1a2 | Ib1 |
| A1a3 | Ib1 |
| A1a4 | Ib1 |
| A1a5 | Ib1 |
| A1a6 | Ib1 |
| A1a7 | Ib1 |
| A1a8 | Ib1 |
| A1a9 | Ib1 |
| A1a10 | Ib1 |
| A1a11 | Ib1 |
| A1a12 | Ib1 |
| A1a13 | Ib1 |
| A1a14 | Ib1 |
| A1a1 | Ib17 |
| A1a2 | Ib17 |
| A1a3 | Ib17 |
| A1a4 | Ib17 |
| A1a5 | Ib17 |
| A1a6 | Ib17 |
| A1a7 | Ib17 |
| A1a8 | Ib17 |
| A1a9 | Ib17 |
| A1a10 | Ib17 |
| A1a11 | Ib17 |
| A1a12 | Ib17 |
| A1a13 | Ib17 |
| A1a14 | Ib17 |
| A1a1 | Ib33 |
| A1a2 | Ib33 |
| A1a3 | Ib33 |
| A1a4 | Ib33 |
| A1a5 | Ib33 |
| A1a6 | Ib33 |
| A1a7 | Ib33 |
| A1a8 | Ib33 |
| A1a9 | Ib33 |
| A1a10 | Ib33 |
| A1a11 | Ib33 |
| A1a12 | Ib33 |
| A1a13 | Ib33 |
| A1a14 | Ib33 |
| A1a1 | Ib49 |
| A1a2 | Ib49 |
| A1a3 | Ib49 |
| A1a4 | Ib49 |
| A1a5 | Ib49 |
| A1a6 | Ib49 |
| A1a7 | Ib49 |
| A1a8 | Ib49 |

TABLE D-continued

| Radical A | Ib |
|---|---|
| A1a9 | Ib49 |
| A1a10 | Ib49 |
| A1a11 | Ib49 |
| A1a12 | Ib49 |
| A1a13 | Ib49 |
| A1a14 | Ib49 |
| A1a1 | Ib65 |
| A1a2 | Ib65 |
| A1a3 | Ib65 |
| A1a4 | Ib65 |
| A1a5 | Ib65 |
| A1a6 | Ib65 |
| A1a7 | Ib65 |
| A1a8 | Ib65 |
| A1a9 | Ib65 |
| A1a10 | Ib65 |
| A1a11 | Ib65 |
| A1a12 | Ib65 |
| A1a13 | Ib65 |
| A1a14 | Ib65 |
| A1a1 | Ib81 |
| A1a2 | Ib81 |
| A1a3 | Ib81 |
| A1a4 | Ib81 |
| A1a5 | Ib81 |
| A1a6 | Ib81 |
| A1a7 | Ib81 |
| A1a8 | Ib81 |
| A1a9 | Ib81 |
| A1a10 | Ib81 |
| A1a11 | Ib81 |
| A1a12 | Ib81 |
| A1a13 | Ib81 |
| A1a14 | Ib81 |
| A1a1 | Ib97 |
| A1a2 | Ib97 |
| A1a3 | Ib97 |
| A1a4 | Ib97 |
| A1a5 | Ib97 |
| A1a6 | Ib97 |
| A1a7 | Ib97 |
| A1a8 | Ib97 |
| A1a9 | Ib97 |
| A1a10 | Ib97 |
| A1a11 | Ib97 |
| A1a12 | Ib97 |
| A1a13 | Ib97 |
| A1a14 | Ib97 |
| A1a1 | Ib113 |
| A1a2 | Ib113 |
| A1a3 | Ib113 |
| A1a4 | Ib113 |
| A1a5 | Ib113 |
| A1a6 | Ib113 |
| A1a7 | Ib113 |
| A1a8 | Ib113 |
| A1a9 | Ib113 |
| A1a10 | Ib113 |
| A1a11 | Ib113 |
| A1a12 | Ib113 |
| A1a13 | Ib113 |
| A1a14 | Ib113 |
| A1a1 | Ib129 |
| A1a2 | Ib129 |
| A1a3 | Ib129 |
| A1a4 | Ib129 |
| A1a5 | Ib129 |
| A1a6 | Ib129 |
| A1a7 | Ib129 |
| A1a8 | Ib129 |
| A1a9 | Ib129 |
| A1a10 | Ib129 |
| A1a11 | Ib129 |
| A1a12 | Ib129 |
| A1a13 | Ib129 |
| A1a14 | Ib129 |
| A1a1 | Ib145 |
| A1a2 | Ib145 |

TABLE D-continued

| Radical A | Ib |
|---|---|
| A1a3 | Ib145 |
| A1a4 | Ib145 |
| A1a5 | Ib145 |
| A1a6 | Ib145 |
| A1a7 | Ib145 |
| A1a8 | Ib145 |
| A1a9 | Ib145 |
| A1a10 | Ib145 |
| A1a11 | Ib145 |
| A1a12 | Ib145 |
| A1a13 | Ib145 |
| A1a14 | Ib145 |
| A1a1 | Ib161 |
| A1a2 | Ib161 |
| A1a3 | Ib161 |
| A1a4 | Ib161 |
| A1a5 | Ib161 |
| A1a6 | Ib161 |
| A1a7 | Ib161 |
| A1a8 | Ib161 |
| A1a9 | Ib161 |
| A1a10 | Ib161 |
| A1a11 | Ib161 |
| A1a12 | Ib161 |
| A1a13 | Ib161 |
| A1a14 | Ib161 |
| A1a1 | Ib177 |
| A1a2 | Ib177 |
| A1a3 | Ib177 |
| A1a4 | Ib177 |
| A1a5 | Ib177 |
| A1a6 | Ib177 |
| A1a7 | Ib177 |
| A1a8 | Ib177 |
| A1a9 | Ib177 |
| A1a10 | Ib177 |
| A1a11 | Ib177 |
| A1a12 | Ib177 |
| A1a13 | Ib177 |
| A1a14 | Ib177 |
| A1a1 | Ib193 |
| A1a2 | Ib193 |
| A1a3 | Ib193 |
| A1a4 | Ib193 |
| A1a5 | Ib193 |
| A1a6 | Ib193 |
| A1a7 | Ib193 |
| A1a8 | Ib193 |
| A1a9 | Ib193 |
| A1a10 | Ib193 |
| A1a11 | Ib193 |
| A1a12 | Ib193 |
| A1a13 | Ib193 |
| A1a14 | Ib193 |
| A1a1 | Ib209 |
| A1a2 | Ib209 |
| A1a3 | Ib209 |
| A1a4 | Ib209 |
| A1a5 | Ib209 |
| A1a6 | Ib209 |
| A1a7 | Ib209 |
| A1a8 | Ib209 |
| A1a9 | Ib209 |
| A1a10 | Ib209 |
| A1a11 | Ib209 |
| A1a12 | Ib209 |
| A1a13 | Ib209 |
| A1a14 | Ib209 |
| A1a1 | Ib225 |
| A1a2 | Ib225 |
| A1a3 | Ib225 |
| A1a4 | Ib225 |
| A1a5 | Ib225 |
| A1a6 | Ib225 |
| A1a7 | Ib225 |
| A1a8 | Ib225 |
| A1a9 | Ib225 |
| A1a10 | Ib225 |

TABLE D-continued

| Radical A | Ib |
|---|---|
| A1a11 | Ib225 |
| A1a12 | Ib225 |
| A1a13 | Ib225 |
| A1a14 | Ib225 |
| A1a1 | Ib241 |
| A1a2 | Ib241 |
| A1a3 | Ib241 |
| A1a4 | Ib241 |
| A1a5 | Ib241 |
| A1a6 | Ib241 |
| A1a7 | Ib241 |
| A1a8 | Ib241 |
| A1a9 | Ib241 |
| A1a10 | Ib241 |
| A1a11 | Ib241 |
| A1a12 | Ib241 |
| A1a13 | Ib241 |
| A1a14 | Ib241 |
| A1a1 | Ib257 |
| A1a2 | Ib257 |
| A1a3 | Ib257 |
| A1a4 | Ib257 |
| A1a5 | Ib257 |
| A1a6 | Ib257 |
| A1a7 | Ib257 |
| A1a8 | Ib257 |
| A1a9 | Ib257 |
| A1a10 | Ib257 |
| A1a11 | Ib257 |
| A1a12 | Ib257 |
| A1a13 | Ib257 |
| A1a14 | Ib257 |
| A1a1 | Ib273 |
| A1a2 | Ib273 |
| A1a3 | Ib273 |
| A1a4 | Ib273 |
| A1a5 | Ib273 |
| A1a6 | Ib273 |
| A1a7 | Ib273 |
| A1a8 | Ib273 |
| A1a9 | Ib273 |
| A1a10 | Ib273 |
| A1a11 | Ib273 |
| A1a12 | Ib273 |
| A1a13 | Ib273 |
| A1a14 | Ib273 |
| A1a1 | Ib289 |
| A1a2 | Ib289 |
| A1a3 | Ib289 |
| A1a4 | Ib289 |
| A1a5 | Ib289 |
| A1a6 | Ib289 |
| A1a7 | Ib289 |
| A1a8 | Ib289 |
| A1a9 | Ib289 |
| A1a10 | Ib289 |
| A1a11 | Ib289 |
| A1a12 | Ib289 |
| A1a13 | Ib289 |
| A1a14 | Ib289 |
| A1a1 | Ib305 |
| A1a2 | Ib305 |
| A1a3 | Ib305 |
| A1a4 | Ib305 |
| A1a5 | Ib305 |
| A1a6 | Ib305 |
| A1a7 | Ib305 |
| A1a8 | Ib305 |
| A1a9 | Ib305 |
| A1a10 | Ib305 |
| A1a11 | Ib305 |
| A1a12 | Ib305 |
| A1a13 | Ib305 |
| A1a14 | Ib305 |
| A1a1 | Ib321 |
| A1a2 | Ib321 |
| A1a3 | Ib321 |
| A1a4 | Ib321 |
| A1a5 | Ib321 |
| A1a6 | Ib321 |
| A1a7 | Ib321 |
| A1a8 | Ib321 |
| A1a9 | Ib321 |
| A1a10 | Ib321 |
| A1a11 | Ib321 |
| A1a12 | Ib321 |
| A1a13 | Ib321 |
| A1a14 | Ib321 |
| A1a1 | Ib337 |
| A1a2 | Ib337 |
| A1a3 | Ib337 |
| A1a4 | Ib337 |
| A1a5 | Ib337 |
| A1a6 | Ib337 |
| A1a7 | Ib337 |
| A1a8 | Ib337 |
| A1a9 | Ib337 |
| A1a10 | Ib337 |
| A1a11 | Ib337 |
| A1a12 | Ib337 |
| A1a13 | Ib337 |
| A1a14 | Ib337 |
| A1a1 | Ib353 |
| A1a2 | Ib353 |
| A1a3 | Ib353 |
| A1a4 | Ib353 |
| A1a5 | Ib353 |
| A1a6 | Ib353 |
| A1a7 | Ib353 |
| A1a8 | Ib353 |
| A1a9 | Ib353 |
| A1a10 | Ib353 |
| A1a11 | Ib353 |
| A1a12 | Ib353 |
| A1a13 | Ib353 |
| A1a14 | Ib353 |
| A1a1 | Ib369 |
| A1a2 | Ib369 |
| A1a3 | Ib369 |
| A1a4 | Ib369 |
| A1a5 | Ib369 |
| A1a6 | Ib369 |
| A1a7 | Ib369 |
| A1a8 | Ib369 |
| A1a9 | Ib369 |
| A1a10 | Ib369 |
| A1a11 | Ib369 |
| A1a12 | Ib369 |
| A1a13 | Ib369 |
| A1a14 | Ib369 |
| A1a1 | Ib385 |
| A1a2 | Ib385 |
| A1a3 | Ib385 |
| A1a4 | Ib385 |
| A1a5 | Ib385 |
| A1a6 | Ib385 |
| A1a7 | Ib385 |
| A1a8 | Ib385 |
| A1a9 | Ib385 |
| A1a10 | Ib385 |
| A1a11 | Ib385 |
| A1a12 | Ib385 |
| A1a13 | Ib385 |
| A1a14 | Ib385 |
| A1a1 | Ib401 |
| A1a2 | Ib401 |
| A1a3 | Ib401 |
| A1a4 | Ib401 |
| A1a5 | Ib401 |
| A1a6 | Ib401 |
| A1a7 | Ib401 |
| A1a8 | Ib401 |
| A1a9 | Ib401 |
| A1a10 | Ib401 |
| A1a11 | Ib401 |
| A1a12 | Ib401 |

TABLE D-continued

| Radical A | Ib |
|---|---|
| A1a13 | Ib401 |
| A1a14 | Ib401 |
| A1a1 | Ib417 |
| A1a2 | Ib417 |
| A1a3 | Ib417 |
| A1a4 | Ib417 |
| A1a5 | Ib417 |
| A1a6 | Ib417 |
| A1a7 | Ib417 |
| A1a8 | Ib417 |
| A1a9 | Ib417 |
| A1a10 | Ib417 |
| A1a11 | Ib417 |
| A1a12 | Ib417 |
| A1a13 | Ib417 |
| A1a14 | Ib417 |
| A1a1 | Ib433 |
| A1a2 | Ib433 |
| A1a3 | Ib433 |
| A1a4 | Ib433 |
| A1a5 | Ib433 |
| A1a6 | Ib433 |
| A1a7 | Ib433 |
| A1a8 | Ib433 |
| A1a9 | Ib433 |
| A1a10 | Ib433 |
| A1a11 | Ib433 |
| A1a12 | Ib433 |
| A1a13 | Ib433 |
| A1a14 | Ib433 |
| A1a1 | Ib449 |
| A1a2 | Ib449 |
| A1a3 | Ib449 |
| A1a4 | Ib449 |
| A1a5 | Ib449 |
| A1a6 | Ib449 |
| A1a7 | Ib449 |
| A1a8 | Ib449 |
| A1a9 | Ib449 |
| A1a10 | Ib449 |
| A1a11 | Ib449 |
| A1a12 | Ib449 |
| A1a13 | Ib449 |
| A1a14 | Ib449 |
| A1a1 | Ib465 |
| A1a2 | Ib465 |
| A1a3 | Ib465 |
| A1a4 | Ib465 |
| A1a5 | Ib465 |
| A1a6 | Ib465 |
| A1a7 | Ib465 |
| A1a8 | Ib465 |
| A1a9 | Ib465 |
| A1a10 | Ib465 |
| A1a11 | Ib465 |
| A1a12 | Ib465 |
| A1a13 | Ib465 |
| A1a14 | Ib465 |
| A1a1 | Ib481 |
| A1a2 | Ib481 |
| A1a3 | Ib481 |
| A1a4 | Ib481 |
| A1a5 | Ib481 |
| A1a6 | Ib481 |
| A1a7 | Ib481 |
| A1a8 | Ib481 |
| A1a9 | Ib481 |
| A1a10 | Ib481 |
| A1a11 | Ib481 |
| A1a12 | Ib481 |
| A1a13 | Ib481 |
| A1a14 | Ib481 |
| A1a1 | Ib497 |
| A1a2 | Ib497 |
| A1a3 | Ib497 |
| A1a4 | Ib497 |
| A1a5 | Ib497 |
| A1a6 | Ib497 |
| A1a7 | Ib497 |
| A1a8 | Ib497 |
| A1a9 | Ib497 |
| A1a10 | Ib497 |
| A1a11 | Ib497 |
| A1a12 | Ib497 |
| A1a13 | Ib497 |
| A1a14 | Ib497 |
| A1a1 | Ib513 |
| A1a2 | Ib513 |
| A1a3 | Ib513 |
| A1a4 | Ib513 |
| A1a5 | Ib513 |
| A1a6 | Ib513 |
| A1a7 | Ib513 |
| A1a8 | Ib513 |
| A1a9 | Ib513 |
| A1a10 | Ib513 |
| A1a11 | Ib513 |
| A1a12 | Ib513 |
| A1a13 | Ib513 |
| A1a14 | Ib513 |
| A1a1 | Ib529 |
| A1a2 | Ib529 |
| A1a3 | Ib529 |
| A1a4 | Ib529 |
| A1a5 | Ib529 |
| A1a6 | Ib529 |
| A1a7 | Ib529 |
| A1a8 | Ib529 |
| A1a9 | Ib529 |
| A1a10 | Ib529 |
| A1a11 | Ib529 |
| A1a12 | Ib529 |
| A1a13 | Ib529 |
| A1a14 | Ib529 |
| A1a1 | Ib545 |
| A1a2 | Ib545 |
| A1a3 | Ib545 |
| A1a4 | Ib545 |
| A1a5 | Ib545 |
| A1a6 | Ib545 |
| A1a7 | Ib545 |
| A1a8 | Ib545 |
| A1a9 | Ib545 |
| A1a10 | Ib545 |
| A1a11 | Ib545 |
| A1a12 | Ib545 |
| A1a13 | Ib545 |
| A1a14 | Ib545 |
| A1a1 | Ib561 |
| A1a2 | Ib561 |
| A1a3 | Ib561 |
| A1a4 | Ib561 |
| A1a5 | Ib561 |
| A1a6 | Ib561 |
| A1a7 | Ib561 |
| A1a8 | Ib561 |
| A1a9 | Ib561 |
| A1a10 | Ib561 |
| A1a11 | Ib561 |
| A1a12 | Ib561 |
| A1a13 | Ib561 |
| A1a14 | Ib561 |
| A1a1 | Ib577 |
| A1a2 | Ib577 |
| A1a3 | Ib577 |
| A1a4 | Ib577 |
| A1a5 | Ib577 |
| A1a6 | Ib577 |
| A1a7 | Ib577 |
| A1a8 | Ib577 |
| A1a9 | Ib577 |
| A1a10 | Ib577 |
| A1a11 | Ib577 |
| A1a12 | Ib577 |
| A1a13 | Ib577 |
| A1a14 | Ib577 |

TABLE D-continued

| Radical A | Ib |
|---|---|
| A1a1 | Ib593 |
| A1a2 | Ib593 |
| A1a3 | Ib593 |
| A1a4 | Ib593 |
| A1a5 | Ib593 |
| A1a6 | Ib593 |
| A1a7 | Ib593 |
| A1a8 | Ib593 |
| A1a9 | Ib593 |
| A1a10 | Ib593 |
| A1a11 | Ib593 |
| A1a12 | Ib593 |
| A1a13 | Ib593 |
| A1a14 | Ib593 |
| A1a1 | Ib609 |
| A1a2 | Ib609 |
| A1a3 | Ib609 |
| A1a4 | Ib609 |
| A1a5 | Ib609 |
| A1a6 | Ib609 |
| A1a7 | Ib609 |
| A1a8 | Ib609 |
| A1a9 | Ib609 |
| A1a10 | Ib609 |
| A1a11 | Ib609 |
| A1a12 | Ib609 |
| A1a13 | Ib609 |
| A1a14 | Ib609 |
| A1a1 | Ib625 |
| A1a2 | Ib625 |
| A1a3 | Ib625 |
| A1a4 | Ib625 |
| A1a5 | Ib625 |
| A1a6 | Ib625 |
| A1a7 | Ib625 |
| A1a8 | Ib625 |
| A1a9 | Ib625 |
| A1a10 | Ib625 |
| A1a11 | Ib625 |
| A1a12 | Ib625 |
| A1a13 | Ib625 |
| A1a14 | Ib625 |
| A1a1 | Ib641 |
| A1a2 | Ib641 |
| A1a3 | Ib641 |
| A1a4 | Ib641 |
| A1a5 | Ib641 |
| A1a6 | Ib641 |
| A1a7 | Ib641 |
| A1a8 | Ib641 |
| A1a9 | Ib641 |
| A1a10 | Ib641 |
| A1a11 | Ib641 |
| A1a12 | Ib641 |
| A1a13 | Ib641 |
| A1a14 | Ib641 |
| A1a1 | Ib657 |
| A1a2 | Ib657 |
| A1a3 | Ib657 |
| A1a4 | Ib657 |
| A1a5 | Ib657 |
| A1a6 | Ib657 |
| A1a7 | Ib657 |
| A1a8 | Ib657 |
| A1a9 | Ib657 |
| A1a10 | Ib657 |
| A1a11 | Ib657 |
| A1a12 | Ib657 |
| A1a13 | Ib657 |
| A1a14 | Ib657 |
| A1a1 | Ib673 |
| A1a2 | Ib673 |
| A1a3 | Ib673 |
| A1a4 | Ib673 |
| A1a5 | Ib673 |
| A1a6 | Ib673 |
| A1a7 | Ib673 |
| A1a8 | Ib673 |
| A1a9 | Ib673 |
| A1a10 | Ib673 |
| A1a11 | Ib673 |
| A1a12 | Ib673 |
| A1a13 | Ib673 |
| A1a14 | Ib673 |
| A1a1 | Ib689 |
| A1a2 | Ib689 |
| A1a3 | Ib689 |
| A1a4 | Ib689 |
| A1a5 | Ib689 |
| A1a6 | Ib689 |
| A1a7 | Ib689 |
| A1a8 | Ib689 |
| A1a9 | Ib689 |
| A1a10 | Ib689 |
| A1a11 | Ib689 |
| A1a12 | Ib689 |
| A1a13 | Ib689 |
| A1a14 | Ib689 |
| A1a1 | Ib705 |
| A1a2 | Ib705 |
| A1a3 | Ib705 |
| A1a4 | Ib705 |
| A1a5 | Ib705 |
| A1a6 | Ib705 |
| A1a7 | Ib705 |
| A1a8 | Ib705 |
| A1a9 | Ib705 |
| A1a10 | Ib705 |
| A1a11 | Ib705 |
| A1a12 | Ib705 |
| A1a13 | Ib705 |
| A1a14 | Ib705 |
| A1a1 | Ib721 |
| A1a2 | Ib721 |
| A1a3 | Ib721 |
| A1a4 | Ib721 |
| A1a5 | Ib721 |
| A1a6 | Ib721 |
| A1a7 | Ib721 |
| A1a8 | Ib721 |
| A1a9 | Ib721 |
| A1a10 | Ib721 |
| A1a11 | Ib721 |
| A1a12 | Ib721 |
| A1a13 | Ib721 |
| A1a14 | Ib721 |
| A1a1 | Ib737 |
| A1a2 | Ib737 |
| A1a3 | Ib737 |
| A1a4 | Ib737 |
| A1a5 | Ib737 |
| A1a6 | Ib737 |
| A1a7 | Ib737 |
| A1a8 | Ib737 |
| A1a9 | Ib737 |
| A1a10 | Ib737 |
| A1a11 | Ib737 |
| A1a12 | Ib737 |
| A1a13 | Ib737 |
| A1a14 | Ib737 |
| A1a1 | Ib753 |
| A1a2 | Ib753 |
| A1a3 | Ib753 |
| A1a4 | Ib753 |
| A1a5 | Ib753 |
| A1a6 | Ib753 |
| A1a7 | Ib753 |
| A1a8 | Ib753 |
| A1a9 | Ib753 |
| A1a10 | Ib753 |
| A1a11 | Ib753 |
| A1a12 | Ib753 |
| A1a13 | Ib753 |
| A1a14 | Ib753 |
| A1a1 | Ib769 |
| A1a2 | Ib417 |

TABLE D-continued

| Radical A | Ib |
|---|---|
| A1a3 | Ib769 |
| A1a4 | Ib769 |
| A1a5 | Ib769 |
| A1a6 | Ib769 |
| A1a7 | Ib769 |
| A1a8 | Ib769 |
| A1a9 | Ib769 |
| A1a10 | Ib769 |
| A1a11 | Ib769 |
| A1a12 | Ib769 |
| A1a13 | Ib769 |
| A1a14 | Ib769 |
| A1a1 | Ib785 |
| A1a2 | Ib785 |
| A1a3 | Ib785 |
| A1a4 | Ib785 |
| A1a5 | Ib785 |
| A1a6 | Ib785 |
| A1a7 | Ib785 |
| A1a8 | Ib785 |
| A1a9 | Ib785 |
| A1a10 | Ib785 |
| A1a11 | Ib785 |
| A1a12 | Ib785 |
| A1a13 | Ib785 |
| A1a14 | Ib785 |
| A1a1 | Ib801 |
| A1a2 | Ib801 |
| A1a3 | Ib801 |
| A1a4 | Ib801 |
| A1a5 | Ib801 |
| A1a6 | Ib801 |
| A1a7 | Ib801 |
| A1a8 | Ib801 |
| A1a9 | Ib801 |
| A1a10 | Ib801 |
| A1a11 | Ib801 |
| A1a12 | Ib801 |
| A1a13 | Ib801 |
| A1a14 | Ib801 |
| A1a1 | Ib817 |
| A1a2 | Ib817 |
| A1a3 | Ib817 |
| A1a4 | Ib817 |
| A1a5 | Ib817 |
| A1a6 | Ib817 |
| A1a7 | Ib817 |
| A1a8 | Ib817 |
| A1a9 | Ib817 |
| A1a10 | Ib817 |
| A1a11 | Ib817 |
| A1a12 | Ib817 |
| A1a13 | Ib817 |
| A1a14 | Ib817 |
| A1a1 | Ib833 |
| A1a2 | Ib833 |
| A1a3 | Ib833 |
| A1a4 | Ib833 |
| A1a5 | Ib833 |
| A1a6 | Ib833 |
| A1a7 | Ib833 |
| A1a8 | Ib833 |
| A1a9 | Ib833 |
| A1a10 | Ib833 |
| A1a11 | Ib833 |
| A1a12 | Ib833 |
| A1a13 | Ib833 |
| A1a14 | Ib833 |
| A1a1 | Ib849 |
| A1a2 | Ib849 |
| A1a3 | Ib849 |
| A1a4 | Ib849 |
| A1a5 | Ib849 |
| A1a6 | Ib849 |
| A1a7 | Ib849 |
| A1a8 | Ib849 |
| A1a9 | Ib849 |
| A1a10 | Ib849 |
| A1a11 | Ib849 |
| A1a12 | Ib849 |
| A1a13 | Ib849 |
| A1a14 | Ib849 |
| A1a1 | Ib865 |
| A1a2 | Ib865 |
| A1a3 | Ib865 |
| A1a4 | Ib865 |
| A1a5 | Ib865 |
| A1a6 | Ib865 |
| A1a7 | Ib865 |
| A1a8 | Ib865 |
| A1a9 | Ib865 |
| A1a10 | Ib865 |
| A1a11 | Ib865 |
| A1a12 | Ib865 |
| A1a13 | Ib865 |
| A1a14 | Ib865 |
| A1a1 | Ib881 |
| A1a2 | Ib881 |
| A1a3 | Ib881 |
| A1a4 | Ib881 |
| A1a5 | Ib881 |
| A1a6 | Ib881 |
| A1a7 | Ib881 |
| A1a8 | Ib881 |
| A1a9 | Ib881 |
| A1a10 | Ib881 |
| A1a11 | Ib881 |
| A1a12 | Ib881 |
| A1a13 | Ib881 |
| A1a14 | Ib881 |
| A1a1 | Ib897 |
| A1a2 | Ib897 |
| A1a3 | Ib897 |
| A1a4 | Ib897 |
| A1a5 | Ib897 |
| A1a6 | Ib897 |
| A1a7 | Ib897 |
| A1a8 | Ib897 |
| A1a9 | Ib897 |
| A1a10 | Ib897 |
| A1a11 | Ib897 |
| A1a12 | Ib897 |
| A1a13 | Ib897 |
| A1a14 | Ib897 |
| A1a1 | Ib913 |
| A1a2 | Ib913 |
| A1a3 | Ib913 |
| A1a4 | Ib913 |
| A1a5 | Ib913 |
| A1a6 | Ib913 |
| A1a7 | Ib913 |
| A1a8 | Ib913 |
| A1a9 | Ib913 |
| A1a10 | Ib913 |
| A1a11 | Ib913 |
| A1a12 | Ib913 |
| A1a13 | Ib913 |
| A1a14 | Ib913 |
| A1a1 | Ib929 |
| A1a2 | Ib929 |
| A1a3 | Ib929 |
| A1a4 | Ib929 |
| A1a5 | Ib929 |
| A1a6 | Ib929 |
| A1a7 | Ib929 |
| A1a8 | Ib929 |
| A1a9 | Ib929 |
| A1a10 | Ib929 |
| A1a11 | Ib929 |
| A1a12 | Ib929 |
| A1a13 | Ib929 |
| A1a14 | Ib929 |
| A1a1 | Ib945 |
| A1a2 | Ib945 |
| A1a3 | Ib945 |
| A1a4 | Ib945 |

TABLE D-continued

| Radical A | Ib |
|---|---|
| A1a5 | Ib945 |
| A1a6 | Ib945 |
| A1a7 | Ib945 |
| A1a8 | Ib945 |
| A1a9 | Ib945 |
| A1a10 | Ib945 |
| A1a11 | Ib945 |
| A1a12 | Ib945 |
| A1a13 | Ib945 |
| A1a14 | Ib945 |
| A1a1 | Ib961 |
| A1a2 | Ib961 |
| A1a3 | Ib961 |
| A1a4 | Ib961 |
| A1a5 | Ib961 |
| A1a6 | Ib961 |
| A1a7 | Ib961 |
| A1a8 | Ib961 |
| A1a9 | Ib961 |
| A1a10 | Ib961 |
| A1a11 | Ib961 |
| A1a12 | Ib961 |
| A1a13 | Ib961 |
| A1a14 | Ib961 |
| A1a1 | Ib977 |
| A1a2 | Ib977 |
| A1a3 | Ib977 |
| A1a4 | Ib977 |
| A1a5 | Ib977 |
| A1a6 | Ib977 |
| A1a7 | Ib977 |
| A1a8 | Ib977 |
| A1a9 | Ib977 |
| A1a10 | Ib977 |
| A1a11 | Ib977 |
| A1a12 | Ib977 |
| A1a13 | Ib977 |
| A1a14 | Ib977 |
| A1a1 | Ib993 |
| A1a2 | Ib993 |
| A1a3 | Ib993 |
| A1a4 | Ib993 |
| A1a5 | Ib993 |
| A1a6 | Ib993 |
| A1a7 | Ib993 |
| A1a8 | Ib993 |
| A1a9 | Ib993 |
| A1a10 | Ib993 |
| A1a11 | Ib993 |
| A1a12 | Ib993 |
| A1a13 | Ib993 |
| A1a14 | Ib993 |
| A1a1 | Ib1009 |
| A1a2 | Ib1009 |
| A1a3 | Ib1009 |
| A1a4 | Ib1009 |
| A1a5 | Ib1009 |
| A1a6 | Ib1009 |
| A1a7 | Ib1009 |
| A1a8 | Ib1009 |
| A1a9 | Ib1009 |
| A1a10 | Ib1009 |
| A1a11 | Ib1009 |
| A1a12 | Ib1009 |
| A1a13 | Ib1009 |
| A1a14 | Ib1009 |
| A1a1 | Ib1025 |
| A1a2 | Ib1025 |
| A1a3 | Ib1025 |
| A1a4 | Ib1025 |
| A1a5 | Ib1025 |
| A1a6 | Ib1025 |
| A1a7 | Ib1025 |
| A1a8 | Ib1025 |
| A1a9 | Ib1025 |
| A1a10 | Ib1025 |
| A1a11 | Ib1025 |
| A1a12 | Ib1025 |
| A1a13 | Ib1025 |
| A1a14 | Ib1025 |
| A1a1 | Ib1041 |
| A1a2 | Ib1041 |
| A1a3 | Ib1041 |
| A1a4 | Ib1041 |
| A1a5 | Ib1041 |
| A1a6 | Ib1041 |
| A1a7 | Ib1041 |
| A1a8 | Ib1041 |
| A1a9 | Ib1041 |
| A1a10 | Ib1041 |
| A1a11 | Ib1041 |
| A1a12 | Ib1041 |
| A1a13 | Ib1041 |
| A1a14 | Ib1041 |
| A1a1 | Ib1057 |
| A1a2 | Ib1057 |
| A1a3 | Ib1057 |
| A1a4 | Ib1057 |
| A1a5 | Ib1057 |
| A1a6 | Ib1057 |
| A1a7 | Ib1057 |
| A1a8 | Ib1057 |
| A1a9 | Ib1057 |
| A1a10 | Ib1057 |
| A1a11 | Ib1057 |
| A1a12 | Ib1057 |
| A1a13 | Ib1057 |
| A1a14 | Ib1057 |
| A1a1 | Ib1073 |
| A1a2 | Ib1073 |
| A1a3 | Ib1073 |
| A1a4 | Ib1073 |
| A1a5 | Ib1073 |
| A1a6 | Ib1073 |
| A1a7 | Ib1073 |
| A1a8 | Ib1073 |
| A1a9 | Ib1073 |
| A1a10 | Ib1073 |
| A1a11 | Ib1073 |
| A1a12 | Ib1073 |
| A1a13 | Ib1073 |
| A1a14 | Ib1073 |
| A1a1 | Ib1089 |
| A1a2 | Ib1089 |
| A1a3 | Ib1089 |
| A1a4 | Ib1089 |
| A1a5 | Ib1089 |
| A1a6 | Ib1089 |
| A1a7 | Ib1089 |
| A1a8 | Ib1089 |
| A1a9 | Ib1089 |
| A1a10 | Ib1089 |
| A1a11 | Ib1089 |
| A1a12 | Ib1089 |
| A1a13 | Ib1089 |
| A1a14 | Ib1089 |
| A1a1 | Ib1105 |
| A1a2 | Ib1105 |
| A1a3 | Ib1105 |
| A1a4 | Ib1105 |
| A1a5 | Ib1105 |
| A1a6 | Ib1105 |
| A1a7 | Ib1105 |
| A1a8 | Ib1105 |
| A1a9 | Ib1105 |
| A1a10 | Ib1105 |
| A1a11 | Ib1105 |
| A1a12 | Ib1105 |
| A1a13 | Ib1105 |
| A1a14 | Ib1105 |
| A1a1 | Ib1121 |
| A1a2 | Ib1121 |
| A1a3 | Ib1121 |
| A1a4 | Ib1121 |
| A1a5 | Ib1121 |
| A1a6 | Ib1121 |

TABLE D-continued

| Radical A | Ib |
|---|---|
| A1a7 | Ib1121 |
| A1a8 | Ib1121 |
| A1a9 | Ib1121 |
| A1a10 | Ib1121 |
| A1a11 | Ib1121 |
| A1a12 | Ib1121 |
| A1a13 | Ib1121 |
| A1a14 | Ib1121 |
| A1a1 | Ib1137 |
| A1a2 | Ib1137 |
| A1a3 | Ib1137 |
| A1a4 | Ib1137 |
| A1a5 | Ib1137 |
| A1a6 | Ib1137 |
| A1a7 | Ib1137 |
| A1a8 | Ib1137 |
| A1a9 | Ib1137 |
| A1a10 | Ib1137 |
| A1a11 | Ib1137 |
| A1a12 | Ib1137 |
| A1a13 | Ib1137 |
| A1a14 | Ib1137 |
| A1a1 | Ib1153 |
| A1a2 | Ib1153 |
| A1a3 | Ib1153 |
| A1a4 | Ib1153 |
| A1a5 | Ib1153 |
| A1a6 | Ib1153 |
| A1a7 | Ib1153 |
| A1a8 | Ib1153 |
| A1a9 | Ib1153 |
| A1a10 | Ib1153 |
| A1a11 | Ib1153 |
| A1a12 | Ib1153 |
| A1a13 | Ib1153 |
| A1a14 | Ib1153 |

Compounds of formula I can be prepared according to the following methods and variations described in schemes 1-5. The variables $R^1$, $R^2$, $R^3$, $R^4$, $R^{5a}$, $R^{5b}$, $R^{5c}$, $R^{5d}$, $A^1$, $A^2$, $A^3$, $A^4$, and p are defined as above for formula I.

Compounds of formula I can, for example, be prepared by reaction of amines (or salts thereof) and quinazolines of the formula 4 as described by, for example, Ananthan et al, Bioorg. Med. Chem. Lett. 2002, 12, 2225 and outlined in Scheme 1. Depending on the conditions, bases such as triethylamine or potassium carbonate may be necessary. The reaction can be run in a wide variety of solvents including Tetrahydrofuran (THF), dioxane, and isopropanol or the like. The corresponding quinazolines of the formula 4 containing a leaving group (LG) wherein LG is a fluorine, chlorine, bromine, iodine, thioethers, sulfonates or another suitable leaving group can be prepared from quinazolinones of the formula 3 for example by reaction with a halogenating agent such as phosphorus oxychloride, phosphorus trichloride, phosphorus pentachloride, thionyl chloride, phosphorus tribromide, phosphorus triiodide as described, for example, by Hayakawa, Bioorg. Med. Chem. 2006, 14, 6847. Depending on the conditions solvents such as dioxane, ether, toluene, DMF or the like can be employed. Quinazolinones of the formula 3 can be prepared from anthranilamides of formula 1 and aldehydes of formula 2 in the presence of reagents such as iron chloride (or hydrates thereof), iodine, sodium bisulfite or 2,3-dichloro-4,5-dicyano-1,4-benzoquinone as described, for example, by Wang et al, Bull. Chem. Soc. Jpn. 2006, 79, 1426.

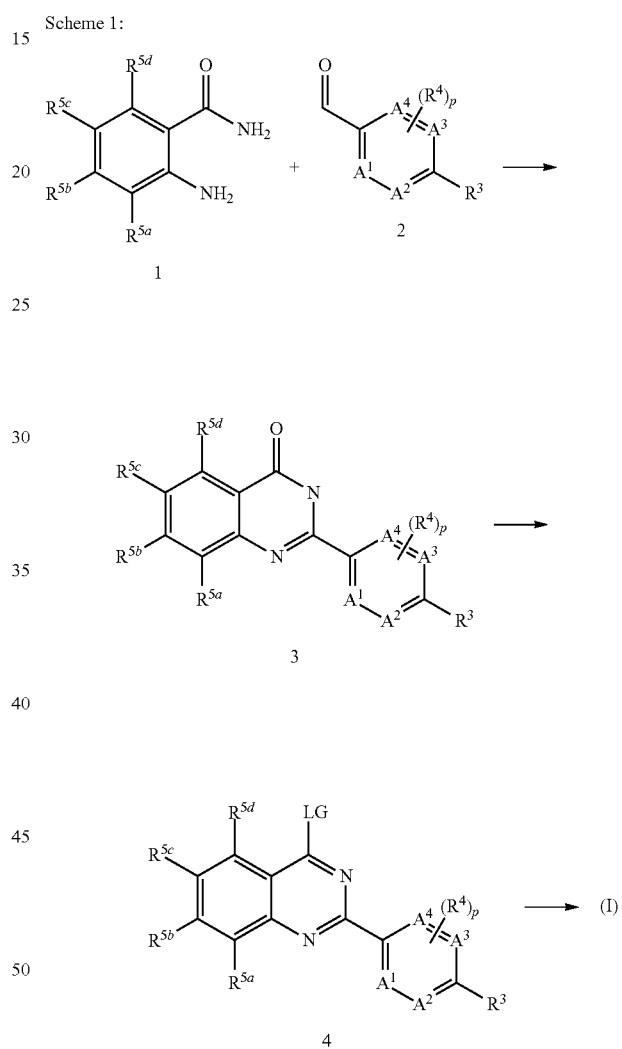

Scheme 1:

Quinazolinones of the formula 3 can also be prepared as outlined in Scheme 2 from arylhalides of the formula 7 and amidines of the formula 8 under copper catalysis as described, for example, by Liu, Angew. Chem. Int. Ed. 2009, 48, 348. Alternatively, quinazolinones of the formula 3 can be prepared from anilines 5 and nitriles 6 under acidic conditions (e.g. hydrochloric acid) as described, for example, by Bogolubsky et al, J. Comb. Chem. 2008, 10, 858 for from amides of the formula 9 under basic conditions (e.g. sodium hydroxide) as described, for example, by Roy et al, J. Org. Chem. 2006, 71, 382.

Scheme 2:

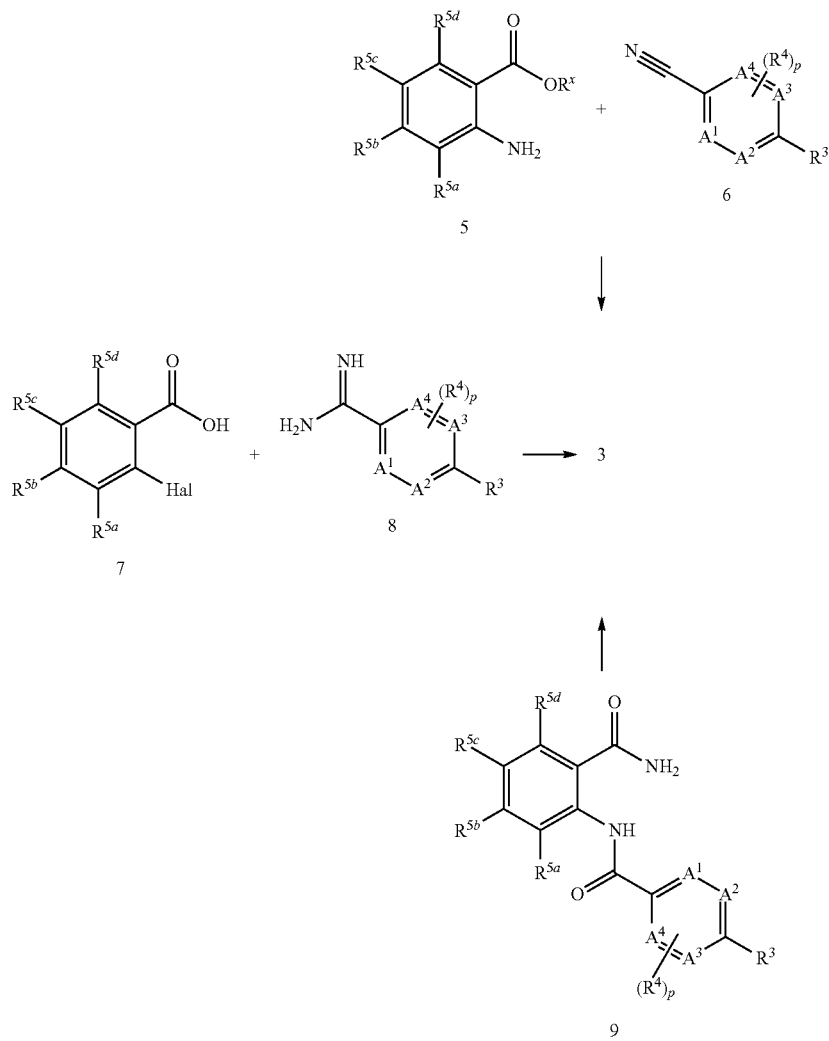

Aminoquinazolines of the formula (I) can be prepared as outlined in Scheme 3 by a coupling reaction between intermediates of the formula 13 and intermediates of the formula 14 in the presence of metal catalyst derived from, for example, palladium, platinum, iron, copper or nickel where LG or Y are, for example, a fluorine, chlorine, bromine, iodine, triflate, thioether, boronic acid, boronate ester, trifluoroborate, or ganoborane or organostannane or other suitable leaving group, A phosphine-, amine-, sulfoxide-derived ligand and base such as potassium carbonate or triethylemine may also be required for the reaction as described, for example, by Itoh et al, Adv. Syn. Cat. 2004, 346, 1859. Intermediate of the formula 13 can be prepared from dichloroquinazoline of the formula 12 where LG is an analogous leaving group as described above. In turn the corresponding quinazolines of the formula 12 can be prepared from quinazoline-2,4-diones of the formula 11 using a similar method to that used to prepare intermediates of the formula 4. Quinazoline-2,4-diones of the formula 11 can be prepared from anthranilic acids of the formula 10 using reagents such as urea, isocyanate, thioisocyanate as described, for example, by Smits et al, J. Med. Chem. 2008, 7855.

Scheme 3:

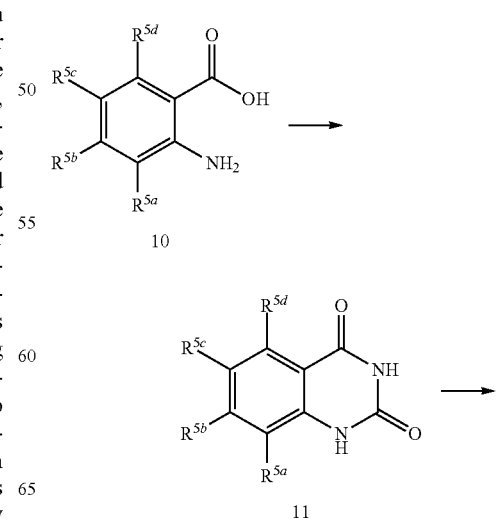

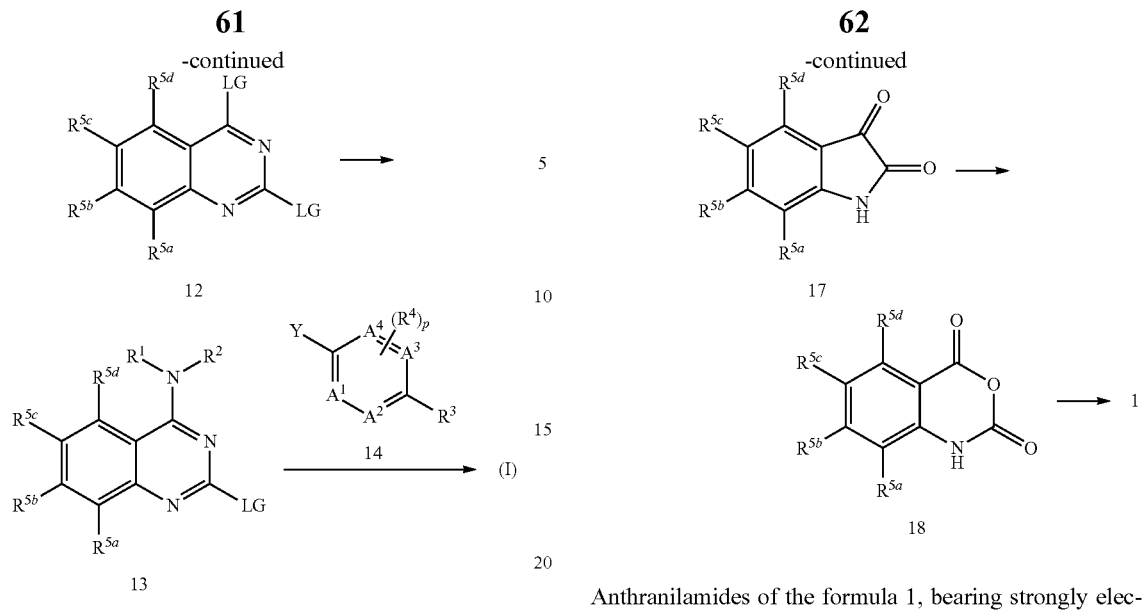

Anthranilamides of the formula 1 can be prepared following an analogous route as that described in Scheme 4 [T. Sandmeyer, Helv. Chinn. Acta 1919, 2, 234 or S. J. Garden et al, Tetrahedron Lett. 1997, 38(9), 1501] starting from isatoic anhydrides of the formula 18 in one step using a reagent such as ammonia or in two steps using an amine-based nucleophile such an benzylamine, hydroxylamine or azide followed by reduction with, for example, hydrogen or ammonium formate as described, for example by Klaubert et al, J. Med. Chem. 1981, 24, 742 and Singh et at J. Heterocyclic Chem. 1990, 27, 2101. Isatoic anhydrides of the formula 18 can be synthesized from indole-2,3-diones of the formula 17 by oxidation with e.g. meta-chloroperbenzoic acid [G. M. Coppola, J. Heterocyclic Chem. 1987, 24, 1249], hydrogen peroxide or chromic acid in a solvent such as dichloromethane, acetic acid or water. In turn indole-2,3-diones of the formula 17 can be prepared in a Friedel-Crafts-type reaction from isonitrosoacetanilides of the formula 16 using a protic or Lewis acid such as sulfuric acid or aluminium trichloride. Finally isonitrosoacetanilides of the formula 16 can be prepared from substituted anilines of the formula 15 using chloral and hydroxylamine as reagents.

Scheme 4:

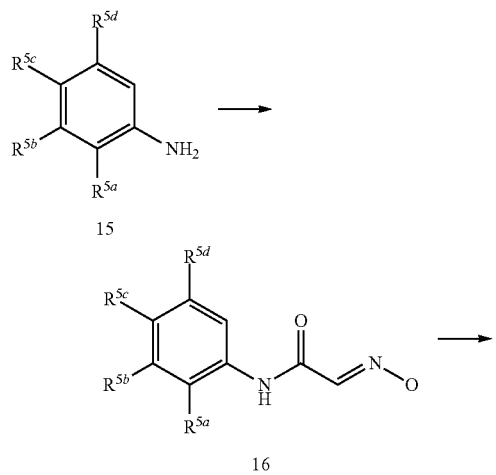

Anthranilamides of the formula 1, bearing strongly electron withdrawing substituents on the phenyl ring, are accessible through corresponding indole-2,3-diones of the formula 17 which in turn can be prepared following a route as that described by P. Hewawasam et al, Tetrahedron Lett. 1994, 35, 7303 and which is outlined in Scheme 5. Indole-2,3-diones of the formula 17 can be prepared by treatment of oxoacetic acid esters of the formula 20 with acids such as hydrochloric acid, trifluoroacetic acid, and triflic acid in solvents such as THF, water or $CH_2Cl_2$ as described, for example, by Hamashima et al., J. Am. Chem. Soc. 2005, 127, 10154. In turn oxoacetic acid esters of the formula 20, $R^x$ being for example ethyl, methyl, can be prepared by exposure of carbamates of the formula 19 to strong carbon bases such as n-, sec-, or t-BuLi followed by reaction of the resultant carbanion with oxoacetic acid diesters. Finally carbamates of the formula 19 can be prepared from anilines of the formula 15 by reaction with di-t-butyldicarbonate.

Scheme 5:

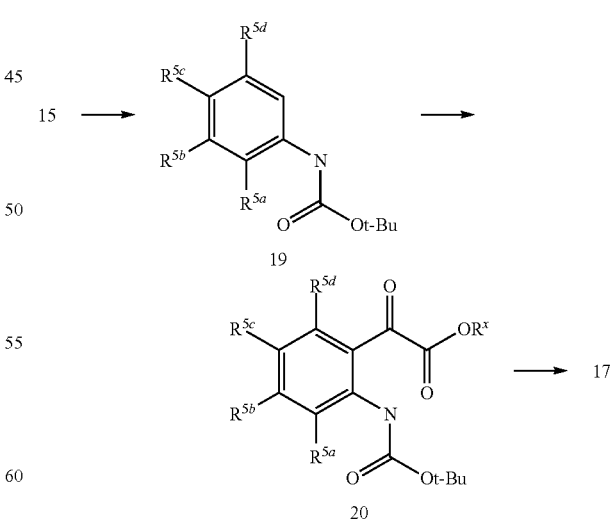

If individual compounds cannot be prepared via the above-described routes, they can be prepared by derivatization of other compounds I or by customary modifications of the synthesis routes described.

The reaction mixtures are worked up in the customary manner, for example by mixing with water, separating the phases, and, if appropriate, purifying the crude products by chromatography, for example on alumina or silica gel. Some of the intermediates and end products may be obtained in the form of colorless or pale brown viscous oils, which are freed or purified from volatile components under reduced pressure and at moderately elevated temperature. If the intermediates and end products are obtained as solids, they may be purified by recrystallization or digestion.

The present invention also provides a method for controlling invertebrate pests which method comprises treating the pests, their food supply, their habitat or their breeding ground or a cultivated plant, plant propagation materials (such as seed), soil, area, material or environment in which the pests are growing or may grow, or the materials, cultivated plants, plant propagation materials (such as seed), soils, surfaces or spaces to be protected from pest attack or infestation with a pesticidally effective amount of a compound of formula I or a salt or N-oxide thereof or a composition as defined above.

Preferably, the method of the invention serves for protecting plant propagation material (such as seed) and the plant which grows therefrom from invertebrate pest attack or infestation and comprises treating the plant propagation material (such as seed) with a pesticidally effective amount of a compound of formula I or an agriculturally acceptable salt or N-oxide thereof as defined above or with a pesticidally effective amount of an agricultural composition as defined above and below. The method of the invention is not limited to the protection of the "substrate" (plant, plant propagation materials, soil material etc.) which has been treated according to the invention, but also has a preventive effect, thus, for example, according protection to a plant which grows from a treated plant propagation materials (such as seed), the plant itself not having been treated.

In the sense of the present invention, "invertebrate pests" are preferably selected from arthropods and nematodes, more preferably from harmful insects, arachnids and nematodes, and even more preferably from insects, acarids and nematodes. In the sense of the present invention, "invertebrate pests" are most preferably insects.

The invention further provides an agricultural composition for combating such invertebrate pests, which comprises such an amount of at least one compound of the general formula I or at least one agriculturally useful salt or N-oxide thereof and at least one inert liquid and/or solid agronomically acceptable carrier that has a pesticidal action and, if desired, at least one surfactant.

Such a composition may contain a single active compound of the formula I or a salt or N-oxide thereof or a mixture of several active compounds I or their salts according to the present invention. The composition according to the present invention may comprise an individual isomer or mixtures of isomers as well as individual tautomers or mixtures of tautomers.

The compounds of the formula I and the pesticidal compositions comprising them are effective agents for controlling arthropod pests and nematodes. Invertebrate pests controlled by the compounds of formula I include for example insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Chematobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusiani* and *Zeiraphera canadensis;* beetles (Coleoptera), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufi-manus, Bruchus pisorum, Bruchus lentis, Byctiscus betulae, Cassida nebulosa, Cero-toma trifurcata, Ceuthorrhynchus assimilis, Ceuthorrhynchus napi, Chaetocnema tibi-alis, Conoderus vespertinus, Crioceris asparagi, Diabrotica longicornis, Diabrotica 12 punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhyn-chus ovatus, Phaedon cochleariae, Phyllotreta chrysocephala, Phyllophaga sp., Phyl-lopertha horticola, Phyllotreta nemorum, Phyllotreta striolata, Popillia japonica, Sitona lineatus* and *Sitophilus granaria;* dipterans (Diptera), for example *Aedes aegypti, Aedes vexans, Anastrepha ludens, Anopheles maculipennis, Ceratitis capitata, Chrysomya bezziana, Chrysomya homi-nivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destruc-tor, Musca domestica, Muscina stabulans, Oestrus ovis, Oscinella frit, Pegomya hyso-cyami, Phorbia antiqua, Phorbia brassicae, Phorbia coarctata, Rhagoletis cerasi, Rhagoletis pomonella, Tabanus bovinus, Tipula oleracea* and *Tipula paludosa;* thrips (Thysanoptera), e.g. *Dichromothrips corbetti, Frankliniella fusca, Frankliniella occidentalis, Frankliniella tritici, Scirtothrips citri, Thrips oryzae, Thrips palmi* and *Thrips tabaci;* hymenopterans (Hymenoptera), e.g. *Athalia rosae, Atta cephalotes, Atta sexdens, Atta texana, Hoplocampa minuta, Hoplocampa testudinea, Monomorium pharaonis, So-lenopsis geminata* and *Solenopsis invicta;* heteropterans (Heteroptera), e.g. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris,*

*Lygus pratensis, Nezara viridula, Piesma quadrata, Solubea insularis* and *Thyanta perditor;* homopterans (Homoptera), e.g. *Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Bemisia tabaci, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus persicae, Myzus varians, Nasonovia ribis-nigri, Nilaparvata lugens, Pemphigus bursarius, Perkinsiella saccharicida, Phorodon humuli, Psylla mali, Psylla pini, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Sogatella furcifera Trialeurodes vaporariorum, Toxoptera aurantiiand,* and *Viteus vitifolii;* termites (Isoptera), e.g. *Calotermes flavicollis, Leucotermes flavipes, Reticulitermes flavipes, Reticulitermes lucifugus* and *Termes natalensis;* orthopterans (Orthoptera), e.g. *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melano-plus spretus, Nomadacris septemfasciata, Periplaneta americana, Schistocerca americana, Schistocerca peregrina, Stauronotus maroccanus* and *Tachycines asynamorus;* arachnoidea, such as arachnids (Acarina), e.g. of the families Argasidae, Ixodidae and Sarcoptidae, such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei,* and *Eriophyidae* spp. such as *Aculus schlechtendali, Phyllocoptrata oleivora* and *Eriophyes sheldoni; Tarsonemidae* spp. such as *Phytonemus pallidus* and *Polyphagotarsonemus latus; Tenuipalpidae* spp. such as *Brevipalpus phoenicis; Tetranychidae* spp. such as *Tetranychus cinnabarinus, Tetranychus kanzawai, Tetranychus pacificus, Tetranychus telarius* and *Tetranychus urticae, Panonychus ulmi, Panonychus citri,* and *oligonychus pratensis;* siphonatera, e.g. *Xenopsylla cheopsis, Ceratophyllus* spp.

The compositions and compounds of formula I are useful for the control of nematodes, especially plant parasitic nematodes such as root knot nematodes, *Meloidogyne hapla, Meloidogyne incognita, Meloidogyne javanica,* and other *Meloidogyne* species;

cyst-forming nematodes, *Globodera rostochiensis* and other *Globodera* species; *Het-erodera avenae, Heterodera glycines, Heterodera schachtii, Heterodera trifolii,* and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nema-todes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Paratylen-chus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species.

In a preferred embodiment of the invention the compounds of formula I are used for controlling insects or arachnids, in particular insects of the orders Lepidoptera, Coleoptera, Thysanoptera and Homoptera and arachnids of the order Acarina. The compounds of the formula I according to the present invention are particularly useful for controlling insects of the order Thysanoptera and Homoptera.

The compounds of formula I or the pesticidal compositions comprising them may be used to protect growing plants and crops from attack or infestation by invertebrate pests, especially insects, acaridae or arachnids by contacting the plant/crop with a pesticidally effective amount of compounds of formula I. The term "crop" refers both to growing and harvested crops.

The compounds of formula I can be converted into the customary formulations, for example solutions, emulsions, suspensions, dusts, powders, pastes and granules. The use form depends on the particular intended purpose; in each case, it should ensure a fine and even distribution of the compound according to the invention.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and of seq. WO 91/13546, U.S. Pat. Nos. 4,172,714, 4,144,050, 3,920,442, 5,180,587, 5,232,701, 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubermann, A., Formulation tech-nology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, anti-freezing agents, for seed treatment formulation also optionally colorants and/or binders and/or gelling agents.

Examples of suitable solvents are water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (N-methylpyrrolidone [NMP], N-octylpyrrolidone [NOP]), acetates (glycol diacetate), glycols, fatty acid dimethylamides, fatty acids and fatty acid esters. In principle, solvent mixtures may also be used.

Suitable emulsifiers are non-ionic and anionic emulsifiers (for example polyoxyethylene fatty alcohol ethers, alkylsulfonates and arylsulfonates).

Examples of dispersants are lignin-sulfite waste liquors and methylcellulose.

Suitable surfactants used are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulphates, alkylsulfonates, fatty alcohol sulfates, fatty acids and sulphated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, tristearylphenyl polyglycol ether, alkylaryl polyether alcohols, alcohol and fatty alcohol ethylene, oxide condensates, ethoxylated castor oil, polyoxyethylene alkyl ethers, ethoxylated polyoxypropyl-ene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, etha-nol, propanol, butanol, cyclohexanol, cyclohexanone, isophorone, highly polar solvents, for example dimethyl sulfoxide, N-methylpyrrolidone or water.

Also anti-freezing agents such as glycerin, ethylene glycol, propylene glycol and bactericides such as can be added to the formulation.

Suitable antiforming agents are for example antiforming agents based on silicon or magnesium stearate.

A suitable preservative is e.g. dichlorophen.

Seed treatment formulations may additionally comprise binders and optionally color-ants.

Binders can be added to improve the adhesion of the active materials on the seeds after treatment. Suitable binders are block copolymers EO/PO surfactants but also polyvinylalcoholsl, polyvinylpyrrolidones, polyacrylates, polymethacrylates, polybute-nes, polyisobutylenes, polystyrene, polyethyleneamines, polyethyleneamides, poly-ethyleneimines (Lupasol®, Polymin®), polyethers, polyurethans, polyvinylacetate, ty-lose and copolymers derived from these polymers.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

An example of a gelling agent is carrageen (Satiagel®).

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers.

Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compound(s). In this case, the active compound(s) are employed in a purity of from 90% to 100 by weight, preferably 95% to 100% % by weight (according to NMR spectrum).

For seed treatment purposes, respective formulations can be diluted 2- to 10-fold leading to concentrations in the ready to use preparations of 0.01 to 60% by weight active compound by weight, preferably 0.1 to 40% by weight.

The compounds of formula I can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compound(s) according to the invention.

Aqueous use forms can be prepared from emulsion concentrates, pastes or wetable powders (sprayable powders, oil dispersions) by adding water. To prepare emulsions, pastes or oil dispersions, the substances, as such or dissolved in an oil or solvent, can be homogenized in water by means of a wetting agent, tackifier, dispersant or emulsifier. However, it is also possible to prepare concentrates composed of active substance, wetting agent, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to %10, preferably from 0.01 to 1% per weight.

The active compound(s) may also be used successfully in the ultra-low-volume process (ULV), it being possible to apply formulations comprising over 95% by weight of active compound, or even to apply the active compound without additives.

The following are examples of formulations:
1. Products for dilution with water for foliar applications. For seed treatment purposes, such products may be applied to the seed diluted or undiluted.
   A) Water-soluble concentrates (SL, LS)
   10 parts by weight of the active compound(s) are dissolved in 90 parts by weight of water or a water-soluble solvent, As an alternative, wetting agents or other auxiliaries are added.

The active compound(s) dissolves upon dilution with water, whereby a formula-tion with 10% (w/w) of active compound(s) is obtained.

B) Dispersible concentrates (DC)

20 parts by weight of the active compound(s) are dissolved in 70 parts by weight of cyclohexanone with addition of 10 parts by weight of a dispersant, for example polyvi-nylpyrrolidone. Dilution with water gives a dispersion, whereby a formulation with 20% (w/w) of active compound(s) is obtained.

C) Emulsifiable concentrates (EC)

15 parts by weight of the active compound(s) are dissolved in 7 parts by weight of xy-lene with addition of calcium dodecylbenzenesulfonate and castor oil ethoxylate (in each case 5 parts by weight). Dilution with water gives an emulsion, whereby a formulation with 15% (w/w) of active compound(s) is obtained.

D) Emulsions (EW, EO, ES)

25 parts by weight of the active compound(s) are dissolved in 35 parts by weight of xylene with addition of calcium dodecylbenzenesulfonate and castor oil ethoxylate (in each case 5 parts by weight). This mixture is introduced into 30 parts by weight of wa-ter by means of an emulsifier machine (e.g. Ultraturrax) and made into a homogeneous emulsion. Dilution with water gives an emulsion, whereby a formulation with 25% (w/w) of active compound(s) is obtained.

E) Suspensions (SC, OD, FS)

In an agitated ball mill, 20 parts by weight of the active compound(s) are comminuted with addition of 10 parts by weight of dispersants, wetting agents and 70 parts by weight of water or of an organic solvent to give a fine active compound(s) suspension. Dilution with water gives a stable suspension of the active compound(s), whereby a formulation with 20% (w/w) of active compound(s) is obtained.

F) Water-dispersible granules and water-soluble granules (WG, SG)

50 parts by weight of the active compound(s) are ground finely with addition of 50 parts by weight of dispersants and wetting agents and made as water-dispersible or water-soluble granules by means of technical appliances (for example extrusion, spray tower, fluidized bed). Dilution with water gives a stable dispersion or solution of the active compound(s), whereby a formulation with 50% (w/w) of active compound(s) is obtained.

G) Water-dispersible powders and water-soluble powders (WP, SP, SS, WS)

75 parts by weight of the active compound(s) are ground in a rotor-stator mill with addition of 25 parts by weight of dispersants, wetting agents and silica gel. Dilution with water gives a stable dispersion or solution of the active compound(s), whereby a formulation with 75% (w/w) of active compound(s) is obtained.

H) Gel-Formulation (GF)

In an agitated ball mill, 20 parts by weight of the active compound(s) are comminuted with addition of 10 parts by weight of dispersants, 1 part by weight of a gelling agent wetting agents and 70 parts by weight of water or of an organic solvent to give a fine active compound(s) suspension. Dilution with water gives a stable suspension of the active compound(s), whereby a formulation with 20% (w/w) of active compound(s) is obtained.

2. Products to be applied undiluted for foliar applications. For seed treatment purposes, such products may be applied to the seed diluted or undiluted.

I) Dustable powders (DP, DS)

5 parts by weight of the active compound(s) are ground finely and mixed intimately with 95 parts by weight of finely divided kaolin. This gives a dustable product having 5% (w/w) of active compound(s)

J) Granules (GR, FG, GG, MG)

0.5 parts by weight of the active compound(s) is ground finely and associated with 95.5 parts by weight of carriers, whereby a formulation with 0.5% (w/w) of active compound(s) is obtained. Current methods are extrusion, spray-drying or the fluidized bed. This gives granules to be applied undiluted for foliar use.

K) ULV solutions (UL)

10 parts by weight of the active compound(s) are dissolved in 90 parts by weight of an organic solvent, for example xylene. This gives a product having 10% (w/w) of active compound(s), which is applied undiluted for foliar use.

The compounds of formula I are also suitable for the treatment of plant propagation materials (such as seed). Conventional seed treatment formulations include for example flowable concentrates FS, solutions LS, powders for dry treatment DS, water dispersible'powders for slurry treatment WS, water-soluble powders SS and emulsion ES and EC and gel formulation GF. These formulations can be applied to the seed diluted or undiluted. Application to the seeds is carried out before sowing, either directly on the seeds or after having pre-germinated the latter In a preferred embodiment a FS formulation is used for seed treatment. Typically, a FS formulation may comprise 1 to 800 g/l of active ingredient, 1 to 200 g/l surfactant, 0 to 200 g/l antifreezing agent, 0 to 400 g/l of binder, 0 to 200 g/l of a pigment and up to 1 liter of a solvent, preferably water.

Other preferred FS formulations of compounds of formula I for seed treatment comprise from 0.5 to 80 wt of the active ingredient, from 0.05 to 5 wt of a wetting agent, from 0.5 to 15 wt of a dispersing agent, from 0.1 to 5 wt of a thickener, from 5 to 20 wt of an anti-freeze agent, from 0.1 to 2 wt of an anti-foam agent, from 1 to 20 wt of a pigment and/or a dye, from 0 to 15 wt of a sticker/adhesion agent, from 0 to 75 wt of a filler/vehicle, and from 0.01 to 1 wt of a preservative.

Various types of oils, wetting agents, adjuvants, herbicides, fungicides, other pesticides, or bactericides may be added to the active ingredients, if appropriate just immediately prior to use (tank mix). These agents usually are admixed with the agents according to the invention in a weight ratio of 1:10 to 10:1.

The compounds of formula I are effective through both contact (via soil, glass, wall, bed net, carpet, plant parts or animal parts), and ingestion (bait, or plant part).

For use against ants, termites, wasps, flies, mosquitoes, crickets, or cockroaches, com-pounds of formula I are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spraying devices, droplet sources, or evaporation sources. Gels can be based on aqueous or oily matrices and can be formulated to particular necessities in terms of stickiness, moisture retention or aging characteristics.

The bait employed in the composition is a product, which is sufficiently attractive to incite insects such as ants, termites, wasps, flies, mosquitoes, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

Formulations of compounds of formula I as aerosols (e.g. in spray cans), oil sprays or pump sprays are highly suitable for the non-professional user for controlling pests such as flies, fleas, ticks, mosquitos or cockroaches. Aerosol recipes are preferably corn-posed of the active compound, solvents such as lower alcohols (e.g. methanol, ethanol, propanol, butanol), ketones (e.g. acetone, methyl ethyl ketone), paraffin hydrocar-bons (e.g. kerosenes) having boiling ranges of approximately 50 to 250° C., dimethyl-formamide, N-methylpyrrolidone, dimethyl sulphoxide, aromatic hydrocarbons such as toluene, xylene, water, furthermore auxiliaries such as emulsifiers such as sorbitol monooleate, oleyl ethoxylate having 3 to 7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, am-photeric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

The compounds of formula I and their respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of formula I and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, non-wovens, netting material or foils and tarpaulins preferably comprise a mixture including the insecticide, optionally a repellent and at least one binder. Suitable repellents for example are N,N-diethyl-meta-toluamide (DEET), N,N-diethylphenylacetamide (DEPA), 1-(3-cyclohexan-1-yl-carbonyl)-2-methylpiperine, (2-hydroxymethyl-cyclohexyl)acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant extracts like limonene, eugenol, (+)-Eucamalol (1), (−)-1-epi-eucamalol or crude plant extracts from plants like Eucalyptus maculata, Vitex rotundifolia, Cymbopogan martinii, Cymbopogan citratus (lemon grass), Cymopogan nartdus (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and diethylenically unsaturated hydrocarbons, such as styrene, and aliphatic diens, such as butadiene.

The impregnation of curtains and bednets is done in general by dipping the textile ma-terial into emulsions or dispersions of the active compounds of formula I or spraying them onto the nets.

Methods which can be employed for treating the seed are, in principle, all suitable seed treatment and especially seed dressing techniques known in the art, such as seed coating (e.g. seed pelleting), seed dusting and seed imbibition (e.g. seed soaking). Here, "seed treatment" refers to all methods that bring seeds and the compounds of formula I into contact with each other, and "seed dressing" to methods of seed treatment which provide the seeds with an amount of the compounds of formula I, i.e. which generate a seed comprising the compound of formula I. In principle, the treatment can be applied to the seed at any time from the harvest of the seed to the sowing of the seed. The seed can be treated immediately before, or during, the planting of the seed, for example using the "planter's box" method. However, the treatment may also be carried out several weeks or months, for example up to 12 months, before planting the seed, for example in the form of a seed dressing treatment, without a substantially reduced efficacy being observed.

Expediently, the treatment is applied to unsown seed. As used herein, the term "unsown seed" is meant to include seed at any period from the harvest of the seed to the sowing of the seed in the ground for the purpose of germination and growth of the plant.

Specifically, a procedure is followed in the treatment in which the seed is mixed, in a suitable device, for example a mixing device for solid or solid/liquid mixing partners, with the desired amount of seed treatment formulations, either as such or after previ-ous dilution with water, until the composition is distributed uniformly on the seed. If ap-propriate, this is followed by a drying step.

The compounds of formula I, or the enantiomers, diastereomers or veterinarily acceptable salts thereof are in particular also suitable for being used for combating parasites in and on animals.

An object of the present invention is therefore also to provide new methods to control parasites in and on animals. Another object of the invention is to provide safer pesticides for animals. Another object of the invention is further to provide pesticides for animals that may be used in lower doses than existing pesticides. And another object of the invention is to provide pesticides for animals, which provide a long residual control of the parasites.

The invention also relates to compositions containing a parasiticidally effective amount of compounds of formula I or the enantiomers or veterinarily acceptable salts thereof and an acceptable carrier, for combating parasites in and on animals.

The present invention also provides a method for treating, controlling, preventing and protecting animals against infestation and infection by parasites, which comprises orally, topically or parenterally administering or applying to the animals a parasiticidally effective amount of a compound of formula I or the enantiomers or veterinarily acceptable salts thereof or a composition comprising it.

The present invention also provides a non-therapeutic method for treating, controlling, preventing and protecting animals against infestation and infection by parasites, which comprises applying to a locus a parasiticidally effective amount of a compound of formula I or the enantiomers or veterinarily acceptable salts thereof or a composition comprising it. The invention also provides a process for the preparation of a composition for treating, controlling, preventing or protecting animals against infestation or infection by parasites which comprises including a parasiticidally effective amount of a compound of formula I or the enantiomers or veterinarily acceptable salts thereof in a composition comprising it.

The invention relates further to the use of compounds of formula I for treating, controlling, preventing or protecting animals against infestation or infection by parasites.

The invention relates also to the use of a compound of formula I, or a composition comprising it, for the manufacture of a medicament for the therapeutic treatment of animals against infections or infestations by parasites.

Activity of compounds against agricultural pests does not suggest their suitability for control of endo- and ectoparasites in and on animals which requires, for example, low, non-emetic dosages in the case of oral application, metabolic compatibility with the animal, low toxicity, and a safe handling.

Surprisingly it has now been found that compounds of formula I are suitable for combating endo- and ectoparasites in and on animals. The compounds of formula I or the enantiomers or veterinarily acceptable salts thereof and compositions comprising them are suitable for systemic and/or non-systemic control of ecto- and/or endoparasites. They are active against all or some stages of development.

Compounds of formula I or the enantiomers or veterinarily acceptable salts thereof and compositions comprising them are preferably used for controlling and preventing infestations and infections animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels.

Compounds of formula I or the enantiomers or veterinarily acceptable salts thereof and compositions comprising them are preferably used for controlling and preventing infestations and infections in domestic animals, such as dogs or cats.

Infestations in warm-blooded animals and fish include, but are not limited to lice, biting lice, ticks, nasal bots, keds, biting flies, muscoid flies, flies, myiasitic fly larvae, chiggers, gnats, mosquitoes and fleas.

The compounds of formula I are especially useful for combating ectoparasites.

The compounds of formula I are especially useful for combating endoparasites.

The compounds of formula I are especially useful for combating parasites of the following orders and species, respectively:

fleas (Siphonaptera), e.g. *Ctenocephalides felis, Ctenocephalides canis, Xenopsylla cheopis, Pulex irritans, Tunga penetrans,* and *Nosopsyllus fasciatus,* cockroaches (Blattaria-Blattodea), e.g. *Blattella germanica, Blattella asahinae, Periplaneta americana, Periplaneta japonica, Periplaneta brunnea, Periplaneta fuligginosa, Periplaneta australasiae,* and *Blatta orientalis,* flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinque fasciatus, Culex tarsalis, Culiseta inornata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma lineata, Leptoconops torrens, Lucilia caprina, Lucilia cuprina, Lucilia sericata, Lycoria pectoralis, Mansonia* spp., *Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga* sp., *Simulium vittatum, Stomoxys calcitrans, Tabanus bovinus, Tabanus atratus, Tabanus lineola,* and *Tabanus similis,* lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus.* ticks and parasitic mites (Parasitiformes): ticks (Ixodida), e.g. *Ixodes scapularis, Ixodes holocyclus, Ixodes pacificus, Rhiphicephalus sanguineus, Dermacentor andersonii Dermacentor variabilis, Amblyomma americanum, Ambryomma maculatum, Ornithodorus hermsi, Ornithodorus turicata* and parasitic mites (Mesostigmata), e.g. *Ornithonyssus bacoti* and *Dermanyssus gallinae,*

Actinedida (Prostigmata) and Acaridida (Astigmata) e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp, Bugs (Heteropterida); *Cimex lectularius, Cimex hemipterus, Reduvius senilis, Triatoma* spp., *Rhodnius* ssp., *Panstrongylus* ssp. and *Arilus critatus,*

Anoplurida, e.g. *Haematopinus* spp., *Linognathus* spp., *Pediculus* spp., *Phtirus* spp., and *Solenopotes* spp, Mallophagida (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp, Roundworms Nematoda:

Wipeworms and Trichinosis (Trichosyringida), e.g. Trichinellidae (*Trichinella* spp.), (Trichuridae) *Trichuris* spp., *Capillaria* spp, Rhabditida, e.g. *Rhabditis* spp, *Strongyloides* spp., *Helicephalobus* spp, Strongylida, e.g. *Strongylus* spp., *Ancylostoma* spp., *Necator americanus, Bunostomum* spp. (Hookworm), *Trichostrongylus* spp., *Haemonchus contortus., Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp. *Aleurostrongylus abstrusus,* and *Dioctophyma renale,*

Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi,*

Camallanida, e.g. *Dracunculus medinensis* (guinea worm)

Spirurida, e.g. *Thelazia* spp. *Wuchereria* spp., *Brugia* spp., *Onchocerca* spp., *Dirofilari* spp.a, *Dipetalonema* spp., *Setaria* spp., *Elaeophora* spp., *Spirocerca lupi,* and *Habronema* spp.,

*Thorny headed* worms (Acanthocephala), e.g. *Acanthocephalus* spp., *Macracanthorhynchus hirudinaceus* and *Oncicola* spp, Planarians (Plathelminthes):

Flukes (Trematoda), e.g. *Faciola* spp., *Fascioloides magna, Paragonimus* spp., *Dicrocoelium* spp., *Fasciolopsis buski, Clonorchis sinensis, Schistosoma* spp., *Trichobilharzia* spp., *Alaria alata, Paragonimus* spp., and *Nanocyetes* spp, Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

Applications

The present invention relates to the therapeutic and the non-therapeutic use of compounds of formula I for controlling and/or combating parasites in and/or on animals.

The compounds of formula I may be used to protect the animals from attack or infestation by parasites by contacting them with a parasitically effective amount of compounds of formula I. As such, "contacting" includes both direct contact (applying the compounds/compositions directly on the parasite, including the application directly on the animal or excluding the application directly on the animal, e.g. at it's locus for the latter) and indirect contact (applying the compounds/compositions to the locus of the parasite). The contact of the parasite through application to its locus is an example of a non-therapeutic use of compounds of formula I.

"Locus" as defined above means the habitat, food supply, breeding ground, area, material or environment in which a parasite is growing or may grow outside of the animal. The compounds of the invention can also be applied preventively to places at which occurrence of the pests or parasites is expected.

The compounds of formula I can be effective through both contact (via soil, glass, wall, bed net, carpet, blankets or animal parts) and ingestion (e.g. baits).

The administration can be carried out prophylactically, therapeutically or non-therapeutically.

Administration of the active compounds is carried out directly or in the form of suitable preparations, orally, topically/dermally or parenterally.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

Generally it is favorable to apply the compounds of formula I in total amounts of 0.5 mg/kg to 100 mg/kg per day, preferably 1 mg/kg to 50 mg/kg per day.

Formulations

For oral administration to warm-blooded animals, the formula I compounds may be formulated as animal feeds, animal feed premixes, animal feed concentrates, pills, solutions, pastes, suspensions, drenches, gels, tablets, boluses and capsules. In addition, the formula I compounds may be administered to the animals in their drinking water. For oral administration, the dosage form chosen should provide the animal with 0.01 mg/kg to 100 mg/kg of animal body weight per day of the formula I compound, preferably with 0.5 mg/kg to 100 mg/kg of animal body weight per day.

Alternatively, the formula I compounds may be administered to animals parenterally, for example, by intraruminal, intramuscular, intravenous or subcutaneous injection. The formula I compounds may be dispersed or dissolved in a physiologically acceptable carrier for subcutaneous injection. Alternatively, the formula I compounds may be formulated into an implant for subcutaneous administration. In addition the formula I compound may be transdermally administered to animals. For parenteral administration, the dosage form chosen should provide the animal with 0.01 mg/kg to 100 mg/kg of animal body weight per day of the formula I compound.

The formula I compounds may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the formula I compound. In addition, the formula I compounds may be formulated as ear tags for animals, particularly quadrupeds such as cattle and sheep.

Suitable preparations are:

Solutions such as oral solutions, concentrates for oral administration after dilution, solutions for use on the skin or in body cavities, pouring-on formulations, gels;

Emulsions and suspensions for oral or dermal administration; semi-solid preparations;

Formulations in which the active compound is processed in an ointment base or in an oil-in-water or water-in-oil emulsion base;

Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further ingredients such as acids, bases, buffer salts, preservatives, and solubilizers. The solutions are filtered and filled sterile.

Suitable solvents are physiologically tolerable solvents such as water, alkanols such as ethanol, butanol, benzyl alcohol, glycerol, propylene glycol, polyethylene glycols, N-methyl-pyrrolidone, 2-pyrrolidone, and mixtures thereof.

The active compounds can optionally be dissolved in physiologically tolerable vegetable or synthetic oils which are suitable for injection.

Suitable solubilizers are solvents which promote the dissolution of the active compound in the main solvent or prevent its precipitation. Examples are polyvinylpyrrolidone, polyvinyl alcohol, polyoxyethylated castor oil, and polyoxyethylated sorbitan ester.

Suitable preservatives are benzyl alcohol, trichlorobutanol, p-hydroxybenzoic acid esters, and n-butanol.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on.

Solutions for use on the skin are prepared according to the state of the art and according to what is described above for injection solutions, sterile procedures not being necessary.

Further suitable solvents are polypropylene glycol, phenyl ethanol, phenoxy ethanol, ester such as ethyl or butyl acetate, benzyl benzoate, ethers such, as alkyleneglycol alkylether, e.g. dipropylenglycol monomethylether, ketons such as acetone, methylethylketone, aromatic hydrocarbons, vegetable and synthetic oils, dimethylformamide, dimethylacetamide, transcutol, solketal, propylencarbonate, and mixtures thereof.

It may be advantageous to add thickeners during preparation. Suitable thickeners are inorganic thickeners such as bentonites, colloidal silicic acid, aluminium monostearate, organic thickeners such as cellulose derivatives, polyvinyl alcohols and their copolymers, acrylates and methacrylates.

Gels are applied to or spread on the skin or introduced into body cavities. Gels are prepared by treating solutions which have been prepared as described in the case of the injection solutions with sufficient thickener that a clear material having an ointment-like consistency results. The thickeners employed are the thickeners given above.

Pour-on formulations are poured or sprayed onto limited areas of the skin, the active compound penetrating the skin and acting systemically.

Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added.

Suitable solvents which are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, cyclic carbonates such as propylene carbonate, ethylene carbonate, aromatic and/or aliphatic hydrocarbons, vegetable or synthetic oils, DMF, dimethyllacetamide, n-alkylpyrrolidones such as methylpyrrolidone, n-butylpyrrolidone or noctylpyrrolidone, N-methylpyrrolidone, 2-pyrrolidone, 2,2-dimethyl-4-oxymethylene-1,3-diox-olane and glycerol formal.

Suitable colorants are all colorants permitted for use on animals and which can be dissolved or suspended.

Suitable absorption-promoting substances are, for example, DMSO, spreading oils such as isopropyl myristate, dipropylene glycol pelargonate, silicone oils and copolymers thereof with polyethers, fatty acid esters, triglycerides, fatty alcohols.

Suitable antioxidants are sulfites or metabisulfites such as potassium metabisulfite, ascorbic acid, butylhydroxytoluene, butyl hydroxyanisole, tocopherol.

Suitable light stabilizers are, for example, novantisolic acid.

Suitable adhesives are, for example, cellulose derivatives, starch derivatives, polyacrylates, natural polymers such as alginates, gelatin.

Emulsions can be administered orally, dermally or as injections.

Emulsions are either of the water-in-oil type or of the oil-in-water type.

They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances.

Suitable hydrophobic phases (oils) are liquid paraffins, silicone oils, natural vegetable oils such as sesame oil, almond oil, castor oil, synthetic triglycerides such as caprylic/capric biglyceride, triglyceride mixture with vegetable fatty acids of the chain length $C_8$-$C_{12}$ or other specially selected natural fatty acids, partial glyceride mixtures of saturated or unsaturated fatty acids possibly also containing hydroxyl groups, mono- and diglycerides of the $C_8$-$C_{10}$ fatty acids, fatty acid esters such as ethyl stearate, di-n-butyryl adipate, hexyl laurate, dipropylene glycol perlargonate, esters of a branched fatty acid of medium chain length with saturated fatty alcohols of chain length $C_{16}$-$C_{18}$, isopropyl myristate, isopropyl palmitate, caprylic/capric acid esters of saturated fatty alcohols of chain length $C_{12}$-$C_{18}$, isopropyl stearate, oleyl oleate, decyl oleate, ethyl oleate, ethyl lactate, waxy fatty acid esters such as synthetic duck coccygeal gland fat, dibutyl phthalate, diisopropyl adipate, and ester mixtures related to the latter, fatty alcohols such as isotridecyl alcohol, 2-octyldodecanol, cetylstearyl alcohol, oleyl alcohol, and fatty acids such as oleic acid and mixtures thereof.

Suitable hydrophilic phases are: water, alcohols such as propylene glycol, glycerol, sorbitol and mixtures thereof.

Suitable emulsifiers are:

non-ionic surfactants, e.g. polyethoxylated castor oil, polyethoxylated sorbitan monooleate, sorbitan monostearate, glycerol monostearate, polyoxyethyl stearate, alkylphenol polyglycol ether;

ampholytic surfactants such as di-sodium N-lauryl-p-iminodipropionate or lecithin; anionic surfactants, such as sodium lauryl sulfate, fatty alcohol ether sulfates, mono/dialkyl polyglycol ether orthophosphoric acid ester monoethanolamine salt; cation-active surfactants, such as cetyltrimethylammonium chloride.

Suitable further auxiliaries are: substances which enhance the viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances mentioned.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers.

Liquid suspending agents are all homogeneous solvents and solvent mixtures.

Suitable wetting agents (dispersants) are the emulsifiers given above.

Other auxiliaries which may be mentioned are those given above.

Semi-solid preparations can be administered orally or topically/dermally. They differ from the suspensions and emulsions described above only by their higher viscosity.

For the production of solid preparations, the active compound is mixed with suitable excipients, if appropriate with addition of auxiliaries, and brought into the desired form.

Suitable excipients are all physiologically tolerable solid inert substances. Those used are inorganic and organic substances. Inorganic substances are, for example, sodium chloride, carbonates such as calcium carbonate, hydrogencarbonates, aluminium oxides, titanium oxide, silicic acids, argillaceous earths, precipitated or colloidal silica, or phosphates. Organic substances are, for example, sugar, cellulose, foodstuffs and feeds such as milk powder, animal meal, grain meals and shreds, starches.

Suitable auxiliaries are preservatives, antioxidants, and/or colorants which have been mentioned above.

Other suitable auxiliaries are lubricants and glidants such as magnesium stearate, stearic acid, talc, bentonites, disintegration-promoting substances such as starch or crosslinked polyvinylpyrrolidone, binders such as starch, gelatin or linear polyvinylpyrrolidone, and dry binders such as microcrystalline cellulose.

The compositions which can be used in the invention can comprise generally from about 0.001 to 95% of the compound of formula I.

Ready-to-use preparations contain the compounds acting against parasites, preferably ectoparasites, in concentrations of 10 ppm to 80 percent by weight, preferably from 0.1 to 65 percent by weight, more preferably from 1 to 50 percent by weight, most preferably from 5 to 40 percent by weight.

Preparations which are diluted before use contain the compounds acting against ectoparasites in concentrations of 0.5 to 90 percent by weight, preferably of 1 to 50 percent by weight.

Furthermore, the preparations comprise the compounds of formula I against endoparasites in concentrations of 10 ppm to 2 percent by weight, preferably of 0.05 to 0.9 percent by weight, very particularly preferably of 0.005 to 0.25 percent by weight.

The compositions comprising the compounds of formula I can be applied orally, parenterally or topically, respectively dermally. For example, optionally the topical application is conducted in the form of compound-containing shaped articles such as collars, medallions, ear tags, bands for fixing at body parts, and adhesive strips and foils.

Generally it is favorable to apply solid formulations which release compounds of formula I in total amounts of 10 mg/kg to 300 mg/kg, preferably 20 mg/kg to 200 mg/kg, most preferably 25 mg/kg to 160 mg/kg body weight of the treated animal in the course of three weeks.

For the preparation of the shaped articles, thermoplastic and flexible plastics as well as elastomers and thermoplastic elastomers are used. Suitable plastics and elastomers are polyvinyl resins, polyurethane, polyacrylate, epoxy resins, cellulose, cellulose derivatives, polyamides and polyester which are sufficiently compatible with the compounds of formula I. A detailed list of plastics and elastomers as well as preparation procedures for the shaped articles is given e.g. in WO 03/086075.

The active compounds can be applied solely or in a mixture with synergists or with other active compounds which act against pathogenic endo- and ectoparasites. For example, the active compounds of formula I can be applied in mixtures with synthetic coccidiosis compounds, polyetherantibiotics as Amprolium, Robenidin, Toltrazuril, Monensin, Salinomycin, Maduramicin, Lasalocid, Narasin or Semduramicin or with other pesticides which are described in the list M below.

Compositions to be used according to this invention for agricultural or veterinary purposes may also contain other active ingredients, for example other pesticides, insecticides, herbicides, fungicides, bactericides, fertilizers such as ammonium nitrate, urea, potash, and super-phosphate, phytotoxicants and plant growth regulators, safeners and nematicides. These additional ingredients may be used sequentially or in combination with the above-described compositions, if appropriate also added only immediately prior to use (tank mix). For example, the plant(s) may be sprayed with a composition of this invention either before or after being treated with other active ingredients.

These agents can be admixed with the agents used according to the invention in a weight ratio of 1:10 to 10:1. Mixing the compounds of formula I or the compositions comprising them in the use form as pesticides with other pesticides frequently results in a broader pesticidal spectrum of action.

The following list M of pesticides together with which the compounds according to the invention can be used and with which potential synergistic effects might be produced, is intended to illustrate the possible combinations, but not to impose any limitation:

M.1. Organo(thio)phosphate compounds: acephate, azamethiphos, azinphos-ethyl, azinphos-methyl, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, flupyrazophos, fosthiazate, heptenophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion;

M.2. Carbamate compounds: aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb, triazamate;

M.3. Pyrethroid compounds: acrinathrin, allethrin, d-cis-trans allethrin, d-trans allethrin, bifenthrin, bioallethrin, bioallethrin S-cylclopentenyl, bioresmethrin, cycloprothrin, cyfluthrin, beta-cyfluthrin, cyhalothrin, lambda-cyhalothrin, gammacyhalothrin, cypermethrin, alpha-cypermethrin, beta-cypermethrin, thetacypermethrin, zeta-cypermethrin, cyphenothrin, deltamethrin, empenthrin, esfenvalerate, etofenprox, fenpropathrin, fenvalerate, flucythrinate, flumethrin, taufluvalinate, halfenprox, imiprothrin, metofluthrin, permethrin, phenothrin, prallethrin, profluthrin, pyrethrin (pyrethrum), resmethrin, silafluofen, tefluthrin, tetramethrin, tralomethrin, transfluthrin;

M.4. Juvenile hormone mimics: hydroprene, kinoprene, methoprene, fenoxycarb, pyriproxyfen;

M.5. Nicotinic receptor agonists/antagonists compounds: acetamiprid, bensultap, cartap hydrochloride, clothianidin, dinotefuran, imidacloprid, thiamethoxam, nitenpyram, nicotine, spinosad (allosteric agonist), spinetoram (allosteric agonist), thiacloprid, thiocyclam, thiosultap-sodium and AKD1022.

M.6. GABA gated chloride channel antagonist compounds: chlordane, endosulfan, gamma-HCH (lindane); ethiprole, fipronil, pyrafluprole, pyriprole M.7. Chloride channel activators: abamectin, emamectin benzoate, milbemectin, lepimectin;

M.8. METI I compounds: fenazaquin, fenpyroximate, pyrimidifen, pyridaben, tebufenpyrad, tolfenpyrad, flufenerim, rotenone;

M.9. METI II and III compounds: acequinocyl, fluacyprim, hydramethylnon;

M.10. Uncouplers of oxidative phosphorylation: chlorfenapyr, DNOC;

M.11. Inhibitors of oxidative phosphorylation: azocyclotin, cyhexatin, diafenthiuron, fenbutatin oxide, propargite, tetradifon;

M.12. Moulting disruptors: cyromazine, chromafenozide, halofenozide, methoxyfenozide, tebufenozide;

M.13. Synergists: piperonyl butoxide, tribufos;

M.14. Sodium channel blocker compounds: indoxacarb, metaflumizone;

M.15. Fumigants: methyl bromide, chloropicrin sulfuryl fluoride;

M.16. Selective feeding blockers: crylotie, pymetrozine, flonicamid;

M.17. Mite growth inhibitors: clofentezine, hexythiazox, etoxazole;

M.18. Chitin synthesis inhibitors: buprofezin, bistrifluoron, chlorfluazuron, diflubenzuron, flucycloxuron, flufenoxuron, hexaflumuron, lufenuron, novaluron, noviflumuron, teflubenzuron, triflumuron;

M.19. Lipid biosynthesis inhibitors: spirodiclofen, spiromesifen, spirotetramat;

M.20. Octapaminergic agonists: amitraz;

M.21. Ryanodine receptor modulators: flubendiamide, (R)-, (S)-3-Chlor-N-1-{2-methyl-4-[1,2,2,2-tetrafluor-1-(trifluormethyl)ethyl]phenyl}-N2-(1-methyl-2-methylsulfonylethyl)phthalamid (M21.1)

M.22. Isoxazoline compounds: 4-[5-(3,5-Dichloro-phenyl)-5-trifluoromethyl-4,5-dihydro-isoxazol-3-yl]-2-methyl-N-pyridin-2-ylmethyl-benzamide (M22.1), 445-(3,5-Dichloro-phenyl)-5-trifluoromethyl-4,5-dihydro-isoxazol-3-yl]-2-methyl-N-(2,2,2-trifluoro-ethyl)-benzamide (M22.2), 4-[5-(3,5-Dichloro-phenyl)-5-trifluoromethyl-4,5-dihydro-isoxazol-3-yl]-2-methyl-N-[(2,2,2-trifluoro-ethylcarbamoyl)-methyl]-benzamide (M22.3), 4-[5-(3,5-Dichloro-phenyl)-5-trifluoromethyl-4,5-dihydro-isoxazol-3-yl]-naphthalene-1-carboxylic acid [(2,2,2-trifluoro-ethylcarbamoyl)-methyl]-amide (M22.4) and 4-[5-(3,5-Dichlorophenyl)-5-trifluoromethyl-4,5-dihydro-isoxazol-3-yl]-N-[(methoxyimino)methyl]-2-methylbenzamide (M22.5);

M.23. Anthranilamide compounds: chloranthraniliprole, cyantraniliprole, 5-Bromo-2-(3-chloro-pyridin-2-yl)-2H-pyrazole-3-carboxylic acid [4-cyano-2-(1-cyclopropyl-ethylcarbamoyl)-6-methyl-phenyl]-amide (M23.1), 5-Bromo-2-(3-chloro-pyridin-2-yl)-2H-pyrazole-3-carboxylic acid [2-chloro-4-cyano-6-(1-cyclopropyl-ethyl-carbamoyl)-phenyl]-amide (M23.2), 5-Bromo-2-(3-chloro-pyridin-2-yl)-2H-pyrazole-3-carboxylic acid [2-bromo-4-cyano-6-(1-cyclopropyl-ethylcarbamoyl)-phenyl]-amide(M23.3), 5-Bromo-2-(3-chloro-pyridin-2-yl)-2H-pyrazole-3-carboxylic acid [2-bromo-4-chloro-6-(1-cyclopropyl-ethylcarbamoyl)-phenyl]-amide(M23.4), 5-Bromo-2-(3-chloro-pyridin-2-yl)-2H-pyrazole-3-carboxylic acid [2,4-dichloro-6-(1-cyclopropyl-ethylcarbamoyl)-phenyl]-amide (M23.5), 5-Bromo-2-(3-chloro-pyridin-2-yl)-2H-pyrazole-3-carboxylic acid [4-chloro-2-(1-cyclopropyl-ethylcarbamoyl)-6-methyl-phenyl]-amide (M23.6), N'-(2-{[5-Bromo-2-(3-chloro-pyridin-2-yl)-2H-pyrazole-3-carbonyl]-amino}-5-chloro-3-methyl-benzoyl)-hydrazinecarboxylic acid methyl ester (M23.7), N'-(2-{[5-Bromo-2-(3-chloro-pyridin-2-yl)-2H-pyrazole-3-carbonyl]-amino}-5-chloro-3-methyl-benzoyl)-N'-methyl-hydrazinecarboxylic acid methyl ester (M23.8), N'-(2-{[5-Bromo-2-(3-chloro-pyridin-2-yl)-2H-pyrazole-3-carbonyl]-amino}-5-chloro-3-methyl-benzoyl)-N,N'-dimethyl-hydrazinecarboxylic acid methyl ester (M23.9), N'-(3,5-Dibromo-2-{[5-bromo-2-(3-chloro-pyridin-2-yl)-2H-pyrazole-3-carbonyl]-amino}-benzoyl)-hydrazinecarboxylic acid methyl ester (M23.10), N'-(3,5-Dibromo-2-{[5-bromo-2-(3-chloro-pyridin-2-yl)-2H-pyrazole-3-carbonyl]-amino}-benzoyl)-n-methyl-hydrazinecarboxylic acid methyl ester (M23.11) and N'-(3,5-Dibromo-2-{[5-bromo-2-(3-chloro-pyridin-2-yl)-2H-pyrazole-3-carbonyl]-amino}-benzoyl)-N,N'-dimethyl-hydrazinecarboxylic acid methyl ester (M23.12);

M.24. Malononitrile compounds: 2-(2,2,3,3,4,4,5,5-octafluoropentyl)-2-(3,3,3-trifluoro-propyl)malononitrile ($CF_2H-CF_2-CF_2-CF_2-CH_2-C(CN)_2-CH_2-CH_2-CF_3$) (M24.1) and 2-(2,2,3,3,4,4,5,5-octafluoropentyl)-2-(3,3,4,4,4-pentafluorobutyl)-malonodinitrile ($CF_2H-CF_2-CF_2-CF_2-CH_2-C(CN)_2-CH_2-CH_2-CF_2-CF_3$) (M24.2);

M.25. Microbial disruptors: *Bacillus thuringiensis* subsp. *Israelensi*, *Bacillus sphaericus*, *Bacillus thuringiensis* subsp. *Aizawai*, *Bacillus thuringiensis* subsp. *Kurstaki*, *Bacillus thuringiensis* subsp. *Tenebrionis*;

M.26. Aminofuranone compounds:
4-{[(6-Bromopyrid-3-yl)methyl](2-fluoroethyl)amino}furan-2(5H)-on (M26.1),
4-{[(6-Fluoropyrid-3-yl)methyl](2,2-difluoroethyl)amino}furan-2(5H)-on (M26.2),
4-{[(2-Chloro1,3-thiazolo-5-yl)methyl](2-fluoroethyl)amino}furan-2(5H)-on (M26.3),
4-{[(6-Chloropyrid-3-yl)methyl](2-fluoroethyl)amino}furan-2(5H)-on (M26.4),
4-{[(6-Chloropyrid-3-yl)methyl](2,2-difluoroethyl)amino}furan-2(5H)-on (M26.5),
4-{[(6-Chloro-5-fluoropyrid-3-yl)methyl](methyl)amino}furan-2(5H)-on (M26.6),
4-{[(5,6-Dichloropyrid-3-yl)methyl](2-fluoroethyl)amino}furan-2(5H)-on (M26.7),
4-{[(6-Chloro-5-fluoropyrid-3-yl)methyl](cyclopropyl)amino}furan-2(5H)-on (M26.8),
4-{[(6-Chloropyrid-3-yl)methyl](cyclopropyl)amino}furan-2(5H)-on (M26.9) and
4-{[(6-Chloropyrid-3-yl)methyl](methyl)amino}furan-2(5H)-on (M26.10);

M.27. Various compounds: aluminium phosphide, amidoflumet, benclothiaz, benzoximate, bifenazate, borax, bromopropylate, cyanide, cyenopyrafen, cyflumetofen, chinomethionate, dicofol, fluoroacetate, phosphine, pyridalyl, pyrifluquinazon, sulfur, organic sulfur compounds, tartar emetic, sulfoxaflor, N—R'-2,2-dihalo-1-R"cyclo-propanecarboxamide-2-(2,6-dichloro-α,α,α-trifluoro-ptolyl)hydrazone or N—R'-2,2-di(R''')propionamide-2-(2,6-dichloro-α,α,α-trifluoro-p-tolyl)-hydrazone, wherein R' is methyl or ethyl, halo is chloro or bromo, R" is hydrogen or methyl and R''' is methyl or ethyl, 4-But-2-ynyloxy-6-(3,5-dimethyl-piperidin-1-yl)-2-fluoro-pyrimidine (M27.1), Cyclopropaneacetic acid, 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-[2-hydroxy-4,6a,12b-trimethyl-11-oxo-9-(3-pyridinyl)-2H,11H-naphtho[2,1-b]pyrano[3,4-e]pyran-3,6-diyl]ester(M27.2) and 8-(2-Cyclopropylmethoxy-4-trifluoromethyl-phenoxy)-3-(6-trifluoromethyl-pyridazin-3-yl)-3-aza-bicyclo[3.2.1]octane(M27.3).

The commercially available compounds of the group M may be found in The Pesticide Manual, 14th Edition, British Crop Protection Council (2006).

Paraoxon and their preparation have been described in Farm Chemicals Handbook, Volume 88, Meister Publishing Company, 2001. Flupyrazofos has been described in Pesticide Science 54, 1988, p. 237-243 and in U.S. Pat. No. 4,822, 779. AKD 1022 and its preparation have been described in U.S. Pat. No. 6,300,348. The anthranilamides M23.1 to M23.6 have been described in WO 2008/72743 and WO 200872783, those M23.7 to M23.12 in WO2007/043677. The phthalamide M 21.1 is known from WO 2007/101540. The alkynylether compound M27.1 is described e.g. in JP 2006131529. Organic sulfur compounds have been described in WO 2007060839. The isoxazoline compounds M 22.1 to M 22.5 have been described in e.g. WO2005/085216, WO 2007/079162 and WO 2007/026965. The aminofuranone compounds M 26.1 to M 26.10 have been described eg. in WO 2007/115644. The pyripyropene derivative M 27.2 has been described in WO 2008/66153 and WO 2008/108491. The pyridazin compound M 27.3 has been described in JP 2008/115155. Malononitrile compounds as those (M24.1) and (M24.2) have been described in WO 02/089579, WO 02/090320, WO 02/090321, WO 04/006677, WO 05/068423, WO 05/068432 and WO 05/063694.

The following list of active substances, in conjunction with which the compounds according to the invention can be used, is intended to illustrate the possible combinations but does not limit them. Fungicidal mixing partners are in particular those selected from the following groups:

F.I) Respiration Inhibitors
F.I-1) Inhibitors of complex III at Qo site (e.g. strobilurins) strobilurins: azoxystrobin, dimoxystrobin, enestroburin, fluoxastrobin, kresoximmethyl, metominostrobin, orysastrobin, picoxystrobin, pyraclostrobin, pyrametostrobin, pyraoxystrobin, pyribencarb, trifloxystrobin, methyl (2-chloro-5[1-(3-methylbenzyloxyimino)ethyl]benzyl) carbamate and 2 (2-(3-(2,6-dichlorophenyl)-1-methyl-allylideneaminooxymethyl)-phenyl)-2-methoxyimino-N methyl-acetamide; oxazolidinediones and imidazolinones: famoxadone, fenamidone;
F.I-2) Inhibitors of complex II (e.g. carboxamides):
carboxanilides: benodanil, bixafen, boscalid, carboxin, fenfuram, fenhexamid, fluopyram, flutolanil, furametpyr, isopyrazam, isotianil, mepronil, oxycarboxin, penflufen, penthiopyrad, sedaxane, tecloftalam, thifluzamide, tiadinil, 2-amino-4 methyl-thiazole-5-carboxanilide, N-(3',4',5' trifluorobiphenyl-2 yl)-3-difluoromethyl-1-methyl-1H-pyrazole-4 carboxamide, N-(4'-trifluoromethylthiobiphenyl-2-yl)-3 difluoromethyl-1-methyl-1H pyrazole-4-carboxamide and N-(2-(1,3,3-trimethyl-butyl)-phenyl)-1,3-dimethyl-5 fluoro-1H-pyrazole-4 carboxamide;
F.I-3) Inhibitors of complex III at Qi site: cyazofamid, amisulbrom;
F.I-4) Other respiration inhibitors (complex I, uncouplers) diflumetorim; tecnazen; ferimzone; ametoctradin; silthiofam;
nitrophenyl derivates: binapacryl, dinobuton, dinocap, fluazinam, nitrthal-isopropyl, organometal compounds: fentin salts, such as fentin-acetate, fentin chloride or fentin hydroxide;
F.II) Sterol biosynthesis inhibitors (SBI fungicides)
F.II-1) C14 demethylase inhibitors (DMI fungicides, e.g. triazoles, imidazoles) triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole;
imidazoles: imazalil, pefurazoate, oxpoconazole, prochloraz, triflumizole; pyrimidines, pyridines and piperazines: fenarimol, nuarimol, pyrifenox, triforine;

F.II-2) Delta14-reductase inhibitors (Amines, e.g. morpholines, piperidines) morpholines: aldimorph, dodemorph, dodemorph-acetate, fenpropimorph, tridemorph;
piperidines: fenpropidin, piperalin;
spiroketalamines: spiroxamine;
F.II-3) Inhibitors of 3-keto reductase: hydroxyanilides: fenhexamid;
F.III) Nucleic acid synthesis inhibitors
F.III-1) RNA, DNA synthesis
phenylamides or acyl amino acid fungicides: benalaxyl, benalaxyl-M, kiralaxyl, metalaxyl, metalaxyl-M (mefenoxam), ofurace, oxadixyl;
isoxazoles and iosothiazolones: hymexazole, octhilinone;
F.III-2) DNA topisomerase inhibitors: oxolinic acid;
F.III-3) Nucleotide metabolism (e.g. adenosin-deaminase) hydroxy (2-amino)-pyrimidines: bupirimate;
F.IV) Inhibitors of cell division and or cytoskeleton
F.IV-1) Tubulin inhibitors: benzimidazoles and thiophanates: benomyl, carbendazim, fuberidazole, thiabendazole, thiophanate-methyl;
triazolopyrimidines: 5-chloro-7 (4-methylpiperidin-1-yl)-6-(2,4,6-trifluorophenyl)-[1,2,4]triazolo[1,5 a]pyrimidine
F.IV-2) Other cell division inhibitors
benzamides and phenyl acetamides: diethofencarb, ethaboxam, pencycuron, fluopicolide, zoxamide;
F.IV-3) Actin inhibitors: benzophenones: metrafenone;
F.V) Inhibitors of amino acid and protein synthesis
F.V-1) Methionine synthesis inhibitors (anilino-pyrimidines) anilino-pyrimidines: cyprodinil, mepanipyrim, nitrapyrin, pyrimethanil;
F.V-2) Protein synthesis inhibitors (anilino-pyrimidines)
antibiotics: blasticidin-S, kasugamycin, kasugamycin hydrochloride-hydrate, mildiomycin, streptomycin, oxytetracyclin, polyoxine, validamycin A;
F.VI) Signal transduction inhibitors
F.VI-1) MAP/Histidine kinase inhibitors (e.g. anilino-pyrimidines) dicarboximides: fluoroimid, iprodione, procymidone, vinclozolin;
phenylpyrroles: fenpiclonil, fludioxonil;
F.VI-2) G protein inhibitors: quinolines: quinoxyfen;
F.VII) Lipid and membrane synthesis inhibitors
F.VII-1) Phospholipid biosynthesis inhibitors organophosphorus compounds: edifenphos, iprobenfos, pyrazophos;
dithiolanes: isoprothiolane;
F.VII-2) Lipid peroxidation
aromatic hydrocarbons: dicloran, quintozene, tecnazene, tolclofos-methyl, biphenyl, chloroneb, etridiazole;
F.VII-3) Carboxyl acid amides (CAA fungicides)
cinnamic or mandelic acid amides: dimethomorph, flumorph, mandipromamid, pyrimorph;
valinamide carbamates: benthiavalicarb, iprovalicarb, pyribencarb, valifenalate and N-(1-(1-(4-cyano-phenyl) ethanesulfonyl)-but-2-yl)carbamic acid-(4-fluorophenyl) ester;
F.VII-4) Compounds affecting cell membrane permeability and fatty acides carbamates: propamocarb, propamocarb-hydrochlorid
F.VIII) Inhibitors with Multi Site Action
F.VIII-1) Inorganic active substances: Bordeaux mixture, copper acetate, copper hydroxide, copper oxychloride, basic copper sulfate, sulfur;
F.VIII-2) Thio- and dithiocarbamates: ferbam, mancozeb, maneb, metam, methasulphocarb, metiram, propineb, thiram, zineb, ziram;
F.VIII-3) Organochlorine compounds (e.g. phthalimides, sulfamides, chloronitriles): anilazine, chlorothalonil, captafol, captan, folpet, dichlofluanid, dichlorophen, flusulfamide, hexachlorobenzene, pentachlorphenole and its salts, phthalide, tolylfluanid, N-(4-chloro-2-nitro-phenyl)-N-ethyl-4-methyl-benzenesulfonamide;

F.VIII-4) Guanidines: guanidine, dodine, dodine free base, guazatine, guazatineacetate, iminoctadine, iminoctadine-triacetate, iminoctadine-tris(albesilate);

F.VIII-5) Ahtraquinones: dithianon;

F.IX) Cell wall synthesis inhibitors

F.IX-1) Inhibitors of glucan synthesis: validamycin, polyoxin B;

F.IX-2) Melanin synthesis inhibitors: pyroquilon, tricyclazole, carpropamide, dicyclomet, fenoxanil;

F.X) Plant defence inducers

F.X-1) Salicylic acid pathway: acibenzolar-5-methyl;

F.X-2) Others: probenazole, isotianil, tiadinil, prohexadione-calcium;

phosphonates: fosetyl, fosetyl-aluminum, phosphorous acid and its salts;

F.XI) Unknown mode of action:

bronopol, chinomethionat, cyflufenamid, cymoxanil, dazomet, debacarb, diclomezine, difenzoquat, difenzoquat-methylsulfate, diphenylamin, flumetover, flusulfamide, flutianil, methasulfocarb, oxin-copper, proquinazid, tebufloquin, tecloftalam, triazoxide, 2-butoxy-6-iodo-3-propylchromen-4-one, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N methyl formamidine, N' (4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2 methyl-4-(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, methoxyacetic acid 6-tert-butyl-8-fluoro-2,3-dimethyl-quinolin-4-yl ester and N-Methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide, 3-[5-(4-chloro-phenyl)-2,3-dimethyl-isoxazolidin-3 yl]-pyridine, 3-[5-(4-methyl-phenyl)-2,3-dimethyl-isoxazolidin-3-yl]-pyridine, 5-amino-2-isopropyl-3-oxo-4-ortho-tolyl-2,3-dihydro-pyrazole-1 carbothioic acid S-allyl ester, N-(6-methoxy-pyridin-3-yl)cyclopropane-carboxylic acid amide, 5-chloro-1 (4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide;

F.XI) Growth regulators:

abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N 6 benzyladenine, paclobutrazol, prohexadione (prohexadione-calcium), prohydrojasmon, thidiazuron, triapenthenol, tributyl phosphorotrithioate, 2,3,5 tri iodobenzoic acid, trinexapac-ethyl and uniconazole;

F.XII) Biological control agents antifungal biocontrol agents: *Bacillus substilis* strain with NRRL No. B-21661 (e.g. RHAPSODY®, SERENADE® MAX and SERENADE® ASO from AgraQuest, Inc., USA.), *Bacillus pumilus* strain with NRRL No. B-30087 (e.g. SONATA® and BALLAD® Plus from AgraQuest, Inc., USA), *Ulocladium oudemansii* (e.g. the product BOTRY-ZEN from BotriZen Ltd., New Zealand), Chitosan (e.g. ARMOUR-ZEN from BotriZen Ltd., New Zealand).

The invertebrate pest, i.e. arthropodes and nematodes, the plant, soil or water in which the plant is growing can be contacted with the compound(s) of formula I or the composition(s) containing them by any application method known in the art. As such, "contacting" includes both direct contact (applying the compounds/compositions directly on the invertebrate pest or plant—typically to the foliage, stem or roots of the plant) and indirect contact (applying the compounds/compositions to the locus of the invertebrate pest or plant).

Moreover, invertebrate pests may be controlled by contacting the target pest, its food supply, habitat, breeding ground or its locus with a pesticidally effective amount of compounds of formula I. As such the application may be carried out before or after the infection of the locus, growing crops, or harvested crops by the pest.

"Locus" in general means a habitat, breeding ground, cultivated plants, plant propagation material (such as seed), soil, area, material or environment in which a pest or parasite is growing or may grow.

In general "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

The compounds of formula I and the compositions comprising said compounds can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of formula I are applied not only to the surrounding soil surface or into the under-floor soil in order to protect wooden materials but it can also be applied to lumbered articles such as surfaces of the under-floor concrete, alcove posts, beams, plywood, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

The compounds of formula I can also be applied preventively to places at which occurrence of the pests is expected.

The compounds of formula I may also be used to protect growing plants from attack or infestation by pests by contacting the plant with a pesticidally effective amount of compounds of formula I. As such, "contacting the plant" includes both direct contact (applying the compounds/compositions directly on the pest and/or plant—typically to the foliage, stem or roots of the plant) and indirect contact (applying the compounds/compositions to the locus of the pest and/or plant).

In the case of soil treatment or of application to the pests dwelling place or nest, the quantity of active ingredient ranges from 0.0001 to 500 g per 100 m², preferably from 0.001 to 20 g per 100 m².

Customary application rates in the protection of materials are, for example, from 0.01 g to 1000 g of active compound per m² treated material, desirably from 0.1 g to 50 g per m².

Insecticidal compositions for use in the impregnation of materials typically contain from 0.001 to 95% by weight, preferably from 0.1 to 45% by weight, and more preferably from 1 to 25% by weight of at least one repellent and/or insecticide.

For use in bait compositions, the typical content of active ingredient is from 0.001% by weight to 15% by weight, desirably from 0.001% by weight to 5% by weight of active compound.

For use in spray compositions, the content of active ingredient is from 0.001% to 80% by weight, preferably from 0.01 to 50% by weight and most preferably from 0.01 to 15% by weight.

For use in treating crop plants, the rate of application of the active ingredients of this invention may be in the range of 0.1 g to 4000 g per hectare, desirably from 5 g to 600 g per hectare, more desirably from 10 g to 300 g per hectare.

In the treatment of seed, the application rates of the active ingredients are generally from 0.1 g to 10 kg per 100 kg of seed, preferably from 1 g to 1 kg per 100 kg of seed, in particular from 1 g to 250 g per 100 kg of seed, in particular from 50 g to 150 g per 100 kg of seed.

The present invention is now illustrated in further detail by the following examples which are not intended to limit the invention to them.

I. PREPARATION EXAMPLES

Products were characterized by HPLC (High Performance Liquid Chromatography Mass Spectrometry). HPLC was carried out using an analytic RP-18 column (Chromolith Speed ROD from Merck KgaA, Germany) which was operated at 40° C. Acetonitrile with 0.1% by volume of a trifluoroacetic acid/water mixture and 0.1% by volume of trifluoroacetic acid served as mobile phase; flow rate: 1.8 mL/min and injection volume: 2 μl.

Example 1

[2-(4-Chloro-phenyl)-7-trifluoromethyl-quinazolin-4-yl]ethylamine (I-99)

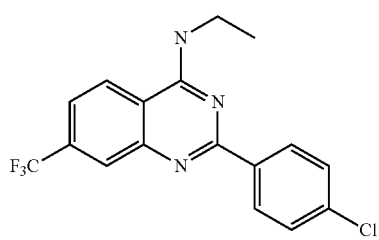

I-99

1.1 2-(4-Chlorophenyl)-7-trifluoromethyl-3H-quinazolin-4-one:

To a stirred suspension of 2-amino-4-(trifluoromethyl) benzamide (33.6 g, 0.16 mol) in water (750 mL) was added dropwise 4-chlorobenzaldehyde. Iron trichloride hexahydrate (133 g) was then added in portions. The reaction mixture was then heated at reflux for 24 h. After allowing the suspension to cool to room temperature, the precipitate was isolated by vacuum filtration washing with water (3×500 mL) and dried under vacuum (10 mbar, 50° C.). Yield=50 g, 94%; HPLC-mass spectrometry (LC-MS): 3.7 min, 325 (M⁺).

1.2 4-Chloro-2-(4-chloro-phenyl)-7-trifluoromethylquinazoline

To a stirred suspension of 2-(4-chlorophenyl)-7-trifluoromethyl-3H-quinazolin-4-one (50 g, 0.15 mol) in dioxane (400 mL) was added dropwise phosphorus oxychloride (43 mL, 0.46 mol). The suspension was then heated at reflux for 2 h then allowed to cool to room temperature and evaporated under reduced pressure. The remaining solid was dissolved in dioxane (1 L) and an aqueous solution of sodium hydroxide (50 mL, 10% weight/weight (w/w)) was added dropwise maintaining the internal temperature≤10° C.). Water (1 L) was then added to the resultant suspension followed by the dropwise addition of a further quantity of aqueous sodium hydroxide (90 mL, 10% w/w). The precipitate was isolated by vacuum filtration washing with water (3×500 mL) and dried under vacuum (10 mbar, 50° C.). Yield=49 g, 93%; LC-MS: 4.7 min, 343 (M⁺); ¹H NMR (dimethylsulfoxide (DMSO)-$d_6$) δ 7.68 (d, 2 H, J=8.9 Hz), 8.12 (dd, 1 H, J=8.9, 1.8 Hz), 8.48-8.54 (m, 4 H).

1.3 [2-(4-Chloro-phenyl)-7-trifluoromethyl-quinazolin-4-yl]ethylamine

To a stirred solution of 4-chloro-2-(4-chloro-phenyl)-7-trifluoromethylquinazoline (52.0 g, 0.15 mol) in THF (400 mL) at 0° C. was added dropwise a solution of ethylamine (0.45 mol, 230 mL, 2 M in THF. The ice-bath was then removed and the reaction mixture was allowed to stir at room temperature for 1 h. The reaction mixture was concentrated under reduced pressure then partitioned between ethyl acetate (400 mL) and water (400 mL) removing any undissolved solid by vacuum filtration. The filtrate was concentrated to approximately 200 mL and the resultant precipitate was removed by vacuum filtration. The filtrate was again concentrated to approximately 100 mL volume and the resultant precipitate was removed by vacuum filtration. Finally the filtrate was cooled to 0° C. upon which [2-(4-chloro-phenyl)-7-trifluoromethyl-quinazolin-4-yl]ethylamine precipitated from solution. The precipitate (30 g) was isolated by vacuum filtration and dried under vacuum (10 mbar, 50° C.). A second amount of the precipitate of equal purity (19.6 g) was obtained following concentration of the filtrate to approximately 50 mL volume, cooling to 0° C., filtration and drying under vacuum. Combined yield=49.6 g, 93%; LC-MS: 2.9 min, 352 (M⁺); ¹H NMR (DMSO-$d_6$): δ 1.38 (t, 1 H, J=7 Hz), 3.77-3.85 (m, 2 H), 7.46 (d, 2 H, J=8.7 Hz), 7.64 (dd, 1 H, J=8.3, 1.8 Hz), 7.72-7.78 (br s, 1 H), 8.09 (s, 1 H), 8.17 (d, 1 H, J=8.3 Hz), 8.59 (d, 2 H, J=8.7 Hz).

Example 2

[2-(4-Trifluoromethylphenyl)-7-trifluoromethyl-quinazolin-4-yl]ethylamine (I-209)

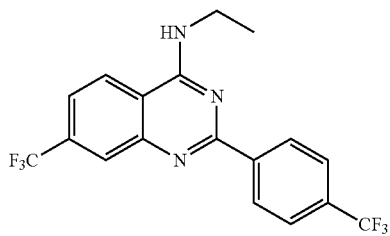

I-209

2.1 7-Trifluoromethyl-1H-quinazoline-2,4-dione

2-Amino-4-trifluoromethylbenzoic acid (25.0 g, 122 mmol) and urea (75.0 g, 1.2 mol) were combined and heated at 200° C. while stirring. After 1 h, the reaction mixture was allowed to cool to 100° C. and water (100 mL) was added. The reaction mixture was then allowed to cool to room temperature and the solid was isolated by vacuum filtration washing with water (500 mL). The solid was then dried under vacuum (10 mbar, 50° C.). Yield=24 g, 86%; LC-MS: 2.1 min, 230 ($M^+$); $^1$H NMR (DMSO-$d_6$) δ 7.44 (s, 1 H) 7.47 (d, 1 H), 8.07 (d, 1 H), 11.43 (br s, 1 H), 11.56 (br s, 1 H).

2.2 (2-Chloro-7-trifluoromethyl-quinazolin-4-yl)ethylamine

To a stirred suspension of 7-trifluoromethyl-1H-quinazoline-2,4-dione (25 g, 0.11 mol) and N,N-dimethylaniline (13.1 g, 0.11 mol) at 0° C. was added phosphorus oxychloride (101 mL, 1.1 mol) and the reaction mixture was heated at reflux for 6 h. The reaction mixture was allowed to cool to room temperature then concentrated under reduced pressure. The resultant solid was dissolved in THF (50 mL) then cooled to 0° C. and a solution of ethylamine (10 mL, 2 molar in THF) was added dropwise with stirring. After 2 h, the reaction mixture was concentrated under reduced pressure, diluted with water (250 mL) and extracted with ethyl acetate (2×150 mL). The combined organic layers were dried over MgSO$_4$, filtered and concentrated under reduced pressure. Yield=14 g, 47%; LC-MS: 3.1 min, 276 ($M^+$); $^1$H NMR (DMSO-$d_6$): δ 1.26 (apparent t, 3 H, J=7 Hz), 3.57 (ddd, 2H, J=12.7, 7.3, 5.6 Hz), 7.84 (dd, 1 H, J=8.7, 1.6 Hz), 7.93 (s, 1 H), 8.49 (d, 1 H, J=8.7 Hz), 9.05 (apparent t, 1 H, J=5 Hz).

2.3 [2-(4-Trifluoromethylphenyl)-7-trifluoromethyl-quinazolin-4-yl]ethylamine A solution of (2-chloro-7-trifluoromethyl-quinazolin-4-yl)ethylamine (276 mg, 1.00 mmol), p-trifluoromethylphenylboronic acid (285 mg, 1.50 mmol), tetrakis(triphenylphosphine)palladium (116 mg, 0.10 mmol) and sodium carbonate (0.21 g, 2.0 mmol) in dimethoxyethane/water (3 mL, 2:1) was heated at 80° C. for 16 h. The reaction mixture was then concentrated under reduced pressure, diluted with water (50 mL) and extracted with CH$_2$Cl$_2$ (3×25 mL). The combined organic layers were dried over MgSO$_4$, filtered, and concentrated under reduced pressure. Purification by flash chromatography using cyclohexane:ethyl acetate (4:1) as solvent afforded [2-(4-trifluoromethylphenyl)-7-trifluoromethyl-quinazolin-4-yl]ethylamine. Yield=0.20 g, 52%; LC-MS: 3.2 min, 385 ($M^+$); $^1$H NMR (DMSO-$d_6$): δ 1.34 (t, 3 H, J=7.2 Hz), 3.68-3-78 (m, 2 H), 7.82 (dd, 1 H, J=8.6, 1.7 Hz), 7.88 (d, 2 H, J=8.1 Hz), 8.07 (s, 1 H), 8.50 (d, 1 H, J=8.6 Hz), 8.67 (d, 2 H, J=8.1 Hz), 8.70-8.76 (m, 1 H).

Example 3

[2-(4-Chlorophenyl)-5,6,difluoro-7-trifluoromethylquinazolin-4-yl]ethylamine (I-401)

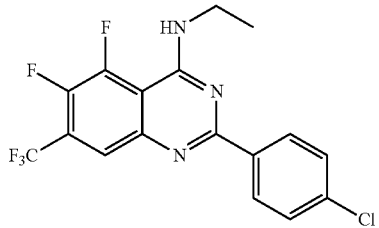

I-401

3.1 2,3-Difluoro-6-iodo-4-trifluoromethylbenzoic acid

A suspension of 2,3-difluoro-4-trifluoromethylbenzoic acid (1.00 g, 4.42 mmol), palladium (II) acetate (0.199 g, 0.88 mmol) and N-iodosuccinimide (1.19 g, 5.31 mmol) in dimethylformamide (10 mL) were heated at 100° C. for 2 d. The reaction mixture was then concentrated under reduced pressure, diluted with ethyl acetate (100 mL) and washed with water (3×25 mL). The organic layer was dried over MgSO$_4$, filtered and concentrated under reduced pressure to afford a brown solid (1.53) g which was used without further purification. LC-MS: 2.6 min, 353 ($M^+$).

3.2 2-(4-Chlorophenyl)-5,6-difluoro-7-trifluoromethyl-3H-quinazolin-4-one

A suspension of crude 2,3-difluoro-6-iodo-4-trifluoromethylbenzoic acid (1.00 g), 4-chlorobenzamide hydrochloride (0.814 g, 4.26 mmol), copper (I) iodide (0.108 g), caesium carbonate (1.85 g, 5.68 mmol) in dimethylformamide (8 mL) were stirred under nitrogen at room temperature for 1 week. The reaction mixture was then diluted with ethyl acetate (100 mL) and washed with hydrochloric acid (1 M, 25 mL) and water (25 mL). The organic phase was dried over MgSO$_4$, filtered and concentrated under reduced pressure (0.98 g). The reaction was repeated with crude 2,3-difluoro-6-iodo-4-trifluoromethylbenzoic acid (0.50 g) to afford an additional portion (0.57 g) of the quinazolin-4-one. LC-MS: 3.6 min, 361 ($M^+$).

3.3 4-chloro-2-(4-chlorophenyl)-5,6-difluoro-7-trifluoromethylquinazoline

To a suspension of the above quinazolin-4-one (1.50 g) in dioxane (45 mL) was added phosphorus oxychloride (3.9 mL, 41 mmol) and the resultant solution was heated at reflux for 16 h. The reaction mixture was then concentrated under reduced pressure to afford a gummy solid which was used without further purification.

3.4 [2-(4-Trifluoromethylphenyl)-5,6,difluoro-7-trifluoromethylquinazolin-4-yl]ethylamine A suspension of the above crude quinazoline and ethylamine (2 M in THF, 25 mL) was stirred at room temperature for 16 h. The reaction mixture was then concentrated under reduced pressure, diluted with ethyl acetate (75 mL) and washed with water (25 mL), aqueous sodium carbonate (25 mL) and water (25 mL). The organic phase was dried over MgSO$_4$, filtered and concentrated under reduced pressure to afford a crystalline solid. Recrystallization from hot cyclohexane:ethyl acetate (4:1) afforded [2-(4-chlorophenyl)-5,6,difluoro-7-trifluoromethylquinazolin-4-yl]ethylamine. Yield=0.10 g, 6% over 4 steps. LC-MS: 4.6 min, 388 (M$^+$); $^1$H NMR (tetrahydrofuran (THF)-d$_6$): δ 1.38 (apparent t, J=7 Hz, 3 H), 3.79-3.87 (m, 2 H), 7.47 (apparent d, J=8.8 Hz, 2 H), 7.51-7.59 (broad s, 1 H), 7.96 (dd, J=6.2, 1.4 Hz, 1 H), 8.54 (apparent d, J=8.8 Hz, 2 H).

Compounds of formula I prepared according to the above mentioned method together with their physico-chemical data are compiled below in Tables E, F and G. The corresponding physico-chemical data (LC/MS) wherein t$_R$ is retention time in minutes and M is the mass of respective molecular ion are listed in the Tables.

In Table E, compounds are of the general formula:

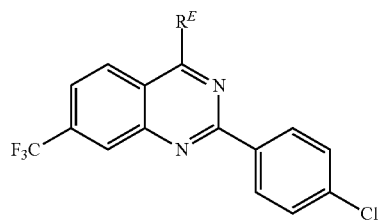

wherein R$^E$ is a mono- or dialkylamino derivative:
R$^E$ is

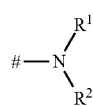

and # denotes the binding site to the remainder

TABLE E

| I | R$^E$ | LC/MS |
|---|---|---|
| I-1 | (structure) | t$_R$: 3.751'<br>M = 470.9 |
| I-2 | (structure) | t$_R$: 3.672'<br>M = 437.9 |
| I-3 | (structure) | t$_R$: 3.591'<br>M = 451.9 |
| I-4 | (structure) | t$_R$: 3.742'<br>M = 437.9 |
| I-5 | (structure) | t$_R$: 2.532'<br>M = 380.8 |
| I-6 | (structure) | t$_R$: 3.057'<br>M = 439.9 |
| I-7 | (structure) | t$_R$: 4.068'<br>M = 447.9 |
| I-8 | cyclopropylamino | t$_R$: 3.183'<br>M = 364.1 |
| I-9 | (structure) | t$_R$: 3.678'<br>M = 461.6 |
| I-10 | cyclopentylamino | t$_R$: 3.421'<br>M = 391.8 |
| I-11 | #-CH$_2$CH$_2$OCH$_2$CH$_3$ | t$_R$: 3.073'<br>M = 396.0 |
| I-12 | (structure) | t$_R$: 3.464'<br>M = 440.0 |
| I-13 | (structure) | t$_R$: 3.083'<br>M = 410.0 |
| I-14 | (structure) | t$_R$: 2.507'<br>M = 409.1 |
| I-15 | (structure) | t$_R$: 4.063'<br>M = 418.8 |

TABLE E-continued

| I | R^E | LC/MS |
|---|-----|-------|
| I-16 | (1,1-dimethylprop-2-ynyl)amino | $t_R$: 3.355'<br>M = 389.8 |
| I-17 | (2-methylpentyl)amino | $t_R$: 3.592'<br>M = 407.8 |
| I-18 | N-(cyanomethyl)-N-propylamino | $t_R$: 3.91'<br>M = 404.8 |
| I-19 | (2-methylsulfonylethyl)amino | $t_R$: 2.974'<br>M = 429.8 |
| I-20 | N-ethylacetamido | $t_R$: 4.559'<br>M = 393.8 |
| I-21 | (2-oxotetrahydrothiophen-3-yl)amino | $t_R$: 3.395'<br>M = 423.8 |
| I-22 | (6,6-dimethylbicyclo[3.1.1]heptan-2-yl)methylamino | $t_R$: 4.275'<br>M = 459.9 |
| I-23 | (2-oxopropyl)amino | $t_R$: 3.286'<br>M = 379.8 |
| I-24 | (3-tert-butoxy-2-methylbutyl)amino | $t_R$: 3.812'<br>M = 465.9 |
| I-25 | (2-neopentyloxypropyl)amino | $t_R$: 3.932'<br>M = 451.9 |
| I-26 | (1-methoxymethyl-2,2-dimethylpropyl)amino | $t_R$: 3.174'<br>M = 423.8 |
| I-27 | (amidinomethyl)amino | $t_R$: 2.746'<br>M = 379.8 |
| I-28 | benzyl | $t_R$: 3.520'<br>M = 414.1 |
| I-29 | propyl | $t_R$: 3.330'<br>M = 366.1 |
| I-30 | cyclohexyl | $t_R$: 3.524'<br>M = 406.0 |
| I-31 | #-CH$_2$C(CH$_3$)$_3$ | $t_R$: 3.461'<br>M = 394.1 |
| I-32 | tert-butyl hydrazinecarboxylate | $t_R$: 3.541'<br>M = 439.0 |
| I-33 | (3-hydroxybutyl)amino | $t_R$: 2.731'<br>M = 396.0 |
| I-34 | (1,5-dimethylhexyl)amino | $t_R$: 3.908'<br>M = 436.1 |
| I-35 | (2-diisopropylaminoethyl)amino | $t_R$: 2.831'<br>M = 451.1 |
| I-36 | (2-acetamidoethyl)amino | $t_R$: 2.560'<br>M = 409.0 |
| I-37 | (2-methylbutyl)amino | $t_R$: 3.457'<br>M = 394.0 |
| I-38 | #-CH$_2$CH$_2$OCH$_3$ | $t_R$: 2.897'<br>M = 382.0 |
| I-39 | (4-tert-butoxycarbonylaminobutyl)amino | $t_R$: 3.201'<br>M = 495.1 |

TABLE E-continued
| I | R^E | LC/MS |
|---|---|---|
| I-40 | 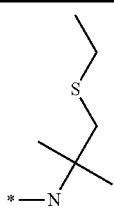 | $t_R$: 3.796'<br>M = 439.9 |
| I-41 | 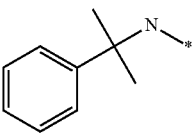 | $t_R$: 3.499'<br>M = 441.9 |
| I-42 | 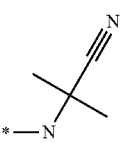 | $t_R$: 3.584'<br>M = 390.8 |
| I-43 | 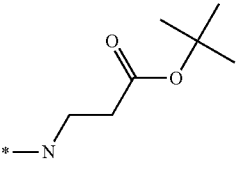 | $t_R$: 3.415'<br>M = 451.9 |
| I-44 | 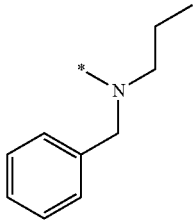 | $t_R$: 3.755'<br>M = 455.9 |
| I-45 | 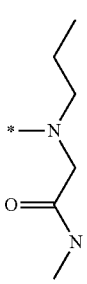 | $t_R$: 2.881'<br>M = 436.9 |
| I-46 | #-CH$_2$cyclopentyl | $t_R$: 3.437'<br>M = 405.8 |
| I-47 | 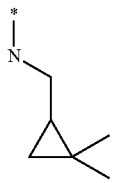 | $t_R$: 3.442'<br>M = 405.9 |
| I-48 | 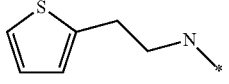 | $t_R$: 3.383'<br>M = 433.9 |
| I-49 | 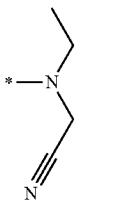 | $t_R$: 3.711'<br>M = 390.8 |
| I-50 | 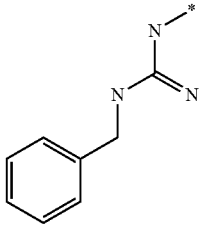 | $t_R$: 3.816'<br>M = 455.9 |
| I-51 | 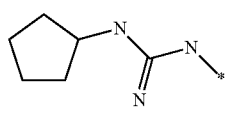 | $t_R$: 3.821'<br>M = 433.8 |
| I-52 | 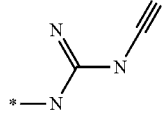 | $t_R$: 4.003'<br>M = 390.7 |
| I-53 | 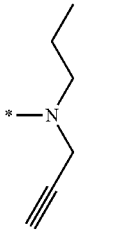 | $t_R$: 3.968'<br>M = 403.8 |
| I-54 | 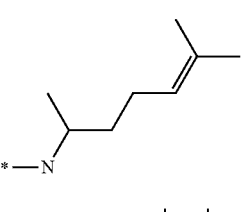 | $t_R$: 3.862'<br>M = 433.9 |
| I-55 | 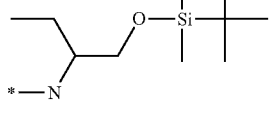 | $t_R$: 4.333'<br>M = 510.1 |
| I-56 | 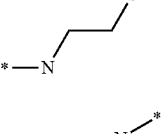 | $t_R$: 3.176'<br>M = 398.0 |
| I-57 |  | $t_R$: 2.885'<br>M = 424.0 |

TABLE E-continued

| I | R^E | LC/MS |
|---|-----|-------|
| I-58 | (CH3-S-CH2-C(CH3)2-N*) | t_R: 3.645'<br>M = 425.9 |
| I-59 | (tert-butyl-C(CH3)2-N*) | t_R: 3.794'<br>M = 435.9 |
| I-60 | (diisopropyl-CH-N*) | t_R: 3.593'<br>M = 421.9 |
| I-61 | (isopropyl-CH(CH3)-N*) | t_R: 3.358'<br>M = 393.8 |
| I-62 | (3-ethylpentan-3-yl-N*) | t_R: 3.704'<br>M = 407.9 |
| I-63 | (HO-C(CH3)2-CH(CH3)-N*) | t_R: 3.021'<br>M = 409.8 |
| I-64 | (cyclopropyl-phenyl-CH-N*) | t_R: 3.54'<br>M = 453.9 |
| I-65 | (2-oxopyrrolidin-1-yl-CH(CH3)-CH2-N*) | t_R: 2.83'<br>M = 448.9 |
| I-66 | (MeO2C-CH2-N(propyl)*) | t_R: 3.551'<br>M = 437.8 |
| I-67 | (2-methyl-1,3-dioxolan-2-yl-CH(CH3)-N*) | t_R: 3.292'<br>M = 437.8 |
| I-68 | (4-methyl-2,6,7-trioxabicyclo[2.2.2]octan-1-yl-CH2-N*) | t_R: 2.895'<br>M = 465.9 |
| I-69 | (MeO2C-CH(phenyl)-N*) | t_R: 4.078'<br>M = 471.9 |
| I-70 | (cyclohexyl-CH(CH3)-CH2-CH2-N*) | t_R: 4.222'<br>M = 461.9 |
| I-71 | #-NCH2cyclopropyl | t_R: 3.214'<br>M = 378.0 |
| I-72 | (2-ethylbutyl-N*) | t_R: 3.646'<br>M = 408.1 |
| I-73 | (isobutyl-N*) | t_R: 3.328'<br>M = 380.0 |
| I-74 | (neopentyl-CH2-N*) | t_R: 3.624'<br>M = 408.1 |
| I-75 | #-N-cyclobutyl | t_R: 3.272'<br>M = 378.0 |
| I-76 | #-NH2 | t_R: 2.652'<br>M = 324.0 |
| I-77 | (3-pentyl-N*) | t_R: 3.417'<br>M = 394.0 |

TABLE E-continued

| I | R^E | LC/MS |
|---|-----|-------|
| I-78 | #-N-allyl | $t_R$: 3.116'<br>M = 364.0 |
| I-79 | *-N-CH2-CH(OEt)2 | $t_R$: 3.359'<br>M = 440.0 |
| I-80 | *-N-CH2CH2CH2-OMe | $t_R$: 2.978'<br>M = 396.0 |
| I-81 | 3-aminotetrahydrofuran | $t_R$: 2.801'<br>M = 394.0 |
| I-82 | *-N-CH(Me)-CH(OMe)2 | $t_R$: 3.028'<br>M = 426.0 |
| I-83 | *-N-CH2-CH(OMe)2 | $t_R$: 2.920'<br>M = 412.0 |
| I-84 | *-N-CH(Me)-(2-methyl-1,3-dioxan-2-yl) | $t_R$: 3.389'<br>M = 451.9 |
| I-85 | *-N-C(Me)2-CH2CH3 (tert-amyl) | $t_R$: 3.422'<br>M = 393.8 |
| I-86 | *-N-CH2-(2,2-diethylcyclopropyl) | $t_R$: 3.725'<br>M = 433.9 |
| I-87 | *-N-CH2CH2-Ph | $t_R$: 3.432'<br>M = 427.) |
| I-88 | *-N-CH2-(2,2-dichlorocyclopropyl) | $t_R$: 3.443'<br>M = 446./ |
| I-89 | *-N-C(=NH)-N(Me)2 | $t_R$: 3.025'<br>M = 393.8 |
| I-90 | *-N-O-Me | $t_R$: 4.21'<br>M = 353.7 |
| I-91 | *-N-CH2-(1,3-dioxolan-2-yl) | $t_R$: 3.088'<br>M = 409.7 |
| I-92 | *-N-CH2-C(=O)-C(Me)3 | $t_R$: 3.529'<br>M = 421.9 |
| I-93 | *-N-CH2CH2CH2-O-CH2-C(Me)3 | $t_R$: 3.9'<br>M = 451.9 |
| I-94 | *-N-CH(Me)-CH=CH-Me | $t_R$: 3.519'<br>M = 391.8 |
| I-95 | *-N-CH2CH2-C(=O)-OMe | $t_R$: 3.069'<br>M = 409.8 |
| I-96 | *-N-CH2CH2-CH(Me)-CH2-(1,3-dioxolan-2-yl) | $t_R$: 3.29'<br>M = 465.9 |
| I-97 | *-N-CH2-CH(Me)-CH2-O-C(Me)3 | $t_R$: 3.795'<br>M = 451.9 |
| I-98 | *-N-CH2-C(=O)-N(OMe) | $t_R$: 2.66'<br>M = 409.8 |

TABLE E-continued
| I | $R^E$ | LC/MS |
|---|---|---|
| I-99 |  | $t_R$: 3.130'<br>M = 352.1 |
| I-100 | 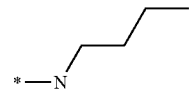 | $t_R$: 3.357'<br>M = 380.0 |
| I-101 | 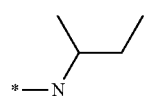 | $t_R$: 3.298'<br>M = 380.0 |
| I-102 | 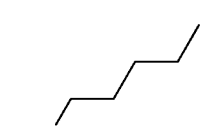 | $t_R$: 3.527'<br>M = 394.0 |
| I-103 | 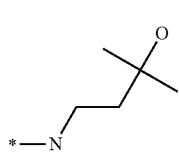 | $t_R$: 2.800'<br>M = 410.0 |
| I-104 | 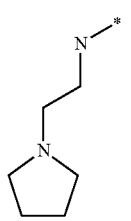 | $t_R$: 2.586'<br>M = 421.0 |
| I-105 | 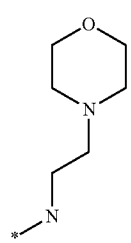 | $t_R$: 2.508'<br>M = 437.0 |
| I-106 | 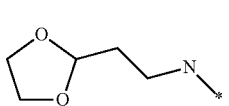 | $t_R$: 2.841'<br>M = 424.0 |
| I-107 | 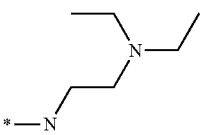 | $t_R$: 2.561'<br>M = 423.1 |
| I-108 | 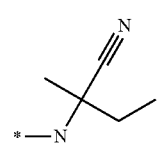 | $t_R$: 3.933'<br>M = 404.8 |
| I-109 | 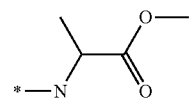 | $t_R$: 3.209'<br>M = 409.8 |
TABLE E-continued
| I | $R^E$ | LC/MS |
|---|---|---|
| I-110 |  | $t_R$: 2.945'<br>M = 338.1 |
| I-111 | 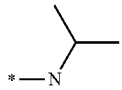 | $t_R$: 3.280'<br>M = 366.1 |
| I-112 | 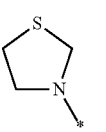 | $t_R$: 3.48'<br>M = 395.8 |
| I-113 | 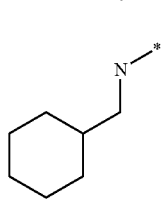 | $t_R$: 3.713'<br>M = 420.1 |
| I-114 | 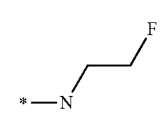 | $t_R$: 2.888'<br>M = 370.0 |
| I-115 | 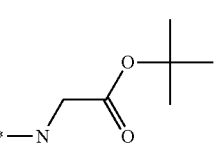 | $t_R$: 3.533'<br>M = 437.8 |
| I-116 | 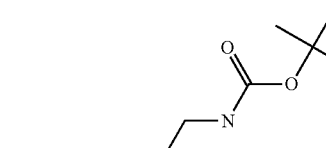 | $t_R$: 3.404'<br>M = 509.1 |
| I-117 | 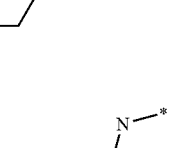 | $t_R$: 3.040'<br>M = 408.0 |
| I-118 | 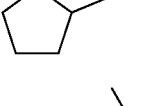 | $t_R$: 3.492'<br>M = 408.1 |
| I-119 | 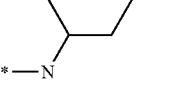 | $t_R$: 3.217'<br>M = 412.0 |
| I-120 | 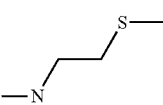 | $t_R$: 3.101'<br>M = 400.0 |

TABLE E-continued

| I | R^E | LC/MS |
|---|---|---|
| I-121 | (2-ethoxyethyl)aminopropyl group, *—N— | t_R: 3.043'  M = 410.0 |
| I-122 | 3-cyano-2-methylbutan-2-yl amino, *—N— | t_R: 3.528'  M = 404.8 |
| I-123 | 3,3-dimethylbutan-2-yl amino, *—N— | t_R: 3.489'  M = 407.9 |
| I-124 | 3-hydroxybutan-2-yl amino, *—N— | t_R: 2.772'  M = 395.8 |
| I-125 | 3-ethylpent-1-yn-3-yl amino, *—N— | t_R: 3.682'  M = 417.9 |
| I-126 | Boc-aminopropyl amino, *—N— | t_R: 3.207'  M = 480.9 |
| I-127 | N-methylguanidino, *—N— | t_R: 3.388'  M = 379.8 |
| I-128 | 2-ethyl-1,3-dioxolan-2-yl ethyl amino | t_R: 3.485'  M = 451.9 |
| I-129 | methyl alaninate, *—N— | t_R: 3.209'  M = 409.8 |
| I-130 | 1-morpholinopropan-2-yl amino, *—N— | t_R: 2.585'  M = 450.9 |
| I-131 | 1-(methylthio)propan-2-yl amino, *—N— | t_R: 3.207'  M = 411.9 |
| I-132 | N-ethyl-N-(2-(methylamino)-2-oxoethyl) amino | t_R: 2.675'  M = 422.8 |
| I-133 | (2-methylcyclopropyl)methyl amino | t_R: 3.295'  M = 391.8 |
| I-134 | N-acetylguanidino | t_R: 3.743'  M = 407.8 |
| I-135 | N-phenylguanidino | t_R: 4.034'  M = 441.8 |
| I-136 | dicyclopropylmethyl amino | t_R: 3.551'  M = 417.9 |
| I-137 | N-ethyl-N-propargyl amino | t_R: 3.721'  M = 389.8 |
| I-138 | 2-oxo-2-phenylethyl amino | t_R: 3.509'  M = 441.8 |
| I-139 | 3-(cyclohexyloxy)propyl amino | t_R: 3.833'  M = 463.93 |

TABLE E-continued

| I | R^E | LC/MS |
|---|---|---|
| I-140 | (N-methyl-cyclohexyloxy-propyl-amine) | $t_R$: 3.896'<br>M = 463.9 |
| I-141 | (2-(2-methoxyethoxy)ethylamine) | $t_R$: 3.038'<br>M = 425.8 |
| I-142 | (2-acetoxyethylamine) | $t_R$: 3.073'<br>M = 409.8 |
| I-143 | (2,5-dimethoxy-tetrahydrofuran-3-ylmethylamine) | $t_R$: 3.219'<br>M = 467.9 |
| I-144 | (1-(4-methyl-1,3-dioxolan-2-yl)-2-methylbutylamine) | $t_R$: 3.619'<br>M = 493.9 |
| I-145 | (2,5-dimethoxy-2,5-dihydrofuran-2-ylmethylamine) | $t_R$: 3.271'<br>M = 465.9 |
| I-146 | (ethyl 2-(thiophen-3-yl)-2-aminoacetate) | $t_R$: 4.146'<br>M = 491.9 |
| I-147 | (3-chlorobutan-2-ylamine) | $t_R$: 3.632'<br>M = 414.3 |
| I-148 | (4-chloro-but-2-ynylamine) | $t_R$: 3.562'<br>M = 410.2 |
| I-149 | (1-(4-methyl-1,3-dioxan-2-yl)-2-methylpropyl-aminomethyl) | $t_R$: 3.932'<br>M = 493.9 |
| I-150 | (3-methoxypropyl-amine) | $t_R$: 2.663'<br>M = 465.9 |
| I-151 | (2,2-difluoroethylamine) | $t_R$: 3.392'<br>M = 388.0 |
| I-152 | (3,3,3-trifluoropropylamine) | $t_R$: 3.428'<br>M = 420.0 |
| I-153 | (thiophen-2-ylmethylamine) | $t_R$: 3.308'<br>M = 420.0 |
| I-154 | (2,2,2-trifluoroethylamine) | $t_R$: 3.807'<br>M = 406.0 |
| I-155 | (norbornylmethylamine) | $t_R$: 3.700'<br>M = 432.1 |
| I-156 | (N,N-dimethylethylenediamine) | $t_R$: 2.471'<br>M = 395.0 |
| I-157 | (isoamylamine) | $t_R$: 3.482'<br>M = 394.0 |
| I-158 | (2-methyl-1,1-dioxo-tetrahydrothiophen-2-ylamine) | $t_R$: 3.152'<br>M = 455.9 |
| I-159 | (1,1,1-trifluoropropan-2-ylamine) | $t_R$: 3.972'<br>M = 419.7 |

TABLE E-continued

| I | R$^E$ | LC/MS |
|---|---|---|
| I-160 | (1,1-dimethylallyl)amino | t$_R$.: 3.552' M = 391.8 |
| I-161 | (1-phenylpropyl)amino | t$_R$.: 3.558' M = 441.9 |
| I-162 | (1-cyclopropylethyl)amino | t$_R$.: 3.296' M = 391.8 |
| I-163 | (1-(thiophen-3-yl)ethyl)amino | t$_R$.: 3.397' M = 433.9 |
| I-164 | ((2-phenylcyclopropyl)methyl)amino | t$_R$.: 3.49' M = 453.9 |
| I-165 | ((2-ethylcyclopropyl)methyl)amino | t$_R$.: 3.432' M = 405.85 |
| I-166 | (2-(phenylamino)propyl)amino | t$_R$.: 3.331' M = 456.9 |
| I-167 | (3-methoxybutyl)amino | t$_R$.: 3.221' M = 409.8 |
| I-168 | (2-isopropoxyethyl)amino | t$_R$.: 3.165' M = 409.8 |
| I-169 | (2-methylallyl)amino | t$_R$.: 3.855' M = 377.8 |
| I-170 | (cyclobutylmethyl)amino | t$_R$.: 3.298' M = 391.8 |
| I-171 | (N-methoxycarbamimidoyl)amino | t$_R$.: 3.823' M = 395.8 |
| I-172 | (methyl valinate)amino | t$_R$.: 3.911' M = 437.8 |
| I-173 | ((1,3-dioxolan-2-yl)methylisobutyl)amino | t$_R$.: 3.402' M = 465.9 |
| I-174 | (2-(pentan-3-yloxy)propyl)amino | t$_R$.: 4.207' M = 479.9 |
| I-175 | ((2-methyl-1,3-dioxolan-4-yl)methyl)amino | t$_R$.: 3.181' M = 423.8 |
| I-176 | (4-methoxybutan-2-yl)amino | t$_R$.: 3.204' M = 409.8 |
| I-177 | ((E)-3-chloroallyl)amino | t$_R$.: 3.463' M = 398.2 |
| I-178 | (methyl serinate methyl ether)amino | t$_R$.: 3.075' M = 425.8 |
| I-179 | (ethyl alaninate)amino | t$_R$.: 3.609' M = 423.82 |

TABLE E-continued

| I | R^E | LC/MS |
|---|-----|-------|
| I-180 | | $t_R$: 3.733'<br>M = 479.9 |
| I-181 | | $t_R$: 4.32'<br>M = 461.9 |
| I-182 | | $t_R$: 3.434'<br>M = 375.8 |
| I-183 | | $t_R$: 3.74'<br>M = 479.9 |
| I-184 | | $t_R$: 3.776'<br>M = 479.9 |
| I-185 | | $t_R$: 3.471'<br>M = 423.9 |
| I-186 | | $t_R$: 3.518'<br>M = 391.8 |
| I-187 | | $t_R$: 3.894'<br>M = 455.9 |
| I-188 | | $t_R$: 2.469'<br>M = 410.8 |
| I-189 | | $t_R$: 2.469'<br>M = 410.8 |
| I-190 | | $t_R$: 3.699'<br>M = 414.3 |
| I-191 | | $t_R$: 3.224'<br>M = 395.8 |
| I-192 | | $t_R$: 3.253'<br>M = 376.8 |
| I-193 | | $t_R$: 3.331'<br>M = 361.7 |
| I-194 | | $t_R$: 3.188'<br>M = 404.0 |
| I-195 | | $t_R$: 3.452'<br>M = 394.0 |
| I-196 | | $t_R$: 3.132'<br>M = 438.0 |
| I-197 | | $t_R$: 3.698'<br>M = 407.9 |
| I-198 | | $t_R$: 3.882'<br>M = 417.9 |
| I-199 | | $t_R$: 4.081'<br>M = 445.9 |
| I-200 | | $t_R$: 3.755'<br>M = 407.9 |

In Table F, compounds are of the general formula:

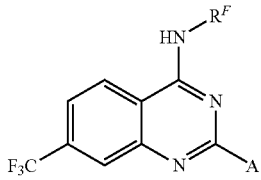

wherein $R^F$ in the above formula is $R^1$ or $R^2$
and $R^F$ is a propyl (Pr) or an ethyl (Et) and A as indicated in Table F:

TABLE F

| I | $R^F$ | A | LC/MS |
|---|---|---|---|
| I-201 | Et | 4-F-C6H4 | $t_R$: 2.654'<br>M = 335.8 |
| I-202 | Et | 4-Br-C6H4 | $t_R$: 3.123'<br>M = 398.1 |
| I-203 | Et | 2-CF3-pyridin-5-yl | $t_R$: 3.404'<br>M = 387.0 |
| I-204 | Pr | 2-CF3-pyridin-5-yl | $t_R$: 3.613'<br>M = 401.0 |
| I-205 | Pr | 3-F-4-Br-C6H3 | $t_R$: 2.778'<br>M = 428.8 |
| I-206 | Et | 3-F-4-Br-C6H3 | $t_R$: 2.922'<br>M = 414.2 |
| I-207 | Pr | 3-F-4-Br-C6H3 | $t_R$: 3.213'<br>M = 428.2 |
| I-208 | Et | 4-NO2-C6H4 | $t_R$: 3.109'<br>M = 363.0 |
| I-209 | Et | 4-CF3-C6H4 | $t_R$: 3.239'<br>M = 386.0 |
| I-210 | Et | 4-PhO-C6H4 | $t_R$: 3.255'<br>M = 410.1 |
| I-211 | Et | 2,4-bis(CF3)-C6H3 | $t_R$: 3.396'<br>M = 454.0 |
| I-212 | Et | 2-F-4-CF3-C6H3 | $t_R$: 3.147'<br>M = 404.0 |
| I-213 | Et | 2-Cl-4-CF3-C6H3 | $t_R$: 3.281'<br>M = 420.0 |
| I-214 | Et | 4-NH-C6H4 | $t_R$: 2.461'<br>M = 333.1 |
| I-215 | Et | 3-Cl-4-CF3-C6H3 | $t_R$: 3.598'<br>M = 420.0 |
| I-216 | Et | 4-NHC(O)CF3-C6H4 | $t_R$: 2.778'<br>M = 429.0 |
| I-217 | Et | 2-CF3-4-Cl-C6H3 | $t_R$: 3.29'<br>M = 419.8 |
| I-218 | Et | 2-F-4-Cl-C6H3 | $t_R$: 2.981'<br>M = 369.8 |
| I-219 | Pr | 2-F-4-Cl-C6H3 | $t_R$: 3.183'<br>M = 383.8 |

TABLE F-continued

| I | R$^F$ | A | LC/MS |
|---|---|---|---|
| I-220 | Et | 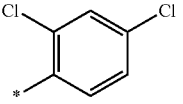 [SMILES: *c1ccc(Cl)cc1Cl] 2,4-dichlorophenyl | $t_R$: 3.101'<br>M = 386.2 |
| I-221 | Pr | 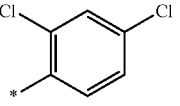 [SMILES: *c1ccc(Cl)cc1Cl] 2,4-dichlorophenyl | $t_R$: 3.279'<br>M = 400.2 |
| I-222 | Et | 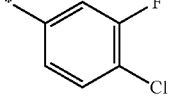 3-F,4-Cl-phenyl | $t_R$: 3.35'<br>M = 369.8 |
| I-223 | Pr | 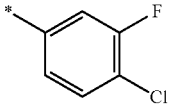 3-F,4-Cl-phenyl | $t_R$: 3.564'<br>M = 383.8 |
| I-224 | Et | 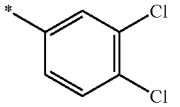 3,4-dichlorophenyl | $t_R$: 3.562'<br>M = 386.2 |
| I-225 | Pr | 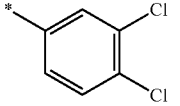 3,4-dichlorophenyl | $t_R$: 3.755'<br>M = 400.2 |
| I-226 | Et | 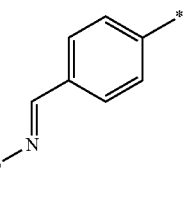 | $t_R$: 3.016'<br>M = 374.4 |
| I-227 | Pr | 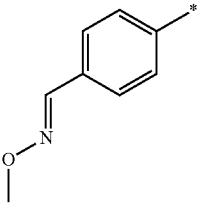 [SMILES: *c1ccc(/C=N/OC)cc1] | $t_R$: 3.201'<br>M = 388.4 |
| I-228 | Et | 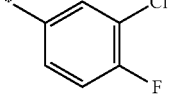 3-Cl,4-F-phenyl | $t_R$: 3.246'<br>M = 369.8 |
| I-229 | Pr | 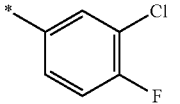 3-Cl,4-F-phenyl | $t_R$: 3.441'<br>M = 383.8 |
| I-230 | Et | 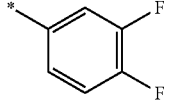 3,4-difluorophenyl | $t_R$: 3.05'<br>M = 353.3 |
| I-231 | Pr | 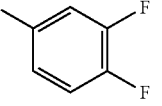 3,4-difluorophenyl | $t_R$: 3.251'<br>M = 367.3 |
| I-232 | Et | 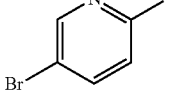 5-Br-pyridin-2-yl | $t_R$: 2.735'<br>M = 397.9 |
| I-233 | Pr | 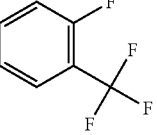 | $t_R$: 3.968'<br>M = 417.3 |
| I-234 | Et | 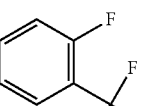 | $t_R$: 3.789'<br>M = 403.3 |
| I-235 | Pr | 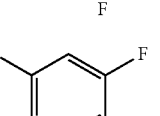 2,4-difluorophenyl | $t_R$: 2.945'<br>M = 367.6 |
| I-236 | Et | 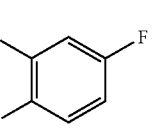 2,4-difluorophenyl | $t_R$: 2.768'<br>M = 353.3 |
| I-237 | Pr | 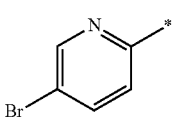 [SMILES: *c1ccc(Br)cn1] 5-Br-pyridin-2-yl | $t_R$: 3.052'<br>M = 411.2 |
| I-238 | Et | 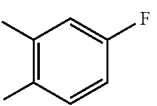 2-Cl,4-F-phenyl | $t_R$: 2.885'<br>M = 369.8 |
| I-239 | Pr | 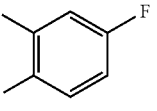 2-Cl,4-F-phenyl | $t_R$: 3.078'<br>M = 383.8 |
| I-240 | Et | 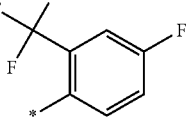 | $t_R$: 3.024'<br>M = 403.3 |
| I-241 | Pr | 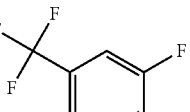 | $t_R$: 3.199'<br>M = 417.3 |
| I-242 | Pr | 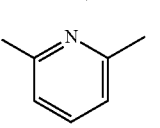 6-Me-pyridin-2-yl | $t_R$: 2.884'<br>M = 346.4 |

TABLE F-continued
| I | R^F | A | LC/MS |
|---|---|---|---|
| I-243 | Et | 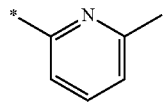 | $t_R$: 2.706'<br>M = 332.3 |
| I-244 | Pr | 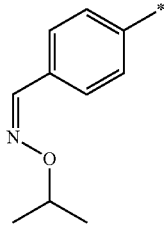 [SMILES: *c1ccc(/C=N\OC(C)C)cc1] | $t_R$: 3.377'<br>M = 416.4 |
| I-245 | Pr | 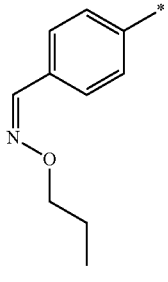 [SMILES: *c1ccc(/C=N\OCCC)cc1] | $t_R$: 3.6'<br>M = 416.4 |
| I-246 | Pr | 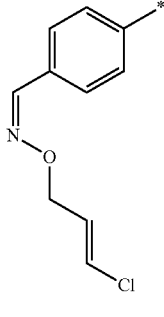 [SMILES: *c1ccc(/C=N\OC/C=C/Cl)cc1] | $t_R$: 3.6'<br>M = 448.8 |
| I-247 | Pr | 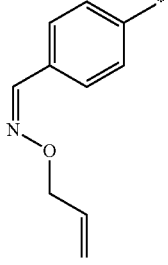 | $t_R$: 3.295'<br>M = 414.4 |
| I-248 | Pr | 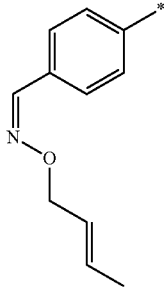 [SMILES: *c1ccc(/C=N\OC/C=C/C)cc1] | $t_R$: 3.458'<br>M = 428.4 |
| I-249 | Pr | 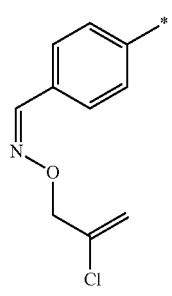 | $t_R$: 3.423'<br>M = 448.8 |
| I-250 | Pr | 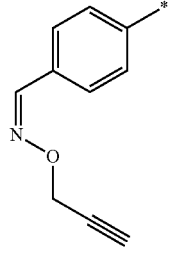 [SMILES: *c1ccc(/C=N\OCC#C)cc1] | $t_R$: 3.125'<br>M = 412.4 |
| I-251 | Pr | 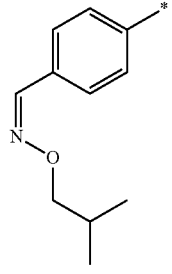 [SMILES: *c1ccc(/C=N\OCC(C)C)cc1] | $t_R$: 3.594'<br>M = 430.4 |
| I-252 | Pr | 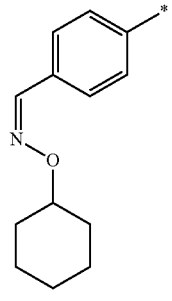 [SMILES: *c1ccc(/C=N\OC2CCCCC2)cc1] | $t_R$: 3.798'<br>M = 456.5 |
| I-253 | Pr | 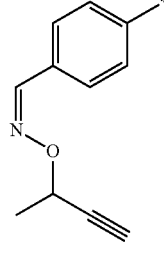 | $t_R$: 3.252'<br>M = 426.4 |

TABLE F-continued
| I | R$^F$ | A | LC/MS |
|---|---|---|---|
| I-254 | Pr | 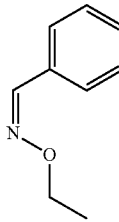 | $t_R$: 3.227'<br>M = 402.4 |
| I-255 | Et | 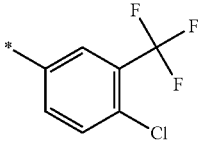 [SMILES: *c1ccc(Cl)c(C(F)(F)F)c1] | $t_R$: 4.007'<br>M = 419.8 |
| I-256 | Pr | 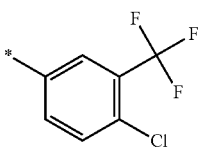 [SMILES: *c1ccc(Cl)c(C(F)(F)F)c1] | $t_R$: 4.146'<br>M = 433.8 |
| I-257 | Et |  | $t_R$: 4.094'<br>M = 454.2 |
| I-258 | Et | 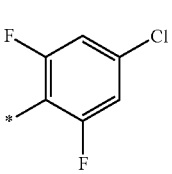 [SMILES: *c1c(F)cc(Cl)cc1F] | $t_R$: 4.252'<br>M = 387.7 |
| I-259 | Et | 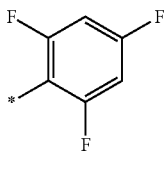 [SMILES: *c1c(F)cc(F)cc1F] | $t_R$: 4.044'<br>M = 371.3 |
| I-260 | Pr | 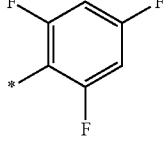 | $t_R$: 4.283'<br>M = 385.3 |
| I-261 | Et | 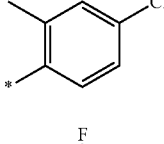 | $t_R$: 3.047'<br>M = 365.8 |
| I-262 | Et | 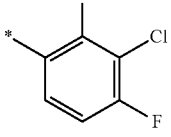 | $t_R$: 3.577'<br>M = 387.7 |
| I-263 | Pr | 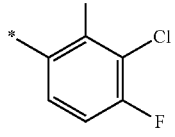 | $t_R$: 3.749'<br>M = 401.8 |
| I-264 | Pr | 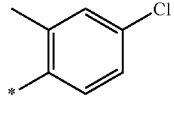 [SMILES: *c1ccc(Cl)cc1C] | $t_R$: 3.223'<br>M = 379.8 |
| I-265 | Pr | 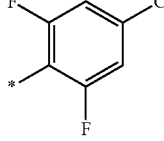 | $t_R$: 4.456'<br>M = 401.8 |
| I-266 | Et | 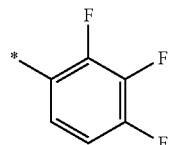 | $t_R$: 3.131'<br>M = 371.3 |
| I-267 | Pr | 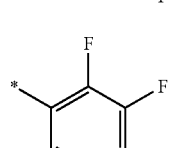 | $t_R$: 3.353'<br>M = 385.3 |
| I-268 | Pr | 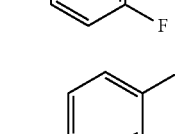 | $t_R$: 3.596'<br>M = 441.4 |
| I-269 | Pr | 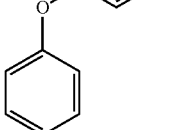 | $t_R$: 3.507'<br>M = 401.8 |
| I-270 | Pr | 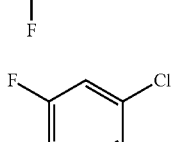 | $t_R$: 3.513'<br>M = 415.3 |
| I-271 | Pr | 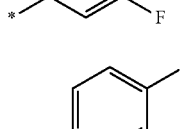 | $t_R$: 3.323'<br>M = 359.3 |

TABLE F-continued
| I | R^F | A | LC/MS |
|---|---|---|---|
| I-272 | Pr | 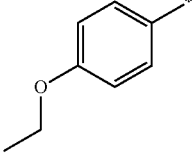 | $t_R$: 3.25'<br>M = 375.4 |
| I-273 | Pr | 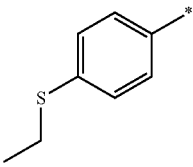 | $t_R$: 3.396'<br>M = 391.4 |
| I-274 | Pr | 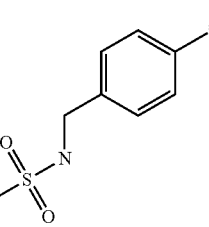 | $t_R$: 2.655'<br>M = 438.5 |
| I-275 | Pr | 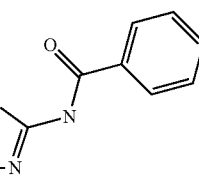 | $t_R$: 2.98'<br>M = 457.5 |
| I-276 | Pr | 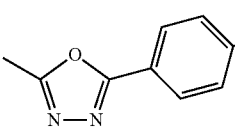 | $t_R$: 2.878'<br>M = 413.4 |
| I-277 | Pr | 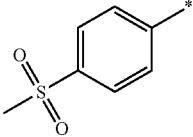 [SMILES: *c1ccc(S(C)(=O)=O)cc1] | $t_R$: 2.833'<br>M = 409.4 |
| I-278 | Pr | 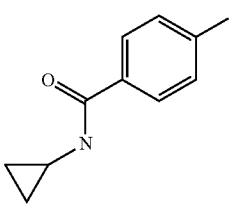 | $t_R$: 2.684'<br>M = 414.4 |
| I-279 | Pr | 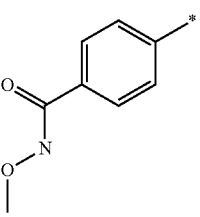 [SMILES: *c1ccc(C(=O)NOC)cc1] | $t_R$: 2.493'<br>M = 404.4 |
| I-280 | Pr | 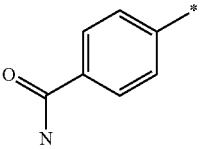 [SMILES: *c1ccc(C(N)=O)cc1] | $t_R$: 2.401'<br>M = 374.4 |
| I-281 | Pr | 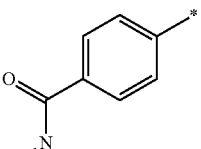 | $t_R$: 2.508'<br>M = 388.4 |
| I-282 | Pr | 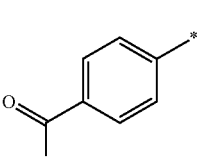 | $t_R$: 3.139'<br>M = 389.4 |
| I-283 | Pr | 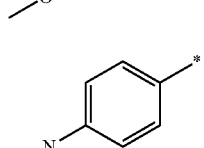 | $t_R$: 2.709'<br>M = 424.4 |
| I-284 | Pr | 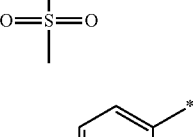 | $t_R$: 2.674'<br>M = 388.4 |
| I-285 | Pr | 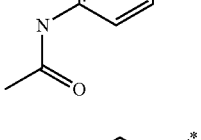 | $t_R$: 2.597'<br>M = 402.4 |
| I-286 | Pr | 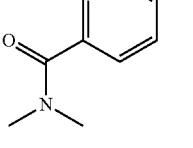 | $t_R$: 2.65'<br>M = 402.4 |
| I-287 | Pr | 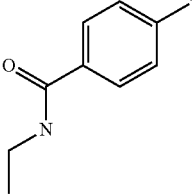 | $t_R$: 2.829'<br>M = 416.4 |

TABLE F-continued
| I | R^F | A | LC/MS |
|---|---|---|---|
| I-288 | Pr | 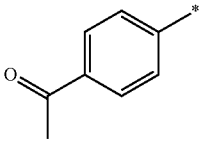 | $t_R$: 2.958'<br>M = 373.4 |
| I-289 | Pr | 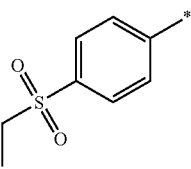 [SMILES: *c1ccc(S(=O)(=O)CC)cc1] | $t_R$: 2.983'<br>M = 423.4 |
| I-290 | Pr | 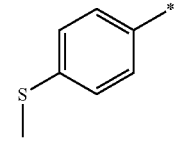 | $t_R$: 3.219'<br>M = 377.4 |
| I-291 | Pr | 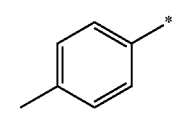 | $t_R$: 3.111'<br>M = 345.4 |
| I-292 | Pr | 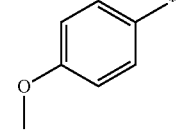 | $t_R$: 3.036'<br>M = 361.4 |
| I-293 | Pr | 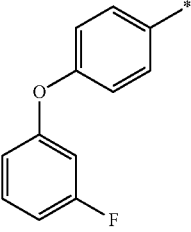 [SMILES: *c1ccc(Oc2cccc(F)c2)cc1] | $t_R$: 3.624'<br>M = 441.4 |
| I-294 | Pr | 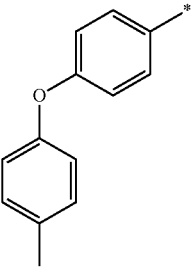 [SMILES: *c1ccc(Oc2ccc(C)cc2)cc1] | $t_R$: 3.767'<br>M = 437.5 |
| I-295 | Pr | 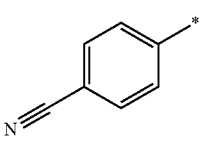 | $t_R$: 3.192'<br>M = 356.3 |
| I-296 | Pr | 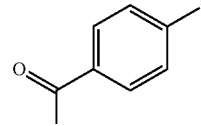 | $t_R$: 3.513'<br>M = 468.4 |
| I-297 | Pr | 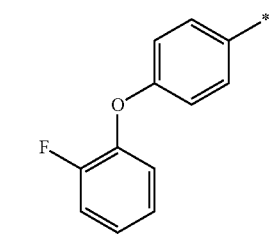 [SMILES: *c1ccc(Oc2ccccc2F)cc1] | $t_R$: 3.508'<br>M = 441.4 |
| I-298 | Pr | 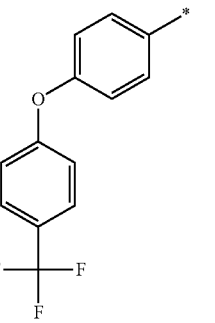 | $t_R$: 3.847'<br>M = 491.4 |
| I-299 | Pr | 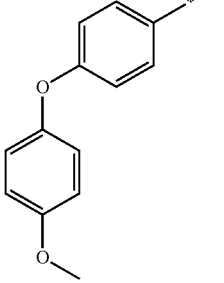 | $t_R$: 3.528'<br>M = 453.5 |
| I-300 | Pr | 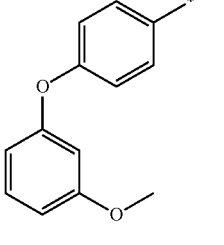 | $t_R$: 3.561'<br>M = 453.5 |
| I-301 | Pr | 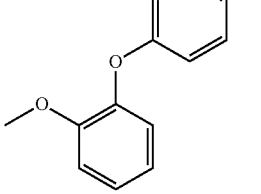 | $t_R$: 3.473'<br>M = 453.5 |

TABLE F-continued

| I | R^F | A | LC/MS |
|---|-----|---|-------|
| I-302 | Pr | 4-(3-(trifluoromethyl)phenoxy)phenyl | $t_R$: 3.791'<br>M = 491.4 |
| I-303 | Pr | 4-(3-(trifluoromethoxy)phenoxy)phenyl | $t_R$: 3.86'<br>M = 507.4 |
| I-304 | Pr | 4-(4-(trifluoromethoxy)phenoxy)phenyl | $t_R$: 3.83'<br>M = 507.4 |
| I-305 | Et | 4-chloro-2,5-difluorophenyl | $t_R$: 3.308'<br>M = 387.7 |
| I-306 | Pr | 4-(phenylamino)phenyl | $t_R$: 3.458'<br>M = 422.4 |
| I-307 | Pr | 4-(2-methylthiazol-4-yl)phenyl | $t_R$: 3.237'<br>M = 428.5 |
| I-308 | Pr | 4-(5-methyl-1,2,4-oxadiazol-3-yl)phenyl | $t_R$: 3.083'<br>M = 413.4 |
| I-309 | Pr | 4-(oxazol-5-yl)phenyl | $t_R$: 2.942'<br>M = 398.4 |
| I-310 | Pr | 4-(3-(trifluoromethyl)-1H-pyrazol-1-yl)phenyl | $t_R$: 3.523'<br>M = 465.4 |
| I-311 | Pr | 4-(1H-pyrazol-1-yl)phenyl | $t_R$: 3.121'<br>M = 398.4 |
| I-312 | Pr | 4-(1H-1,2,4-triazol-1-yl)phenyl | $t_R$: 2.695'<br>M = 398.4 |
| I-313 | Pr | 4-(furan-2-yl)phenyl | $t_R$: 3.359'<br>M = 397.4 |
| I-314 | Pr | methyl 2-(4-methylenebenzyl)hydrazinecarboxylate | $t_R$: 2.731'<br>M = 431.4 |
| I-315 | Et | 4-(1-(ethoxyimino)ethyl)phenyl | $t_R$: 3.294'<br>M = 402.4 |

TABLE F-continued

| I | R^F | A | LC/MS |
|---|-----|---|-------|
| I-316 | Et | 4-[C(CH3)=N-OMe]-phenyl | $t_R$: 3.075'; M = 388.4 |
| I-317 | Pr | 4-[CH=N-NH-C(O)CH3]-phenyl | $t_R$: 2.611'; M = 415.4 |
| I-318 | Pr | 4-[CH=N-N(CH3)2]-phenyl | $t_R$: 3.184'; M = 401.4 |
| I-319 | Pr | 4-[CH=N-NH-C(O)O-tBu]-phenyl | $t_R$: 3.188'; M = 473.5 |
| I-320 | Pr | 4-[CH=N-NH-Ph]-phenyl | $t_R$: 3.532'; M = 449.5 |
| I-321 | Pr | 4-(pyrazol-3-yl)-phenyl | $t_R$: 3.501'; M = 397.4 |
| I-322 | Pr | 4-(imidazol-1-yl)-phenyl | $t_R$: 2.183'; M = 397.4 |
| I-323 | Pr | 4-(3,5-dimethylpyrazol-1-yl)-phenyl | $t_R$: 3.076'; M = 425.5 |
| I-324 | Pr | 4-[CH=N-NH-C(O)CH2-C≡CH]-phenyl | $t_R$: 2.668'; M = 440.4 |
| I-325 | Pr | 4-[CH=N-NH-C(O)CH2-Ph]-phenyl | $t_R$: 3.067'; M = 491.5 |
| I-326 | Pr | 4-[CH=N-NH-C(O)Pr]-phenyl | $t_R$: 2.922'; M = 457.5 |

TABLE F-continued

| I | R^F | A | LC/MS |
|---|---|---|---|
| I-327 | Pr | 4-(1-methyl-1H-pyrazol-4-yl)phenyl | $t_R$: 2.876'<br>M = 411.4 |
| I-328 | Pr | 4-(1-methyl-1H-pyrazol-4-yl)phenyl | $t_R$: 2.876'<br>M = 411.4 |
| I-329 | Pr | 4-[(E)-N-ethyl-N'-hydroxycarbamimidoyl]phenyl | $t_R$: 2.282'<br>M = 417.4 |
| I-330 | Pr | 4-[(E)-N'-hydroxy-N-isopropylcarbamimidoyl]phenyl | $t_R$: 2.132'<br>M = 403.4 |
| I-331 | Pr | 4-[(E)-N'-hydroxy-N-isopropylcarbamimidoyl]phenyl | $t_R$: 2.46'<br>M = 431.5 |
| I-332 | Pr | 4-[(E)-N'-hydroxy-N-propylcarbamimidoyl]phenyl | $t_R$: 2.476'<br>M = 431.5 |
| I-333 | Pr | 4-[(E)-N'-hydroxy-N-isobutylcarbamimidoyl]phenyl | $t_R$: 2.597'<br>M = 445.5 |
| I-334 | Pr | N'-[(E)-(4-methylphenyl)methylidene]pyridine-3-carbohydrazide | $t_R$: 2.334'<br>M = 478.4 |
| I-335 | Pr | 4-hydroxyphenyl | $t_R$: 2.678'<br>M = 347.3 |
| I-336 | Pr | phenyl | $t_R$: 2.867'<br>M = 331.3 |
| I-337 | Pr | 4-[(E)-(pyrrolidin-1-ylimino)methyl]phenyl | $t_R$: 3.392'<br>M = 427.5 |
| I-338 | Pr | 4-[(E)-N'-hydroxy-N-phenylcarbamimidoyl]phenyl | $t_R$: 2.763'<br>M = 465.5 |
| I-339 | Pr | 4-[(E)-N'-hydroxy-N-methoxycarbamimidoyl]phenyl | $t_R$: 2.182'<br>M = 419.4 |
| I-340 | Pr | 4-(pyridin-3-yloxy)phenyl | $t_R$: 2.527'<br>M = 424.4 |

TABLE F-continued

| I | R^F | A | LC/MS |
|---|---|---|---|
| I-341 | Pr | (4-substituted phenyl)-CH=N-NH-C(=O)-NH-CH2-CF3 | $t_R$: 3.043'<br>M = 498.4 |
| I-342 | Pr | benzo[1,3]dioxol-5-yl | $t_R$: 2.994'<br>M = 375.4 |
| I-343 | Pr | 2-(hydroxy)-4-fluorophenyl (ether linkage) | $t_R$: 4.077'<br>M = 365.3 |
| I-344 | Pr | 2,3-dihydrobenzofuran-5-yl | $t_R$: 3.11'<br>M = 373.4 |
| I-345 | Pr | 1H-indol-6-yl | $t_R$: 3.161'<br>M = 370.4 |
| I-346 | Pr | 1H-indazol-5-yl | $t_R$: 2.679'<br>M = 371.4 |
| I-347 | Pr | 4-(pyridin-4-ylcarbonyl-hydrazonomethyl)phenyl | $t_R$: 2.337'<br>M = 478.5 |
| I-348 | Pr | 4-(thiophen-2-ylcarbonyl-hydrazonomethyl)phenyl | $t_R$: 2.995'<br>M = 483.5 |
| I-349 | Pr | 4-(pyridin-2-ylcarbonyl-hydrazonomethyl)phenyl | $t_R$: 2.804'<br>M = 478.5 |
| I-350 | Pr | 4-(pyrazol-1-yl)phenyl | $t_R$: 2.974'<br>M = 397.4 |
| I-351 | Pr | 3-(isobutyl-NH-C(=O)-NH-N=CH-)phenyl | $t_R$: 3.144'<br>M = 472.5 |
| I-352 | Pr | 3-(CF3-CH2-NH-C(=O)-NH-N=CH-)phenyl | $t_R$: 3.062'<br>M = 498.4 |
| I-353 | Pr | 3-(phenyl-NH-C(=O)-NH-N=CH-)phenyl | $t_R$: 3.225'<br>M = 492.5 |

TABLE F-continued

| I | R^F | A | LC/MS |
|---|---|---|---|
| I-354 | Pr | (ethyl-NH-C(O)-NH-N=CH-(3-phenyl)-*) | $t_R$: 2.843' M = 444.5 |
| I-355 | Pr | (3-nitro-4-methylphenyl-*) | $t_R$: 3.483' M = 390.4 |
| I-356 | Pr | (3-(acetylamino)phenyl-*) | $t_R$: 2.749' M = 388.4 |
| I-357 | Pr | (3,5-dichlorophenyl-*) | $t_R$: 4.394' M = 400.2 |
| I-358 | Pr | (3,5-bis(trifluoromethyl)phenyl-*) | $t_R$: 4.769' M = 467.3 |
| I-359 | Pr | (2-methylphenyl-*) | $t_R$: 2.96' M = 345.4 |
| I-360 | Pr | (ethyl-NH-C(O)-NH-N=CH-(4-phenyl)-*) | $t_R$: 2.794' M = 444.5 |
| I-361 | Pr | (phenyl-NH-C(O)-NH-N=CH-(4-phenyl)-*) | $t_R$: 3.18' M = 492.5 |
| I-362 | Pr | (cyclopropyl-NH-C(O)-NH-N=CH-(4-phenyl)-*) | $t_R$: 2.789' M = 456.5 |
| I-363 | Pr | (isobutyl-NH-C(O)-NH-N=CH-(4-phenyl)-*) | $t_R$: 3.094' M = 472.5 |
| I-364 | Pr | (3-(methylsulfonyl)phenyl-*) | $t_R$: 2.751' M = 409.4 |
| I-365 | Pr | (3-((tert-butoxycarbonylamino)methyl)phenyl-*) | $t_R$: 3.27' M = 460.5 |
| I-366 | Pr | (3-vinylphenyl-*) | $t_R$: 3.155' M = 357.3 |

TABLE F-continued

| I | R^F | A | LC/MS |
|---|---|---|---|
| I-367 | Pr | 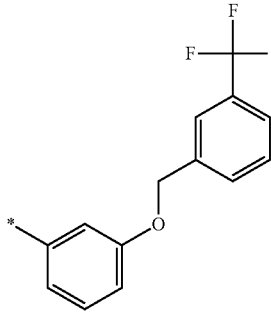 | $t_R$: 3.697'<br>M = 505.5 |
| I-368 | Pr | 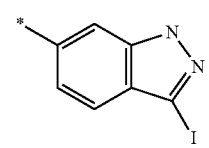 [SMILES: *c1ccc2c(I)n[nH]c2c1] | $t_R$: 3.222'<br>M = 497.3 |
| I-369 | Pr | 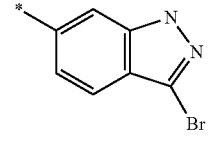 | $t_R$: 3.199'<br>M = 450.3 |
| I-370 | Pr | 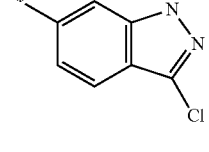 | $t_R$: 3.227'<br>M = 405.8 |
| I-371 | Pr | 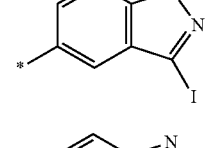 | $t_R$: 3.055'<br>M = 497.3 |
| I-372 | Pr | 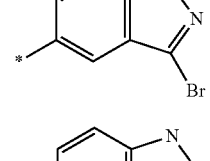 | $t_R$: 3.032'<br>M = 450.3 |
| I-373 | Pr | 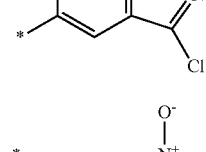 | $t_R$: 3.01'<br>M = 405.8 |
| I-374 | Pr | 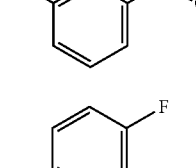 | $t_R$: 3.524'<br>M = 376.3 |
| I-375 | Pr | 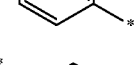 | $t_R$: 2.956'<br>M = 349.3 |
| I-376 | Pr | 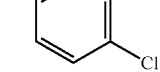 | $t_R$: 3.582'<br>M = 379.8 |

TABLE F-continued

| I | R^F | A | LC/MS |
|---|---|---|---|
| I-377 | Pr | 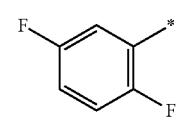 | $t_R$: 3.102'<br>M = 367.3196 |
| I-378 | Pr | 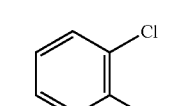 | $t_R$: 3.066'<br>M = 365.8 |
| I-379 | Pr | 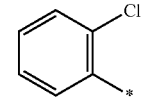 [SMILES: *c1ccccc1Cl] | $t_R$: 3.239'<br>M = 345.4 |
| I-380 | Pr | 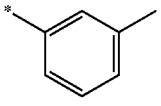 [SMILES: *c1cccc(C)c1] | $t_R$: 3.445'<br>M = 359.4 |
| I-381 | Pr | 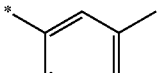 | $t_R$: 3.009'<br>M = 391.4 |
| I-382 | Pr | 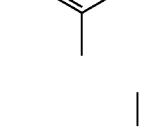 | $t_R$: 3.223'<br>M = 349.3 |
| I-383 | Pr | 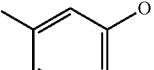 | $t_R$: 3.203'<br>M = 399.3 |
| I-384 | Pr | 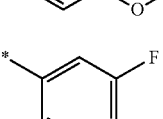 | $t_R$: 3.205'<br>M = 359.4 |
| I-385 | Pr | 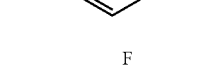 | $t_R$: 3.229'<br>M = 391.4 |
| I-386 | Pr | 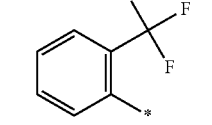 | $t_R$: 3.257'<br>M = 359.4 |
| I-387 | Pr | 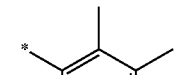 | $t_R$: 3.32'<br>M = 391.4 |

TABLE F-continued

| I | R^F | A | LC/MS |
|---|---|---|---|
| I-388 | Pr | 3-methoxyphenyl | $t_R$: 3.145' M = 361.4 |
| I-389 | Pr | 4-chloro-2-methoxyphenyl | $t_R$: 3.325' M = 395.8 |
| I-390 | Pr | 3-(methylthio)phenyl | $t_R$: 3.221' M = 377.4 |
| I-391 | Pr | biphenyl-3-yl | $t_R$: 3.529' M = 407.4 |
| I-392 | Pr | 3-(benzyloxy)phenyl | $t_R$: 3.471' M = 437.5 |
| I-393 | Pr | 3-((4-fluorobenzyl)oxy)phenyl | $t_R$: 3.498' M = 455.4 |
| I-394 | Pr | 3-((4-(trifluoromethoxy)benzyl)oxy)phenyl | $t_R$: 3.828' M = 521.5 |

In Table 3, further examples compounds of the general formula (I)

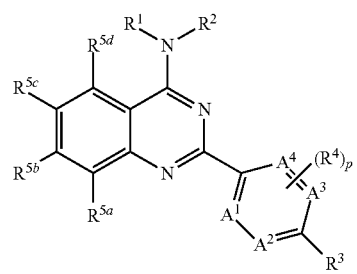

(I)

wherein $R^1$, $R^2$, $R^3$, $R^4$, $R^{5a}$, $R^{5b}$, $R^{5c}$, $R^{5d}$, $A^1$ and $A^2$ in each case have the meaning given in the corresponding line and wherein $A^3$ and $A^4$ are each CH.

TABLE 3

| I | $R^1$ | $R^2$ | $R^3$ | $R^4$ | $R^{5a}$ | $R^{5b}$ | $R^{5c}$ | $R^{5d}$ | $A^1$ | $A^2$ | LC/MS |
|---|---|---|---|---|---|---|---|---|---|---|---|
| I-395 | #-CH$_2$CN | H | Br | H | H | CF$_2$ | H | H | CH | CH | $t_R$: 3.383' M = 406.1 |
| I-396 | n-butyl | H | Br | H | H | CHF$_2$ | H | H | CH | CH | $t_R$: 3.300' M = 424.0 |
| I-397 | #-CH(CH$_2$CH$_3$)$_2$ | H | Br | H | H | CF$_3$ | H | H | CH | CH | $t_R$: 3.373' M = 438.0 |
| I-398 | cyclohexyl | H | Br | H | H | CF$_3$ | H | H | CH | CH | $t_R$: 3.486' M = 452.0 |
| I-399 | propargyl | H | Br | H | H | CF$_3$ | H | H | CH | CH | $t_R$: 3.119' M= 405.9 |
| I-400 | #-CH$_2$-thiophen-2-yl | H | Br | H | H | CF$_3$ | H | H | CH | CH | $t_R$: 3.378' M = 465.9 |
| I-401 | ethyl | H | Cl | H | H | CF$_3$ | F | F | CH | CH | $t_R$: 4.647' M = 387.7 |
| I-402 | H | H | CF$_3$ | A1-NH$_2$ | H | CF$_3$ | H | H | C | CH | $t_R$: 2.774' M = 372.7 |
| I-403 | 2-fluoro-ethyl | H | Br | H | H | CF$_3$ | H | H | CH | CH | $t_R$: 3.018' M = 414.2 |
| I-404 | 2,2,2-t$_R$ifluoroethyl | H | Br | H | H | CF$_3$ | H | H | CH | CH | $t_R$: 3.952' M = 450.2 |
| I-405 | #-CH$_2$C(O)OC(CH$_3$)$_3$ | H | Br | H | H | CF$_3$ | H | H | CH | CH | $t_R$: 3.722' M = 482.3 |
| I-406 | propyl | H | Cl | H | F | CF$_3$ | H | H | CH | CH | $t_R$: 4.848' M = 383.8 |
| I-407 | ethyl | H | Cl | H | H | 1,1,2,2-tetrafluoro-ethoxy | H | H | CH | CH | $t_R$: 3.144' M = 399.8 |
| I-408 | propargyl | H | Cl | H | H | 1,1,2,2-tetrafluoro-ethoxy | H | H | CH | CH | $t_R$: 3.135' M = 410.1 |
| I-409 | propyl | H | Cl | A1-F | Cl | CF$_3$ | H | H | C | CH | $t_R$: 4.544' M = 418.2 |
| I-410 | ethyl | H | Cl | H | H | CF$_3$ | CH$_3$ | H | CH | CH | $t_R$: 3.235' M = 365.8 |

TABLE 3-continued

| I | R$^1$ | R$^2$ | R$^3$ | R$^4$ | R$^{5a}$ | R$^{5b}$ | R$^{5c}$ | R$^{5d}$ | A$^1$ | A$^2$ | LC/MS |
|---|---|---|---|---|---|---|---|---|---|---|---|
| I-411 | propyl | H | Cl | H | H | CF$_3$ | NEt | H | CH | CH | t$_R$: 3.493' M = 408.8 |
| I-412 | cyclopropyl-methyl | H | Br | H | H | CF$_3$ | H | H | CH | CH | t$_R$: 3.165' M = 424.0 |
| I-413 | cyclopentyl | H | Br | H | H | CF$_3$ | H | H | CH | CH | t$_R$: 3.355' M = 436.0 |
| I-414 | #-CH$_2$CH(CH$_3$)$_2$ | H | Br | H | H | CF$_3$ | H | H | CH | CH | t$_R$: 3.272' M = 424.0 |
| I-415 | #-CH(CH$_3$)CH$_2$CH$_3$ | H | Br | H | H | CF$_3$ | H | H | CH | CH | t$_R$: 3.244' M = 424.0 |
| I-416 | #-CH(CH$_3$)$_2$ | H | Br | H | H | CF$_3$ | H | H | CH | CH | t$_R$: 3.098' M = 412.0 |
| I-417 | #-CH(=NH)-cyclopropyl | H | Br | H | H | CF$_3$ | H | H | CH | CH | t$_R$: 3.384' M = 437.0 |
| I-418 | #-CH(=NH)thien-2-yl | H | Br | H | H | CF$_3$ | H | H | CH | CH | t$_R$: 4.474' M = 477.3 |
| I-419 | ethyl | H | Cl | H | H | CF$_3$ | H | H | CH | CH | t$_R$: 3.213' M = 369.7 |
| I-420 | propyl | H | Cl | H | Cl | CF$_3$ | H | H | CH | CH | t$_R$: 4.711' M = 400.2 |
| I-421 | #-CH$_2$-cyclopropyl | H | Cl | H | H | CF$_3$ | OCH$_3$ | H | CH | CH | t$_R$: 3.412' M = 407.8 |
| I-422 | propyl | H | Cl | H | H | CF$_3$ | OCH$_3$ | H | CH | CH | t$_R$: 3.386' M = 395.8 |
| I-423 | propyl | H | Cl | H | H | CF$_3$ | CH$_3$ | H | CH | CH | t$_R$: 3.445' M = 379.8 |
| I-424 | benzyl | H | Br | H | H | CF$_3$ | H | H | CH | CH | t$_R$: 3.595' M = 458.1 |
| I-425 | ethyl | H | Cl | H | H | CHF$_2$ | H | H | CH | CH | t$_R$: 2.738' M = 333.8 |
| I-426 | #-CH$_2$-cyclohexyl | H | Br | H | H | CF$_3$ | H | H | CH | CH | t$_R$: 3.635' M = 466.0 |
| I-427 | allyl | H | Br | H | H | CF$_3$ | H | H | CH | CH | t$_R$: 3.070' M = 410.0 |
| I-428 | #-CH$_2$C(CH$_3$)3 | H | Br | H | H | CF$_3$ | H | H | CH | CH | t$_R$: 3.410' M = 440.0 |
| I-429 | #-CH$_2$-2-furyl | H | Br | H | H | CF$_3$ | H | H | CH | CH | t$_R$: 3.260' M = 450.0 |
| I-430 | propyl | H | Cl | H | CH$_3$ | CF$_3$ | H | H | CH | CH | t$_R$: 4.892' M = 379.8 |
| I-431 | propyl | H | Cl | A1-F | CH$_3$ | CF$_3$ | H | H | C | CH | t$_R$: 4.078' M = 397.8 |
| I-432 | propyl | H | F | H | H | C$_3$F$_7$ | H | H | CH | CH | t$_R$: 3.428' M = 449.3 |
| I-433 | methyl | methyl | F | H | H | CF$_3$ | H | H | CH | CH | t$_R$: 2.537' M = 335.8 |
| I-434 | #-CH(CH$_3$)$_2$ | cyclopropyl | F | H | H | CF$_3$ | H | H | CH | CH | t$_R$: 3.120' M = 389.8 |
| I-435 | H | H | Br | H | H | CF$_3$ | H | H | CH | CH | t$_R$: 2.759' M = 370.0 |
| I-436 | ethyl | H | Cl | H | H | OCF$_3$ | H | H | CH | CH | t$_R$: 2.966' M = 368.1 |
| I-437 | propyl | H | F | A2-Cl | Cl | CF$_3$ | H | H | CH | C | t$_R$: 4.516' M = 418.2 |
| I-438 | n-pentyl | H | Br | H | H | CF$_3$ | H | H | CH | CH | t$_R$: 3.474' M = 440.0 |
| I-439 | #-CH$_2$CH(CH$_2$CH$_3$)$_2$ | H | Br | H | H | CF$_3$ | H | H | CH | CH | t$_R$: 3.592' M = 452.0 |
| I-440 | 3,3,3-trifluoropropyl | H | Br | H | H | CF$_3$ | H | H | CH | CH | t$_R$: 3.366' M = 463.9 |
| I-441 | CH(=NH)phenyl | H | Br | H | H | CF$_3$ | H | H | CH | CH | t$_R$: 3.947' M = 473.0 |
| I-442 | #-CH(CH$_3$)CH(OCH$_3$)$_2$ | H | F | A1-F | H | CF$_3$ | H | H | C | CH | t$_R$: 2.967' M = 427.4 |
| I-443 | propyl | H | Cl | H | H | CF$_3$ | NSO$_2$CH$_3$ | H | CH | CH | t$_R$: 3.049' M = 458.9 |
| I-444 | propyl | H | Cl | H | H | CF$_3$ | NAc | H | CH | CH | t$_R$: 2.914' M = 422.8 |
| I-445 | ethyl | ethyl | F | H | H | CF$_3$ | H | H | CH | CH | t$_R$: 2.903' M = 363.8 |
| I-446 | 2,2-difluoroethyl | H | Br | H | H | CF$_3$ | H | H | CH | CH | t$_R$: 3.324' M = 431.9 |
| I-447 | ethyl | methyl | Br | H | H | CF$_3$ | H | H | CH | CH | t$_R$: 2.968' M = 410.0 |
| I-448 | #-NH(CO)OC(CH$_3$)$_3$ | H | Br | H | H | CF$_3$ | H | H | CH | CH | t$_R$: 3.694' M = 483.0 |
| I-449 | propyl | H | Cl | H | H | OCF$_3$ | H | H | CH | CH | t$_R$: 3.248' M = 382.0 |
| I-450 | CH(=NH)cyclohexyl | H | Br | H | H | CF$_3$ | H | H | CH | CH | t$_R$: 3.566' M = 477.3 |
| I-451 | propyl | H | Cl | H | H | CF$_3$ | I | H | CH | CH | t$_R$: 3.971' M = 491.7 |

II. Evaluation Of Pesticidal Activity

The activity of the compounds of formula I of the present invention can be demonstrated and evaluated by the following biological test.

B.1 Southern Armyworm (*Spodoptera eridania*, 2nd instar larvae)

The active compounds were formulated in cyclohexanone as a 10,0000 ppm solution supplied in 1.3 ml ABgene® tubes. These tubes were inserted into an automated electrostatic sprayer equipped with an atomizing nozzle and they served as stock solutions for which lower dilutions were made in 50% acetone: 50% water (v/v). A nonionic surfactant (Kinetic®) was included in the solution at a volume of 0.01% (v/v). Lima bean plants (variety Sieva) were grown 2 plants to a pot and selected for treatment at the 1$^{st}$ true leaf stage. Test solutions were sprayed onto the foliage by an automated electrostatic plant sprayer equipped with an atomizing spray nozzle. The plants were dried in the sprayer fume hood and then removed from the sprayer. Each pot was placed into perforated plastic bags with a zip closure. Ten to 11 armyworm larvae were placed into the bag and the bags zipped closed. Test plants were maintained in a growth room at at 25° C. and 20-40% relative humidity for 4 days, avoiding direct exposure to fluorescent light (24 hour photoperiod) to prevent trapping of heat inside the bags. Mortality and reduced feeding were assessed 4 days after treatment, compared to untreated control plants.

In this test, compounds I-1, I-2, I-3, I-4, I-5, I-8, I-10, I-11, I-13, I-16, I-17, I-21, I-23, I-28, I-29, I-30, I-31, I-37, I-38, I-40, I-41, I-46, I-47, I-49, I-53, I-54, I-56, I-57, I-58, I-60, I-61, I-63, I-64, I-67, I-71, I-72, I-73, I-74, I-75, I-77, I-78, I-79, I-80, I-82, I-83, I-84, a85, I-88, I-91, I-94, I-99, I-100, I-101, I-102, I-109, I-110, I-111, I-114, I-117, I-118, I-119, -a120, I-123, I-124, I-125, I-128, I-130, I-132, I-133, I-136, I-143, I-151, I-152, I-153, I-154, I-155, I-157, I-159, I-160, I-161, I-162, I-163, I-167, I-168, I-169, I-170, I-172, I-175, I-176, I-177, I-182, I-183, I-184, I-185, I-186, I-187, I-191, I-192, I-193, I-194, I-195, I-196, I-197, I-198, I-200, I-201, I-202, I-204, I-205, I-206, I-207, I-208, I-210, I-218, I-219, I-222, I-223, I-224, I-225, I-226, I-227, I-229, I-230, I-231, I-233, I-234, I-235, I-236, I-244, I-245, I-246, I-248, I-249, I-250, I-251, I-252, I-253, I-254, I-264, I-266, I-268, I-269, I-270, I-273, I-292, I-295, I-297, I-299, I-300, I-301, I-302, I-303, I-304, I-305, I-306, I-307, I-308, I-309, I-310, I-311, I-312, I-323, I-327, I-329, I-330, I-331, I-332, I-335, I-395, I-396, I-397, I-399, I-400, I-403, I-406, I-407, I-408, I-412, I-413, I-414, I-415, I-416, I-417, I-420, I-421, I-424, I-430, I-431, I-433, I-438, I-440, I-445, I-446, I-447 and I-451 at 300 ppm showed a mortality of at least 50% in comparison with untreated controls.

B.2 Silverleaf Whitefly (*Bemisia argentifolii*, adult)

The active compounds were formulated in cyclohexanone as a 10,0000 ppm solution supplied in 1.3 ml ABgene® tubes.

These tubes were inserted into an automated electrostatic sprayer equipped with an atomizing nozzle and they served as stock solutions for which lower dilutions were made in 50% acetone: 50% water (v/v). A nonionic surfactant (Kinetic®) was included in the solution at a volume of 0.01% (v/v). Cotton plants at the cotyledon stage (one plant per pot) were sprayed by an automated electrostatic plant sprayer equipped with an atomizing spray nozzle. The plants were dried in the sprayer fume hood and then removed from the sprayer. Each pot was placed into a plastic cup and 10 to 12 whitefly adults (approximately 3-5 days old) were introduced. The insects were collected using an aspirator and 0.6 cm, nontoxic Tygon® tubing (R-3603) connected to a barrier pipette tip. The tip, containing the collected insects, was then gently inserted into the soil containing the treated plant, allowing insects to crawl out of the tip to reach the foliage for feeding. Cups were covered with a reusable screened lid (150-micron mesh polyester screen PeCap from Tetko, Inc.). Test plants were maintained in a growth room at 25° C. and 20-40% relative humidity for 3 days, avoiding direct exposure to fluorescent light (24 hour photoperiod) to prevent trapping of heat inside the cup. Mortality was assessed 3 days after treatment, compared to untreated control plants.

In this test, compounds I-11, I-78, I-120, I-121, I-182, I-195, I-196, I-244, I-413 and I-442 at a test concentration of 500 ppm showed a mortality of at least 50% in comparison with untreated controls.

B.3 Colorado potato beetle (*Leptinotarsa decemlineata*, adult)

The active compounds were formulated in cyclohexanone as a 10,0000 ppm solution supplied in 1.3 ml ABgene® tubes. These tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v). Eggplants were grown 2 plants to a pot and were selected for treatment at the $1^{st}$ true leaf stage. Test solutions were sprayed onto the foliage by an automated electrostatic plant sprayer equipped with an atomizing spray nozzle. The plants were dried in the sprayer fume hood and then removed from the sprayer. The treated foliage was then cut and removed from the pot and placed in a 5-inch Petri dish lined with moistened filter paper. Five beetle larvae were introduced into each Petri dish and the dish was covered by a Petri dish lid. Petri dishes were maintained in a growth room at 25° C. and 20-40% relative humidity for 4 days, avoiding direct exposure to fluorescent light (24 hour photoperiod) to prevent trapping of heat inside the dishes. Mortality and reduced feeding were assessed 4 days after treatment, compared to untreated control plants.

In this test, compound I-201 at a test concentration of 300 ppm showed a mortality of at least 50% in comparison with untreated controls.

B.4 Diamondback moth (*Plutella xylostella*)

The active compound was dissolved at the desired concentration in a mixture of 1:1 (vol:vol) distilled water:acetone. The test solution was prepared at the day of use.

The activity against *Plutella xylostella* can be tested by the following experiments:

Leaves of Chinese cabbage were dipped in test solution and air-dried. Treated leaves were placed in petri dished lined with moist filter paper. Mortality was recorded 24, 72, and 120 hours after treatment.

In this test, compounds I-1, I-4, I-5, I-8, I-10, I-11, I-13, I-16, I-17, I-23, I-28, I-29, I-33, I-36, I-37, I-38, I-46, I-47, I-48, I-51, I-52, I-54, I-56, I-57, I-58, I-60, I-61, I-63, I-71, I-73, I-74, I-75, I-76, I-77, I-78, I-79, I-82, I-83, I-84, I-85, I-88, I-94, I-99, I-100, I-101, I-102, I-103, I-105, I-109, I-110, I-111, I-114, I-117, I-118, I-120, I-121, I-124, I-125, I-131, I-133, I-135, I-136, I-142, I-143, I-151, I-152, I-153, I-154, I-157, I-159, I-160, I-162, I-163, I-169, I-170, I-176, I-177, I-185, I-186, I-187, I-191, I-193, I-194, I-195, I-196, I-198, I-201, I-202, I-204, I-205, I-206, I-207, I-209, I-210, I-211, I-212, I-213, I-215, I-218, I-219, I-21, I-223, I-224, I-225, I-227, I-228, I-229, I-230, I-231, I-233, I-234, I-235, I-236, I-238, I-241, I-61, I-264, I-266, I-267, I-268, I-270, I-272, I-285, I-292, I-296, I-297, I-299, I-300, I-301, I-302, I-303, I-304, I-306, I-307, I-313, I-395, I-396, I-397, I-399, I-403 and I-404 at a test concentration of 500 ppm showed a mortality of at least 50% in comparison with untreated controls.

B.5 Orchid thrips (*Dichromothrips corbetti*)

*Dichromothrips corbetti* adults used for bioassay were obtained from a colony maintained continuously under laboratory conditions. For testing purposes, the test compound was diluted to a concentration of 300 ppm (wt compound: vol diluent) in a 1:1 mixture of acetone:water (vol:vol), plus 0.01% vol/vol Kinetic® surfactant. Thrips potency of each compound was evaluated by using a floral-immersion technique. Plastic petri dishes were used as test arenas. All petals of individual, intact orchid flowers were dipped into treatment solution and allowed to dry. Treated flowers were placed into individual petri dishes along with 10-15 adult thrips. The petri dishes were then covered with lids. All test arenas were held under continuous light and a temperature of about 28° C. for duration of the assay. After 4 days, the numbers of live thrips were counted on each flower, and along inner walls of each petri dish. The level of thrips mortality was extrapolated from pre-treatment thrips numbers.

In this test, compounds I-5, I-8, I-29, I-56, I-71, I-100, I-101, I-111, I-124, I-131, I-133, I-162, I-169, I-170, I-201, I-202, I-225, I-227, I-231, I-235, I-242, I-243, I-412, I-434 and I-445 at a test concentration of 500 ppm showed a mortality of at least 50% in comparison with untreated controls.

B.6 Vetch aphid (*Megoura viciae*)

For evaluating control of vetch aphid (*Megoura viciae*) through contact or systemic means the test unit consists of 24-well-microtiter plates containing broad bean leaf disks. The compounds were formulated using a solution containing 75% v/v water and 25% v/v DMSO. Different concentrations of formulated compounds were sprayed onto the leaf disks at 2.5 μl, using a custom built micro atomizer, at two replications. After application, the leaf disks were air-dried and 5-8 adult aphids placed on the leaf disks inside the microtiter plate wells. The aphids were then allowed to suck on the treated leaf disks and incubated at about 23±1° C. and about 50±5% relative humidity for 5 days. Aphid mortality and fecundity was then visually assessed.

In this test, compounds I-11, I-32, I-34, I-35, I-47, I-66, I-78, I-84, I-86, I-87, I-122, I-162, I-164, I-165, I-169, I-170, I-197, I-205, I-217, I-220, I-232, I-233, I-235, I-240, I-241, I-264, I-282, I-330, I-413, I-415, I-418 and I-425 at a test concentration of 800 ppm showed a mortality of at least 50%.

B.7 Green Peach Aphid (*Myzus persicae*, mixed life stages)

The active compounds were formulated in cyclohexanone as a 10,000 ppm solution supplied in tubes. The tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v).

Bell pepper plants at the first true-leaf stage were infested prior to treatment by placing heavily infested leaves from the main colony on top of the treatment plants. Aphids were allowed to transfer overnight to accomplish an infestation of 30-50 aphids per plant and the host leaves were removed. The infested plants were then sprayed by an automated electrostatic plant sprayer equipped with an atomizing spray nozzle. The plants were dried in the sprayer fume hood, removed, and then maintained in a growth room under fluorescent lighting in a 24-hr photoperiod at about 25° C. and about 20-40% relative humidity. Aphid mortality on the treated plants, relative to mortality on untreated control plants, was determined after 5 days.

In this test, compounds I-29, I-32, I-33, I-35, I-57, I-60, I-77, I-100, I-101, I-102, I-105, I-109, I-114, I-118, I-119, I-120, I-150, I-162, I-165, I-169, I-191, I-195, I-217, I-218, I-221, I-223, I-225, I-227, I-228, I-235, I-239, I-240, I-241, I-270, I-271, I-272, I-273, I-274, I-279, I-280, I-283, I-284, I-286, I-288, I-289, I-290, I-291, I-292, I-296, I-332, I-335, I-402, I-415, I-418, I-425, I-436 and I-448 at a test concentration of 800 ppm showed a mortality of at least 50%.

B.8 Boll weevil (*Anthonomus grandis*)

For evaluating control of boll weevil (*Anthonomus grandis*) the test unit consists of 24-well-microtiter plates containing an insect diet and 20-30 *A. grandis* eggs. The compounds were formulated using a solution containing 75% v/v water and 25% v/v DMSO. Different concentrations of formulated compounds were sprayed onto the insect diet at 20 µl, using a custom built micro atomizer, at two replications. After application, microtiter plates were incubated at about 23±1° C. and about 50±5% relative humidity for 5 days. Egg and larval mortality was then visually assessed.

In this test, compounds I-10, I-11, I-13, I-17, I-28, I-29, I-31, I-34, I-37, I-38, I-40, I-41, I-46, I-58, I-60, I-61, I-64, I-71, I-73, I-77, I-78, I-79, I-80, I-82, I-83, I-100, I-101, I-102, I-108, I-109, I-111, I-113, I-114, I-116, I-119, I-120, I-121, I-124, I-132, I-133, I-152, I-153, I-154, I-157, I-159, I-162, I-163, I-169, I-182, I-191, I-193, I-194, I-195, I-199, I-201, I-202, I-205, I-207, I-208, I-211, I-218, I-219, I-221, I-222, I-223, I-25, I-227, I-229, I-230, I-231, I-232, I-233, I-234, I-235, I-236, I-240, I-243, I-255, I-261, I-264, I-267, I-269, I-271, I-272, I-273, I-277, I-280, I-281, I-282, I-283, I-284, I-285, I-289, I-290, I-291, I-92, I-295, I-330, I-335, I-336, I-395, I-396, I-397, I-399, I-403, I-406, I-412, I-415, I-416, I-420, I-24, I-425, I-427, I-428, I-430, I-431, I-435, I-438 and I-449 at a test concentration of 800 ppm showed a mortality of at least 50%.

B. 9 Mediterranean fruitfly (*Ceratitis capitata*)

For evaluating control of Mediterranean fruitfly (*Ceratitis capitata*) the test unit consisted of microtiter plates containing an insect diet and 50-80 *C. capitata* eggs. The compounds were formulated using a solution containing 75% v/v water and 25% v/v DMSO. Different concentrations of formulated compounds were sprayed onto the insect diet at 5 µl, using a custom built micro atomizer, at two replications. After application, microtiter plates were incubated at about 28±1° C. and about 80±5% relative humidity for 5 days. Egg and larval mortality was then visually assessed.

In this test, compounds I-10, I-11, I-12, I-13, I-14, I-16, I-17, I-19, I-28, I-29, I-34, I-37, I-38, I-45, I-46, I-47, I-49, I-56, I-57, I-61, I-64, I-71, I-72, I-73, I-74, I-75, I-77, I-78, I-79, I-80, I-81, I-82, I-83, I-87, I-98, I-99, I-100, I-101, I-102, I-105, I-107, I-109, I-111, I-114, I-115, I-117, I-118, I-119, I-120, I-121, I-125, I-133, I-151, I-152, I-153, I-154, I-155, I-157, I-159, I-162, I-163, I-169, I-182, I-191, I-193, I-195, I-196, I-199, I-201, I-202, I-205, I-206, I-207, I-208, I-209, I-210, I-213, I-215, I-218, I-219, I-221, I-222, I-223, I-224, I-225, I-226, I-227, I-228, I-229, I-230, I-231, I-233, I-234, I-235, I-236, I-237, I-239, I-241, I-255, I-257, I-264, I-267, I-269, I-270, I-272, I-276, I-295, I-330, I-331, I-332, I-335, I-395, I-396, I-397, I-399, I-400, I-403, I-404, I-406, I-407, I-408, I-409, I-412, I-414, I-415, I-416, I-417, I-418, I-420, I-424, I-427, I-431, I-434, I-437, I-438, I-440, I-441, I-445, I-446, I-447, I-448 and I-449 at a test concentration of 800 ppm showed a mortality of at least 50%.

B.10 Tobacco budworm (*Heliothis virescens*)

For evaluating control of tobacco budworm (*Heliothis virescens*) the test unit consists of 96-well-microtiter plates containing an insect diet and 15-25 *H. virescens* eggs. The compounds were formulated using a solution containing 75% v/v water and 25% v/v DMSO. Different concentrations of formulated compounds were sprayed onto the insect diet at 10 µl, using a custom built micro atomizer, at two replications. After application, microtiter plates were incubated at about 28±1° C. and about 80±5% relative humidity for 5 days. Egg and larval mortality was then visually assessed.

In this test, compounds I-8, I-10, I-11, I-12, I-13, I-16, I-17, I-19, I-28, I-29, I-32, I-34, I-37, I-38, I-39, I-40, I-41, I-46, I-47, I-49, I-56, I-57, I-60, I-61, I-63, I-64, I-71, I-72, I-73, I-74, I-75, I-76, I-77, I-78, I-79, I-80, I-82, I-83, I-84, I-85, I-99, I-100, I-101, I-102, I-109, I-111, I-114, I-115, I-116, I-117, I-118, I-119, I-120, I-121, I-122, I-124, I-125, I-126, I-130, I-132, I-133, I-151, I-152, I-153, I-154, I-157, I-158, I-159, I-160, I-161, I-162, I-163, I-168, I-169, I-182, I-191, I-193, I-194, I-195, I-196, I-197, I-199, I-200, I-201, I-202, I-204, I-205, I-206, I-207, I-208, I-209, I-210, I-212, I-215, I-216, I-218, I-219, I-221, I-222, I-223, I-224, I-225, I-226, I-227, I-228, I-229, I-230, I-231, I-232, I-233, I-234, I-235, I-236, I-237, I-238, I-239, I-241, I-255, I-256, I-257, I-261, I-264, I-266, I-267, I-269, I-270, I-271, I-272, I-273, I-280, I-282, I-283, I-284, I-287, I-290, I-291, I-292, I-295, I-329, I-330, I-331, I-332, I-335, I-395, I-396, I-397, I-399, I-400, I-403, I-404, I-405, I-406, I-407, I-408, I-409, I-412, I-413, I-414, I-415, I-416, I-420, I-424, I-425, I-427, I-430, I-431, I-433, I-435, I-436, I-437, I-438, I-439, I-440, I-445, I-446, I-447, I-448, I-449 at a test concentration of 800 ppm showed a mortality of at least 50%.

We claim:

1. A method for controlling or combating invertebrate pests attack or infestation which method comprises treating the pests, their food supply, their habitat, their breeding ground, the plant, the plant propagation material, soil, area, material or environment in which the pests are growing or may grow, with a pesticidally effective amount of a compound of the formula (I)

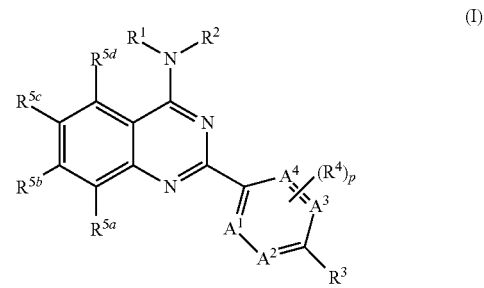

wherein $A^1, A^2, A^3$ and $A^4$ are N, NX or $CR^4$ wherein X is a lone pair or O, with the proviso that at most three of $A^1, A^2, A^3$ and $A^4$ are N or NX;

$R^1$, $R^2$ are selected independently from one another from the group consisting of hydrogen, CN, $NO_2$, $C_1$-$C_{10}$-alkyl, $C_3$-$C_8$-cycloalkyl, $C_2$-$C_{10}$-alkenyl, $C_2$-$C_{10}$-alkynyl,
    wherein the carbon atoms of the aforementioned aliphatic and cycloaliphatic radicals may be unsubstituted or substituted with one or more $R^6$;
    $Si(R^{11})_2R^{12}$, $OR^7$, $S(O)_mR^7$, $NR^8R^9$, $N=C(R^6)_2$, $C(=O)R^6$, $C(=S)R^6$, $C(=NR^8)R^6$
and a 3-, 4-, 5-, 6- or 7- membered heterocyclic ring, wherein said heterocyclic ring
    is saturated or partially saturated,
        comprises 1, 2 or 3 heteroatoms selected from the group consisting of oxygen, nitrogen and sulfur, wherein the nitrogen and/or the sulfur atom(s) may be oxidized,
    is unsubstituted or substituted with one to five $R^{10}$, and
    wherein one or two $CH_2$ groups in said heterocyclic ring may be replaced by one or two C=O groups;

$R^3$ is selected from the group consisting of hydrogen, halogen, cyano, azido, nitro, SCN, $SF_5$, $C_1$-$C_{10}$-alkyl, $C_3$-$C_8$-cycloalkyl, $C_2$-$C_{10}$-alkenyl, $C_2$-$C_{10}$-alkynyl,
    wherein the carbon atoms of the aforementioned aliphatic and cycloaliphatic radicals may be unsubstituted or substituted with one or more $R^6$;
    $Si(R^{11})_2R^{12}$, $OR^7$, $S(O)_mR^7$, $N(R^8)R^9$, $N=C(R^6)_2$, $C(=O)R^6$, $C(=S)R^6$, $C(=NR^8)R^6$, phenyl which may be substituted with 1, 2, 3, 4 or 5 radicals $R^{10}$;
and a 3-, 4-, 5-, 6- or 7-membered heterocyclic ring, wherein said heterocyclic ring
    is saturated or partially saturated,
        comprises 1, 2 or 3 heteroatoms or heteroatom groups selected from the group consisting of N, O, S, NO, SO and $SO_2$,
    is unsubstituted or substituted with one to five radicals $R^{10}$, and
    wherein one or two $CH_2$ groups in said heterocyclic ring may be replaced by one or two C=O groups;

each $R^4$ is selected independently from the group consisting of hydrogen, halogen, cyano, azido, nitro, SCN, $SF_5$, $C_1$-$C_{10}$-alkyl, $C_3$-$C_8$-cycloalkyl, $C_2$-$C_{10}$-alkenyl, $C_2$-$C_{10}$-alkynyl,
    wherein the carbon atoms of the aforementioned aliphatic and cycloaliphatic radicals may be unsubstituted or substituted with one or more $R^6$;
    $Si(R^{11})_2R^{12}$, $OR^7$, $S(O)_mR^7$, $N(R^8)R^9$, $N=C(R^6)_2$, $C(=O)R^6$, $C(=S)R^6$, $C(=NR^8)R^6$, $C(=O)N(R^8)R^9$, $C(=S)N(R^8)R^9$, phenyl which may be substituted with 1, 2, 3, 4 or 5 radicals $R^{10}$;
and a 3-, 4-, 5-, 6- or 7-membered heterocyclic ring, wherein said heterocyclic ring
    is saturated or partially unsaturated or aromatic,
        comprises 1, 2 or 3 heteroatoms or heteroatom groups selected from the group consisting of N, O, S, NO, SO and $SO_2$,
    is unsubstituted or substituted with one to five radicals $R^{10}$, and
    wherein one or two $CH_2$ groups in said saturated or partially saturated rings may be replaced by one or two C=O groups;
or two radicals $R^4$ bound on adjacent carbon atoms together form a group selected from the group consisting of —$CH_2CH_2CH_2CH_2$—, —CH=CH—CH=CH—, —N=CH—CH=CH—, —CH=N—CH=CH—, —N=CH—N=CH—, —$OCH_2CH_2CH_2$—, —OCH=$CHCH_2$—, —$CH_2OCH_2CH_2$—, —$OCH_2CH_2O$—, —$OCH_2OCH_2$—, —$CH_2CH_2CH_2$—, —CH=$CHCH_2$—, —$CH_2CH_2O$—, —CH=CHO—, —$CH_2OCH_2$—, —$CH_2C(=O)O$—, —C(=O)$OCH_2$—, —$O(CH_2)O$—, —$SCH_2CH_2CH_2$—, —SCH=$CHCH_2$—, —$CH_2SCH_2CH_2$—, —$SCH_2CH_2S$—, —$SCH_2SCH_2$—, —$CH_2CH_2S$—, —CH=CHS—, —$CH_2SCH_2$—, —$CH_2C(=S)S$—, —C(=S)$SCH_2$—, —$S(CH_2)S$—, —$CH_2CH_2NR^8$—, —$CH_2CH=N$—, —CH=CH—$NR^8$—, —OCH=N— and —SCH=N—,
wherein in each of the above group,
    one to five hydrogen atoms independently of each other may be replaced by one to five substituents selected from the group consisting of halogen, methyl, halomethyl, hydroxyl, methoxy and halomethoxy, or
    one or two $CH_2$ groups of the above groups may be replaced by one or two C=O groups;

$R^{5a}$ is selected from the group consisting of hydrogen, halogen, cyano, azido, nitro, SCN, $SF_5$, $C_1$-$C_{10}$-alkyl, $C_3$-$C_8$-cycloalkyl, $C_2$-$C_{10}$-alkenyl, $C_2$-$C_{10}$-alkynyl,
    wherein the carbon atoms of the aforementioned aliphatic and cycloaliphatic radicals may be unsubstituted or substituted with one or more $R^6$;
    $Si(R^{11})_2R^{12}$, $OR^7$, $S(O)_mR^7$, $N(R^8)R^9$, $N=C(R^6)_2$, $C(=O)R^6$, $C(=S)R^6$, $C(=NR^8)R^6$, phenyl which may be substituted with 1, 2, 3, 4 or 5 radicals $R^{10}$;
and a 3-, 4-, 5-, 6- or 7-membered heterocyclic ring, wherein said heterocyclic ring
    is saturated or partially unsaturated or aromatic,
        comprises 1, 2 or 3 heteroatoms or heteroatom groups selected from the group consisting of N, O, S, NO, SO and $SO_2$,
    is unsubstituted or substituted with one to five radicals $R^{10}$, and
    wherein one or two $CH_2$ groups in said saturated or partially saturated rings may be replaced by one or two C=O groups;
or $R^{5a}$ may form together with the adjacent carbon atom $R^{5b}$ a 5- or 6-membered ring which is at least substituted with one halogen;

$R^{5b}$ is selected from the group consisting of $C_1$-$C_6$-alkyl, $C_3$-$C_6$-cycloalkyl, $C_1$-$C_6$-alkoxy and $C_1$-$C_6$-cycloalkoxy, wherein each mentioned radical
    is substituted with at least one halogen,
    may be further partially or fully halogenated, and
    may be substituted with one to five radicals $R^6$;
or $R^{5b}$ may form together with the adjacent carbon atom $R^{5c}$ or $R^{5a}$ a 5- or 6-membered ring which is substituted with at least one halogen;

$R^{5c}$ is selected from the group consisting of hydrogen, halogen, cyano, azido, nitro, SCN, $SF_5$, $C_1$-$C_{10}$-alkyl, $C_3$-$C_8$-cycloalkyl, $C_2$-$C_{10}$-alkenyl, $C_2$-$C_{10}$-alkynyl,
    wherein the carbon atoms of the aforementioned aliphatic and cycloaliphatic radicals may be unsubstituted or substituted with one or more $R^6$;
    $Si(R^{11})_2R^{12}$, $OR^7$, $S(O)_mR^7$, $N(R^8)R^9$, $N=C(R^6)_2$, $C(=O)OR^7$, $C(=S)OR^7$, $C(=NR^8)R^6$, $C(=O)N(R^8)R^9$, $C(=S)N(R^8)R^9$, phenyl which may be substituted with 1, 2, 3, 4 or 5 radicals $R^{10}$;
and a 3-, 4-, 5-, 6- or 7-membered heterocyclic ring, wherein said heterocyclic ring
    is saturated, partially unsaturated or aromatic,
        comprises 1, 2 or 3 heteroatoms or heteroatom groups selected from the group consisting of N, O, S, NO, SO and $SO_2$, is unsubstituted or substituted with one to five radicals $R^{10}$, and
wherein one or two $CH_2$ groups in said saturated or partially saturated rings may be replaced by one or two C=O groups;
or $R^{5c}$ may form together with the adjacent carbon atom $R^{5b}$ or $R^{5d}$ a 5- or 6-membered ring which is substituted with at least one halogen in case of $R^{5b}$ being involved;
$R^{5d}$ is selected from the group consisting of hydrogen, halogen, cyano, azido, nitro, SCN, $SF_5$, $C_1$-$C_{10}$-alkyl, $C_3$-$C_8$-cycloalkyl, $C_2$-$C_{10}$-alkenyl, $C_2$-$C_{10}$-alkynyl,
wherein the carbon atoms of the aforementioned aliphatic and cycloaliphatic radicals may be unsubstituted or substituted with one or more $R^6$;
$Si(R^{11})_2R^{12}$, $OR^7$, $S(O)_mR^7$, $S(O)_mN(R^8)R^9$, $N(R^8)R^9$, $N=C(R^6)_2$, $C(=O)R^6$, $C(=S)R^6$, $C(=NR^8)R^6$, phenyl
which may be substituted with 1, 2, 3, 4 or 5 radicals $R^{10}$;
and a 3-, 4-, 5-, 6- or 7-membered heterocyclic ring, wherein said heterocyclic ring
is saturated, partially unsaturated or aromatic,
comprises 1, 2 or 3 heteroatoms or heteroatom groups selected from the group consisting of N, O, S, NO, SO and $SO_2$,
is unsubstituted or substituted with one to five radicals $R^{10}$, and
wherein one or two $CH_2$ groups in said saturated or partially saturated rings may be replaced by one or two C=O groups;
or $R^{5d}$ may form together with the adjacent carbon atom $R^{5c}$ or with $R^1$ or $R^2$ a 5- or 6-membered ring;
$R^6$ is selected independently from the group consisting of hydrogen, halogen, cyano, azido, nitro, SCN, $SF_5$, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_3$-$C_8$-cycloalkyl, $C_3$-$C_8$-cycloalkyl-$C_1$-$C_4$-alkyl, $C_2$-$C_6$-alkenyl, $C_2$-$C_6$-alkynyl,
wherein the carbon atom of the aforementioned aliphatic and cycloaliphatic radicals may be substituted with one or more $R^c$;
$Si(R^{11})_2R^{12}$, $OR^o$, $O(CO)R^c$, $O(CS)R^c$, $S(O)_mR^o$, $S(O)_mN(R'')_2$, $S(CO)R^c$, $S(CS)R^c$, $S(C=NR'')R^c$, $N(R'')_2$, $N(R'')C(=O)R^c$, $N(R'')C(=S)R^c$, $NS(O)_mR^o$, $N=C(R^c)_2$, $C(=O)R^c$, $C(=S)R^c$, $C(=NR'')R^c$, $C(=O)N(R'')_2$, $C(=S)N(R'')_2$, phenyl
which may be substituted with 1, 2, 3, 4 or 5 radicals $R^{10}$;
and a 3-, 4-, 5-, 6- or 7-membered heterocyclic ring, wherein said heterocyclic ring
is saturated, partially unsaturated or aromatic,
comprises 1, 2 or 3 heteroatoms or heteroatom groups selected from the group consisting of N, O, S, NO, SO and $SO_2$,
is unsubstituted or substituted with one to five radicals $R^{10}$, and
wherein one or two $CH_2$ groups in said saturated or partially saturated rings may be replaced by one or two C=O groups;
or two vicinally bound radicals $R^6$ together form a group selected from $=C(R^c)_2$, $=S(O)_mR^o$, $=S(O)_mN(R'')_2$, $=NR''$ and $=NN(R'')_2$;
$R^7$ is selected independently from the group consisting of hydrogen, cyano, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_3$-$C_8$-cycloalkyl, $C_3$-$C_8$-cycloalkyl-$C_1$-$C_4$-alkyl, $C_2$-$C_6$-alkenyl, $C_2$-$C_6$-alkynyl, wherein the carbon atom of the aforementioned aliphatic and cycloaliphatic radicals may be substituted with one or more $R^c$;
$Si(R^{11})_2R^{12}$, $OR^o$, $O(CO)R^c$, $O(CS)R^c$, $S(O)_mR^o$, $S(O)_mN(R'')_2$, $S(CO)R^c$, $S(CS)R^c$, $S(C=NR'')R^c$, $N(R'')_2$, $N(R'')C(=O)R^c$, $N(R'')C(=S)R^c$, $NS(O)_mR^o$, $N=C(R^c)_2$, $C(=O)R^c$, $C(=S)R^c$, $C(=NR'')R^c$, $C(=O)N(R'')_2$, $C(=S)N(R'')_2$, phenyl
which may be substituted with 1, 2, 3, 4 or 5 radicals $R^{10}$;
and a 3-, 4-, 5-, 6- or 7-membered heterocyclic ring, wherein said heterocyclic ring
is saturated, partially unsaturated or aromatic,
comprises 1, 2 or 3 heteroatoms or heteroatom groups selected from the group consisting of N, O, S, NO, SO and $SO_2$,
is unsubstituted or substituted with one to five radicals $R^{10}$, and
wherein one or two $CH_2$ groups in said saturated or partially saturated rings may be replaced by one or two C=O groups;
with the proviso that $R^7$ is not $C_1$-$C_6$-alkoxy or $C_1$-$C_6$-haloalkoxy if it is bound to an oxygen atom;
$R^8$, $R^9$ are selected independently from one another and independently of each occurrence from the group consisting of hydrogen, CN, $NO_2$, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_3$-$C_8$-cycloalkyl, $C_3$-$C_8$-cycloalkyl-$C_1$-$C_4$-alkyl, $C_2$-$C_6$-alkenyl, $C_2$-$C_6$-alkynyl,
wherein the carbon atom of the aforementioned aliphatic and cycloaliphatic radicals may be substituted with one or more $R^c$;
$Si(R^{11})_2R^{12}$, $OR^o$, $O(CO)R^c$, $O(CS)R^c$, $S(O)_mR^o$, $S(O)_mN(R'')_2$, $S(CO)R^c$, $S(CS)R^c$, $S(C=NR'')R^c$, $N(R'')_2$, $N(R'')C(=O)R^c$, $N(R'')C(=S)R^c$, $NS(O)_mR^o$, $N=C(R^c)_2$, $C(=O)R^c$, $C(=S)R^c$, $C(=NR'')R^c$, $C(=O)N(R'')_2$, $C(=S)N(R'')_2$ phenyl
which may be substituted with 1, 2, 3, 4 or 5 radicals $R^{10}$;
and a 3-, 4-, 5-, 6- or 7-membered heterocyclic ring, wherein said heterocyclic ring
is saturated, partially unsaturated or aromatic,
comprises 1, 2 or 3 heteroatoms or heteroatom groups selected from the group consisting of N, O, S, NO, SO and $SO_2$,
is unsubstituted or substituted with one to five radicals $R^{10}$, and
wherein one or two $CH_2$ groups in said saturated or partially saturated rings may be replaced by one or two C=O groups;
$R^{10}$ is selected independently from the group consisting of halogen, cyano, azido, nitro, SCN, $SF_5$, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_3$-$C_8$-cycloalkyl, $C_3$-$C_8$-cycloalkyl-$C_1$-$C_4$-alkyl, $C_2$-$C_6$-alkenyl, $C_2$-$C_6$-alkynyl,
wherein the carbon atom of the aforementioned aliphatic and cycloaliphatic radicals may be substituted with one or more $R^c$;
$Si(R^{11})_2R^{12}$, $OR^o$, $O(CO)R^c$, $O(CS)R^c$, $S(O)_mR^o$, $S(O)_mN(R'')_2$, $S(CO)R^c$, $S(CS)R^c$, $S(C=NR'')R^c$, $N(R'')_2$, $N(R'')C(=O)R^c$, $N(R'')C(=S)R^c$, $NS(O)_mR^o$, $N=C(R^c)_2$, $C(=O)R^c$, $C(=S)R^c$, $C(=NR'')R^c$, $C(=O)N(R'')_2$, $C(=S)N(R'')_2$, phenyl
which may be substituted with one to five radicals selected independently from halogen, cyano, nitro, $C_1$-$C_6$-alkyl, $C_1$-$C_6$-haloalkyl, $C_1$-$C_6$-alkoxy and $C_1$-$C_6$-haloalkoxy;
and a 3-, 4-, 5-, 6- or 7-membered heterocyclic ring, wherein said heterocyclic ring is saturated or unsaturated,
comprises 1, 2 or 3 heteroatoms or heteroatom groups selected from the group consisting of N, O, S, NO, SO and $SO_2$,
is unsubstituted or substituted with one to five radicals selected independently from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy;
or two radicals $R^{10}$ bound on adjacent atoms together form a group selected from —$CH_2CH_2CH_2CH_2$—, —CH=CH—CH=CH—, —N=CH—CH=CH—, —CH=N—CH=CH—, —N=CH—N=CH—, —$OCH_2CH_2CH_2$—, —OCH=$CHCH_2$—, —$CH_2OCH_2CH_2$—, —$OCH_2CH_2O$—, —$OCH_2OCH_2$—, —$CH_2CH_2CH_2$—, —CH=$CHCH_2$—, —$CH_2CH_2O$—, —CH=CHO—, —$CH_2OCH_2$—, —$CH_2C$(=O)O—, —C(=O)$OCH_2$—, —O($CH_2$)O—, —$SCH_2CH_2CH_2$—, —SCH=$CHCH_2$—, —$CH_2SCH_2CH_2$—, —$SCH_2CH_2S$—, —$SCH_2SCH_2$—, —$CH_2CH_2S$—, —CH=CHS—, —$CH_2SCH_2$—, —$CH_2C$(=S)S—, —C(=S)$SCH_2$—, —S($CH_2$)S—, —$CH_2CH_2NR^8$—, —$CH_2$CH=N—, —CH=CH—$NR^8$—, —OCH=N— and —SCH=N—,
wherein in each of the above groups,
one to five hydrogen atoms independently of each other may be replaced by one to five substituents selected from the group consisting of halogen, methyl, halomethyl, hydroxyl, methoxy and halomethoxy, or
one or two or more $CH_2$ groups of the above groups may be replaced by one or two C=O groups;
$R^{11}$, $R^{12}$ are selected independently of each other and independently of each occurrence from the group consisting of $C_1$-$C_4$-alkyl, $C_3$-$C_6$-cycloalkyl, $C_1$-$C_4$-alkoxy-$C_1$-$C_4$-alkyl, phenyl and benzyl;
$R^c$ is selected independently from the group consisting of hydrogen, halogen, cyano, azido, nitro, SCN, $SF_5$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkyl, $C_3$-$C_8$-cycloalkyl-$C_1$-$C_4$-alkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl, and a 3-, 4-, 5-, 6- or 7-membered heterocyclic ring,
wherein said heterocyclic ring
is saturated, partially unsaturated or aromatic,
comprises 1, 2 or 3 heteroatoms or heteroatom groups selected from CO, N, O, S, NO, SO and $SO_2$,
is unsubstituted or substituted with one to five radicals, which are selected independently of each other from halogen, cyano, nitro, $C_1$-$C_4$-alkyl, $C_1$-$C_4$-haloalkyl, $C_1$-$C_4$-alkoxy and $C_1$-$C_4$-haloalkoxy;
$R^o$ is selected independently from the group consisting of hydrogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkyl, $C_3$-$C_8$-cycloalkyl-$C_1$-$C_4$-alkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl, and a 3-, 4-, 5-, 6- or 7-membered heterocyclic ring, wherein said heterocyclic ring
is saturated, partially unsaturated or aromatic,
comprises 1, 2 or 3 heteroatoms or heteroatom groups selected from CO, N, O, S, NO, SO and $SO_2$,
is unsubstituted or substituted with one to five radicals, which are selected independently of each other from halogen, cyano, nitro, $C_1$-$C_4$-alkyl, $C_1$-$C_4$-haloalkyl, $C_1$-$C_4$-alkoxy and $C_1$-$C_4$-haloalkoxy;
with the proviso that $R^o$ is not $C_1$-$C_6$-alkoxy or $C_1$-$C_6$-haloalkoxy if it is bound to an oxygen atom;
$R^n$ is selected independently from the group consisting of hydrogen, CN, $NO_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkyl, $C_3$-$C_8$-cycloalkyl-$C_1$-$C_4$-alkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl, and a 3-, 4-, 5-, 6- or 7-membered saturated heterocyclic ring,
wherein said heterocyclic ring
is saturated, partially unsaturated or aromatic,
comprises 1, 2 or 3 heteroatoms or heteroatom groups selected from CO, N, O, S, NO, SO and $SO_2$,
is unsubstituted or substituted with one to five radicals, which are selected independently of each other from halogen, cyano, nitro, $C_1$-$C_4$-alkyl, $C_1$-$C_4$-haloalkyl, $C_1$-$C_4$-alkoxy and $C_1$-$C_4$-haloalkoxy;
m is independently 0, 1 or 2;
p is 0, 1, 2, 3 or 4;
or enantiomers or diastereoisomers thereof or their agriculturally or veterinarily acceptable salts, or a composition comprising at least one compound of formula I.

2. The method according to claim 1, wherein $R^{5b}$ is selected from the group consisting of $C_1$-$C_6$-alkyl, $C_3$-$C_6$-cycloalkyl, $C_1$-$C_6$-alkoxy and $C_1$-$C_6$-cycloalkoxy, wherein each mentioned radical is at least substituted with one halogen.

3. The method according to claim 1, wherein $R^3$ is selected from the group consisting of hydrogen, halogen, cyano, azido, nitro, SCN, $SF_5$, $C_1$-$C_6$-haloalkyl, $C_3$-$C_6$-halocycloalkyl, $C_1$-$C_6$-haloalkoxy, $C_3$-$C_6$-halocycloalkoxy, Si($R^{11}$)$_2R^{12}$, $OR^7$, S(O)$_mR^7$, N($R^8$)$R^9$, N=($R^6$)$_2$, C(=O)$R^6$, C(=S)$R^6$ and C(=$NR^8$)$R^6$.

4. The method according to claim 1, wherein
$R^{5b}$ is selected from the group consisting of $C_1$-$C_6$-haloalkyl and $C_1$-$C_6$-haloalkoxy;
$R^3$ is selected from the group consisting of hydrogen, halogen, CN, $NO_2$, C(=$NR^8$)$R^6$, $C_1$-$C_6$-haloalkyl, $C_3$-$C_6$-halocycloalkyl, $C_1$-$C_6$-haloalkoxy and $C_3$-$C_6$-halocycloalkoxy.

5. The method according to claim 1, wherein
$R^{5b}$ is $CF_3$;
$R^3$ is halogen;
$A^1$, $A^2$, $A^3$ and $A^4$ are $CR^4$;
$R^{5c}$ and $R^{5d}$ are independently from one another hydrogen, halogen, $C_1$-$C_6$-alkyl or $C_1$-$C_6$-haloalkyl;
$R^{5a}$ and each $R^4$ are independently from one another hydrogen, halogen, CN, $NO_2$, $C_1$-$C_6$-alkyl, $C_3$-$C_6$-cycloalkyl, $C_1$-$C_6$-alkoxy or $C_1$-$C_6$-cycloalkoxy.

6. The method according to claim 1, wherein
$R^{5b}$ is $CF_3$;
$R^3$ is halogen;
$A^1$, $A^2$, $A^3$ and $A^4$ are $CR^4$;
$R^{5c}$ and $R^{5d}$ are hydrogen;
$R^{5a}$ and each $R^4$ are independently from one another hydrogen, halogen, $C_1$-$C_6$-alkyl, or $C_1$-$C_6$-haloalkyl.

7. A method for protecting plants or plant propagation materials from attack or infestation by invertebrate pests, which method comprises treating the plants or the plant propagation materials or the materials, surfaces or spaces in which they grow with a pesticidally effective amount of a compound of formula (I)

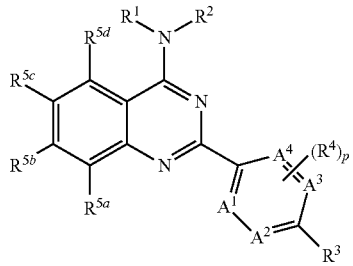

wherein
$A^1, A^2, A^3$ and $A^4$ are N, NX or $CR^4$ wherein X is a lone pair or O, with the proviso that at most three of $A^1, A^2, A^3$ and $A^4$ are N or NX;
$R^1$, $R^2$ are selected independently from one another from the group consisting of hydrogen, CN, $NO_2$, $C_1$-$C_{10}$-alkyl, $C_3$-$C_8$-cycloalkyl, $C_2$-$C_{10}$-alkenyl, $C_2$-$C_{10}$-alkynyl,
wherein the carbon atoms of the aforementioned aliphatic and cycloaliphatic radicals may be unsubstituted or substituted with one or more $R^6$;
$Si(R^{11})_2R^{12}$, $OR^7$, $S(O)_mR^7$, $NR^8R^9$, $N=C(R^6)_2$, $C(=O)R^6$, $C(=S)R^6$, $C(=NR^8)R^6$ and a 3-, 4-, 5-, 6- or 7-membered heterocyclic ring,
wherein said heterocyclic ring
is saturated or partially saturated,
comprises 1, 2 or 3 heteroatoms selected from the group consisting of oxygen, nitrogen and sulfur, wherein the nitrogen and/or the sulfur atom(s) may be oxidized,
is unsubstituted or substituted with one to five $R^{10}$, and
wherein one or two $CH_2$ groups in said heterocyclic ring may be replaced by one or two C=O groups;
$R^3$ is selected from the group consisting of hydrogen, halogen, cyano, azido, nitro, SCN, $SF_5$, $C_1$-$C_{10}$-alkyl, $C_3$-$C_8$-cycloalkyl, $C_2$-$C_{10}$-alkenyl, $C_2$-$C_{10}$-alkynyl,
wherein the carbon atoms of the aforementioned aliphatic and cycloaliphatic radicals may be unsubstituted or substituted with one or more $R^6$;
$Si(R^{11})_2R^{12}$, $OR^7$, $S(O)_mR^7$, $N(R^8)R^9$, $N=C(R^6)_2$, $C(=O)R^6$, $C(=S)R^6$, $C(=NR^8)R^6$, phenyl
which may be substituted with 1, 2, 3, 4 or 5 radicals $R^{10}$;
and a 3-, 4-, 5-, 6- or 7-membered heterocyclic ring,
wherein said heterocyclic ring
is saturated or partially saturated,
comprises 1, 2 or 3 heteroatoms or heteroatom groups selected from the group consisting of N, O, S, NO, SO and $SO_2$,
is unsubstituted or substituted with one to five radicals $R^{10}$, and
wherein one or two $CH_2$ groups in said heterocyclic ring may be replaced by one or two C=O groups;
each $R^4$ is selected independently from the group consisting of hydrogen, halogen, cyano, azido, nitro, SCN, $SF_5$, $C_1$-$C_{10}$-alkyl, $C_3$-$C_8$-cycloalkyl, $C_2$-$C_{10}$-alkenyl, $C_2$-$C_{10}$-alkynyl,
wherein the carbon atoms of the aforementioned aliphatic and cycloaliphatic radicals may be unsubstituted or substituted with one or more $R^6$;
$Si(R^{11})_2R^{12}$, $OR^7$, $S(O)_mR^7$, $N(R^8)R^9$, $N=C(R^6)_2$, $C(=O)R^6$, $C(=S)R^6$, $C(=NR^8)R^6$, $C(=O)N(R^8)R^9$, $C(=S)N(R^8)R^9$, phenyl
which may be substituted with 1, 2, 3, 4 or 5 radicals $R^{10}$;
and a 3-, 4-, 5-, 6- or 7-membered heterocyclic ring,
wherein said heterocyclic ring
is saturated or partially unsaturated or aromatic,
comprises 1, 2 or 3 heteroatoms or heteroatom groups selected from the group consisting of N, O, S, NO, SO and $SO_2$,
is unsubstituted or substituted with one to five radicals $R^{10}$, and
wherein one or two $CH_2$ groups in said saturated or partially saturated rings may be replaced by one or two C=O groups;
or two radicals $R^4$ bound on adjacent carbon atoms together form a group selected from the group consisting of —$CH_2CH_2CH_2CH_2$—, —CH=CH—CH=CH—, —N=CH—CH=CH—, —CH=N—CH=CH—, —N=CH—N=CH—, —$OCH_2CH_2CH_2$—, —OCH=$CHCH_2$—, —$CH_2OCH_2CH_2$—, —$OCH_2CH_2O$—, —$OCH_2OCH_2$—, —$CH_2CH_2CH_2$—, —CH=$CHCH_2$—, —$CH_2CH_2O$—, —CH=CHO—, —$CH_2OCH_2$—, —$CH_2C(=O)O$—, —$C(=O)OCH_2$—, —$O(CH_2)O$—, —$SCH_2CH_2CH_2$—, —SCH=$CHCH_2$—, —$CH_2SCH_2CH_2$—, —$SCH_2CH_2S$—, —$SCH_2SCH_2$—, —$CH_2CH_2S$—, —CH=CHS—, —$CH_2SCH_2$—, —$CH_2C(=S)S$—, —$C(=S)SCH_2$—, —$S(CH_2)S$—, —$CH_2CH_2NR^8$—, —$CH_2CH=N$—, —CH=CH—$NR^8$—, —OCH=N— and —SCH=N—,
wherein in each of the above group,
one to five hydrogen atoms independently of each other may be replaced by one to five substituents selected from the group consisting of halogen, methyl, halomethyl, hydroxyl, methoxy and halomethoxy, or
one or two $CH_2$ groups of the above groups may be replaced by one or two C=O groups;
$R^{5a}$ is selected from the group consisting of hydrogen, halogen, cyano, azido, nitro, SCN, $SF_5$, $C_1$-$C_{10}$-alkyl, $C_3$-$C_8$-cycloalkyl, $C_2$-$C_{10}$-alkenyl, $C_2$-$C_{10}$-alkynyl,
wherein the carbon atoms of the aforementioned aliphatic and cycloaliphatic radicals may be unsubstituted or substituted with one or more $R^6$;
$Si(R^{11})_2R^{12}$, $OR^7$, $S(O)_mR^7$, $N(R^8)R^9$, $N=C(R^6)_2$, $C(=O)R^6$, $C(=S)R^6$, $C(=NR^8)R^6$, phenyl
which may be substituted with 1, 2, 3, 4 or 5 radicals $R^{10}$;
and a 3-, 4-, 5-, 6- or 7-membered heterocyclic ring,
wherein said heterocyclic ring
is saturated or partially unsaturated or aromatic,
comprises 1, 2 or 3 heteroatoms or heteroatom groups selected from the group consisting of N, O, S, NO, SO and $SO_2$,
is unsubstituted or substituted with one to five radicals $R^{10}$, and
wherein one or two $CH_2$ groups in said saturated or partially saturated rings may be replaced by one or two C=O groups;
or $R^{5a}$ may form together with the adjacent carbon atom $R^{5b}$ a 5- or 6-membered ring which is at least substituted with one halogen;
$R^{5b}$ is selected from the group consisting of $C_1$-$C_6$-alkyl, $C_3$-$C_6$-cycloalkyl, $C_1$-$C_6$-alkoxy and $C_1$-$C_6$-cycloalkoxy, wherein each mentioned radical
is substituted with at least one halogen, may be further partially or fully halogenated, and may be substituted with one to five radicals $R^6$;

or $R^{5b}$ may form together with the adjacent carbon atom $R^{5c}$ or $R^{5a}$ a 5- or 6-membered ring which is substituted with at least one halogen;

$R^{5c}$ is selected from the group consisting of hydrogen, halogen, cyano, azido, nitro, SCN, $SF_5$, $C_1$-$C_{10}$-alkyl, $C_3$-$C_8$-cycloalkyl, $C_2$-$C_{10}$-alkenyl, $C_2$-$C_{10}$-alkynyl, wherein the carbon atoms of the aforementioned aliphatic and cycloaliphatic radicals may be unsubstituted or substituted with one or more $R^6$;

$Si(R^{11})_2R^{12}$, $OR^7$, $S(O)_mR^7$, $N(R^8)R^9$, $N=C(R^6)_2$, $C(=O)OR^7$, $C(=S)OR^7$, $C(=NR^8)R^6$, $C(=O)N(R^8)R^9$, $C(=S)N(R^8)R^9$, phenyl which may be substituted with 1, 2, 3, 4 or 5 radicals $R^{10}$;

and a 3-, 4-, 5-, 6- or 7-membered heterocyclic ring,
wherein said heterocyclic ring
is saturated, partially unsaturated or aromatic,
comprises 1, 2 or 3 heteroatoms or heteroatom groups selected from the group consisting of N, O, S, NO, SO and $SO_2$,
is unsubstituted or substituted with one to five radicals $R^{10}$, and
wherein one or two $CH_2$ groups in said saturated or partially saturated rings may be replaced by one or two C=O groups;

or $R^{5c}$ may form together with the adjacent carbon atom $R^{5b}$ or $R^{5d}$ a 5- or 6-membered ring which is substituted with at least one halogen in case of $R^{5b}$ being involved;

$R^{5d}$ is selected from the group consisting of hydrogen, halogen, cyano, azido, nitro, SCN, $SF_5$, $C_1$-$C_{10}$-alkyl, $C_3$-$C_8$-cycloalkyl, $C_2$-$C_{10}$-alkenyl, $C_2$-$C_{10}$-alkynyl, wherein the carbon atoms of the aforementioned aliphatic and cycloaliphatic radicals may be unsubstituted or substituted with one or more $R^6$;

$Si(R^{11})_2R^{12}$, $OR^7$, $S(O)_mR^7$, $S(O)_mN(R^8)R^9$, $N(R^8)R^9$, $N=C(R^6)_2$, $C(=O)R^6$, $C(=S)R^6$, $C(=NR^8)R^6$, phenyl which may be substituted with 1, 2, 3, 4 or 5 radicals $R^{10}$;

and a 3-, 4-, 5-, 6- or 7-membered heterocyclic ring,
wherein said heterocyclic ring
is saturated, partially unsaturated or aromatic,
comprises 1, 2 or 3 heteroatoms or heteroatom groups selected from the group consisting of N, O, S, NO, SO and $SO_2$,
is unsubstituted or substituted with one to five radicals $R^{10}$, and
wherein one or two $CH_2$ groups in said saturated or partially saturated rings may be replaced by one or two C=O groups;

or $R^{5d}$ may form together with the adjacent carbon atom $R^{5c}$ or with $R^1$ or $R^2$ a 5- or 6-membered ring;

$R^6$ is selected independently from the group consisting of hydrogen, halogen, cyano, azido, nitro, SCN, $SF_5$, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_3$-$C_8$-cycloalkyl, $C_3$-$C_8$-cycloalkyl-$C_1$-$C_4$-alkyl, $C_2$-$C_6$-alkenyl, $C_2$-$C_6$-alkynyl, wherein the carbon atom of the aforementioned aliphatic and cycloaliphatic radicals may be substituted with one or more $R^c$;

$Si(R^{11})_2R^{12}$, $OR^o$, $O(CO)R^c$, $O(CS)R^c$, $S(O)_mR^o$, $S(O)_mN(R'')_2$, $S(CO)R^c$, $S(CS)R^c$, $S(C=NR'')R^c$, $N(R'')_2$, $N(R'')C(=O)R^c$, $N(R'')C(=S)R^c$, $NS(O)_mR^o$, $N=C(R^c)_2$, $C(=O)R^c$, $C(=S)R^c$, $C(=NR'')R^c$, $C(=O)N(R'')_2$, $C(=S)N(R'')_2$, phenyl which may be substituted with 1, 2, 3, 4 or 5 radicals $R^{10}$;

and a 3-, 4-, 5-, 6- or 7-membered heterocyclic ring,
wherein said heterocyclic ring
is saturated, partially unsaturated or aromatic,
comprises 1, 2 or 3 heteroatoms or heteroatom groups selected from the group consisting of N, O, S, NO, SO and $SO_2$,
is unsubstituted or substituted with one to five radicals $R^{10}$, and
wherein one or two $CH_2$ groups in said saturated or partially saturated rings may be replaced by one or two C=O groups;

or two vicinally bound radicals $R^6$ together form a group selected from $=C(R^c)_2$, $=S(O)_mR^o$, $=S(O)_mN(R'')_2$, $=NR''$ and $=NN(R'')_2$;

$R^7$ is selected independently from the group consisting of hydrogen, cyano, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_3$-$C_8$-cycloalkyl, $C_3$-$C_8$-cycloalkyl-$C_1$-$C_4$-alkyl, $C_2$-$C_6$-alkenyl, $C_2$-$C_6$-alkynyl, wherein the carbon atom of the aforementioned aliphatic and cycloaliphatic radicals may be substituted with one or more $R^c$;

$Si(R^{11})_2R^{12}$, $OR^o$, $O(CO)R^c$, $O(CS)R^c$, $S(O)_mR^o$, $S(O)_mN(R'')_2$, $S(CO)R^c$, $S(CS)R^c$, $S(C=NR'')R^c$, $N(R'')_2$, $N(R'')C(=O)R^c$, $N(R'')C(=S)R^c$, $NS(O)_mR^o$, $N=C(R^c)_2$, $C(=O)R^c$, $C(=S)R^c$, $C(=NR'')R^c$, $C(=O)N(R'')_2$, $C(=S)N(R'')_2$, phenyl which may be substituted with 1, 2, 3, 4 or 5 radicals $R^{10}$;

and a 3-, 4-, 5-, 6- or 7-membered heterocyclic ring,
wherein said heterocyclic ring
is saturated, partially unsaturated or aromatic,
comprises 1, 2 or 3 heteroatoms or heteroatom groups selected from the group consisting of N, O, S, NO, SO and $SO_2$,
is unsubstituted or substituted with one to five radicals $R^{10}$, and
wherein one or two $CH_2$ groups in said saturated or partially saturated rings may be replaced by one or two C=O groups;

with the proviso that $R^7$ is not $C_1$-$C_6$-alkoxy or $C_1$-$C_6$-haloalkoxy if it is bound to an oxygen atom;

$R^8$, $R^9$ are selected independently from one another and independently of each occurrence from the group consisting of hydrogen, CN, $NO_2$, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_3$-$C_8$-cycloalkyl, $C_3$-$C_8$-cycloalkyl-$C_1$-$C_4$-alkyl, $C_2$-$C_6$-alkenyl, $C_2$-$C_6$-alkynyl, wherein the carbon atom of the aforementioned aliphatic and cycloaliphatic radicals may be substituted with one or more $R^c$;

$Si(R^{11})_2R^{12}$, $OR^o$, $O(CO)R^c$, $O(CS)R^c$, $S(O)_mR^o$, $S(O)_mN(R'')_2$, $S(CO)R^c$, $S(CS)R^c$, $S(C=NR'')R^c$, $N(R'')_2$, $N(R'')C(=O)R^c$, $N(R'')C(=S)R^c$, $NS(O)_mR^o$, $N=C(R^c)_2$, $C(=O)R^c$, $C(=S)R^c$, $C(=NR'')R^c$, $C(=O)N(R'')_2$, $C(=S)N(R'')_2$ phenyl which may be substituted with 1, 2, 3, 4 or 5 radicals $R^{10}$;

and a 3-, 4-, 5-, 6- or 7-membered heterocyclic ring,
wherein said heterocyclic ring
is saturated, partially unsaturated or aromatic,
comprises 1, 2 or 3 heteroatoms or heteroatom groups selected from the group consisting of N, O, S, NO, SO and $SO_2$,
is unsubstituted or substituted with one to five radicals $R^{10}$, and
wherein one or two $CH_2$ groups in said saturated or partially saturated rings may be replaced by one or two C=O groups;

$R^{10}$ is selected independently from the group consisting of halogen, cyano, azido, nitro, SCN, $SF_5$, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_3$-$C_8$-cycloalkyl, $C_3$-$C_8$-cycloalkyl-$C_1$-$C_4$-alkyl, $C_2$-$C_6$-alkenyl, $C_2$-$C_6$-alkynyl,
  wherein the carbon atom of the aforementioned aliphatic and cycloaliphatic radicals may be substituted with one or more $R^c$;
$Si(R^{11})_2R^{12}$, $OR^o$, $O(CO)R^c$, $O(CS)R^c$, $S(O)_mR^o$, $S(O)_mN(R'')_2$, $S(CO)R^c$, $S(CS)R^c$, $S(C=NR'')R^c$, $N(R'')_2$, $N(R'')C(=O)R^c$, $N(R'')C(=S)R^c$, $NS(O)_mR^o$, $N=C(R^c)_2$, $C(=O)R^c$, $C(=S)R^c$, $C(=NR'')R^c$, $C(=O)N(R'')_2$, $C(=S)N(R'')_2$, phenyl
  which may be substituted with one to five radicals selected independently from halogen, cyano, nitro, $C_1$-$C_6$-alkyl, $C_1$-$C_6$-haloalkyl, $C_1$-$C_6$-alkoxy and $C_1$-$C_6$-haloalkoxy;
and a 3-, 4-, 5-, 6- or 7-membered heterocyclic ring, wherein said heterocyclic ring
  is saturated or unsaturated,
  comprises 1, 2 or 3 heteroatoms or heteroatom groups selected from the group consisting of N, O, S, NO, SO and $SO_2$,
  is unsubstituted or substituted with one to five radicals selected independently from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy;
or two radicals $R^{10}$ bound on adjacent atoms together form a group selected from —$CH_2CH_2CH_2CH_2$—, —CH=CH—CH=CH—, —N=CH—CH=CH—, —CH=N—CH=CH—, —N=CH—N=CH—, —$OCH_2CH_2CH_2$—, —OCH=$CHCH_2$—, —$CH_2OCH_2CH_2$—, —$OCH_2CH_2O$—, —$OCH_2OCH_2$—, —$CH_2CH_2CH_2$—, —CH=$CHCH_2$—, —$CH_2CH_2O$—, —CH=CHO—, —$CH_2OCH_2$—, —$CH_2C(=O)O$—, —C(=O)$OCH_2$—, —O($CH_2$)O—, —$SCH_2CH_2CH_2$—, —SCH=$CHCH_2$—, —$CH_2SCH_2CH_2$—, —$SCH_2CH_2S$—, —$SCH_2SCH_2$—, —$CH_2CH_2S$—, —CH=CHS—, —$CH_2SCH_2$—, —$CH_2C(=S)S$—, —C(=S)$SCH_2$—, —S($CH_2$)S—, —$CH_2CH_2NR^8$—, —$CH_2CH$=N—, —CH=CH—$NR^8$—, —OCH=N— and —SCH=N—,
  wherein in each of the above groups,
  one to five hydrogen atoms independently of each other may be replaced by one to five substituents selected from the group consisting of halogen, methyl, halomethyl, hydroxyl, methoxy and halomethoxy, or
  one or two or more $CH_2$ groups of the above groups may be replaced by one or two C=O groups;
$R^{11}$, $R^{12}$ are selected independently of each other and independently of each occurrence from the group consisting of $C_1$-$C_4$-alkyl, $C_3$-$C_6$-cycloalkyl, $C_1$-$C_4$-alkoxy-$C_1$-$C_4$-alkyl, phenyl and benzyl;
$R^c$ is selected independently from the group consisting of hydrogen, halogen, cyano, azido, nitro, SCN, $SF_5$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkyl, $C_3$-$C_8$-cycloalkyl-$C_1$-$C_4$-alkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl, and a 3-, 4-, 5-, 6- or 7-membered heterocyclic ring,
  wherein said heterocyclic ring
  is saturated, partially unsaturated or aromatic,
  comprises 1, 2 or 3 heteroatoms or heteroatom groups selected from CO, N, O, S, NO, SO and $SO_2$,
  is unsubstituted or substituted with one to five radicals, which are selected independently of each other from halogen, cyano, nitro, $C_1$-$C_4$-alkyl, $C_1$-$C_4$-haloalkyl, $C_1$-$C_4$-alkoxy and $C_1$-$C_4$-haloalkoxy;
$R^o$ is selected independently from the group consisting of hydrogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkyl, $C_3$-$C_8$-cycloalkyl-$C_1$-$C_4$-alkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl, and a 3-, 4-, 5-, 6- or 7-membered heterocyclic ring, wherein said heterocyclic ring
  is saturated, partially unsaturated or aromatic,
  comprises 1, 2 or 3 heteroatoms or heteroatom groups selected from CO, N, O, S, NO, SO and $SO_2$,
  is unsubstituted or substituted with one to five radicals, which are selected independently of each other from halogen, cyano, nitro, $C_1$-$C_4$-alkyl, $C_1$-$C_4$-haloalkyl, $C_1$-$C_4$-alkoxy and $C_1$-$C_4$-haloalkoxy;
with the proviso that $R^o$ is not $C_1$-$C_6$-alkoxy or $C_1$-$C_6$-haloalkoxy if it is bound to an oxygen atom;
$R''$ is selected independently from the group consisting of hydrogen, CN, $NO_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkyl, $C_3$-$C_8$-cycloalkyl-$C_1$-$C_4$-alkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl, and a 3-, 4-, 5-, 6- or 7-membered saturated heterocyclic ring,
  wherein said heterocyclic ring
  is saturated, partially unsaturated or aromatic,
  comprises 1, 2 or 3 heteroatoms or heteroatom groups selected from CO, N, O, S, NO, SO and $SO_2$,
  is unsubstituted or substituted with one to five radicals, which are selected independently of each other from halogen, cyano, nitro, $C_1$-$C_4$-alkyl, $C_1$-$C_4$-haloalkyl, $C_1$-$C_4$-alkoxy and $C_1$-$C_4$-haloalkoxy;
m is independently 0, 1 or 2;
p is 0, 1, 2, 3 or 4;
or enantiomers or diastereoisomers thereof or their agriculturally or veterinarily acceptable salts;
or a composition comprising the compound.

8. The method according to claim 7, wherein $R^{5b}$ is selected from the group consisting of $C_1$-$C_6$-alkyl, $C_3$-$C_6$-cycloalkyl, $C_1$-$C_6$-alkoxy and $C_1$-$C_6$-cycloalkoxy, wherein each mentioned radical is at least substituted with one halogen.

9. The method according to claim 7, wherein $R^3$ is selected from the group consisting of hydrogen, halogen, cyano, azido, nitro, SCN, $SF_5$, $C_1$-$C_6$-haloalkyl, $C_3$-$C_6$-halocycloalkyl, $C_1$-$C_6$-haloalkoxy, $C_3$-$C_6$-halocycloalkoxy, $Si(R^{11})_2R^{12}$, $OR^7$, $S(O)_mR^7$, $N(R^8)R^9$, $N=(R^6)_2$, $C(=O)R^6$, $C(=S)R^6$ and $C(=NR^8)R^6$.

10. The method according to claim 7, wherein
$R^{5b}$ is selected from the group consisting of $C_1$-$C_6$-haloalkyl and $C_1$-$C_6$-haloalkoxy;
$R^3$ is selected from the group consisting of hydrogen, halogen, CN, $NO_2$, $C(=NR^8)R^6$, $C_1$-$C_6$-haloalkyl, $C_3$-$C_6$-halocycloalkyl, $C_1$-$C_6$-haloalkoxy and $C_3$-$C_6$-halocycloalkoxy.

11. The method according to claim 7, wherein
$R^{5b}$ is $CF_3$;
$R^3$ is halogen;
$A^1, A^2, A^3$ and $A^4$ are $CR^4$;
$R^{5c}$ and $R^{5d}$ are independently from one another hydrogen, halogen, $C_1$-$C_6$-alkyl or $C_1$-$C_6$-haloalkyl;
$R^{5a}$ and each $R^4$ are independently from one another hydrogen, halogen, CN, $NO_2$, $C_1$-$C_6$-alkyl, $C_3$-$C_6$-cycloalkyl, $C_1$-$C_6$-alkoxy or $C_1$-$C_6$-cycloalkoxy.

12. The method according to claim 7, wherein
$R^{5b}$ is $CF_3$;
$R^3$ is halogen;
$A^1, A^2, A^3$ and $A^4$ are $CR^4$;
$R^{5c}$ and $R^{5d}$ are hydrogen;
$R^{5a}$ and each $R^4$ are independently from one another hydrogen, halogen, $C_1$-$C_6$-alkyl, or $C_1$-$C_6$-haloalkyl.

13. A method for combating invertebrate pests attack or infestation which method comprises treating the pests, their food supply, their habitat, their breeding ground, the plant, the plant propagation material, soil, area, material or environment in which the pests are growing or may grow, with a pesticidally effective amount of at least one compound of the formula I as defined in claim 1 or a composition comprising it.

14. Plant propagation material treated with the compound of claim 1 or a composition comprising the compound.

15. Seeds treated with a compound of claim 1 in an amount of from 0.1 g to 10 kg per 100 kg of seed.

16. A method for treating, controlling, preventing or protecting an animal from infestation or infection by invertebrate pests which comprises bringing the animal in contact with a pesticidally effective amount of at least one compound of the formula I as defined in claim 1.

17. A compound of formula (I)

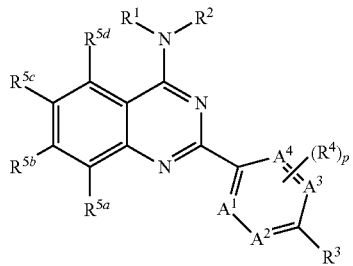

(I)

wherein
$A^1, A^2, A^3$ and $A^4$ are N, NX or $CR^4$ wherein X is a lone pair or O, with the proviso that at most three of $A^1, A^2, A^3$ and $A^4$ are N or NX;
$R^1, R^2$ are selected independently from one another from the group consisting of hydrogen, CN, $NO_2$, $C_1$-$C_{10}$-alkyl, $C_3$-$C_8$-cycloalkyl, $C_2$-$C_{10}$-alkenyl, $C_2$-$C_{10}$-alkynyl,
wherein the carbon atoms of the aforementioned aliphatic and cycloaliphatic radicals may be unsubstituted or substituted with one or more $R^6$;
$Si(R^{11})_2R^{12}$, $OR^7$, $S(O)_mR^7$, $NR^8R^9$, $N=C(R^6)_2$, $C(=O)R^6$, $C(=S)R^6$, $C(=NR^8)R^6$
and a 3-, 4-, 5-, 6- or 7-membered heterocyclic ring,
wherein said heterocyclic ring
is saturated or partially saturated,
comprises 1, 2 or 3 heteroatoms selected from the group consisting of oxygen, nitrogen and sulfur, wherein the nitrogen and/or the sulfur atom(s) may be oxidized,
is unsubstituted or substituted with one to five $R^{10}$, and
wherein one or two $CH_2$ groups in said heterocyclic ring may be replaced by one or two C=O groups;
$R^3$ is selected from the group consisting of hydrogen, halogen, cyano, azido, nitro, SCN, $SF_5$, $C_1$-$C_{10}$-alkyl, $C_3$-$C_8$-cycloalkyl, $C_2$-$C_{10}$-alkenyl, $C_2$-$C_{10}$-alkynyl,
wherein the carbon atoms of the aforementioned aliphatic and cycloaliphatic radicals may be unsubstituted or substituted with one or more $R^6$;
$Si(R^{11})_2R^{12}$, $OR^7$, $S(O)_mR^7$, $N(R^8)R^9$, $N=C(R^6)_2$, $C(=O)R^6$, $C(=S)R^6$, $C(=NR^8)R^6$, phenyl
which may be substituted with 1, 2, 3, 4 or 5 radicals $R^{10}$;
and a 3-, 4-, 5-, 6- or 7-membered heterocyclic ring,
wherein said heterocyclic ring
is saturated or partially saturated,
comprises 1, 2 or 3 heteroatoms or heteroatom groups selected from the group consisting of N, O, S, NO, SO and $SO_2$,
is unsubstituted or substituted with one to five radicals $R^{10}$, and
wherein one or two $CH_2$ groups in said heterocyclic ring may be replaced by one or two C=O groups;
each $R^4$ is selected independently from the group consisting of hydrogen, halogen, cyano, azido, nitro, SCN, $SF_5$, $C_1$-$C_{10}$-alkyl, $C_3$-$C_8$-cycloalkyl, $C_2$-$C_{10}$-alkenyl, $C_2$-$C_{10}$-alkynyl,
wherein the carbon atoms of the aforementioned aliphatic and cycloaliphatic radicals may be unsubstituted or substituted with one or more $R^6$;
$Si(R^{11})_2R^{12}$, $OR^7$, $S(O)_mR^7$, $N(R^8)R^9$, $N=C(R^6)_2$, $C(=O)R^6$, $C(=S)R^6$, $C(=NR^8)R^6$, $C(=O)N(R^8)R^9$, $C(=S)N(R^8)R^9$, phenyl
which may be substituted with 1, 2, 3, 4 or 5 radicals $R^{10}$;
and a 3-, 4-, 5-, 6- or 7-membered heterocyclic ring,
wherein said heterocyclic ring
is saturated or partially unsaturated or aromatic,
comprises 1, 2 or 3 heteroatoms or heteroatom groups selected from the group consisting of N, O, S, NO, SO and $SO_2$,
is unsubstituted or substituted with one to five radicals $R^{10}$, and
wherein one or two $CH_2$ groups in said saturated or partially saturated rings may be replaced by one or two C=O groups;
or two radicals $R^4$ bound on adjacent carbon atoms together form a group selected from the group consisting of —$CH_2CH_2CH_2CH_2$—, —CH=CH—CH=CH—, —N=CH—CH=CH—, —CH=N—CH=CH—, —N=CH—N=CH—, —$OCH_2CH_2CH_2$—, —OCH=CHCH_2—, —$CH_2OCH_2CH_2$—, —$OCH_2CH_2O$—, —$OCH_2OCH_2$—, —$CH_2CH_2CH_2$—, —CH=CHCH_2—, —$CH_2CH_2O$—, —CH=CHO—, —$CH_2OCH_2$—, —$CH_2C(=O)O$—, —$C(=O)OCH_2$—, —$O(CH_2)O$—, —$SCH_2CH_2CH_2$—, —SCH=CHCH_2—, —$CH_2SCH_2CH_2$—, —$SCH_2CH_2S$—, —$SCH_2SCH_2$—, —$CH_2CH_2S$—, —CH=CHS—, —$CH_2SCH_2$—, —$CH_2C(=S)S$—, —$C(=S)SCH_2$—, —$S(CH_2)S$—, —$CH_2CH_2NR^8$—, —$CH_2CH=N$—, —CH=CH—$NR^8$—, —OCH=N— and —SCH=N—,
wherein in each of the above group,
one to five hydrogen atoms independently of each other may be replaced by one to five substituents selected from the group consisting of halogen, methyl, halomethyl, hydroxyl, methoxy and halomethoxy, or
one or two $CH_2$ groups of the above groups may be replaced by one or two $C=O$ groups;
$R^{5a}$ is selected from the group consisting of hydrogen, halogen, cyano, azido, nitro, SCN, $SF_5$, $C_1$-$C_{10}$-alkyl, $C_3$-$C_8$-cycloalkyl, $C_2$-$C_{10}$-alkenyl, $C_2$-$C_{10}$-alkynyl,
wherein the carbon atoms of the aforementioned aliphatic and cycloaliphatic radicals may be unsubstituted or substituted with one or more $R^6$;
$Si(R^{11})_2R^{12}$, $OR^7$, $S(O)_mR^7$, $N(R^8)R^9$, $N=C(R^6)_2$, $C(=O)R^6$, $C(=S)R^6$, $C(=NR^8)R^6$, phenyl
which may be substituted with 1, 2, 3, 4 or 5 radicals $R^{10}$;
and a 3-, 4-, 5-, 6- or 7-membered heterocyclic ring,
wherein said heterocyclic ring
is saturated or partially unsaturated or aromatic,
comprises 1, 2 or 3 heteroatoms or heteroatom groups selected from the group consisting of N, O, S, NO, SO and $SO_2$,
is unsubstituted or substituted with one to five radicals $R^{10}$, and
wherein one or two $CH_2$ groups in said saturated or partially saturated rings may be replaced by one or two $C=O$ groups;
or $R^{5a}$ may form together with the adjacent carbon atom $R^{5b}$ a 5- or 6-membered ring which is at least substituted with one halogen;
$R^{5b}$ is selected from the group consisting of $C_1$-$C_6$-alkyl, $C_3$-$C_6$-cycloalkyl, $C_1$-$C_6$-alkoxy and $C_1$-$C_6$-cycloalkoxy, wherein each mentioned radical
is substituted with at least one halogen,
may be further partially or fully halogenated, and
may be substituted with one to five radicals $R^6$;
or $R^{5b}$ may form together with the adjacent carbon atom $R^{5c}$ or $R^{5a}$ a 5- or 6-membered ring which is substituted with at least one halogen;
$R^{5c}$ is selected from the group consisting of hydrogen, halogen, cyano, azido, nitro, SCN, $SF_5$, $C_1$-$C_{10}$-alkyl, $C_3$-$C_8$-cycloalkyl, $C_2$-$C_{10}$-alkenyl, $C_2$-$C_{10}$-alkynyl,
wherein the carbon atoms of the aforementioned aliphatic and cycloaliphatic radicals may be unsubstituted or substituted with one or more $R^6$;
$Si(R^{11})_2R^{12}$, $OR^7$, $S(O)_mR^7$, $N(R^8)R^9$, $N=C(R^6)_2$, $C(=O)OR^7$, $C(=S)OR^7$, $C(=NR^8)R^6$, $C(=O)N(R^8)R^9$, $C(=S)N(R^8)R^9$, phenyl
which may be substituted with 1, 2, 3, 4 or 5 radicals $R^{10}$;
and a 3-, 4-, 5-, 6- or 7-membered heterocyclic ring,
wherein said heterocyclic ring
is saturated, partially unsaturated or aromatic,
comprises 1, 2 or 3 heteroatoms or heteroatom groups selected from the group consisting of N, O, S, NO, SO and $SO_2$,
is unsubstituted or substituted with one to five radicals $R^{10}$, and
wherein one or two $CH_2$ groups in said saturated or partially saturated rings may be replaced by one or two $C=O$ groups;
or $R^{5c}$ may form together with the adjacent carbon atom $R^{5b}$ or $R^{5d}$ a 5- or 6-membered ring which is substituted with at least one halogen in case of $R^{5b}$ being involved;
$R^{5d}$ is selected from the group consisting of hydrogen, halogen, cyano, azido, nitro, SCN, $SF_5$, $C_1$-$C_{10}$-alkyl, $C_3$-$C_8$-cycloalkyl, $C_2$-$C_{10}$-alkenyl, $C_2$-$C_{10}$-alkynyl,
wherein the carbon atoms of the aforementioned aliphatic and cycloaliphatic radicals may be unsubstituted or substituted with one or more $R^6$;
$Si(R^{11})_2R^{12}$, $OR^7$, $S(O)_mR^7$, $S(O)_mN(R^8)R^9$, $N(R^8)R^9$, $N=C(R^6)_2$, $C(=O)R^6$, $C(=S)R^6$, $C(=NR^8)R^6$, phenyl
which may be substituted with 1, 2, 3, 4 or 5 radicals $R^{10}$;
and a 3-, 4-, 5-, 6- or 7-membered heterocyclic ring,
wherein said heterocyclic ring
is saturated, partially unsaturated or aromatic,
comprises 1, 2 or 3 heteroatoms or heteroatom groups selected from the group consisting of N, O, S, NO, SO and $SO_2$,
is unsubstituted or substituted with one to five radicals $R^{10}$, and
wherein one or two $CH_2$ groups in said saturated or partially saturated rings may be replaced by one or two $C=O$ groups;
or $R^{5d}$ may form together with the adjacent carbon atom $R^{5c}$ or with $R^1$ or $R^2$ a 5- or 6-membered ring;
$R^6$ is selected independently from the group consisting of hydrogen, halogen, cyano, azido, nitro, SCN, $SF_5$, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_3$-$C_8$-cycloalkyl, $C_3$-$C_8$-cycloalkyl-$C_1$-$C_4$-alkyl, $C_2$-$C_6$-alkenyl, $C_2$-$C_6$-alkynyl,
wherein the carbon atom of the aforementioned aliphatic and cycloaliphatic radicals may be substituted with one or more $R^c$;
$Si(R^{11})_2R^{12}$, $OR^o$, $O(CO)R^c$, $O(CS)R^c$, $S(O)_mR^o$, $S(O)_mN(R'')_2$, $S(CO)R^c$, $S(CS)R^c$, $S(C=NR'')R^c$, $N(R'')_2$, $N(R'')C(=O)R^c$, $N(R'')C(=S)R^c$, $NS(O)_mR^o$, $N=C(R^c)_2$, $C(=O)R^c$, $C(=S)R^c$, $C(=NR'')R^c$, $C(=O)N(R'')_2$, $C(=S)N(R'')_2$, phenyl
which may be substituted with 1, 2, 3, 4 or 5 radicals $R^{10}$;
and a 3-, 4-, 5-, 6- or 7-membered heterocyclic ring,
wherein said heterocyclic ring
is saturated, partially unsaturated or aromatic,
comprises 1, 2 or 3 heteroatoms or heteroatom groups selected from the group consisting of N, O, S, NO, SO and $SO_2$,
is unsubstituted or substituted with one to five radicals $R^{10}$, and
wherein one or two $CH_2$ groups in said saturated or partially saturated rings may be replaced by one or two $C=O$ groups;
or two vicinally bound radicals $R^6$ together form a group selected from $=C(R^c)_2$, $=S(O)_mR^o$, $=S(O)_mN(R'')_2$, $=NR''$ and $=NN(R'')_2$;
$R^7$ is selected independently from the group consisting of hydrogen, cyano, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_3$-$C_8$-cycloalkyl, $C_3$-$C_8$-cycloalkyl-$C_1$-$C_4$-alkyl, $C_2$-$C_6$-alkenyl, $C_2$-$C_6$-alkynyl,
wherein the carbon atom of the aforementioned aliphatic and cycloaliphatic radicals may be substituted with one or more $R^c$;
$Si(R^{11})_2R^{12}$, $OR^o$, $O(CO)R^c$, $O(CS)R^c$, $S(O)_mR^o$, $S(O)_mN(R'')_2$, $S(CO)R^c$, $S(CS)R^c$, $S(C=NR'')R^c$, $N(R'')_2$, $N(R'')C(=O)R^c$, $N(R'')C(=S)R^c$, $NS(O)_mR^o$, $N=C(R^c)_2$, $C(=O)R^c$, $C(=S)R^c$, $C(=NR'')R^c$, $C(=O)N(R'')_2$, $C(=S)N(R'')_2$, phenyl
which may be substituted with 1, 2, 3, 4 or 5 radicals $R^{10}$;
and a 3-, 4-, 5-, 6- or 7-membered heterocyclic ring,
wherein said heterocyclic ring
is saturated, partially unsaturated or aromatic,
comprises 1, 2 or 3 heteroatoms or heteroatom groups selected from the group consisting of N, O, S, NO, SO and $SO_2$, is unsubstituted or substituted with one to five radicals $R^{10}$, and wherein one or two $CH_2$ groups in said saturated or partially saturated rings may be replaced by one or two C=O groups;

with the proviso that $R^7$ is not $C_1$-$C_6$-alkoxy or $C_1$-$C_6$-haloalkoxy if it is bound to an oxygen atom;

$R^8$, $R^9$ are selected independently from one another and independently of each occurrence from the group consisting of hydrogen, CN, $NO_2$, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_3$-$C_8$-cycloalkyl, $C_3$-$C_8$-cycloalkyl-$C_1$-$C_4$-alkyl, $C_2$-$C_6$-alkenyl, $C_2$-$C_6$-alkynyl, wherein the carbon atom of the aforementioned aliphatic and cycloaliphatic radicals may be substituted with one or more $R^c$;

$Si(R^{11})_2R^{12}$, $OR^o$, $O(CO)R^c$, $O(CS)R^c$, $S(O)_mR^o$, $S(O)_mN(R'')_2$, $S(CO)R^c$, $S(CS)R^c$, $S(C=NR'')R^c$, $N(R'')_2$, $N(R'')C(=O)R^c$, $N(R'')C(=S)R^c$, $NS(O)_mR^o$, $N=C(R^c)_2$, $C(=O)R^c$, $C(=S)R^c$, $C(=NR'')R^c$, $C(=O)N(R'')_2$, $C(=S)N(R'')_2$ phenyl which may be substituted with 1, 2, 3, 4 or 5 radicals $R^{10}$;

and a 3-, 4-, 5-, 6- or 7-membered heterocyclic ring, wherein said heterocyclic ring is saturated, partially unsaturated or aromatic, comprises 1, 2 or 3 heteroatoms or heteroatom groups selected from the group consisting of N, O, S, NO, SO and $SO_2$, is unsubstituted or substituted with one to five radicals $R^{10}$, and wherein one or two $CH_2$ groups in said saturated or partially saturated rings may be replaced by one or two C=O groups;

$R^{10}$ is selected independently from the group consisting of halogen, cyano, azido, nitro, SCN, $SF_5$, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_3$-$C_8$-cycloalkyl, $C_3$-$C_8$-cycloalkyl-$C_1$-$C_4$-alkyl, $C_2$-$C_6$-alkenyl, $C_2$-$C_6$-alkynyl, wherein the carbon atom of the aforementioned aliphatic and cycloaliphatic radicals may be substituted with one or more $R^c$;

$Si(R^{11})_2R^{12}$, $OR^o$, $O(CO)R^c$, $O(CS)R^c$, $S(O)_mR^o$, $S(O)_mN(R'')_2$, $S(CO)R^c$, $S(CS)R^c$, $S(C=NR'')R^c$, $N(R'')_2$, $N(R'')C(=O)R^c$, $N(R'')C(=S)R^c$, $NS(O)_mR^o$, $N=C(R^c)_2$, $C(=O)R^c$, $C(=S)R^c$, $C(=NR'')R^c$, $C(=O)N(R'')_2$, $C(=S)N(R'')_2$, phenyl which may be substituted with one to five radicals selected independently from halogen, cyano, nitro, $C_1$-$C_6$-alkyl, $C_1$-$C_6$-haloalkyl, $C_1$-$C_6$-alkoxy and $C_1$-$C_6$-haloalkoxy;

and a 3-, 4-, 5-, 6- or 7-membered heterocyclic ring, wherein said heterocyclic ring is saturated or unsaturated, comprises 1, 2 or 3 heteroatoms or heteroatom groups selected from the group consisting of N, O, S, NO, SO and $SO_2$, is unsubstituted or substituted with one to five radicals selected independently from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy;

or two radicals $R^{10}$ bound on adjacent atoms together form a group selected from —$CH_2CH_2CH_2CH_2$—, —CH=CH—CH=CH—, —N=CH—CH=CH—, —CH=N—CH=CH—, —N=CH—N=CH—, —$OCH_2CH_2CH_2$—, —OCH=CHCH_2—, —$CH_2OCH_2CH_2$—, —$OCH_2CH_2O$—, —$OCH_2OCH_2$—, —$CH_2CH_2CH_2$—, —CH=$CHCH_2$—, —$CH_2CH_2O$—, —CH=CHO—, —$CH_2OCH_2$—, —$CH_2C(=O)O$—, —C(=O)$OCH_2$—, —$O(CH_2)O$—, —$SCH_2CH_2CH_2$—, —SCH=$CHCH_2$—, —$CH_2SCH_2CH_2$—, —$SCH_2CH_2S$—, —$SCH_2SCH_2$—, —$CH_2CH_2S$—, —CH=CHS—, —$CH_2SCH_2$—, —$CH_2C(=S)S$—, —C(=S)$SCH_2$—, —$S(CH_2)S$—, —$CH_2CH_2NR^8$—, —$CH_2CH=N$—, —CH=CH—$NR^8$—, —OCH=N— and —SCH=N—, wherein in each of the above groups, one to five hydrogen atoms independently of each other may be replaced by one to five substituents selected from the group consisting of halogen, methyl, halomethyl, hydroxyl, methoxy and halomethoxy, or one or two or more $CH_2$ groups of the above groups may be replaced by one or two C=O groups;

$R^{11}$, $R^{12}$ are selected independently of each other and independently of each occurrence from the group consisting of $C_1$-$C_4$-alkyl, $C_3$-$C_6$-cycloalkyl, $C_1$-$C_4$-alkoxy-$C_1$-$C_4$-alkyl, phenyl and benzyl;

$R^c$ is selected independently from the group consisting of hydrogen, halogen, cyano, azido, nitro, SCN, $SF_5$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkyl, $C_3$-$C_8$-cycloalkyl-$C_1$-$C_4$-alkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl, and a 3-, 4-, 5-, 6- or 7-membered heterocyclic ring, wherein said heterocyclic ring is saturated, partially unsaturated or aromatic, comprises 1, 2 or 3 heteroatoms or heteroatom groups selected from CO, N, O, S, NO, SO and $SO_2$, is unsubstituted or substituted with one to five radicals, which are selected independently of each other from halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^o$ is selected independently from the group consisting of hydrogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkyl, $C_3$-$C_8$-cycloalkyl-$C_1$-$C_4$-alkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl, and a 3-, 4-, 5-, 6- or 7-membered heterocyclic ring, wherein said heterocyclic ring is saturated, partially unsaturated or aromatic, comprises 1, 2 or 3 heteroatoms or heteroatom groups selected from CO, N, O, S, NO, SO and $SO_2$, is unsubstituted or substituted with one to five radicals, which are selected independently of each other from halogen, cyano, nitro, $C_1$-$C_4$-alkyl, $C_1$-$C_4$-haloalkyl, $C_1$-$C_4$-alkoxy and $C_1$-$C_4$-haloalkoxy;

with the proviso that $R^o$ is not $C_1$-$C_6$-alkoxy or $C_1$-$C_6$-haloalkoxy if it is bound to an oxygen atom;

$R''$ is selected independently from the group consisting of hydrogen, CN, $NO_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkyl, $C_3$-$C_8$-cycloalkyl-$C_1$-$C_4$-alkyl, $C_3$-$C_8$-halocycloalkyl, $C_2$-$C_6$-alkenyl, $C_2$-$C_6$- haloalkenyl, $C_2$-$C_6$-alkynyl, $C_2$-$C_6$-haloalkynyl, phenyl, and a 3-, 4-, 5-, 6- or 7-membered saturated heterocyclic ring,
  wherein said heterocyclic ring
    is saturated, partially unsaturated or aromatic,
    comprises 1, 2 or 3 heteroatoms or heteroatom groups selected from CO, N, O, S, NO, SO and $SO_2$,
    is unsubstituted or substituted with one to five radicals, which are selected independently of each other from halogen, cyano, nitro, $C_1$-$C_4$-alkyl, $C_1$-$C_4$-haloalkyl, $C_1$-$C_4$-alkoxy and $C_1$-$C_4$-haloalkoxy;
  m is independently 0, 1 or 2;
  p is 0, 1, 2, 3 or 4;
or enantiomers or diastereoisomers thereof or their agriculturally or veterinarily acceptable salts,
with the exception of 2-[4-[2-aminoethyamino]-7-trifluoromethyl-quinazolin-2-yl]-phenol, and the salts and N-oxides thereof.

18. The compound of claim 13, wherein $R^{5b}$ is selected from the group consisting of $C_1$-$C_6$-alkyl, $C_3$-$C_6$-cycloalkyl, $C_1$-$C_6$-alkoxy and $C_3$-$C_6$-cycloalkoxy, wherein each mentioned radical is at least substituted with one halogen.

19. The compound of claim 13, wherein $R^3$ is selected from the group consisting of hydrogen, halogen, cyano, azido, nitro, SCN, $SF_5$, $C_1$-$C_6$-haloalkyl, $C_3$-$C_6$-halocycloalkyl, $C_1$-$C_6$-haloalkoxy, $C_3$-$C_6$-halocycloalkoxy, $Si(R^{11})_2R^{12}$, $OR^7$, $S(O)_mR^7$, $N(R^8)R^9$, $N=(R^6)_2$, $C(=O)R^6$, $C(=S)R^6$ and $C(=NR^8)R^6$.

20. The compound of claim 13, wherein
  $R^{5b}$ is selected from the group consisting of $C_1$-$C_6$-haloalkyl and $C_1$-$C_6$-haloalkoxy;
  $R^3$ is selected from the group consisting of hydrogen, halogen, CN, $NO_2$, $C(=NR^8)R^6$, $C_1$-$C_6$-haloalkyl, $C_3$-$C_6$-halocycloalkyl, $C_1$-$C_6$-haloalkoxy and $C_3$-$C_6$-halocycloalkoxy.

21. The compound of claim 13, wherein
  $R^{5b}$ is $CF_3$;
  $R^3$ is halogen;
  $A^1$, $A^2$, $A^3$ and $A^4$ are $CR^4$;
  $R^{5c}$ and $R^{5d}$ are independently from one another hydrogen, halogen, $C_1$-$C_6$-alkyl or $C_1$-$C_6$-haloalkyl;
  $R^{5a}$ and each $R^4$ are independently from one another hydrogen, halogen, CN, $NO_2$, $C_1$-$C_6$-alkyl, $C_3$-$C_6$-cycloalkyl, $C_1$-$C_6$-alkoxy or $C_1$-$C_6$-cycloalkoxy.

22. The compound of claim 13, wherein
  $R^{5b}$ is $CF_3$;
  $R^3$ is halogen;
  $A^1$, $A^2$, $A^3$ and $A^4$ are $CR^4$;
  $R^{5c}$ and $R^{5d}$ are hydrogen;
  $R^{5a}$ and each $R^4$ are independently from one another hydrogen, halogen, $C_1$-$C_6$-alkyl, or $C_1$-$C_6$-haloalkyl.

* * * * *